United States Patent
Gori et al.

(10) Patent No.: US 11,518,985 B2
(45) Date of Patent: Dec. 6, 2022

(54) DETERGENT COMPOSITION COMPRISING A DNASE

(71) Applicant: Novozymes A/S, Bagsvaerd (DK)

(72) Inventors: Klaus Gori, Copenhagen (DK); Henrik Marcus Geertz-Hansen, Copenhagen (DK); Jesper Salomon, Holte (DK); Thomas Holberg Blicher, Copenhagen (DK); Mary Ann Stringer, Soborg (DK); Nikolaj Spodsberg, Holte (DK); Tianqi Sun, Beijing (CN); Morten Gjermansen, Greve (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/158,077

(22) Filed: Jan. 26, 2021

(65) Prior Publication Data
US 2021/0189362 A1    Jun. 24, 2021

Related U.S. Application Data

(62) Division of application No. 15/766,962, filed as application No. PCT/EP2016/074102 on Oct. 7, 2016, now Pat. No. 10,934,535.

(30) Foreign Application Priority Data

| Oct. 7, 2015 | (DK) | .......................... PA 2015 00615 |
| Oct. 7, 2015 | (DK) | .......................... PA 2015 00617 |
| Oct. 7, 2015 | (DK) | .......................... PA 2015 00618 |

(51) Int. Cl.
| *C12N 9/22* | (2006.01) |
| *C11D 3/386* | (2006.01) |
| *C11D 3/20* | (2006.01) |
| *C11D 3/22* | (2006.01) |
| *C11D 3/37* | (2006.01) |
| *C11D 11/00* | (2006.01) |

(52) U.S. Cl.
CPC .............. *C12N 9/22* (2013.01); *C11D 3/2065* (2013.01); *C11D 3/22* (2013.01); *C11D 3/3707* (2013.01); *C11D 3/38627* (2013.01); *C11D 3/38636* (2013.01); *C11D 3/38681* (2013.01); *C11D 11/0017* (2013.01); *C12Y 301/21* (2013.01); *C12Y 301/21001* (2013.01)

(58) Field of Classification Search
None
See application file for complete search history.

(56) References Cited

U.S. PATENT DOCUMENTS

| 6,340,566 | B1 | 1/2002 | McCutchen-Maloney |
| 6,365,355 | B1 | 4/2002 | McCutchen-Maloney |
| 10,954,497 | B2 | 3/2021 | Gjermansen et al. |
| 2010/0061971 | A1 | 3/2010 | Genkin et al. |
| 2012/0060300 | A1 | 3/2012 | Kim et al. |
| 2013/0189760 | A1 | 7/2013 | Mori |
| 2019/0055528 | A1 | 2/2019 | Gori et al. |
| 2020/0123476 | A1 | 4/2020 | Gjermansen et al. |

FOREIGN PATENT DOCUMENTS

| EP | 2617824 A1 | 7/2013 |
| WO | 01/98214 A1 | 12/2001 |
| WO | 2009/107091 A2 | 9/2009 |
| WO | 2009/111258 A2 | 9/2009 |
| WO | 2011/015327 A1 | 2/2011 |
| WO | 2011/098579 A1 | 8/2011 |
| WO | 2014/087011 A1 | 6/2014 |
| WO | 2015/181286 A1 | 12/2015 |
| WO | 2017/162836 A1 | 9/2017 |
| WO | 2018/011276 A1 | 1/2018 |

OTHER PUBLICATIONS

Chen et al. (BMC Genomics 2013, 14, 339, 2013).*
He et al. (Scientific Reports, 5: 9747; DOI:1010.1038/srep09747, May 2015).*
Ngo et al. in The Protein Folding Problem and Tertiary Structure Prediction, 1994, Merz et al. (ed.), Birkhauser, Boston, MA, pp. 433 and 492-495.*
Anonymous, NCBI Accession No. WP_004251670 (2013).
Anonymous, UniParc Accession No. UPI0003A82032 (2013).
Anonymous, NCBI Accession No. WP_025722554 (2014).
Anonymous, NCBI Accession No. WP_027924635 (2014).
Anonymous, NCBI Accession No. WP_028551502 (2014).
Anonymous, NCBI Accession No. WP_029440352 (2014).
Anonymous, NCBI Accession No. WP_034664156 (2014).
Anonymous, NCBI Accession No. WP_039304398 (2015).
Anonymous, NCBI Accession No. WP_041089515 (2015).
Anonymous, NCBI Accession No. WP_045521827 (2015).
Anonymous, NCBI Accession No. WP_047969415 (2015).
Anonymous, NCBI Accession No. WP_051450038 (2015).
Anonymous, NCBI Accession No. WP_030603405 (2016).
Anonymous, NCBI Accession No. WP_031424130 (2016).
Anonymous, NCBI Accession No. WP_034817012 (2016).
Anonymous, NCBI Accession No. WP_035510436 (2016).
Anonymous, Merriam-Webster Dictionary Definition & Granule (2020).
Baumgarten et al., GenBank Accession No. KXJ07836 (2015).
Birren et al., EBI Accession No. A5ARC4 (2005).
Birren et al., EBI Accession No. Q2GRF9 (2006).
Birren et al., GenBank Accession No. EAT79147.2 (2007).
Birren et al., GenBank Accession No. EAQ85431.1 (2015).
Chancey et al., UniProt Accession No. J1GWI8 (2012).
Chen et al., UniProt Accession No. S3D1S1 (2013).
Chen et al., UniProt Accession No. S3DWR8 (2013).
Coleman et al., EBI Accession No. C7YPZ7 (2009).

(Continued)

*Primary Examiner* — Richard G Hutson
(74) *Attorney, Agent, or Firm* — Elias Lambiris

(57) ABSTRACT

The present invention relates to new polypeptides, nucleotides encoding the polypeptide, as well as methods of producing the polypeptides. The present invention also relates to detergent composition comprising polypeptides, a laundering method and the use of polypeptides.

11 Claims, No Drawings

Specification includes a Sequence Listing.

(56) References Cited

OTHER PUBLICATIONS

Cuomo et al., EBI Accession No. U7Q814 (2014).
Cuomo et al., EBI Accession No. AOAOD2ITS4 (2015).
Cuomo et al., GenBank Accession No. ERT03205.1 (2015).
Cuomo et al., GenBank Accession No. KIX09484.1 (2015).
Daniel et al., UniProt Accession No. AOAOE4HDQ4 (2015).
Federova et al, EBI Accession No. A1D7DL (2007).
Feldgarden et al., GenBank Accession No. EJR08198 (2012).
Franco et al., UniProt Accession No. AOAOL1HKH6 (2015).
Gao et al., PLoS Genetics, vol. 7, Issue 1, Article No. E1001264, pp. 1-18 (2011).
Gibson et al., EBI Accession No. AOAOA1V6B7 (2015).
Giuliano et al., GenBank Accession No. EXV05759.1 (2014).
Goh et al., UniProt Accession No. AOAOC2VMI6 (2015).
Gori et al., ip.com Prior Art Database Technical Disclosure, IP.com No. IPCOM000237363D, pp. 1-94 (2014).
Gostin et al., EBI Accession No. AOA074YFK3 (2014).
Greiner-Stoeffele et al., EBI Accession No. JA286959 (2011).
Hane et al., EBI Accession No. Q0U4Q1 (2006).
Hymes et al., Journal of Infectious Disease, vol. 207, No. 10, pp. 1491-1497 (2013).
Klosterman et al., EBI Accession No. G2WSK6 (2011).
Kwak et al., UniProt Accession No. AOA086GGG3 (2014).
Lawrence et al., EBI Accession No. AOA)G2FAG3 (2015).
Lian et al., GenBank Accession No. AFK65439 (2013).
Liu et al., GenBank Accession No. ET577558.1 (2014).
Liu et al., GenBank Accession No. KMY52255 (2015).
Ma et al., GenBank Accession No. EGY17920.1 (2011).
Ma et al., EBI Accession No. H6NAU2 (2012).
Ma et al., GenBank Accession No. CCF36160.1 (2012).
Marincowitz et al., GenBank Accession No. EU552123 (2008).
Martin et al., Trends in Biochemical Sciences, vol. 21, No. 8, pp. 283-285 (1996).
McCutchen-Mulaney et al., EBI Accession No. AAE89259 (2014).
McCutchen-Mulaney et al., EBI Accession No. AAM56188 (2014).
Morales-Cruz et al., GenBank Accession No. KKY31181.1 (2015).
Murphy et al., UniProt Accession No. AOAOT9L4U8 (2015)h.
Neafsy et al., UniProt Accession No. AOAOJ8TUN1 (2010).
Ngo et al., The Protein Folding Problem and Tertiary Structure Prediction, chapter 14, pp. 433 and 492-495 (1994).
Nierman et al., GenBank Accession No. EAW21625.1 (2006).
Njiland et al., PLoS One, vol. 5, Issue 12, Article e15668, pp. 1-7 (2010).
O'Connell et al., UniProt Accession No. H1V7F8 (2012).
Ohm et al., EBI Accession No. M2N7N4 (2013).
Ohm et al., EBI Accession No. M2S5C4 (2013).
Ohm et al., GenBank Accession No. EMC94815.1 (2013).
Ohm et al., GenBank Accession No. EMD62363.1 (2013).
Osei et al., UniProt Accession No. AOAOP8GOA5 (2016).
Pel et al., EBI Accession No. A2QFZ2 (2007).
Pel et al., GenBank Accession No. CAK38102.1 (2011).
Sharma et al., UniProt Accession No. AOAOF5R1U3 (2015).
Shields et al., PLoS One, vol. 8, Issue 2, Article e55339, pp. 1-13 (2013).
Traeger et al., EBI Accession No. U4LM18 (2013).
Traeger et al., GenBank Accession No. 00X32983.1 (2013).
Tran et al., UniProt Accession No. AOAOK6K3H5 (2015).
Vandeputte et al., GenBank Accession No. KEZ43987.1 (2014).
Vandeputte et al., UniProt Accession No. AOA084G9H5 (2014).
Wang et al., EBI Accession No. W3WUK5 (2014).
Wang et al., GenBank Accession No. AJK28734 (2015).
Wang et al., UniProt Accession No. AOAOC5AGR7 (2015).
Wortman et al., GenBank Accession No. CBF82427.1 (2015).
Yaakop et al., UniProt Accession No. AOAOB5ASW2 (2015).
Yoon et al., UniProt Accession No. AOA084H293 (2005).
Yoon et al., GenBank Accession No. KF753705.1 (2014).
Zhu et al., UniProt Accession No. AOAOF7TT23 (2014).
Petrusso, 2022, Toothpaste, obtained from encyclopedia.com.
Singh et al, 2017, Current protein and peptide science 18, 1-11.
Zhang et al, 2018, Structure 26, 1474-1485.
Greiner-Stoeffele et al, WO 2011-015327—2011, EBI Accession No. JA286959.
Greiner-Stoeffele et al, WO 2011-015327 A1—EBI Access No. JA286954.
McCutchen-Maloney, U.S. Pat. No. 6,340,566—EBI Access No. AAE89259.
McCutchen-Maloney, U.S. Pat. No. 6,365,355—EBI Access No. AAM56188.

* cited by examiner

DETERGENT COMPOSITION COMPRISING A DNASE

CROSS-REFERENCE TO RELATED APPLICATIONS

This application is a divisional of U.S. application Ser. No. 15/766,962 filed Apr. 9, 2018, now U.S. Patent No. 10,934,535, which is a 35 U.S.C. 371 national application of international application no. PCT/EP2016/074102 filed Oct. 7, 2016, which claims priority or the benefit under 35 U.S.C. 119 of Danish application nos. PA 2015 00615, PA 2015 00617 and PA 2015 00618, each filed Oct. 7, 2015. The contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to new polypeptides having deoxyribonuclease (DNase) activity, nucleotides encoding the polypeptide, as well as methods of producing the polypeptides. The present invention also relates to detergent composition comprising a DNase, a laundering method and the use of DNase.

BACKGROUND OF THE INVENTION

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces, where biofilm colonisation can form the base component of a localised ecosystem which can disrupt and interfere with industrial processes and components.

When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result, the laundry item is more "soiled" after wash than before wash. Further, these bacteria are a source of bad odour, which develops after use of the laundry item. The bad odour (malodour) is difficult to remove and may remain even after wash. The reason for this bad odour is adhesion of bacteria to the textile surface. Because of the adhesion to the textile, the bacteria may remain even after wash, and continue to be a source of bad odour.

International patent applications WO 2011/098579 (University of Newcastle) and WO 2014/087011 (Novozymes A/S) relate to deoxyribonuclease compounds and methods for biofilm disruption and prevention.

SUMMARY OF THE INVENTION

The invention relates to polypeptides having DNase (deoxyribonuclease) activity and polynucleotides encoding these.

One aspect of the invention relates to a composition comprising a polypeptide having DNase activity, wherein the polypeptide comprises any of the motifs [G/Y/W/F/A/H]NI[R/Q/D/E/V] (SEQ ID NO: 73), SDH[D/H/L]P (SEQ ID NO: 74) or GGNI[RIQ] (SEQ ID NO: 75), and at least on additional component, selected from
  i. a polyol,
  ii. an enzyme preferably selected from protease and lipases,
  iii. a surfactant preferably selected from anionic or non-ionic surfactants, and
  iv. one or more polymer.

A second aspect of the invention relates to a detergent composition comprising a polypeptide having DNase activity selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 or DNases having at least 80% sequence identity thereto and a detergent adjunct ingredient.

A third aspect of the invention relates to a polypeptide having DNase activity, wherein the polypeptide comprises one or more of the motifs [G/Y/W/F/A/H] NI[R/Q/D/E/V] (SEQ ID NO: 73), SDH [D/H/L] P (SEQ ID NO: 74) or GGNI [RIQ] (SEQ ID NO: 75) and wherein the polypeptide is selected from the polypeptides:
  a) a polypeptide having at least 72% sequence identity to the polypeptide of SEQ ID NO: 6,
  b) a polypeptide having at least 90% sequence identity to the polypeptide of SEQ ID NO: 7,
  c) a polypeptide having at least 84.5% sequence identity to the polypeptide of SEQ ID NO: 10,
  d) a polypeptide having at least 82% sequence identity to the polypeptide of SEQ ID NO: 27,
  e) a polypeptide having at least 80% sequence identity to the polypeptide of SEQ ID NO: 30,
  f) a polypeptide having at least 60% sequence identity to the polypeptide of SEQ ID NO: 33,
  g) a polypeptide having at least 65% sequence identity to the polypeptide of SEQ ID NO: 36,
  h) a polypeptide having at least 91% sequence identity to the polypeptide of SEQ ID NO: 39,
  i) a polypeptide having at least 99% sequence identity to the polypeptide of SEQ ID NO: 42,
  j) a polypeptide having at least 68% sequence identity to the polypeptide of SEQ ID NO: 45,
  k) a polypeptide having at least 94% sequence identity to the polypeptide of SEQ ID NO: 48, l) a polypeptide having at least 80% sequence identity to the polypeptide of SEQ ID NO: 51, m) a polypeptide having at least 73% sequence identity to the polypeptide of SEQ ID NO: 57, n) a polypeptide having at least 90% sequence identity to the polypeptide of SEQ ID NO: 60, o) a polypeptide having at least 84% sequence identity to the polypeptide of SEQ ID NO: 63, p) a polypeptide having at least 80% sequence identity to the polypeptide of SEQ ID NO: 66, q) a polypeptide having at least 72% sequence identity to the polypeptide of SEQ ID NO: 69, and r) a polypeptide having at least 68% sequence identity to the polypeptide of SEQ ID NO: 72.

One aspect of the invention relates to a polypeptide having DNase activity, selected from the group consisting of:

(a) a polypeptide having at least 60% sequence identity to the polypeptide comprising SEQ ID NOS: 2, 3, 4, 5, 6, 7, 8, 9 or 10;

(b) a variant of the mature polypeptide of SEQ ID NOS: 2, 3, 4, 5, 6, 7, 8, 9 or 10 comprising a substitution, deletion, and/or insertion at one or more positions; and (c) a fragment of the polypeptide of (a) or (b), that has DNase activity.

Another aspect the invention relates to detergent compositions comprising a polypeptide having DNase activity and preferably a detergent adjunct ingredient, such as surfactants, builders etc. One aspect of the invention relates to a composition comprising a polypeptide having DNase activity and having at least 60% sequence identity to a polypeptide selected from the group consisting of SEQ ID NOS: 2, 3, 4, 5, 6, 7, 8, 9 and 10 and a detergent adjunct.

The invention further relates to a cleaning or laundering method for cleaning or laundering an item comprising the steps of:

a. Exposing an item to a wash liquor comprising a polypeptide having DNase activity or a detergent composition comprising a polypeptide having DNase activity;

b. Completing at least one wash cycle; and c. Optionally rinsing the item, wherein the item is a textile and wherein the DNase is selected from the group consisting of polypeptides with SEQ ID NOS: 2, 3, 4, 5, 6, 7, 8, 9 and 10 or a polypeptide having at least 60% sequence identity to any of the polypeptides with SEQ ID NOS: 2, 3, 4, 5, 6, 7, 8, 9 and 10.

In addition is claimed the use of a DNase selected from the group consisting of polypeptides with SEQ ID NOS: 2, 3, 4, 5, 6, 7, 8, 9 and 10 or a polypeptide having at least 60% sequence identity to any of the polypeptides with SEQ ID NOS: 2, 3, 4, 5, 6, 7, 8, 9 and 10 for preventing, reducing or removing the biofilm of an item.

The present invention further relates to polynucleotides encoding polypeptides having DNase activity selected from the group consisting of polypeptides with SEQ ID NOS: 2, 3, 4, 5, 6, 7, 8, 9 and 10 and methods of producing the polypeptides.

SEQUENCES

SEQ ID NO: 1 DNA sequence obtained from *Vibrissea flavovirens*
SEQ ID NO: 2 is the polypeptide sequence derived from SEQ ID NO: 1
SEQ ID NO: 3 mature polypeptide obtained from *Vibrissea flavovirens*
SEQ ID NO: 4 mature polypeptide obtained from *Penicillium reticulisporum*
SEQ ID NO: 5 mature polypeptide obtained from *Acremonium dichromosporum*
SEQ ID NO: 6 mature polypeptide obtained from *Preussia aemulans*
SEQ ID NO: 7 mature polypeptide obtained from *Colletotrichum circinans*
SEQ ID NO: 8 mature polypeptide obtained from *Clavicipitaceae*
SEQ ID NO: 9 mature polypeptide obtained from *Preussia aemulans*
SEQ ID NO: 10 mature polypeptide obtained from *Trichurus spiralis*
SEQ ID NO: 11 DNA obtained from *Penicillium reticulisporum*
SEQ ID NO: 12 polypeptide obtained SEQ ID NO: 11
SEQ ID NO: 13 DNA obtained from *Acremonium dichromosporum*
SEQ ID NO: 14 polypeptide obtained from SEQ ID NO: 13
SEQ ID NO: 15 DNA obtained from *Preussia aemulans*
SEQ ID NO: 16 polypeptide obtained from SEQ ID NO: 15
SEQ ID NO: 17 DNA obtained from *Colletotrichum circinans*
SEQ ID NO: 18 polypeptide obtained from SEQ ID NO: 17
SEQ ID NO: 19 DNA obtained from *Clavicipitaceae*
SEQ ID NO: 20 polypeptide obtained from SEQ ID NO: 19
SEQ ID NO: 21 DNA obtained from *Preussia aemulans*
SEQ ID NO: 22 polypeptide obtained from SEQ ID NO: 21
SEQ ID NO: 23 DNA obtained from *Trichurus spiralis*
SEQ ID NO: 24 polypeptide obtained from SEQ ID NO: 23
SEQ ID NO: 25 DNA sequence obtained from *Pyrenochaetopsis* sp.
SEQ ID NO: 26 is the polypeptide sequence derived from SEQ ID NO: 25
SEQ ID NO: 27 mature polypeptide obtained from *Pyrenochaetopsis* sp.
SEQ ID NO: 28 DNA sequence obtained from *Aspergillus sydowii*
SEQ ID NO: 29 is the polypeptide sequence derived from SEQ ID NO: 28
SEQ ID NO: 30 mature polypeptide obtained from *Aspergillus sydowii*
SEQ ID NO: 31 DNA sequence obtained from *Cladosporium cladosporioides*
SEQ ID NO: 32 is the polypeptide sequence derived from SEQ ID NO: 31
SEQ ID NO: 33 mature polypeptide obtained from *Cladosporium cladosporioides*
SEQ ID NO: 34 DNA sequence obtained from *Rhinocladiella* sp.
SEQ ID NO: 35 is the polypeptide sequence derived from SEQ ID NO: 34
SEQ ID NO: 36 mature polypeptide obtained from *Rhinocladiella* sp.
SEQ ID NO: 37 DNA sequence obtained from *Pyronema domesticum*
SEQ ID NO: 38 is the polypeptide sequence derived from SEQ ID NO: 37
SEQ ID NO: 39 mature polypeptide obtained from *Pyronema domesticum*
SEQ ID NO: 40 DNA sequence obtained from *Aspergillus niger*
SEQ ID NO: 41 is the polypeptide sequence derived from SEQ ID NO: 40
SEQ ID NO: 42 mature polypeptide obtained from *Aspergillus niger*

SEQ ID NO: 43 DNA sequence obtained from *Phialophora geniculata*
SEQ ID NO: 44 is the polypeptide sequence derived from SEQ ID NO: 43
SEQ ID NO: 45 mature polypeptide obtained from *Phialophora geniculata*
SEQ ID NO: 46 DNA sequence obtained from *Paradendryphiella salina*
SEQ ID NO: 47 is the polypeptide sequence derived from SEQ ID NO: 46
SEQ ID NO: 48 mature polypeptide obtained from *Paradendryphiella salina*
SEQ ID NO: 49 DNA sequence obtained from *Aspergillus insuetus*
SEQ ID NO: 50 is the polypeptide sequence derived from SEQ ID NO: 49
SEQ ID NO: 51 mature polypeptide obtained from *Aspergillus insuetus*
SEQ ID NO: 52 DNA sequence obtained from *Purpureocillium lilacinum*
SEQ ID NO: 53 is the polypeptide sequence derived from SEQ ID NO: 52
SEQ ID NO: 54 mature polypeptide obtained from *Purpureocillium lilacinum*
SEQ ID NO: 55 DNA sequence obtained from *Warcupiella spinulosa*
SEQ ID NO: 56 is the polypeptide sequence derived from SEQ ID NO: 55
SEQ ID NO: 57 mature polypeptide obtained from *Warcupiella spinulosa*
SEQ ID NO: 58 DNA sequence obtained from *Stenocarpella maydis*
SEQ ID NO: 59 is the polypeptide sequence derived from SEQ ID NO: 58
SEQ ID NO: 60 mature polypeptide obtained from *Stenocarpella maydis*
SEQ ID NO: 61 DNA sequence obtained from *Acrophialophora fusispora*
SEQ ID NO: 62 is the polypeptide sequence derived from SEQ ID NO: 61
SEQ ID NO: 63 mature polypeptide obtained from *Acrophialophora fusispora*
SEQ ID NO: 64 DNA sequence obtained from *Chaetomium luteum*
SEQ ID NO: 65 is the polypeptide sequence derived from SEQ ID NO: 64
SEQ ID NO: 66 mature polypeptide obtained from *Chaetomium luteum*
SEQ ID NO: 67 DNA sequence obtained from *Arthrinium arundinis*
SEQ ID NO: 68 is the polypeptide sequence derived from SEQ ID NO: 67
SEQ ID NO: 69 mature polypeptide obtained from *Arthrinium arundinis*
SEQ ID NO: 70 DNA sequence obtained from *Phialophora geniculata*
SEQ ID NO: 71 is the polypeptide sequence derived from SEQ ID NO: 70
SEQ ID NO: 72 mature polypeptide obtained from *Phialophora geniculata*
SEQ ID NO: 73 motif [G/Y/W/F/A/H]NI[R/Q/D/E/V]
SEQ ID NO: 74 motif SDH[D/H/L]P
SEQ ID NO: 75 motif GGNI[R/Q]

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Colour difference (L value): A Lab colour space is a colour-opponent space with dimension L for lightness. L value, L* represents the darkest black at L*=0, and the brightest white at L*=100. In the context of the present invention L value is also referred to as colour difference.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant disruption or removal of a biofilm or components of a biofilm such as polysaccharides, proteins, DNA, soil or other components present in the biofilm.

Detergent adjunct ingredient: The detergent adjunct ingredient is different to the DNase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the DNases of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity that catalyzes the hydrolytic cleavage of phosphodiester linkages in the DNA backbone, thus degrading DNA. The term "DNases" and the expression "a polypeptide with DNase activity" are used interchangeably throughout the application. For purposes of the present invention, DNase activity is determined according to the procedure described in the Assay I. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide shown in SEQ ID NOS: 2, or the mature polypeptide shown in 3, 4, 5, 6, 7, 8, 9 or 10. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide shown in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72. In one embodiment, the polypeptides of the present invention have improved DNase activity, e.g., such that the DNase activity of the polypeptide is at least 105%, e.g., at least 110%, at least 120%, at least 130%, at least 140%, at least 160%, at least 170%, at least 180%, or at least 200% with reference to the DNase activity of the mature polypeptide of SEQ ID NOS: 2, or the mature polypeptide shown in 3, 4, 5, 6, 7, 8, 9 or 10.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has DNase activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved wash performance: The term "improved wash performance" is defined herein as an enzyme displaying an increased wash performance in a detergent composition relative to the wash performance of same detergent composition without the enzyme, e.g., by increased stain removal or less redeposition. The term "improved wash performance" includes wash performance in laundry.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g., a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

Malodour: By the term "malodour" is meant an odour which is not desired on clean items. The cleaned item should smell fresh and clean without malodour s adhered to the item. One example of malodour is compounds with an unpleasant smell, which may be produced by microorganisms. Another example is unpleasant smells can be sweat or body odour adhered to an item which has been in contact with human or animal. Another example of malodour can be the odour from spices, which sticks to items for example curry or other exotic spices which smells strongly. One way of measuring the ability of an item to adhere malodour is by using Assay II disclosed herein.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptides are SEQ ID NOS: 3, 4, 5, 6, 7, 2, 3, 4, 5, 6, 7, 8, 9 and 10. In one aspect, the mature polypeptides are any of the following SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72. In another aspect the mature polypeptide is amino acid 20 to 209 of SEQ ID NO: 2. In another aspect the mature polypeptide is amino acid 1 to 191 of SEQ ID NO: 12. In another aspect the mature polypeptide is amino acid 1 to 182 of SEQ ID NO: 14. In another aspect the mature polypeptide is amino acid 1 to 590 of SEQ ID NO: 16. In another aspect the mature polypeptide is amino acid 1 to 589 of SEQ ID NO: 18. In another aspect the mature polypeptide is amino acid 1 to 186 of SEQ ID NO: 20. In another aspect the mature polypeptide is amino acid 1 to 281 of SEQ ID NO: 22. In another aspect the mature polypeptide is amino acid 1 to 585 of SEQ ID NO: 24. In another aspect the mature polypeptide is amino acid 1 to 592 of SEQ ID NO: 26. In another aspect the mature polypeptide is amino acid 1 to 589 of SEQ ID NO: 29. In another aspect the mature polypeptide is amino acid 1 to 597 of SEQ ID NO: 32. In another aspect the mature polypeptide is amino acid 1 to 600 of SEQ ID NO: 35. In another aspect the mature polypeptide is amino acid 1 to 588 of SEQ ID NO: 38. In another aspect the mature polypeptide is amino acid 1 to 585 of SEQ ID NO: 41. In another aspect the mature polypeptide is amino acid 1 to 587 of SEQ ID NO: 44. In another aspect the mature polypeptide is amino acid 1 to 592 of SEQ ID NO: 47. In another aspect the mature polypeptide is amino acid 1 to 594 of SEQ ID NO: 50. In another aspect the mature polypeptide is amino acid 1 to 588 of SEQ ID NO: 53. In another aspect the mature polypeptide is amino acid 1 to 586 of SEQ ID NO: 56. In another aspect the mature polypeptide is amino acid 1 to 590 of SEQ ID NO: 59. In another aspect the mature polypeptide is amino acid 1 to 596 of SEQ ID NO: 62. In another aspect the mature polypeptide is amino acid 1 to 598 of SEQ ID NO: 65. In another aspect the mature polypeptide is amino acid 1 to 592 of SEQ ID NO: 68. In another aspect the mature polypeptide is amino acid 1 to 766 of SEQ ID NO: 71. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. The mature polypeptide of SEQ ID NO: 2 is SEQ ID NO: 3.

Mature polypeptide coding sequence: The term "mature polypeptide coding sequence" means a polynucleotide that encodes a mature polypeptide having DNase activity. In one aspect, the mature polypeptide coding sequence is the nucleotides 60 to 627 of SEQ ID NO: 1.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pharmaceutical adjunct ingredient means any pharmaceutical excipient suitable for formulating the pharmaceutical compound. Such excipients, carriers, vehicles etc. are well known to those of skill in the art and are described in text books such as Remington's Pharmaceutical Sciences, Mack Publishing Co., Easton, Pa., 1985. Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. For hard gelatin capsule formulations, the active ingredient can be mixed with an inert solid diluent, for example, calcium carbonate, calcium phosphate or kaolin. For soft gelatin capsule formulations the active ingredient can be mixed with water or an oil medium, for example peanut oil, liquid paraffin or olive oil. Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters obtained from fatty acids and a hexitol such as polyoxyethylene sorbitol monooleate, or condensation products of ethylene oxide with partial esters obtained from fatty acids and hexitol anhydrides, for example polyethylene sorbitan monooleate. Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin. Oily suspensions may be formulated by suspending the active ingredients in a vegetable oil, for example arachis oil, olive oil, sesame oil or coconut oil, or in a mineral oil such as liquid paraffin The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Remission value: Wash performance maybe expressed as a Remission value of the stained swatches. After washing and rinsing the swatches are spread out flat and allowed to air dry at room temperature overnight. All washes swatches are evaluated the day after the wash. Light reflectance evaluations of the swatches may be done using a Macbeth Colour Eye 7000 reflectance spectrophotometer with very small aperture. Measurements are made without UV in the incident light and remission at 460 nm is extracted.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows: (Identical Residues×100)/(Length of Alignment−Total Number of Gaps in Alignment). For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EM-BOSS: The European Molecular Biology Open Software Suite, Rice et al., 2000, supra), prefer-ably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows: (Identical Deoxyribonucleotides×100)/(Length of Alignment−Total Number of Gaps in Alignment).

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having DNase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and toweling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fibre (e.g., polyamide fibre, acrylic fibre, polyester fiber, polyvinyl chloride fiber, polyurethane fiber, polyurea fiber, aramid fibre), such as polyester/cotton, and/or cellulose-containing fiber (e.g., rayon/viscose, ramie, flax/linen, jute, cellulose acetate fibre, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same activity as the parent enzyme comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e., the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g., the polypeptides of SEQ ID NOS: 2, 3, 4, 5, 6, 7, 8, 9 or 10.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is defined herein as the solution or mixture of water and detergent components optionally including the enzyme of the invention.

Wash time: The term "wash time" is defined herein as the time it takes for the entire washing process; i.e., the time for the wash cycle(s) and rinse cycle(s) together.

Whiteness: The term "Whiteness" is defined herein as a broad term with different meanings in different regions and for different consumers. Loss of whiteness can, e.g., be due to greying, yellowing, or removal of optical brighteners/hueing agents. Greying and yellowing can be due to soil redeposition, body soils, colouring from, e.g., iron and copper ions or dye transfer. Whiteness might include one or several issues from the list below: colourant or dye effects; incomplete stain removal (e.g., body soils, sebum etc.); redeposition (greying, yellowing or other discolourations of the object) (removed soils reassociate with other parts of textile, soiled or unsoiled); chemical changes in textile during application; and clarification or brightening of colours.

Nomenclature

For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The present invention relates to polypeptides having deoxyribonuclease (DNase) activity (DNases). The DNases can be used for preventing, reducing or removing biofilm on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably throughout the application.

Polypeptides

Polypeptides having DNase activity have been described previously, e.g., in WO 2015/155350 (Novozymes A/S) and WO 2015/155351 (Novozymes A/S), describing fungal DNases and the use of such, e.g., in detergents. The present invention describes novel polypeptides having DNase activity and the use of such polypeptides and compositions for, e.g., preventing, reduction or removal of a biofilm. The polypeptides of the present invention comprise not previously described motifs and domains, which are structurally different and distinguishable from the domains of the DNases described in WO 2015/155350 (Novozymes A/S) and WO 2015/155351 (Novozymes A/S), in fact the domain and motifs described in the present invention have been identified by the inventors and have not previously been described.

Examples of such a domain is a domain termed NUC1 by the inventors, this domain comprises the motifs [E/D/H]H[I/V/L/F/M]X[P/A/S], [T/D/S][G/N]PQL, [G/T]Y[D/S][R/K/L], [F/L]AND[L/I], C[D/N]T[A/R] and [D/Q][I/V]D[H], the amino acids are in one letter code and the brackets indicate that the amino acids within the bracket are alternatives. Polypeptides having DNase activity and comprising these motif(s) effectively prevent, remove or reduce biofilm and the DNases are particularly useful in cleaning processes, such as laundry and dish wash. Examples of DNases of the invention comprising this domain are the polypeptide shown in SEQ ID NO: 3 (mature polypeptide from *Vibrissea flavovirens*) and the polypeptide shown in SEQ ID NO: 4 (mature polypeptide from *Penicillium reticulisporum*).

An example of another domain is a domain termed NUC2 by the inventors; this domain comprises the motif [G/Y/W/F/A/H]NI[R/Q/D/E/V] (SEQ ID NO: 73), where amino acids in brackets are alternatives. The polypeptides of the invention having DNase activity preferably comprises the motif [G/Y/W/F/A/H]NI[R/Q/D/E/V] (SEQ ID NO: 73). Polypeptides having DNase activity and comprising thesis motif have shown to effectively prevent, remove or reduce biofilm and the DNases are particularly useful in cleaning processes, such as laundry and dish wash.

Another distinguishable domain also identified by the inventors is the NUC2_B domain. The polypeptides in NUC2 can be separated into at least one distinct sub-clusters, which were denoted NUC2_B and is defined with motif SDH[D/H/L]P (SEQ ID NO: 74), corresponding to position 610 to 614 of SEQ ID NO: 36. In one embodiment of the invention the polypeptides having DNase activity comprises the motif SDH[D/H/L]P (SEQ ID NO: 74), wherein the positions correspond to positions 610 to 614 in SEQ ID NO: 36. The polypeptides of the NUC2_B domain may also comprise the motif GGNI[R/Q] (SEQ ID NO: 75), corresponding to positions 395 to 399 of SEQ ID NO: 36. In one embodiment of the invention, the polypeptides having DNase activity comprise the motif GGNI[R/Q] (SEQ ID NO: 75), wherein the positions correspond to positions 610 to 614 in SEQ ID NO: 36.

The NUC2_B domain have a trusted domain cut-off score of at least 100.0, preferably a score of at least 135, preferably a score of at least 150, preferably a score of at least 250 when queried using a Profile Hidden Markov Model prepared as described in Methods.

Polypeptides belonging to the NUC2_B domain group may share this motif, which is thus common to the DNase polypeptides in the NUC2_B domain. In one embodiment, the invention relates to polypeptides comprising the motif SDH[D/H/L]P (SEQ ID NO:74), wherein the polypeptides have DNase activity. Polypeptides having DNase activity and which comprise this motif SDH[D/H/L]P (SEQ ID NO:75) effectively remove or reduce biofilm and the DNases are particularly useful in cleaning processes, such as laundry and dish wash.

In one embodiment, the invention relates to polypeptides comprising the motif GGNI[R/Q] (SEQ ID NO: 75), wherein the polypeptides have DNase activity. Polypeptides having DNase activity and which comprise this motif GGNI[R/Q] (SEQ ID NO: 76) effectively remove or reduce biofilm and the DNases are particularly useful in cleaning processes, such as laundry and dish wash.

Examples of DNases of the invention of the NUC2_B domain group are the polypeptide shown in SEQ ID NO: 6 (mature polypeptide from *Preussia aemulans*), the polypeptide shown in SEQ ID NO: 7 (mature polypeptide from *Colletotrichum circinans*), the polypeptide shown in SEQ ID NO: 10 (mature polypeptide from *Trichurus spiralis*), the polypeptide shown in SEQ ID NO: 27 (mature polypeptide from *Pyrenochaetopsis* sp.), the polypeptide shown in SEQ ID NO: 30 (mature polypeptide from *Aspergillus sydowii*), the polypeptide shown in SEQ ID NO: 33 (mature polypeptide from *Cladosporium cladosporioides*), the polypeptide shown in SEQ ID NO: 36 (mature polypeptide from *Rhinocladiella* sp.), the polypeptide shown in SEQ ID NO: 39 (mature polypeptide from *Pyronema domesticum*), the polypeptide shown in SEQ ID NO: 42 (mature polypeptide from *Aspergillus niger*), the polypeptide shown in SEQ ID NO: 45 (mature polypeptide from *Phialophora geniculata*), the polypeptide shown in SEQ ID NO: 48 (mature polypeptide from *Paradendryphiella salina*), the polypeptide shown in SEQ ID NO: 51 (mature polypeptide from *Aspergillus insuetus*), the polypeptide shown in SEQ ID NO: 54 (mature polypeptide from *Purpureocillium lilacinum*), the polypeptide shown in SEQ ID NO: 57 (mature polypeptide from *Warcupiella spinulosa*), the polypeptide shown in SEQ ID NO: 60 (mature polypeptide from *Stenocarpella maydis*), the polypeptide shown in SEQ ID NO: 63 (mature polypeptide from *Acrophialophora fusispora*), the polypeptide shown in SEQ ID NO: 66 (mature polypeptide from *Chaetomium luteum*), the polypeptide shown in SEQ ID NO: 69 (mature polypeptide from *Arthrinium arundinis*) and the polypeptide shown in SEQ ID NO: 72 (mature polypeptide from *Phialophora geniculata*). The DNases listed above preferably further comprise one or more of the motifs [G/Y/W/F/A/H]NI[R/Q/D/E/V] (SEQ ID NO: 73), SDH[D/H/L]P (SEQ ID NO: 74) or GGNI[R/Q] (SEQ ID NO: 75).

One embodiment of the invention relates to a polypeptide having DNase activity, wherein the polypeptide preferably comprises one or more of the motifs [G/Y/W/F/A/H]NI[R/Q/D/E/V] (SEQ ID NO: 73), SDH[D/H/L]P (SEQ ID NO: 74) or GGNI[R/Q] (SEQ ID NO: 75), wherein the polypeptide is selected from the polypeptides:

a) a polypeptide having at least 72% sequence identity to the polypeptide of SEQ ID NO: 6,
b) a polypeptide having at least 90% sequence identity to the polypeptide of SEQ ID NO: 7,
c) a polypeptide having at least 84.5% sequence identity to the polypeptide of SEQ ID NO: 10,
d) a polypeptide having at least 82% sequence identity to the polypeptide of SEQ ID NO: 27,
e) a polypeptide having at least 80% sequence identity to the polypeptide of SEQ ID NO: 30,
f) a polypeptide having at least 60% sequence identity to the polypeptide of SEQ ID NO: 33,
g) a polypeptide having at least 65% sequence identity to the polypeptide of SEQ ID NO: 36,
h) a polypeptide having at least 91% sequence identity to the polypeptide of SEQ ID NO: 39,
i) a polypeptide having at least 99% sequence identity to the polypeptide of SEQ ID NO: 42,
j) a polypeptide having at least 68% sequence identity to the polypeptide of SEQ ID NO: 45,
k) a polypeptide having at least 94% sequence identity to the polypeptide of SEQ ID NO: 48,
l) a polypeptide having at least 80% sequence identity to the polypeptide of SEQ ID NO: 51,
m) a polypeptide having at least 73% sequence identity to the polypeptide of SEQ ID NO: 57,
n) a polypeptide having at least 90% sequence identity to the polypeptide of SEQ ID NO: 60,
o) a polypeptide having at least 84% sequence identity to the polypeptide of SEQ ID NO: 63,
p) a polypeptide having at least 80% sequence identity to the polypeptide of SEQ ID NO: 66,
q) a polypeptide having at least 72% sequence identity to the polypeptide of SEQ ID NO: 69, and
r) a polypeptide having at least 68% sequence identity to the polypeptide of SEQ ID NO: 72.

A DNase of the present invention may be obtained from *Vibrissea flavovirens* (SEQ ID NO: 3 or the mature polypeptide of SEQ ID NO: 2), *Penicillium reticulisporum* (SEQ ID NO: 4), *Acremonium dichromosporum* (SEQ ID NO: 5), *Preussia aemulans* (SEQ ID NO: 6), *Colletotrichum circinans* (SEQ ID NO: 7), *Clavicipitaceae* (SEQ ID NO: 8), *Preussia aemulans* (SEQ ID NO: 9) or *Trichurus spiralis* (SEQ ID NO: 10). A DNase of the invention may further be obtained from *Pyrenochaetopsis* sp. (SEQ ID NO: 27), *Aspergillus sydowii* (SEQ ID NO: 30), *Cladosporium cladosporioides* (SEQ ID NO: 33), *Rhinocladiella* sp. (SEQ ID NO: 36), *Pyronema domesticum* (SEQ ID NO: 39), *Aspergillus niger* (SEQ ID NO: 42), *Phialophora geniculata* (SEQ ID NO: 45), *Paradendryphiella salina* (SEQ ID NO: 48), *Aspergillus insuetus* (SEQ ID NO: 51), *Purpureocillium lilacinum* (SEQ ID NO: 54), *Warcupiella spinulosa* (SEQ ID NO: 57), *Stenocarpella maydis* (SEQ ID NO: 60), *Acrophialophora fusispora* (SEQ ID NO: 63), *Chaetomium luteum* (SEQ ID NO: 66), *Arthrinium arundinis* (SEQ ID NO: 69) and *Phialophora geniculata* (SEQ ID NO: 72).

The DNase of the present invention includes the polypeptides of SEQ ID NOS: 2, 3, 4, 5, 6, 7, 8, 9 or 10 or polypeptides having a sequence identity to the mature polypeptide of SEQ ID NOS: 2, 3, 4, 5, 6, 7, 8, 9 or 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity. The DNases of the present invention have all shown to have deep cleaning performance, i.e., they have demonstrated to effectively prevent, reduce or limit the presence of biofilm on or in, e.g., fabrics/textiles.

A DNase of the present invention includes the polypeptide shown in SEQ ID NO: 3, or polypeptides having a sequence identity to the polypeptide shown in SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 5, or polypeptides having a sequence identity to the polypeptide shown in SEQ ID NO: 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 6, or polypeptides having a sequence identity to the polypeptide shown in SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 7, or polypeptides having a sequence identity to the polypeptide shown in SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 8, or polypeptides having a sequence identity to the polypeptide shown in SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 9, or polypeptides having a sequence identity to the polypeptide shown in SEQ ID NO: 9 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 10, or polypeptides having a sequence identity to the polypeptide shown in SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 27, or polypeptides having a sequence identity to the polypeptide shown in SEQ ID NO: 27 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 30, or polypeptides having a sequence identity to the polypeptide shown in SEQ ID NO: 30 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 33, or polypeptides having a sequence identity to the polypeptide shown in SEQ ID NO: 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 36, or polypeptides having a sequence identity to the polypeptide shown in SEQ ID NO: 36 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 39, or polypeptides having a sequence identity to the polypeptide shown in SEQ ID NO: 39 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 42, or polypeptides having a sequence identity to the polypeptide shown in SEQ ID NO: 42 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 45, or polypeptides having a sequence identity to the polypeptide shown in SEQ ID NO: 45 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 48, or polypeptides having a sequence identity to the polypeptide shown in SEQ ID NO: 48 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 51, or polypeptides having a sequence identity to the polypeptide shown in SEQ ID NO: 51 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 54, or polypeptides having a sequence identity to the polypeptide shown in SEQ ID NO: 54 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 57, or polypeptides having a sequence identity to the polypeptide shown in SEQ ID NO: 57 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 60, or polypeptides having a sequence identity to the polypeptide shown in SEQ ID NO: 60 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 63, or polypeptides having a sequence identity to the polypeptide shown in SEQ ID NO: 63 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 66, or polypeptides having a sequence identity to the polypeptide shown in SEQ ID NO: 66 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 69, or polypeptides having a sequence identity to the polypeptide shown in SEQ ID NO: 69 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

A DNase of the present invention includes the polypeptide shown in SEQ ID NO: 72, or polypeptides having a sequence identity to the polypeptide shown in SEQ ID NO: 72 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and which have DNase activity.

The DNases of the present invention have all shown to have deep cleaning performance, i.e., they have demonstrated to effectively prevent, reduce or limit the presence of biofilm on or in, e.g., fabrics/textiles.

The DNase may be obtained from *Vibrissea*, preferably, *Vibrissea flavovirens*. The DNase of the invention may be a polypeptide comprising the polypeptide of SEQ ID NO: 3 or a polypeptide closely related hereto. The DNase of the invention may be obtained from *Vibrissea flavovirens* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3.

The DNase may be obtained from *Penicillium*, preferably, *Penicillium reticulisporum*. The DNase of the invention may be a polypeptide comprising the polypeptide of SEQ ID NO: 4 or a polypeptide closely related hereto. The DNase of the invention may be obtained from *Penicillium reticulisporum* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4.

The DNase may be obtained from *Acremonium*, preferably, *Acremonium dichromosporum*. The DNase of the invention may be a polypeptide comprising the polypeptide of SEQ ID NO: 5 or a polypeptide closely related hereto. The DNase of the invention may be obtained from *Penicillium reticulisporum* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5.

The DNase may be obtained from *Preussia*, preferably, *Preussia aemulans*. The DNase of the invention may be a polypeptide comprising the polypeptide of SEQ ID NO: 6 or a polypeptide closely related hereto. The DNase of the invention may be obtained from *Preussia aemulans* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6.

The DNase of the invention may be obtained from *Preussia aemulans*. The DNase of the invention may be a polypeptide comprising the polypeptide of SEQ ID NO: 9 or a polypeptide closely related hereto. The DNase of the invention may be obtained from *Preussia aemulans* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 9.

The DNase may be obtained from *Colletotrichum*, preferably, *Colletotrichum circinans*. The DNase of the invention may be a polypeptide comprising the polypeptide of SEQ ID NO: 7 or a polypeptide closely related hereto. The DNase of the invention may be obtained from *Colletotrichum circinans* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 7.

The DNase may be obtained from *Clavicipitaceae*. The DNase of the invention may be a polypeptide comprising the polypeptide of SEQ ID NO: 8 or a polypeptide closely related hereto. The DNase of the invention may be obtained from *Clavicipitaceae* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 8.

The DNase may be obtained from *Trichurus*, preferably, *Trichurus spiralis*. The DNase of the invention may be a polypeptide comprising the polypeptide of SEQ ID NO: 10 or a polypeptide closely related hereto. The DNase of the invention may be obtained from *Trichurus spiralis* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 10.

The DNase may be obtained from *Pyrenochaetopsis*, preferably, *Pyrenochaetopsis* sp. The DNase of the invention may be a polypeptide comprising the polypeptide shown in SEQ ID NO: 27 or a polypeptide closely related hereto. The DNase of the invention may be obtained from *Pyrenochaetopsis* sp. and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 27.

The DNase may be obtained from *Aspergillus*, preferably, *Aspergillus sydowii*. The DNase of the invention may be a polypeptide comprising the polypeptide shown in SEQ ID NO: 30 or a polypeptide closely related hereto. The DNase of the invention may be obtained from *Aspergillus sydowii* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 30.

The DNase may be obtained from *Cladosporium*, preferably, *Cladosporium cladosporioides*. The DNase of the invention may be a polypeptide comprising the polypeptide shown in SEQ ID NO: 33 or a polypeptide closely related hereto. The DNase of the invention may be obtained from *Cladosporium cladosporioides* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 33.

The DNase may be obtained from *Rhinocladiella*, preferably, *Rhinocladiella* sp. The DNase of the invention may be a polypeptide comprising the polypeptide shown in SEQ ID NO: 36 or a polypeptide closely related hereto. The DNase of the invention may be obtained from *Rhinocladiella* sp. and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 36.

The DNase may be obtained from *Pyronema*, preferably, *Pyronema domesticum*. The DNase of the invention may be a polypeptide comprising the polypeptide shown in SEQ ID NO: 39 or a polypeptide closely related hereto. The DNase of the invention may be obtained from *Pyronema domesticum* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 39.

The DNase may be obtained from *Aspergillus*, preferably, *Aspergillus niger*. The DNase of the invention may be a polypeptide comprising the polypeptide shown in SEQ ID NO: 42 or a polypeptide closely related hereto. The DNase of the invention may be obtained from *Aspergillus niger* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 42.

The DNase may be obtained from *Phialophora*, preferably, *Phialophora geniculata*. The DNase of the invention may be a polypeptide comprising the polypeptide shown in SEQ ID NO: 45 or a polypeptide closely related hereto. The DNase of the invention may be obtained from *Phialophora geniculata* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 45.

The DNase may be obtained from *Paradendryphiella*, preferably, *Paradendryphiella salina*. The DNase of the invention may be a polypeptide comprising the polypeptide shown in SEQ ID NO: 48 or a polypeptide closely related hereto. The DNase of the invention may be obtained from *Paradendryphiella salina* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 48.

The DNase may be obtained from *Aspergillus*, preferably, *Aspergillus insuetus*. The DNase of the invention may be a polypeptide comprising the polypeptide shown in SEQ ID NO: 51 or a polypeptide closely related hereto. The DNase of the invention may be obtained from *Aspergillus insuetus* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 51.

The DNase may be obtained from *Warcupiella*, preferably, *Warcupiella spinulosa*. The DNase of the invention may be a polypeptide comprising the polypeptide shown in SEQ ID NO: 57 or a polypeptide closely related hereto. The DNase of the invention may be obtained from *Warcupiella spinulosa* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 57.

The DNase may be obtained from *Stenocarpella*, preferably, *Stenocarpella maydis*. The DNase of the invention may be a polypeptide comprising the polypeptide shown in SEQ ID NO: 60 or a polypeptide closely related hereto. The DNase of the invention may be obtained from *Stenocarpella maydis* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 60.

The DNase may be obtained from *Acrophialophora*, preferably, *Acrophialophora fusispora*. The DNase of the invention may be a polypeptide comprising the polypeptide shown in SEQ ID NO: 63 or a polypeptide closely related hereto. The DNase of the invention may be obtained from *Acrophialophora fusispora* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 63.

The DNase may be obtained from *Chaetomium*, preferably, *Chaetomium luteum*. The DNase of the invention may be a polypeptide comprising the polypeptide shown in SEQ ID NO: 66 or a polypeptide closely related hereto. The DNase of the invention may be obtained from *Chaetomium luteum* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 66.

The DNase may be obtained from *Arthrinium*, preferably, *Arthrinium arundinis*. The DNase of the invention may be a polypeptide comprising the polypeptide shown in SEQ ID NO: 69 or a polypeptide closely related hereto. The DNase of the invention may be obtained from *Arthrinium arundinis* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 69.

The DNase may be obtained from *Phialophora*, preferably, *Phialophora geniculata*. The DNase of the invention may be a polypeptide comprising the polypeptide shown in SEQ ID NO: 72 or a polypeptide closely related hereto. The DNase of the invention may be obtained from *Phialophora geniculata* and comprise a polypeptide having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 72.

In one aspect of the invention, the polypeptide having DNase activity is obtained from *Vibrissea*, in particular, from *Vibrissea flavovirens*. In one aspect of the invention the polypeptide having DNase activity is obtained from *Penicillium*, in particular, from *Penicillium reticulisporum*. In one aspect of the invention the polypeptide having DNase activity is obtained from *Acremonium*, in particular, from *Acremonium dichromosporum*. In one aspect of the invention the polypeptide having DNase activity is obtained from *Preussia*, in particular, from *Preussia aemulans*. In one aspect of the invention the polypeptide having DNase activity is obtained from *Colletotrichum*, in particular, from *Colletotrichum circinans*. In one aspect of the invention the polypeptide having DNase activity is obtained from *Clavicipitaceae*. In one aspect of the invention the polypeptide having DNase activity is obtained from *Trichurus*, in particular, from *Trichurus spiralis*. In one aspect of the invention the polypeptide having DNase activity is obtained from *Pyrenochaetopsis* sp. In one aspect of the invention the polypeptide having DNase activity is obtained from *Aspergillus* in particular, from *Aspergillus sydowii*. In one aspect of the invention the polypeptide having DNase activity is obtained from *Cladosporium*, in particular, *Cladosporium cladosporioides*. In one aspect of the invention the polypeptide having DNase activity is obtained from *Rhinocladiella* sp. In one aspect of the invention the polypeptide having DNase activity is obtained from *Pyronema*, in particular, *Pyronema domesticum*. In one aspect of the invention the polypeptide having DNase activity is obtained from *Aspergillus*, in particular, *Aspergillus niger*. In one aspect of the invention the polypeptide having DNase activity is obtained from *Phialophora*, in particular, *Phialophora geniculata*. In one aspect of the invention the polypeptide having DNase activity is obtained from *Paradendryphiella*, in particular, *Paradendryphiella salina*. In one aspect of the invention the polypeptide having DNase activity is obtained from *Aspergillus*, in particular, *Aspergillus insuetus*. In one aspect of the invention the polypeptide having DNase activity is obtained from *Warcupiella*, in particular, *Warcupiella spinulosa*. In one aspect of the invention the polypeptide having DNase activity is obtained from *Stenocarpella maydis*, in particular, *Stenocarpella maydis*. In one aspect of the invention the polypeptide having DNase activity is obtained from *Acrophialophora*, in particular, *Acrophialophora fusispora*. In one aspect of the invention the polypeptide having DNase activity is obtained from *Chaetomium*, in particular, *Chaetomium luteum*. In one aspect of the invention the polypeptide having DNase activity is obtained from *Arthrinium*, in particular, *Arthrinium arundinis*. In one aspect of the invention the polypeptide having DNase activity is obtained from *Phialophora*, in particular, *Phialophora geniculata*.

In one aspect of the invention, the polypeptide having DNase activity is obtained from *Vibrissea flavovirens* and comprises the mature polypeptide of SEQ ID NO: 2, i.e., the polypeptide with SEQ ID NO: 3. In a preferred aspect of the invention the DNase is obtained from *Penicillium reticulisporum* and comprises the polypeptide sequence with SEQ ID NO: 4. In a preferred aspect of the invention the DNase is obtained from *Acremonium dichromosporum* and comprises the polypeptide sequence with SEQ ID NO: 5. In a preferred aspect of the invention the DNase is obtained from *Preussia aemulans* and comprises any of the polypeptide sequence with SEQ ID NO: 6 or SEQ ID NO: 9. In a preferred aspect of the invention the DNase is obtained from *Colletotrichum circinans* and comprises the polypeptide sequence with SEQ ID NO: 7. In a preferred aspect of the invention the DNase is obtained from *Clavicipitaceae* and comprises the polypeptide sequence with SEQ ID NO: 8. In a preferred aspect of the invention the DNase is obtained from *Trichurus spiralis* and comprises the polypeptide sequence with SEQ ID NO: 10.

In one aspect of the invention, the polypeptide having DNase activity is obtained from *Vibrissea flavovirens* and consists of the mature polypeptide of SEQ ID NO: 2, i.e., the polypeptide with SEQ ID NO: 3. In a preferred aspect of the invention the DNase is obtained from *Penicillium reticulisporum* and consists of the sequence of SEQ ID NO: 4. In a preferred aspect of the invention the DNase is obtained from *Acremonium dichromosporum* and consists of the sequence of SEQ ID NO: 5. In a preferred aspect of the invention the DNase is obtained from *Preussia aemulans* and consists of the sequence of SEQ ID NO: 6 or SEQ ID NO: 9. In a preferred aspect of the invention the DNase is obtained from *Colletotrichum circinans* and consists of the sequence of SEQ ID NO: 7. In a preferred aspect of the invention the DNase is obtained from *Clavicipitaceae* and consists of the sequence of SEQ ID NO: 8. In a preferred aspect of the invention the DNase is obtained from *Trichurus spiralis* and consists of the sequence of SEQ ID NO: 10.

In a preferred aspect of the invention the DNase is obtained from *Pyrenochaetopsis* sp. and consists of the sequence with SEQ ID NO: 27. In a preferred aspect of the invention the DNase is obtained from *Pyrenochaetopsis* sp. and comprises the sequence with SEQ ID NO: 27.

In a preferred aspect of the invention the DNase is obtained from *Aspergillus sydowii* and consists of the sequence of SEQ ID NO: 30. In a preferred aspect of the invention the DNase is obtained from *Aspergillus sydowii* and comprises the sequence with SEQ ID NO: 30.

In a preferred aspect of the invention the DNase is obtained from *Cladosporium cladosporioides* and consists of the sequence with SEQ ID NO: 33. In a preferred aspect of the invention the DNase is obtained from *Cladosporium cladosporioides* and comprises the sequence with SEQ ID NO: 33.

In a preferred aspect of the invention the DNase is obtained from *Rhinocladiella* sp. and consists of the sequence of SEQ ID NO: 36. In a preferred aspect of the invention the DNase is obtained from *Rhinocladiella* sp. and comprises the sequence of SEQ ID NO: 36.

In a preferred aspect of the invention the DNase is obtained from *Pyronema domesticum* and consists of the sequence of SEQ ID NO: 39. In a preferred aspect of the invention the DNase is obtained from *Pyronema domesticum* and comprises the sequence of SEQ ID NO: 39.

In a preferred aspect of the invention the DNase is obtained from *Aspergillus niger* and consists of the sequence of SEQ ID NO: 42. In a preferred aspect of the invention the DNase is obtained from *Aspergillus niger* and comprises the sequence of SEQ ID NO: 42.

In a preferred aspect of the invention the DNase is obtained from *Phialophora geniculata* and consists of the sequence of SEQ ID NO: 45. In a preferred aspect of the invention the DNase is obtained from *Phialophora geniculata* and comprises the sequence of SEQ ID NO: 45.

In a preferred aspect of the invention the DNase is obtained from *Paradendryphiella salina* and consists of the sequence with SEQ ID NO: 48. In a preferred aspect of the invention the DNase is obtained from *Paradendryphiella salina* and comprises the sequence of SEQ ID NO: 48.

In a preferred aspect of the invention the DNase is obtained from *Aspergillus insuetus* and consists of the sequence of SEQ ID NO: 51. In a preferred aspect of the invention the DNase is obtained from *Aspergillus insuetus* and comprises the sequence of SEQ ID NO: 51.

In a preferred aspect of the invention the DNase is obtained from *Warcupiella spinulosa* and consists of the sequence of SEQ ID NO: 57. In a preferred aspect of the invention the DNase is obtained from *Warcupiella spinulosa* and comprises the sequence of SEQ ID NO: 57.

In a preferred aspect of the invention the DNase is obtained from *Stenocarpella maydis* and consists of the sequence of SEQ ID NO: 60. In a preferred aspect of the invention the DNase is obtained from *Stenocarpella maydis* and comprises the sequence of SEQ ID NO: 60.

In a preferred aspect of the invention the DNase is obtained from *Acrophialophora fusispora* and consists of the sequence of SEQ ID NO: 63. In a preferred aspect of the invention the DNase is obtained from *Acrophialophora fusispora* and comprises the sequence of SEQ ID NO: 63.

In a preferred aspect of the invention the DNase is obtained from *Chaetomium luteum* and consists of the sequence of SEQ ID NO: 66. In a preferred aspect of the invention the DNase is obtained from *Chaetomium luteum* and comprises the sequence of SEQ ID NO: 66.

In a preferred aspect of the invention the DNase is obtained from *Arthrinium arundinis* and consists of the sequence of SEQ ID NO: 69. In a preferred aspect of the invention the DNase is obtained from *Arthrinium arundinis* and comprises the sequence of SEQ ID NO: 69.

In a preferred aspect of the invention the DNase is obtained from *Phialophora geniculata* and consists of the sequence with SEQ ID NO: 72. In a preferred aspect of the invention the DNase is obtained from *Phialophora geniculata* and comprises the sequence of SEQ ID NO: 72.

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, biofilm adhere soil due to the sticky nature of the biofilm. The commercial laundry detergent compositions available on the marked do not remove such adhered microorganisms or biofilm.

The present invention relates to polypeptides having DNase activity and the use of such polypeptides for preventing, reducing or removing a biofilm from an item, such as textiles. In one embodiment of the invention the polypeptide having DNase activity is used for preventing, reducing or removing the stickiness of an item. In one embodiment of the invention, the polypeptide having DNase activity improves whiteness of an item, such as a textile. In one embodiment the polypeptide of the invention having DNase activity helps maintaining the colour on textiles. When textiles are repeatedly washed the colours tend to be less bright. In one embodiment a polypeptide of the invention having DNase has an improved effect of maintaining the colour of coloured textiles even after repeated washes. In one embodiment the polypeptide of the invention also reduced the colouring of non-coloured part of the same or additional textile present in the wash.

The polypeptide having DNase activity can further be used for pretreating stains on textile such as textile with a pronounced amount of biofilm adhered to the textile.

Additionally, the invention relates to the use of a polypeptide having DNase activity for preventing, reducing or removing redeposition of soil during a wash cycle. When the polypeptide is used for example in the laundering of textile, the polypeptides hinders deposition of soil present in the wash liquor to deposit on the textile.

Further, the invention relates to the use of a polypeptide having DNase activity for preventing, reducing or removing the adherence of soil to an item. In one embodiment, the item is textile. When the soil does not adhere to the item, the item appears cleaner. Thus, the invention further concerns the use of a polypeptide having DNase activity for maintaining or improving the whiteness of the item.

When items like T-shirts or sportswear are used, they are exposed to bacteria from the body of the user and from the rest of the environment in which they are used. This may cause malodour on the item even after the item is washed. The present invention therefore also concerns removal or reduction of malodour on textile. The malodour may be caused by bacteria producing compounds with an unpleasant smell. One example of such unpleasant smelling compounds is E-2-nonenal. The malodour can be present on newly washed textile which is still wet. Or the malodour can be present on newly washed textile, which has subsequently been dried. The malodour may also be present on textile, which has been stored for some time after wash. The present invention relates to the use of DNases of the invention for reduction or removal of malodour such as E-2-nonenal from wet or dry textile.

The polypeptides of the invention having DNase activity, i.e., the DNases of the invention have very good cleaning performance in detergents. Examples of beneficial effects of the DNases with SEQ ID NOS: 2, 3, 4, 5, 6, 7, 8, 9 and 10 are the deep-cleaning effect as shown in example 2, e.g., preventing laundry in becoming grey. Examples of beneficial effects of the DNases comprising any of the motifs [G/Y/W/F/A/H]NI[R/Q/D/E/V] (SEQ ID NO: 73), SDH[D/H/L]P (SEQ ID NO: 74) or GGNI[RIQ] (SEQ ID NO: 75, e.g., the polypeptides having DNase activity and comprising the polypeptides shown in SEQ ID NO: 6, SEQ ID NO: 7, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72 are the deep-cleaning effect as shown in examples, such effects includes preventing laundry in becoming grey, e.g., anti-redeposition effect. Another effect is prevention of static electricity. The polypeptides of the invention having DNase activity can further be used for preventing, reducing or removing static electricity from an item on which static electricity may accumulate, such item maybe a textile or a hard surface. The polypeptide having DNase activity can further be used for preventing, reducing and/or removing a biofilm from an item, such item may be a hard surface, e.g., dishes, cutlery, porcelain, china, crockery etc. Thus, in some aspect the polypeptide having DNase activity may be used in an ADW (Automatic dishwash) process.

The polypeptides comprising SEQ ID NOS: 2, 3, 4, 5, 6, 7, 8, 9 and 10 are novel polypeptides having DNase activity and having deep cleaning effect in detergents particular in liquid detergents. The DNase comprising SEQ ID NO: 3 also shows deep cleaning effect when tested in powder detergent as shown in example 3.

The polypeptides having DNase activity and comprising the amino acid sequence selected from the sequences shown in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69 and SEQ ID NO: 72 are novel polypeptides having DNase activity and having deep cleaning effect in detergents such as liquid or powder detergents.

The polypeptide comprising SEQ ID NO: 3 is preferably obtained from *Vibrissea flavovirens*. The polypeptide comprising SEQ ID NO: 4 is preferably obtained from *Penicillium reticulisporum*. The polypeptide comprising SEQ ID NO: 5 is preferably obtained from *Acremonium dichromosporum*. The polypeptide comprising SEQ ID NO: 6 is preferably obtained from *Preussia aemulans*. The polypeptide comprising SEQ ID NO: 7 is preferably obtained from *Colletotrichum circinans*. The polypeptide comprising SEQ ID NO: 8 is preferably obtained from *Clavicipitaceae*. The polypeptide comprising SEQ ID NO: 9 is preferably obtained from *Preussia aemulans*. The polypeptide comprising SEQ ID NO: 3 is preferably obtained from *Trichurus spiralis*. The invention relates to polypeptides having a sequence identity to any of the polypeptides with SEQ ID NOS: 2, 3, 4, 5, 6, 7, 8, 9 or 10 of at least 60% which have DNase activity and wherein the polypeptides are used for preventing, reducing or removing a biofilm from an item.

In an embodiment, the present invention relates to a polypeptide having a sequence identity to the polypeptide of SEQ ID NO: 3 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 4 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 5 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 6 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 7 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 8 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 60%, which have DNase activity and wherein the polypeptide is used for preventing, reducing or removing a biofilm from an item.

In one embodiment, the present invention relates to a polypeptide having a sequence identity to the polypeptide of SEQ ID NO: 33 of at least 60%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In an embodiment, the present invention relates to a polypeptide having a sequence identity to the polypeptide of SEQ ID NO: 3 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 4 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 5 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 6 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 7 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 8 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 70%, which have DNase activity and wherein the polypeptide is used for preventing, reducing or removing a biofilm from an item.

In one embodiment, the present invention relates to a polypeptide having a sequence identity to the polypeptide of SEQ ID NO: 33 of at least 70%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 36 of at least 70%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 45 of at least 70%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 72 of at least 70%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In an embodiment, the present invention relates to a polypeptide having a sequence identity to the polypeptide of SEQ ID NO: 3 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 4 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 5 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 6 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 7 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 8 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 80%, which have DNase activity and wherein the polypeptide is used for preventing, reducing or removing a biofilm from an item.

In one embodiment, the present invention relates to a polypeptide having a sequence identity to the polypeptide of SEQ ID NO: 33 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 36 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 45 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 72 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 6 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 30 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 57 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 69 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 51 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 66 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In an embodiment, the present invention relates to a polypeptide having a sequence identity to the polypeptide of SEQ ID NO: 3 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 4 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 5 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 6 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 7 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 8 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 90%, which have DNase activity and wherein the polypeptide is used for preventing, reducing or removing a biofilm from an item.

In one embodiment, the present invention relates to a polypeptide having a sequence identity to the polypeptide of SEQ ID NO: 33 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 36 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 45 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 72 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 6 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 30 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 57 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 69 of at least 80%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 51 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 66 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 7 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 10 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 63 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 27 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 60 of at least 90%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In an embodiment, the present invention relates to a polypeptide having a sequence identity to the polypeptide of SEQ ID NO: 3 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 4 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 5 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 6 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 7 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 8 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 95%, which have DNase activity and wherein the polypeptide is used for preventing, reducing or removing a biofilm from an item.

In one embodiment, the present invention relates to a polypeptide having a sequence identity to the polypeptide of SEQ ID NO: 33 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 36 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 45 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 72 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 6 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 30 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 57 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 69 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 51 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 66 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 7 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 10 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 63 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 27 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 39 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 60 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 48 of at least 95%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

In one embodiment, the present invention relates to a polypeptide having a sequence identity to the polypeptide of SEQ ID NO: 42 of at least 99%, which have DNase activity and wherein the polypeptide is capable of reducing at least 10%, such as at least 20%, at least 30%, at least 40%, at last 50%, at least 60%, at least 70%, at last 80%, at least 90% or 100% of at least one biofilm from an item when the biofilm reduction is measured, e.g., as described in example 2 or 3.

The deep cleaning effect of the polypeptides comprising SEQ ID NO: 2, 3, 4, 5, 6, 7, 8, 9 and 10 is shown in example 2. As described above the term "deep cleaning" mean disruption or removal of a biofilm or components of a biofilm such as polysaccharides, proteins, DNA, soil or other components present in the biofilm. A polypeptide of the present invention preferably comprises or consists of the amino acid sequence of SEQ ID NO: 2, 3, 4, 5, 6, 7, 8, 9 or 10 or an allelic variant thereof; or is a fragment thereof having DNase activity. A polypeptide of the present invention preferably comprises or consists of the amino acid sequence of SEQ ID NO: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69, SEQ ID NO: 72 or an allelic variant thereof; or is a fragment thereof having DNase activity In one aspect, the polypeptide of the invention comprises or consists of a polypeptide selected from the group consisting of SEQ ID NOS: 2, 3, 4, 5, 6, 7, 8, 9 and 10. In one aspect, the polypeptide of the invention comprises or consists of a polypeptide selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69 or SEQ ID NO: 72.

In one embodiment, the present invention relates to an isolated polypeptide with SEQ ID NOS: 2, 3, 4, 5, 6, 7, 8, 9 or 10 or a polypeptide with SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69 or SEQ ID NO: 72 having DNase activity and which is encoded by a polynucleotide that hybridizes under low stringency conditions with (i) the mature polypeptide coding sequence, (ii) the cDNA sequence thereof, or (iii) the full-length complement of (i) or (ii) (Sambrook et al., 1989, Molecular Cloning, A Laboratory Manual, 2d edition, Cold Spring Harbor, New York). In an embodiment, the polypeptide has been isolated.

In another embodiment, the present invention relates to an isolated polypeptide having DNase activity which is encoded by a polynucleotide that hybridizes under low-medium stringency conditions with (i) the mature polypeptide coding sequence, (ii) the cDNA sequence thereof, or (iii) the full-length complement of (i) or (ii). In an embodiment, the polypeptide has been isolated.

In another embodiment, the present invention relates to an isolated polypeptide having DNase activity which is encoded by a polynucleotide that hybridizes under medium stringency conditions with (i) the mature polypeptide coding sequence, (ii) the cDNA sequence thereof, or (iii) the full-length complement of (i) or (ii). In an embodiment, the polypeptide has been isolated.

In another embodiment, the present invention relates to an isolated polypeptide having DNase activity which is encoded by a polynucleotide that hybridizes under medium-high stringency conditions with (i) the mature polypeptide coding sequence, (ii) the cDNA sequence thereof, or (iii) the full-length complement of (i) or (ii). In an embodiment, the polypeptide has been isolated.

In another embodiment, the present invention relates to an isolated polypeptide having DNase activity which is encoded by a polynucleotide that hybridizes under high stringency conditions with (i) the mature polypeptide coding sequence, (ii) the cDNA sequence thereof, or (iii) the full-length complement of (i) or (ii). In an embodiment, the polypeptide has been isolated.

In another embodiment, the present invention relates to an isolated polypeptide having DNase activity which is encoded by a polynucleotide that hybridizes under very high stringency conditions with (i) the mature polypeptide coding sequence, (ii) the cDNA sequence thereof, or (iii) the full-length complement of (i) or (ii). In an embodiment, the polypeptide has been isolated.

The polynucleotide or a subsequence thereof, as well as the polypeptides of SEQ ID NOS: 2, 3, 4, 5, 6, 7, 8, 9 or 10 or the polypeptides comprising an amino acid sequence shown in any of SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69 or SEQ ID NO: 72 or a fragment thereof, may be used to design nucleic acid probes to identify and clone DNA encoding polypeptides having DNase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with the DNA sequences that encodes SEQ ID NO: 2, 3, 4, 5, 6, 7, 8, 9 or 10 or SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 57, SEQ ID NO: 60, SEQ ID NO: 63, SEQ ID NO: 66, SEQ ID NO: 69, SEQ ID NO: 72 or a subsequence thereof, the carrier material is used in a Southern blot.

For purposes of the present invention, hybridization indicates that the polynucleotide hybridizes to a labeled nucleic acid probe corresponding to (i) the mature polypeptide coding sequence; (ii) the cDNA sequence thereof; (iii) the full-length complement thereof; or (iv) a subsequence thereof; under very low, low stringency conditions, low-medium stringency conditions, medium stringency conditions, medium-high stringency conditions, high stringency conditions to very high stringency conditions. Molecules to which the nucleic acid probe hybridizes under these conditions can be detected using, for example, X-ray film or any other detection means known in the art.

In another embodiment, the present invention relates to variants of the polypeptide of SEQ ID NOS: 3, 4, 5, 6, 7, 8, 9 or 10 comprising a substitution, deletion, and/or insertion at one or more (e.g., several) positions. In an embodiment, the number of amino acid substitutions, deletions and/or insertions introduced into the mature polypeptide of SEQ ID NOS: 3, 4, 5, 6, 7, 8, 9 or 10 is up to 10, e.g., 1, 2, 3, 4, 5, 6, 7, 8, 9, or 10.

In another embodiment, the present invention relates to variants of the mature polypeptide of SEQ ID NO: 3 comprising a substitution, deletion, and/or insertion at one or more (e.g., several) positions. In an embodiment, the number of amino acid substitutions, deletions and/or insertions introduced into the polypeptide with SEQ ID NO: 3 is up to 10, e.g., 1, 2, 3, 4, 5, 6, 7, 8, 9, or 10.

In another embodiment, the present invention relates to variants of the mature polypeptide of SEQ ID NO: 4 comprising a substitution, deletion, and/or insertion at one or more (e.g., several) positions. In an embodiment, the number of amino acid substitutions, deletions and/or insertions introduced into the polypeptide of SEQ ID NO: 4 is up to 10, e.g., 1, 2, 3, 4, 5, 6, 7, 8, 9, or 10.

In another embodiment, the present invention relates to variants of the mature polypeptide of SEQ ID NO: 5 comprising a substitution, deletion, and/or insertion at one or more (e.g., several) positions. In an embodiment, the number of amino acid substitutions, deletions and/or insertions introduced into the polypeptide of SEQ ID NO: 5 is up to 10, e.g., 1, 2, 3, 4, 5, 6, 7, 8, 9, or 10.

In another embodiment, the present invention relates to variants of the mature polypeptide of SEQ ID NO: 6 comprising a substitution, deletion, and/or insertion at one or more (e.g., several) positions. In an embodiment, the number of amino acid substitutions, deletions and/or insertions introduced into the polypeptide of SEQ ID NO: 6 is up to 10, e.g., 1, 2, 3, 4, 5, 6, 7, 8, 9, or 10.

In another embodiment, the present invention relates to variants of the mature polypeptide of SEQ ID NO: 7 comprising a substitution, deletion, and/or insertion at one or more (e.g., several) positions. In an embodiment, the number of amino acid substitutions, deletions and/or insertions introduced into the polypeptide of SEQ ID NO: 7 is up to 10, e.g., 1, 2, 3, 4, 5, 6, 7, 8, 9, or 10.

In another embodiment, the present invention relates to variants of the mature polypeptide of SEQ ID NO: 8 comprising a substitution, deletion, and/or insertion at one or more (e.g., several) positions. In an embodiment, the number of amino acid substitutions, deletions and/or insertions introduced into the polypeptide of SEQ ID NO: 8 is up to 10, e.g., 1, 2, 3, 4, 5, 6, 7, 8, 9, or 10.

In another embodiment, the present invention relates to variants of the mature polypeptide of SEQ ID NO: 9 comprising a substitution, deletion, and/or insertion at one or more (e.g., several) positions. In an embodiment, the number of amino acid substitutions, deletions and/or insertions introduced into the polypeptide of SEQ ID NO: 9 is up to 10, e.g., 1, 2, 3, 4, 5, 6, 7, 8, 9, or 10.

In another embodiment, the present invention relates to variants of the mature polypeptide of SEQ ID NO: 10 comprising a substitution, deletion, and/or insertion at one or more (e.g., several) positions. In an embodiment, the number of amino acid substitutions, deletions and/or insertions introduced into the polypeptide of SEQ ID NO: 10 is up to 10, e.g., 1, 2, 3, 4, 5, 6, 7, 8, 9, or 10.

In another embodiment, the present invention relates to variants of the mature polypeptide of SEQ ID NO: 27 comprising a substitution, deletion, and/or insertion at one or more (e.g., several) positions. In an embodiment, the number of amino acid substitutions, deletions and/or insertions introduced into the polypeptide of SEQ ID NO: 27 is up to 10, e.g., 1, 2, 3, 4, 5, 6, 7, 8, 9, or 10.

In another embodiment, the present invention relates to variants of the mature polypeptide of SEQ ID NO: 30 comprising a substitution, deletion, and/or insertion at one or more (e.g., several) positions. In an embodiment, the number of amino acid substitutions, deletions and/or insertions introduced into the polypeptide of SEQ ID NO: 30 is up to 10, e.g., 1, 2, 3, 4, 5, 6, 7, 8, 9, or 10.

In another embodiment, the present invention relates to variants of the mature polypeptide of SEQ ID NO: 33 comprising a substitution, deletion, and/or insertion at one or more (e.g., several) positions. In an embodiment, the number of amino acid substitutions, deletions and/or insertions introduced into the polypeptide of SEQ ID NO: 33 is up to 10, e.g., 1, 2, 3, 4, 5, 6, 7, 8, 9, or 10.

In another embodiment, the present invention relates to variants of the mature polypeptide of SEQ ID NO: 36 comprising a substitution, deletion, and/or insertion at one or more (e.g., several) positions. In an embodiment, the number of amino acid substitutions, deletions and/or insertions introduced into the polypeptide of SEQ ID NO: 36 is up to 10, e.g., 1, 2, 3, 4, 5, 6, 7, 8, 9, or 10.

In another embodiment, the present invention relates to variants of the mature polypeptide of SEQ ID NO: 39 comprising a substitution, deletion, and/or insertion at one or more (e.g., several) positions. In an embodiment, the number of amino acid substitutions, deletions and/or insertions introduced into the polypeptide of SEQ ID NO: 39 is up to 10, e.g., 1, 2, 3, 4, 5, 6, 7, 8, 9, or 10.

In another embodiment, the present invention relates to variants of the mature polypeptide of SEQ ID NO: 42 comprising a substitution, deletion, and/or insertion at one or more (e.g., several) positions. In an embodiment, the number of amino acid substitutions, deletions and/or insertions introduced into the polypeptide of SEQ ID NO: 42 is up to 10, e.g., 1, 2, 3, 4, 5, 6, 7, 8, 9, or 10.

In another embodiment, the present invention relates to variants of the mature polypeptide of SEQ ID NO: 45 comprising a substitution, deletion, and/or insertion at one or more (e.g., several) positions. In an embodiment, the number of amino acid substitutions, deletions and/or insertions introduced into the polypeptide of SEQ ID NO: 45 is up to 10, e.g., 1, 2, 3, 4, 5, 6, 7, 8, 9, or 10.

In another embodiment, the present invention relates to variants of the mature polypeptide of SEQ ID NO: 48 comprising a substitution, deletion, and/or insertion at one or more (e.g., several) positions. In an embodiment, the number of amino acid substitutions, deletions and/or insertions introduced into the polypeptide of SEQ ID NO: 48 is up to 10, e.g., 1, 2, 3, 4, 5, 6, 7, 8, 9, or 10.

In another embodiment, the present invention relates to variants of the mature polypeptide of SEQ ID NO: 51 comprising a substitution, deletion, and/or insertion at one or more (e.g., several) positions. In an embodiment, the number of amino acid substitutions, deletions and/or insertions introduced into the polypeptide of SEQ ID NO: 51 is up to 10, e.g., 1, 2, 3, 4, 5, 6, 7, 8, 9, or 10.

In another embodiment, the present invention relates to variants of the mature polypeptide of SEQ ID NO: 54 comprising a substitution, deletion, and/or insertion at one or more (e.g., several) positions. In an embodiment, the number of amino acid substitutions, deletions and/or insertions introduced into the polypeptide of SEQ ID NO: 54 is up to 10, e.g., 1, 2, 3, 4, 5, 6, 7, 8, 9, or 10.

In another embodiment, the present invention relates to variants of the mature polypeptide of SEQ ID NO: 57 comprising a substitution, deletion, and/or insertion at one or more (e.g., several) positions. In an embodiment, the number of amino acid substitutions, deletions and/or insertions introduced into the polypeptide of SEQ ID NO: 57 is up to 10, e.g., 1, 2, 3, 4, 5, 6, 7, 8, 9, or 10.

In another embodiment, the present invention relates to variants of the mature polypeptide of SEQ ID NO: 60 comprising a substitution, deletion, and/or insertion at one or more (e.g., several) positions. In an embodiment, the number of amino acid substitutions, deletions and/or insertions introduced into the polypeptide of SEQ ID NO: 60 is up to 10, e.g., 1, 2, 3, 4, 5, 6, 7, 8, 9, or 10.

In another embodiment, the present invention relates to variants of the mature polypeptide of SEQ ID NO: 63 comprising a substitution, deletion, and/or insertion at one or more (e.g., several) positions. In an embodiment, the number of amino acid substitutions, deletions and/or insertions introduced into the polypeptide of SEQ ID NO: 63 is up to 10, e.g., 1, 2, 3, 4, 5, 6, 7, 8, 9, or 10.

In another embodiment, the present invention relates to variants of the mature polypeptide of SEQ ID NO: 66 comprising a substitution, deletion, and/or insertion at one or more (e.g., several) positions. In an embodiment, the number of amino acid substitutions, deletions and/or insertions introduced into the polypeptide of SEQ ID NO: 66 is up to 10, e.g., 1, 2, 3, 4, 5, 6, 7, 8, 9, or 10.

In another embodiment, the present invention relates to variants of the mature polypeptide of SEQ ID NO: 69 comprising a substitution, deletion, and/or insertion at one or more (e.g., several) positions. In an embodiment, the number of amino acid substitutions, deletions and/or insertions introduced into the polypeptide of SEQ ID NO: 69 is up to 10, e.g., 1, 2, 3, 4, 5, 6, 7, 8, 9, or 10.

In another embodiment, the present invention relates to variants of the mature polypeptide of SEQ ID NO: 72 comprising a substitution, deletion, and/or insertion at one or more (e.g., several) positions. In an embodiment, the number of amino acid substitutions, deletions and/or insertions introduced into the polypeptide of SEQ ID NO: 72 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

The present invention also relates to polynucleotides encoding a polypeptide, as described herein. In an embodiment, the polynucleotide encoding the polypeptide of the present invention has been isolated. In one another embodiment, the polynucleotide encoding a polypeptide of the present invention comprises or consists of the polynucleotide sequence set forth in SEQ ID NO: 1.

In one embodiment, the polynucleotide encoding a polypeptide of the present invention comprises or consists of the polynucleotide sequence set forth in SEQ ID NO: 11.

In one embodiment, the polynucleotide encoding a polypeptide of the present invention comprises or consists of the polynucleotide sequence set forth in SEQ ID NO: 13.

In one embodiment, the polynucleotide encoding a polypeptide of the present invention comprises or consists of the polynucleotide sequence set forth in SEQ ID NO: 15.

In one embodiment, the polynucleotide encoding a polypeptide of the present invention comprises or consists of the polynucleotide sequence set forth in SEQ ID NO: 17.

In one embodiment, the polynucleotide encoding a polypeptide of the present invention comprises or consists of the polynucleotide sequence set forth in SEQ ID NO: 19.

In one embodiment, the polynucleotide encoding a polypeptide of the present invention comprises or consists of the polynucleotide sequence set forth in SEQ ID NO: 21.

In one embodiment, the polynucleotide encoding a polypeptide of the present invention comprises or consists of the polynucleotide sequence set forth in SEQ ID NO: 23.

In one embodiment, the polynucleotide encoding a polypeptide of the present invention comprises or consists of the polynucleotide sequence set forth in SEQ ID NO: 25.

In one embodiment, the polynucleotide encoding a polypeptide of the present invention comprises or consists of the polynucleotide sequence set forth in SEQ ID NO: 28.

In one embodiment, the polynucleotide encoding a polypeptide of the present invention comprises or consists of the polynucleotide sequence set forth in SEQ ID NO: 31.

In one embodiment, the polynucleotide encoding a polypeptide of the present invention comprises or consists of the polynucleotide sequence set forth in SEQ ID NO: 33.

In one embodiment, the polynucleotide encoding a polypeptide of the present invention comprises or consists of the polynucleotide sequence set forth in SEQ ID NO: 17.

In one embodiment, the polynucleotide encoding a polypeptide of the present invention comprises or consists of the polynucleotide sequence set forth in SEQ ID NO: 19.

In one embodiment, the polynucleotide encoding a polypeptide of the present invention comprises or consists of the polynucleotide sequence set forth in SEQ ID NO: 21.

In one embodiment, the polynucleotide encoding a polypeptide of the present invention comprises or consists of the polynucleotide sequence set forth in SEQ ID NO: 23.

In one embodiment, the polynucleotide encoding a polypeptide of the present invention comprises or consists of the polynucleotide sequence set forth in SEQ ID NO: 25.

In one embodiment, the polynucleotide encoding a polypeptide of the present invention comprises or consists of the polynucleotide sequence set forth in SEQ ID NO: 28.

In one embodiment, the polynucleotide encoding a polypeptide of the present invention comprises or consists of the polynucleotide sequence set forth in SEQ ID NO: 31.

In one embodiment, the polynucleotide encoding a polypeptide of the present invention comprises or consists of the polynucleotide sequence set forth in SEQ ID NO: 34.

In one embodiment, the polynucleotide encoding a polypeptide of the present invention comprises or consists of the polynucleotide sequence set forth in SEQ ID NO: 37.

In one embodiment, the polynucleotide encoding a polypeptide of the present invention comprises or consists of the polynucleotide sequence set forth in SEQ ID NO: 40.

In one embodiment, the polynucleotide encoding a polypeptide of the present invention comprises or consists of the polynucleotide sequence set forth in SEQ ID NO: 43.

In one embodiment, the polynucleotide encoding a polypeptide of the present invention comprises or consists of the polynucleotide sequence set forth in SEQ ID NO: 46.

In one embodiment, the polynucleotide encoding a polypeptide of the present invention comprises or consists of the polynucleotide sequence set forth in SEQ ID NO: 49.

In one embodiment, the polynucleotide encoding a polypeptide of the present invention comprises or consists of the polynucleotide sequence set forth in SEQ ID NO: 52.

In one embodiment, the polynucleotide encoding a polypeptide of the present invention comprises or consists of the polynucleotide sequence set forth in SEQ ID NO: 55.

In one embodiment, the polynucleotide encoding a polypeptide of the present invention comprises or consists of the polynucleotide sequence set forth in SEQ ID NO: 58.

In one embodiment, the polynucleotide encoding a polypeptide of the present invention comprises or consists of the polynucleotide sequence set forth in SEQ ID NO: 61.

In one embodiment, the polynucleotide encoding a polypeptide of the present invention comprises or consists of the polynucleotide sequence set forth in SEQ ID NO: 64.

In one embodiment, the polynucleotide encoding a polypeptide of the present invention comprises or consists of the polynucleotide sequence set forth in SEQ ID NO: 67.

In one embodiment, the polynucleotide encoding a polypeptide of the present invention comprises or consists of the polynucleotide sequence set forth in SEQ ID NO: 70.

In one embodiment, the present invention relates to a polynucleotide encoding a polypeptide having DNase activity, wherein the polynucleotide has a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 11 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 13 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 15 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 17 or the cDNA sequence thereof of at least 60%, e.g., at least 65%, at least 70%, at least 75%, at least 80%, at least 85%, In one embodiment, the present invention relates to a polynucleotide encoding a polypeptide having DNase activity, wherein the polynucleotide has a sequence identity to the mature polypeptide coding sequence of SEQ ID NO: 19 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 21 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 23 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 25 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 28 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 31 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 34 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 37 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 40 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 43 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 46 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 49 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 52 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 55 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 58 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 61 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 64 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 67 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In one embodiment, the present invention relates to a polynucleotide encoding a polypeptide having DNase activity, wherein the polynucleotide has a sequence identity to the mature polypeptide coding sequence of SEQ ID NO: 70 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolour* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by RomaNOS: et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by RomaNOS: et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos: et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolour, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolour, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

One aspect of the invention relates to a method of producing a polypeptide, wherein the polypeptide is selected from the group consisting of polypeptides in shown in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and polypeptide having at least 80% sequence identity hereto, wherein the polypeptide has DNase activity (a) cultivating the recombinant host cell under conditions conducive for production of the polypeptide; and (b) recovering the polypeptide.

In one aspect, the cell is *Aspergillus*, however the host cell may be any of those described under the heading "host cells"

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

In one embodiment, the invention further comprises producing the polypeptide by cultivating the recombinant host cell further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, manNOS:idase, mutanase, oxidase, pectinolytic enzyme, peroxidase, phytase, polyphenoloxidase, proteolytic enzyme, ribonuclease, transglutaminase, or a xylanase.

In one embodiment, the second polypeptide of interest is heterologous or homologous to the host cell.

In one embodiment, the recombinant host cell is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolour, Trichoderma harzianum, Trichoderma koningii, Trichoderma longibrachiatum, Trichoderma reesei,* or *Trichoderma viride* cell.

In one embodiment, a method of producing the second polypeptide of interest comprises cultivating the host cell under conditions conducive for production of the second polypeptide of interest.

In one embodiment, the method further comprises recovering the second polypeptide of interest.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention relates to compositions comprising a DNase according to the invention.

Some aspect of the invention relates to a composition comprising at least 0.002 ppm of a polypeptide having DNase activity, wherein the polypeptide comprises any of the motifs [G/Y/W/F/A/H]NI[R/Q/D/E/V] (SEQ ID NO: 73), SDH[D/H/L]P (SEQ ID NO: 74) or GGNI[R/Q] (SEQ ID NO: 75).

The amount of DNase is preferably at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. The amount of DNase is preferably at least 0.02 ppm but may be from 0.00008 to 100, in the range of 0.0001-100, in the range of 0.0002-100, in the range of 0.0004-100, in the range of 0.0008-100, in the range of 0.001-100 ppm enzyme protein, 0.01-100 ppm enzyme protein, 0.01-50 ppm enzyme protein, preferably 0.05-50 ppm enzyme protein, preferably 0.02-50 ppm enzyme protein, 0.015-50 ppm enzyme protein, preferably 0.01-50 ppm enzyme protein, preferably 0.1-50 ppm enzyme protein, preferably 0.2-50 ppm enzyme protein, preferably 0.1-30 ppm enzyme protein, preferably 0.5-20 ppm enzyme protein or preferably 0.5-10 ppm enzyme protein per gram composition.

Some aspect of the invention relates to a composition comprising a polypeptide having DNase activity, wherein the polypeptide having DNase activity comprises the NUC2_B domain, comprises one or both of the motifs SDH[D/H/L]P (SEQ ID NO: 74) or GGNI[R/Q] (SEQ ID NO: 75). Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition Some aspect of the invention relates to a composition comprising a polypeptide having DNase activity, wherein the polypeptide having DNase activity comprises one or both of the motifs SDH[D/H/L]P (SEQ ID NO: 74) or GGNI[R/Q] (SEQ ID NO: 75). Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition.

Some aspects of the invention relates to a composition comprising a polypeptide having DNase activity, wherein the polypeptide comprises one or more of the motifs selected from the motifs [G/Y/W/F/A/H]NI[R/Q/D/E/V] (SEQ ID NO: 73), SDH[D/H/L]P (SEQ ID NO: 74) or GGNI[R/Q] (SEQ ID NO: 75), wherein the polypeptide having DNase activity is selected from the group consisting SEQ ID NO: 6, SEQ ID NO: 7, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and polypeptides having at least 80% sequence identity hereto.

Some aspects of the invention relates to a composition comprising a polypeptide having DNase activity, wherein the polypeptide having DNase activity is selected from the group consisting of:

a) a polypeptide having at least 70%, at least 80%, at least 85%, at least 90%, at least 95%, at least 98%, at least 99% or 100% sequence identity to the polypeptide of SEQ ID NO: 3, b) a polypeptide having at least 70%, at least 80%, at least 85%, at least 90%, at least 95%, at least 98%, at least 99% or 100% sequence identity to the polypeptide of SEQ ID NO: 4, c) a polypeptide having at least 70%, at least 80%, at least 85%, at least 90%, at least 95%, at least 98%, at least 99% or 100% sequence identity to the polypeptide of SEQ ID NO: 5, d) a polypeptide having at least 70%, at least 80%, at least 85%, at least 90%, at least 95%, at least 98%, at least 99% or 100% sequence identity to the polypeptide of SEQ ID NO: 6, e) a polypeptide having at least 70%, at least 80%, at least 85%, at least 90%, at least 95%, at least 98%, at least 99% or 100% sequence identity to the polypeptide of SEQ ID NO: 7, f) a polypeptide having at least 70%, at least 80%, at least 85%, at least 90%, at least 95%, at least 98%, at least 99% or 100% sequence identity to the polypeptide of SEQ ID NO: 8, g) a polypeptide having at least 70%, at least 80%, at least 85%, at least 90%, at least 95%, at least 98%, at least 99% or 100% sequence identity to the polypeptide of SEQ ID NO: 9, h) a polypeptide having at least 70%, at least 80%, at least 85%, at least 90%, at least 95%, at least 98%, at least 99% or 100% sequence identity to the polypeptide of SEQ ID NO: 10, i) a polypeptide having at least 70%, at least 80%, at least 85%, at least 90%, at least 95%, at least 98%, at least 99% or 100% sequence identity to the polypeptide of SEQ ID NO: 27, j) a polypeptide having at least 70%, at least 80%, at least 85%, at least 90%, at least 95%, at least 98%, at least 99% or 100% sequence identity to the polypeptide of SEQ ID NO: 30, k) a polypeptide having at least 70%, at least 80%, at least 85%, at least 90%, at least 95%, at least 98%, at least 99% or 100% sequence identity to the polypeptide of SEQ ID NO: 33, l) a polypeptide having at least 70%, at least 80%, at least 85%, at least 90%, at least 95%, at least 98%, at least 99% or 100% sequence identity to the polypeptide of SEQ ID NO: 36, m) a polypeptide having at least 70%, at least 80%, at least 85%, at least 90%, at least 95%, at least 98%, at least 99% or 100% sequence identity to the polypeptide of SEQ ID NO: 39, n) a polypeptide having at least 70%, at least 80%, at least 85%, at least 90%, at least 95%, at least 98%, at least 99% or 100% sequence identity to the polypeptide of SEQ ID NO: 42, o) a polypeptide having at least 70%, at least 80%, at least 85%, at least 90%, at least 95%, at least 98%, at least 99% or 100% sequence identity to the polypeptide of SEQ ID NO: 45, p) a polypeptide having at least 70%, at least 80%, at least 85%, at least 90%, at least 95%, at least 98%, at least 99% or 100% sequence identity to the polypeptide of SEQ ID NO: 48, q) a polypeptide having at least 70%, at least 80%, at least 85%, at least 90%, at least 95%, at least 98%, at least 99% or 100% sequence identity to the polypeptide of SEQ ID NO: 51, r) a polypeptide having at least 70%, at least 80%, at least 85%, at least 90%, at least 95%, at least 98%, at least 99% or 100% sequence identity to the polypeptide of SEQ ID NO: 54, s) a polypeptide having at least 70%, at least 80%, at least 85%, at least 90%, at least 95%, at least 98%, at least 99% or 100% sequence identity to the polypeptide of SEQ ID NO: 57, t) a polypeptide having at least 70%, at least 80%, at least 85%, at least 90%, at least 95%, at least 98%, at least 99% or 100% sequence identity to the polypeptide of SEQ ID NO: 60, u) a polypeptide having at least 70%, at least 80%, at least 85%, at least 90%, at least 95%, at least 98%, at least 99% or 100% sequence identity to the polypeptide of SEQ ID NO: 63, v) a polypeptide having at least 70%, at least 80%, at least 85%, at least 90%, at least 95%, at least 98%, at least 99% or 100% sequence identity to the polypeptide of SEQ ID NO: 66, x) a polypeptide having at least 70%, at least 80%, at least 85%, at least 90%, at least 95%, at least 98%, at least 99% or 100% sequence identity to the polypeptide of SEQ ID NO: 69, and y) a polypeptide having at least 70%, at least 80%, at least 85%, at least 90%, at least 95%, at least 98%, at least 99% or 100% sequence identity to the polypeptide of SEQ ID NO: 72.

The present invention further concerns a detergent composition comprising a polypeptide having DNase activity and preferably a detergent adjunct ingredient. The detergent composition can be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodour from an item, such as E-2-nonenal as described in Assay II. The detergent compositions comprising the polypeptides of the present invention overcomes the problems of the prior art.

The polypeptides of the invention having DNase activity are useful in powder and liquid detergent. In one embodiment of the invention, the detergent composition comprises a DNase, selected from the group consisting of SEQ ID NOS: 2, 3, 4, 5, 6, 7, 8, 9 and 10 or SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and a detergent adjunct. In one embodiment of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may be a surfactant. One advantage of including a surfactant in a detergent composition comprising a DNase is that the wash performance may be improved. In one embodiment, the detergent adjunct ingredient is a builder or a clay soil removal/anti-redeposition agent. In one embodiment, detergent adjunct ingredient is an enzyme.

The detergent composition may comprise one or more enzymes, as specified below. The one or more enzymes may be selected from the group consisting of proteases, lipases, cutinases, amylases, carbohydrases, cellulases, pectinases, mannanases, arabinases, galactanases, xylanases and oxidases. Specific enzymes suitable for the detergent compositions of the invention are described below.

In one embodiment, the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere.

Biofilm which growth in laundry items may originate from many organisms as described previously. One particular abundant bacterium in biofilm originates from *Brevundimonas*. As shown in the examples the DNases of the invention are particularly effective in reducing the growth of the bacterium and reducing the malodour, stickiness and/or re-deposition coursed by these bacteria. One embodiment of the invention relates to the use of a DNase, selected from the group consisting of SEQ ID NOS: 2, 3, 4, 5, 6, 7, 8, 9 and 10 or SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 or SEQ ID NO: 72 in reduction of malodour, reducing stickiness and/or re-deposition. One embodiment relates to the use in laundering of a DNase, selected from the group consisting of SEQ ID NOS: 2, 3, 4, 5, 6, 7, 8, 9 and 10 or SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 or SEQ ID NO: 72, wherein the DNase reducing adhesion of bacteria from *Brevundimonas*.

In one embodiment of the invention, the surface is a textile surface. The textile can be made of cotton, Cotton/Polyester, Polyester, Polyamide, Polyacryl and/or silk.

The detergent composition may be formulated as a bar, a homogenous tablet, a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The DNases of the invention are suitable for use in cleaning such as laundry. The invention further relates a method for laundering an item, which method comprises the steps of:

a. Exposing an item to a wash liquor comprising a polypeptide having DNase activity selected from the group consisting of polypeptides comprising SEQ ID NOS: 2, 3, 4, 5, 6, 7, 8, 9 and 10 or a detergent composition comprising the polypeptide;

b. Completing at least one wash cycle; and c. Optionally rinsing the item, wherein the item is a textile.

The invention further relates a method for laundering an item, which method comprises the steps of:

a. Exposing an item to a wash liquor comprising a polypeptide having DNase activity selected from the group consisting of polypeptides comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72. or a detergent composition comprising the polypeptide;

b. Completing at least one wash cycle; and c. Optionally rinsing the item, wherein the item is a textile.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment the item is rinsed after being exposed to the wash liquor. The item can be rinsed with water or with water comprising a conditioner.

The invention further concerns an item washed according to the inventive method.

The detergent composition comprising a polypeptide selected from the group consisting of polypeptides comprising SEQ ID NOS: 2, 3, 4, 5, 6, 7, 8, 9 and 10 having DNase activity can be used for releasing or removing a biofilm or preventing biofilm formation.

The detergent composition comprising a polypeptide selected from the group consisting of polypeptides comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and having DNase activity can be used for releasing or removing a biofilm or preventing biofilm formation.

The DNases of the invention may be added to a wash liquor.

Thus, one embodiment of the invention relates to a detergent composition comprising one or more anionic surfactants; an enzyme selected from the group consisting of: a protease, a lipase, a cutinase, an amylase, a carbohydrase, a cellulase, a pectinase, a mannanase, an arabinase, a galactanase, a xylanase, and an oxidase; and a DNase, selected from the group consisting of SEQ ID NOS: 2, 3, 4, 5, 6, 7, 8, 9 and 10.

Thus, one embodiment of the invention relates to a detergent composition comprising one or more anionic surfactants; an enzyme selected from the group consisting of: a protease, a lipase, a cutinase, an amylase, a carbohydrase, a cellulase, a pectinase, a mannanase, an arabinase, a galactanase, a xylanase, and an oxidase; and a DNase, selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72.

One embodiment further relates to a washing method for textile comprising:

a. exposing a textile to a wash liquor comprising a DNase or a detergent composition comprising at least one of the DNases, b. completing at least one wash cycle; and c. optionally rinsing the textile, wherein the DNases are selected from the group consisting of SEQ ID NOS: 2, 3, 4, 5, 6, 7, 8, 9 and 10.

One embodiment further relates to a washing method for textile comprising:

a. exposing a textile to a wash liquor comprising a DNase or a detergent composition comprising at least one of the DNases, b. completing at least one wash cycle; and c. optionally rinsing the textile, wherein the DNases are selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72.

Another embodiment relates to a textile washed according to the inventive method.

The concentration of the DNase in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

An enzyme present in a detergent of the invention may be stabilized using conventional stabilizing agents, e.g., a polyol such as propylene glycol or glycerol, a sugar or sugar alcohol, different salts such as NaCl or KCl. The proteases of the invention may be stabilized by lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or CI2 or SSI. The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In one embodiment, the polypeptides are stabilized using peptide aldehydes or ketones Suitable peptide aldehydes are described in WO 94/04651, WO 95/25791, WO 98/13458, WO 98/13459, WO 98/13460, WO 98/13461, WO 98/13462, WO 2007/141736, WO 2007/145963, WO 2009/118375, WO10/055052 and WO 2011/036153. A polypeptide of the present invention may also be incorporated in the detergent formulations disclosed in WO 97/07202, which is hereby incorporated by reference.

In another embodiment, the polypeptides are stabilized using a phenyl boronic acid derivative is 4-formylphenyl-boronic acid (4-FPBA) with the following formula:

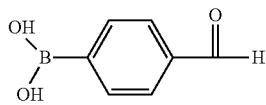 [SMILES: O=Cc1ccc(B(O)O)cc1]

The detergent compositions may comprise two or more stabilizing agents, e.g., such as those selected from the group consisting of propylene glycol, glycerol, 4-formylphenyl boronic acid and borate.

The detergent compositions may comprise two or more stabilizing agents, e.g., such as those selected from the group consisting of propylene glycol, glycerol, 4-formylphenyl boronic acid and borate.

The stabilizing agent(s) is preferably present in the detergent composition in a quantity of from 0.001 to about 5.0 wt. %, from 0.01 to about 2.0 wt. %, from 0.1 to about 3 wt. % or from 0.5% to about 1.5 wt. %.

Liquid Detergent Composition

The DNases of the invention may also be formulated in liquid laundry compositions such as a liquid laundry compositions composition comprising:

a) at least 0.005 mg of active DNase protein per litre detergent wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or a DNase having at least 80% sequence identity hereto, b) 2 wt. % to 60 wt. % of at least one surfactant, and c) 5 wt. % to 50 wt. % of at least one builder.

The DNases of the invention may also be formulated in liquid laundry compositions such as a liquid laundry compositions composition comprising:

a) at least 0.002 ppm DNase polypeptide, wherein the DNase polypeptide is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 or a DNase having at least 80% sequence identity hereto, b) 2 wt. % to 60 wt. % of at least one surfactant, and c) 5 wt. % to 50 wt. % of at least one builder The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and, in particular, alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™ Lutensol™ and Pluronic™ range from BASF, Dehypon™ series from Cognis and Genapol™ series from Clariant.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N, N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MI DA), serine-N,N-diacetic acid (SEDA), isoserine-N,N-diacetic acid (ISDA), phenylalanine-N, N-diacetic acid (PH DA), anthranilic acid-N,N-diacetic acid (ANDA), sulfanilic acid-N, N-diacetic acid (SLDA), taurine-N,N-diacetic acid (TUDA) and N''-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis(methylenephosphonic acid) (HDTMP).

The composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly(acrylic acid/maleic acid) (PAA/PMA) or polyaspartic acid. Further exemplary builders and/or co-builders are described in, e.g., WO 2009/102854, U.S. Pat. No. 5,977,053.

In one preferred embodiment, the builder is a non-phosphorus based builder such as citric acid and/or methylglycine-N, N-diacetic acid (MGDA) and/or glutamic-N, N-diacetic acid (GLDA) and/or salts thereof. The laundry composition may also be phosphate free in the instance the preferred builders includes citrate and/or methylglycine-N, N-diacetic acid (MGDA) and/or glutamic-N,N-diacetic acid (GLDA) and/or salts thereof.

One embodiment of the invention concerns a liquid laundry compositions composition comprising:

a) at least 0.005 mg of active DNase per litre of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or DNases having at least 80% sequence identity hereto, b) 1% to 15% by weight of at least one surfactant wherein the surfactant is LAS, AEOS and/or SLES, and c) 5% to 50% by weight of at least one builder selected from HEDP, DTMPA or DTPMPA.

One embodiment of the invention concerns a liquid laundry compositions composition comprising:

a) at least 0.005 mg of active DNase per litre of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 or DNases having at least 80% sequence identity hereto, b) 1% to 15% by weight of at least one surfactant wherein the surfactant is LAS, AEOS and/or SLES, and c) 5% to 50% by weight of at least one builder selected from HEDP, DTMPA or DTPMPA.

The liquid detergent composition may typically contain at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Powder Compositions

The detergent composition may also be formulated into a granular detergent for laundry or dish wash. One embodiment of the invention concerns a granular detergent composition comprising a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or a DNase having at least 80% sequence identity hereto, b) 5 wt. % to 50 wt. % anionic surfactant, c) 1 wt. % to 8 wt. % nonionic surfactant, and d) 5 wt. % to 40 wt. % builder such as carbonates, zeolites, phosphate builder, calcium sequestering builders or complexing agents One embodiment of the invention concerns a granular detergent composition comprising a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and a DNase having at least 80% sequence identity hereto, b) 5 wt. % to 50 wt. % anionic surfactant, c) 1 wt. % to 8 wt. % nonionic surfactant, and d) 5 wt. % to 40 wt. % builder such as carbonates, zeolites, phosphate builder, calcium sequestering builders or complexing agents The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and, in particular, alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants include Plurafac™, Lutensol™ and Pluronic™ range from BASF, Dehypon™ series from Cognis and Genapol™ series from Clariant.

The builder is may be non-phosphate such as citrate preferably as a sodium salt and/or zeolites. Phosphonate builder may be any of those described above.

The builder is preferably selected among phosphates and sodium citrate builders, sodium carbonate, sodium silicate, sodium aluminiumsilicate (zeolite) as described above under the compositions. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP).

Preferred phosphonates include 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition.

The laundry composition may also be phosphate free in the instance the preferred builders includes citrate, carbonates and/or sodium aluminiumsilicate (zeolite).

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymoNOS:ulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclo-nonane (Me4-TACN), in particular, Me3-TACN, such as the dinuclear manganese complex [(Me3-TACN)Mn(O)3Mn (Me3-TACN)](PF6)2, and [2,2',2''-nitrilotris(ethane-1,2-diylazanylylidene-κN-methanylylidene)triphenolato-κ3O] manganese(III). The bleach catalysts may also be other metal compounds, such as iron or cobalt complexes.

In some embodiments, where a source of a peracid is included, an organic bleach catalyst or bleach booster may be used having one of the following formulae:

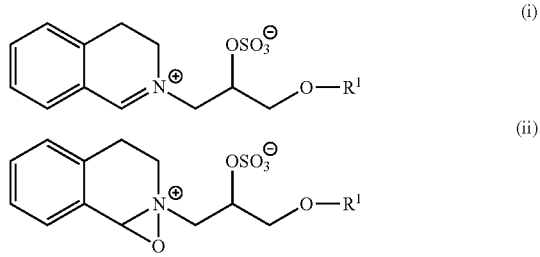

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminium phthalocyanines.

According to one embodiment and any of the previous embodiments, the invention also relates to a cleaning composition comprising;
a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 or a DNase having at least 80% sequence identity hereto,
b) 10-50 wt. % builder and
c) at least one bleach component, wherein the bleach is a peroxide and the bleach catalyst is a manganese compound.

According to one embodiment and any of the previous embodiments the invention also relates to a cleaning composition comprising;
a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and a DNase having at least 80% sequence identity hereto,
b) 10-50 wt. % builder and
c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triaza-cyclononane or manganese (III) acetate tetrahydrate.

According to one embodiment and any of the previous embodiments the invention also relates to a cleaning composition comprising;
a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10,
b) 10-50 wt. % builder selected from citric acid, methyl glycine-N,N-diacetic acid (MGDA) and/or glutamic-N,N-diacetic acid (GLDA) and mixtures thereof, and
c) at least one bleach component, wherein the bleach is an oxygen bleach and the bleach catalyst is a manganese compound.

According to one embodiment and any of the previous embodiments the invention also relates to a cleaning composition comprising;
a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and a DNase having at least 80% sequence identity hereto,
b) 10-50 wt. % builder selected from citric acid, methyl glycine-N,N-diacetic acid (MGDA) and/or glutamic-N,N-diacetic acid (GLDA) and mixtures thereof, and
c) at least one bleach component, wherein the bleach is an oxygen bleach and the bleach catalyst is a manganese compound. The oxygen bleach is preferably percarbonate and the manganese catalyst preferably 1,4,7-trimethyl-1,4,7-triazacyclo-nonane or manganese (II) acetate tetrahydrate.

According to one embodiment and any of the previous embodiments the invention also relates to a cleaning composition comprising;
a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 or a DNase having at least 80% sequence identity hereto,
b) 10-50 wt. % builder selected from citric acid, methyl glycine-N,N-diacetic acid (MGDA) and/or glutamic-N,N-diacetic acid (GLDA) and mixtures thereof, and
c) 0.1-40 wt. %, preferably from 0.5-30 wt. %, of bleaching components, wherein the bleach components are a peroxide, preferably percarbonate and a metal-containing bleach catalyst preferably 1,4,7-trimethyl-1,4,7-triazacyclo-nonane or manganese (II) acetate tetrahydrate (MnTACN).

According to one embodiment and any of the previous embodiments the invention also relates to a cleaning composition comprising;

a) at least 0.005 mg of active DNase per gram of composition wherein the DNase is selected from a polypeptide comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and a DNase having at least 80% sequence identity hereto, b) 10-50 wt. % builder selected from citric acid, methyl glycine-N,N-diacetic acid (MGDA) and/or glutamic-N,N-diacetic acid (GLDA) and mixtures thereof, and c) 0.1-40 wt. %, preferably from 0.5-30 wt. %, of bleaching components, wherein the bleach components are a peroxide, preferably percarbonate and a metal-containing bleach catalyst preferably 1,4,7-trimethyl-1,4,7-triazacyclononane or manganese (II) acetate tetrahydrate (MnTACN).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C. I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt. % to 0.2 wt. % fabric hueing agent, this may be especially preferred when the composition is in the form of a unit dose pouch. Suitable hueing agents are also disclosed in, e.g., WO 2007/087257 and WO 2007/087243.

Enzymes

The cleaning compositions of the invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

The term "subtilases" refers to a sub-group of serine protease according to Siezen et al., 1991, *Protein Engng.* 4: 719-737 and Siezen et al., 1997, *Protein Science* 6: 501-523. Serine proteases are a subgroup of proteases characterized by having a serine in the active site, which forms a covalent adduct with the substrate. The subtilases may be divided into 6 sub-divisions, i.e., the Subtilisin family, the Thermitase family, the Proteinase K family, the Lantibiotic peptidase family, the Kexin family and the Pyrolysin family. Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO 2009/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/016285, WO 02/026024 and WO 02/016547. Examples of trypsin-like proteases are trypsin (e.g., of porcine or bovine origin) and the *Fusarium* protease described in WO 89/06270, WO 94/25583 and WO 2005/040372, and the chymotrypsin proteases obtained from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Genencor Int.) such as those obtained from *Bacillus amyloliquefaciens*.

Examples of useful proteases are the variants described in: WO 92/19729, WO 96/34946, WO 98/20115, WO 98/20116, WO 99/11768, WO 01/44452, WO 03/006602, WO 2004/03186, WO 2004/041979, WO 2007/006305, WO 2011/036263, WO 2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Specific examples of useful proteases are the variants described in: WO 92/19729, WO 96/034946, WO 98/20115, WO 98/20116, WO 99/011768, WO 01/44452, WO 03/006602, WO 2004/03186, WO 2004/041979, WO 2007/006305, WO 2011/036263, WO 2011/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus Lentus* protease shown in SEQ ID NO: 1 of WO 2016/001449. More preferred the subtilase variants may comprise the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, 597A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N2125, M216S, A226V, K229L, Q230H, Q239R, N246K, N255W, N255D, N255E, L256E, L256D T268A, R269H. The protease variants preferably variants of the *Bacillus Lentus* protease (Savinase®) shown in SEQ ID NO: 1 of WO 2016/001449, the *Bacillus* amylolichenifaciens protease (BPN') shown in SEQ ID NO: 2 of WO 2016/001449. The protease variants preferably have at least 80% sequence identity to SEQ ID NO: 1 or SEQ ID NO: 2 of WO 2016/001449.

Or a protease selected from a protease variant comprising a substitution at one or more positions corresponding to positions 171, 173, 175, 179, or 180 of SEQ ID NO: 1 of WO 2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N. V.), BLAP (sequence shown in FIG. 29 of U.S. Pat. No. 5,352,604) and variants hereof (Henkel AG) and KAP (*Bacillus alkalophilus* subtilisin) from Kao.

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and polypeptides having at least 60%, e.g., 70%, e.g., 80%, e.g., at least 90% sequence identity hereto, wherein the composition further comprises: at least 0.01 ppm of one or more protease variant comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO: 1 of WO 2011/036263.

Lipases and Cutinases

Suitable lipases and cutinases include those of bacterial or fungal origin. Chemically modified or protein engineered mutant enzymes are included. Examples include lipase from *Thermomyces*, e.g., from T. lanugiNOS:us (previously named *Humicola lanuginosa*) as described in EP 258068 and EP305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), P. sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades). Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/56782), perhydrolases from the CE 7 family (WO 2009/67279), and variants of the *M. smegmatis* perhydrolase, in particular, the S54V variant used in the commercial product Gentle Power Bleach from Huntsman Textile Effects Pte Ltd (WO 2010/100028).

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and polypeptides having at least 60%, e.g., 70%, e.g., 80%, e.g., at least 90% sequence identity hereto, wherein the composition further comprises: at least 0.01 ppm one or more lipase.

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128O+K178L+T182G+F202Y+Y305R+D319T+G475K;
S125A+N128C+K178L+T182G+Y305R+G475K; or
S125A+N128C+T131I+T165I+K178L+T182G+Y305R+G475K, wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and D184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Some aspect of the invention relates to a composition, such as a detergent, e.g., cleaning composition comprising a polypeptide having DNase activity, wherein the polypeptide having DNase activity is selected from the group consisting of the polypeptides shown in: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 and polypeptides having at least 60%, e.g., 70%, e.g., 80%, e.g., at least 90% sequence identity hereto, wherein the composition further comprises:

a) at least 0.01 ppm of one or more amylase variant, wherein the variant comprises:
(i) one or more substitutions in the following positions: 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, wherein the positions corresponds to positions of SEQ ID NO: 2 of WO 00/60060;
(ii) exhibiting at least 90 percent identity with SEQ ID NO: 2 of WO 96/023873, with deletions in the 183 and 184 positions; or
(iii) variants exhibiting at least 95 percent identity with SEQ ID NO:3 of WO 2008/112459, comprising mutations in one or more of the following positions M202, M208, S255, R172 and/or M261.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E. C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular, from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular, *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolour*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular, a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular, non-dusting granulates, liquids, in particular, stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4.4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt. % to upper levels of 0.5 or even 0.75 wt. %.

Soil Release Polymers

The cleaning compositions of the present invention may also include one or more soil release polymers which aid the removal of soils from fabrics such as cotton and polyester based fabrics, in particular, the removal of hydrophobic soils from polyester based fabrics. The soil release polymers may for example be nonionic or anionic terephthalate based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Anti-Parasitic/Viral Compounds

The cleaning composition may further comprise an antiparasitic compound can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin. The antibacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Formulation of DNases in Microcapsule

The DNases of the invention may be formulated in microcapsules or in liquid detergents comprising microcapsules. A liquid cleaning composition of the invention may comprise a surfactant and a detergent builder in a total concentration of at least 3% by weight, and an enzyme, which may be a DNase, containing microcapsule, wherein the membrane of the microcapsule is produced by cross-linking of a polybranched polyamine having a molecular weight of more than 1 kDa. Encapsulating of enzymes such as DNases in a microcapsule with a semipermeable membrane having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of enzymes such as DNases in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes such as the DNases of the invention against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g., CMC) (cellulase), and dextrin and cyclodextrin (amylase).

Also, sensitive detergent ingredients can be encapsulated, and thus stabilized, in the microcapsules of the invention. Sensitive detergent ingredients are prone to degradation during storage. Such detergent ingredients include bleaching compounds, bleach activators, perfumes, polymers, builder, surfactants, etc.

Generally, the microcapsules can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be coloured.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule may be a small aqueous sphere with a uniform membrane around it. The material inside the microcapsule is referred to as the core, internal phase, or fill, whereas the membrane is sometimes called a shell, coating, or wall. The microcapsules typically have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present.

Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favorable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared—it is not formed in situ from other starting materials. To obtain the attractive properties, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear diamine will allow one or more primary amine(s) to be introduced at the end of the introduced branch(es). In this context we the primary amino group is understood as part of the branch, i.e., the endpoint of the branch. For example, both tris(2-aminoethyl)amine and 1,2,3-propanetriamine is considered as molecules having one branching point. The polyamine preferably has at least four primary amines. Branching points can be introduced from an aliphatic hydrocarbon chain from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

The reactive amino groups preferably constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

The polybranched polyamine may be a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa.

Combinations of different polybranched polyamines may be used for preparing the microcapsule.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

The liquid detergent composition may comprise a microcapsule, and thus form part of, any detergent composition in any form, such as liquid and powder detergents, and soap and detergent bars.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be isotropic or structured, preferably isotropic. It may be a formulation useful for washing in automatic washing machines or for hand washing. It may also be a personal care product, such as a shampoo, toothpaste, or hand soap.

The microcapsule is further described in WO 2014/177709 which is incorporated by reference.

Formulation of Enzyme in Co-Granule

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt. % moisture sink component and the composition additionally comprises from 20 to 80 wt. % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase of the invention. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm.

The core may include additional materials such as fillers, fibre materials (cellulose or synthetic fibres), stabilizing agents, solubilising agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should, in particular, be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 µm, such as less than 10 µm or less than 5 µm.

The salt coating may comprise a single salt or a mixture of two or more salts. The salt may be water soluble, in particular, having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%).

Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e., a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

Thus, in a further aspect, the present invention provides a granule, which comprises:

(a) a core comprising a DNase according to the invention, and (b) optionally a coating consisting of one or more layer(s) surrounding the core. Some aspect of the invention relates to a granule, which comprises:

a) a core comprising a polypeptide having DNase activity wherein the polypeptide is selected from the group consisting of polypeptides shown in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72 or polypeptides having at least 60%, e.g., 70%, e.g., 80%, e.g., at least 90%, e.g., at least 95%, e.g., at least 98%, e.g., at least 69% sequence identity hereto, and (b) optionally a coating consisting of one or more layer(s) surrounding the core.

Formulation of Detergent

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e., if a solid object (e.g., laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants, e.g., anionic synthetic surfactants, builders, polymeric soil release agents, detergent chelators, stabilizing agents, fillers, dyes, colour ants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, DNase, optionally one or more additional enzymes, a protease inhibitor, and a salt of a monovalent cation and an organic anion may be prepared and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Pharmaceutical Compositions and Uses

The invention further concerns a pharmaceutical composition comprising a polypeptide having DNase activity and a pharmaceutical adjunct ingredient, wherein the polypeptide having DNase activity. The adjunct ingredient may be any excipient suitable for pharmaceutical compositions. The adjunct/expient is within the choice of the skilled artisan. The pharmaceutical composition further comprises a polypeptide selected from the group consisting of polypeptides comprising SEQ ID NOS: 2, 3, 4, 5, 6, 7, 8, 9, 10 and 11, or DNases having at least 80% sequence identity hereto. The pharmaceutical compositions can be used for releasing or removing a biofilm or preventing biofilm formation on surfaces such as medical devices.

The use may be indwelling medical device characterised in that at least a portion of a patient-contactable surface of said device is coated with the pharmaceutical composition comprising the DNases of the invention.

The device can be a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument. The pharmaceutical composition can be formulated as a liquid, lotion, cream, spray, gel or ointment. The pharmaceutical composition can be for administration to an animal patient. The animal patient can be a mammalian patient. The mammalian patient can be a human The invention is further summarized in the following paragraphs:

1. Use of a polypeptide having DNase activity, wherein the polypeptide is selected from the group consisting of SEQ ID NOS: 2, 3, 4, 5, 6, 7, 8, 9 and 10 or selected from the group of polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72, or a DNase having at least 80% sequence identity hereto for preventing, reducing or removing a biofilm from an item, wherein the item is a textile.
2. Use according to paragraph 1 for preventing, reducing or removing stickiness of the item.
3. Use according to any of paragraphs 1 or 2 for pretreating stains on the item.
4. Use according to any of paragraphs 1-3 for preventing, reducing or removing redeposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein the polypeptide is the polypeptide of paragraphs 45-50.
8. Use according to any of the preceding paragraphs, wherein a malodour is reduced or removed from the item.
9. Use according to any of the preceding paragraphs, wherein the malodour is caused by E-2-nonenal.
10. Use according to any of the preceding paragraphs, wherein the amount of E-2-nonenal present on a wet textile is reduced or removed.
11. Use according to any of the preceding paragraphs, wherein the amount of E-2-nonenal present on a dry textile is reduced or removed.
12. A detergent composition comprising a polypeptide having deoxyribonuclease (DNase) activity selected from the group consisting of SEQ ID NOS: 2, 3, 4, 5, 6, 7, 8, 9 and 10 or selected from the group of polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72 or DNases having at least 80% sequence identity hereto and a detergent adjunct ingredient.
13. Detergent composition according to paragraph 12, wherein the polypeptide is obtained from *Vibrissea flavovirens, Penicillium reticulisporum, Acremonium dichromosporum, Preussia aemulans, Colletotrichum circinans, Clavicipitaceae, Preussia aemulans* or *Trichurus spiralis*.
14. Detergent composition according to paragraph 12 or 13, wherein the polypeptide having DNase activity is selected from the group consisting of polypeptides with; SEQ ID NOS: 2 and 3 obtained from *Vibrissea flavovirens*, SEQ ID NO: 4 obtained from *Penicillium reticulisporum*, SEQ ID NO: 5 obtained from *Acremonium dichromosporum*, SEQ ID NO: 6 and SEQ ID NO: 9 obtained from *Preussia aemulans*, SEQ ID NO: 7 obtained from *Colletotrichum circinans*, SEQ ID NO: 8 obtained from *Clavicipitaceae* and SEQ ID NO: 10 obtained from *Trichurus spiralis*.
15. Detergent composition according to any of paragraphs 12-14, wherein the polypeptide is the polypeptide of paragraphs 45-50.
16. Detergent composition according to any of paragraphs 12-15, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.
17. Detergent composition according to any of paragraphs 12-16, wherein the composition further comprises one or more enzymes selected from the group consisting of proteases, lipases, cutinases, amylases, carbohydrases, cellulases, pectinases, mannanases, arabinases, galactanases, xylanases and oxidases.
18. Detergent composition according to any of paragraphs 12-17, wherein the enzyme is a protease, which is of animal, vegetable or microbial origin.
19. Detergent composition according to any of paragraphs 12-18, wherein the protease is chemically modified or protein engineered.
20. Detergent composition according to any of paragraphs 12-19, wherein the protease is a serine protease or a metalloprotease, preferably an alkaline microbial protease or a trypsin-like protease.
21. Detergent composition according to any of paragraphs 12-20, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

22. Detergent composition according to any of paragraphs 12-21, wherein the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere.

23. Detergent composition according to any of paragraphs 12-22, wherein the surface is a textile surface.

24. Detergent composition according to any of paragraphs 12-23, wherein the textile is made of cotton, Cotton/Polyester, Polyester, Polyamide, Polyacryl and/or silk.

25. Detergent composition according to any of paragraphs 12-24, wherein the composition is a bar, a homogenous tablet, a tablet having two or more layers, a pouch having one or more compartments, a regular or compact powder, a granule, a paste, a gel, or a regular, compact or concentrated liquid.

26. Detergent composition according to any of paragraphs 12-25, wherein the composition is a liquid detergent, a powder detergent or a granule detergent.

27. A laundering method for laundering an item comprising the steps of:
  a. Exposing an item to a wash liquor comprising a polypeptide of paragraphs 45-50 or a detergent composition according to any of paragraphs 12-26;
  b. Completing at least one wash cycle; and
  c. Optionally rinsing the item,
wherein the item is a textile.

28. Method according to paragraph 27, wherein the pH of the wash liquor is in the range of 1 to 11.

29. Method according to paragraph 27 or 28, wherein the pH of the wash liquor is in the range 5.5 to 11, such as in the range of 7 to 9, in the range of 7 to 8 or in the range of 7 to 8.5.

30. Method according to any of paragraphs 27-29, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.

31. Method according to any of paragraphs 27-30, wherein the temperature of the wash liquor is 30° C.

32. Method according to any of paragraphs 27-31, wherein the method further comprises draining of the wash liquor or part of the wash liquor after completion of a wash cycle.

33. Method according to any of paragraphs 27-32, wherein the item is exposed to the wash liquor during a first and optionally a second or a third wash cycle.

34. Method according to any of paragraphs 27-33, wherein the item is rinsed after being exposed to the wash liquor.

35. Method according to any of paragraphs 27-34, wherein the item is rinsed with water or with water comprising a conditioner.

36. Method according to any of paragraphs 27-35, wherein stickiness of the item is reduced.

37. Method according to any of paragraphs 27-36, wherein stains present on the item is pretreated with a polypeptide of paragraphs 45-50 or a detergent composition according to any of paragraphs 12-26.

38. Method according to any of paragraphs 27-37, wherein redeposition of soil is reduced.

39. Method according to any of paragraphs 27-38, wherein adherence of soil to the item is reduced or removed.

40. Method according to any of paragraphs 27-39, wherein whiteness of the item is maintained or improved.

41. Method according to any of paragraphs 27-40, wherein malodour is reduced or removed from the item.

42. Method according to any of paragraphs 27-41, wherein the malodour is caused by E-2-nonenal.

43. Method according to any of paragraphs 27-42, wherein the amount of E-2-nonenal present on a wet or dry textile is reduced or removed.

44. Method according to any of paragraphs 27-43, wherein the concentration of the polypeptide in the wash liquor is at least 1 mg of DNase protein, such as at least 5 mg of protein, preferably at least 10 mg of protein, more preferably at least 15 mg of protein, even more preferably at least 20 mg of protein, most preferably at least 30 mg of protein, and even most preferably at least 40 mg of protein per liter of wash liquor.

45. A polypeptide having DNase activity, selected from the group consisting of:
  a. a polypeptide having at least 60% sequence identity to the polypeptide of SEQ ID NOS: 2, 3, 4, 5, 6, 7, 8, 9 or 10 or selected from the group of polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72 or a polypeptide having at least 60% sequence identity hereto;
  b. a polypeptide encoded by a polynucleotide that hybridizes under low stringency conditions with
    i. the mature polypeptide coding sequence,
    ii. the cDNA sequence thereof, or
    iii. the full-length complement of (i) or (ii);
  c. a polypeptide encoded by a polynucleotide having at least 60% sequence identity to the mature polypeptide coding sequence or the cDNA sequence thereof;
  d. a variant of the mature polypeptide of SEQ ID NOS: 2, 3, 4, 5, 6, 7, 8, 9 or 10 or aby of the polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 or SEQ ID NO: 72 comprising a substitution, deletion, and/or insertion at one or more positions; and
  e. a fragment of the polypeptide of (a), (b), (c), or (d) that has DNase activity;

46. The polypeptide of paragraph 45, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide with SEQ ID NOS: 2, 3, 4, 5, 6, 7, 8, 9 or 10 or polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 72.

47. The polypeptide according to paragraph 45 or 46, which is encoded by a polynucleotide that hybridizes under low stringency conditions, low-medium stringency conditions, medium stringency conditions, medium-high stringency conditions, high stringency conditions, or very high stringency conditions with i. the mature polypeptide coding sequence,
ii. the cDNA sequence thereof, or
iii. the full-length complement of (i) or (ii).

48. The polypeptide according to any of paragraphs 45-47, comprising or consisting of SEQ ID NO: 2, 3, 4, 5, 6, 7, 8, 9 or 10 or polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 7.

49. The polypeptide according to any of paragraphs 45-48, which is a variant of the polypeptides selected from the group consisting of SEQ ID NOS: 2, 3, 4, 5, 6, 7, 8, 9 and 10 or polypeptides shown in SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69 and SEQ ID NO: 7 comprising a substitution, deletion, and/or insertion at one or more positions.

50. The polypeptide according to paragraph 49, which is a fragment of SEQ ID NOS: 2, 3, 4, 5, 6, 7, 8, 9 or 10, wherein the fragment has DNase activity.

51. A polynucleotide encoding the polypeptide according to any of paragraphs 45-50.

52. A nucleic acid construct or expression vector comprising the polynucleotide of paragraph 51 operably linked to one or more control sequences that direct the production of the polypeptide in an expression host.

53. A recombinant host cell comprising the polynucleotide of paragraph 51 operably linked to one or more control sequences that direct the production of the polypeptide.

54. A method of producing the polypeptide of any of paragraphs 45-50, comprising cultivating a cell, which in its wild-type form produces the polypeptide, under conditions conducive for production of the polypeptide.

55. The method of paragraph 54, further comprising recovering the polypeptide.

56. A method of producing a polypeptide having DNase activity, comprising cultivating the host cell of paragraph 53 under conditions conducive for production of the polypeptide.

57. The method of paragraph 56, further comprising recovering the polypeptide.

58. A method of producing a protein, comprising cultivating the recombinant host cell comprising a gene encoding a protein operably linked to the polynucleotide of paragraph 51, wherein the gene is foreign to the polynucleotide encoding the propeptide, under conditions conducive for production of the protein.

59. The method of paragraph 58, further comprising recovering the protein.

60. A whole broth formulation or cell culture composition comprising a polypeptide of any of paragraphs 45-50.

61. An Item laundered according to the method of any of paragraphs 27-44.

62. A pharmaceutical composition comprising a polypeptide having DNase activity and a pharmaceutical adjunct ingredient, wherein the polypeptide is obtained from a fungal source.

63. Pharmaceutical composition according to paragraph 62, wherein the polypeptide having DNase activity is obtained from *Vibrissea flavovirens, Penicillium reticulisporum, Acremonium dichromosporum, Preussia aemulans, Colletotrichum circinans, Clavicipitaceae, Preussia aemulans* or *Trichurus spiralis*.

64. Pharmaceutical composition according to paragraph 62 or 63, wherein the polypeptide having DNase activity is selected from the group consisting of polypeptides with; SEQ ID NOS: 2 and 3 obtained from *Vibrissea flavovirens,* SEQ ID NO: 4 obtained from *Penicillium reticulisporum,* SEQ ID NO: 5 obtained from *Acremonium dichromosporum,* SEQ ID NO: 6 and SEQ ID NO: 9 obtained from *Preussia aemulans,* SEQ ID NO: 7 obtained from *Colletotrichum circinans,* SEQ ID NO: 8 obtained from *Clavicipitaceae* and SEQ ID NO: 10 obtained from *Trichurus spiralis*.

65. Pharmaceutical composition according to any of paragraphs 62-64, wherein the polypeptide is the polypeptide of paragraphs 45-50.

66. Pharmaceutical composition according to any of paragraphs 62-65, wherein the composition is formulated as a dental paste, a liquid dentifrice, a mouthwash, a troche or a gingival massage ointment.

67. Pharmaceutical composition according to any of paragraphs 62-66, further comprising one or more of an antimicrobial compound, such as an antibacterial compound, an antiparasitic compound, an antifungal compound and an antiviral compound.

68. An indwelling medical device characterised in that at least a portion of a patient-contactable surface of said device is coated with the pharmaceutical composition of any of paragraphs 62-67.

69. The device according to paragraph 68, wherein said device is a catheter such as a central venous catheter, intravascular catheter, urinary catheter, Hickman catheter, peritoneal dialysis catheter, endotracheal catheter, or wherein the device is a mechanical heart valve, a cardiac pacemaker, an arteriovenous shunt, a schleral buckle, a prosthetic joint, a tympaNOS:tomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

70. A method of producing the polypeptide of any of paragraphs 45-50, comprising cultivating the host cell of paragraph 53 under conditions conducive for production of the polypeptide.

71. The method of paragraph 70, further comprising recovering the polypeptide.

72. The recombinant host cell of paragraph 53 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

73. The recombinant host cell of paragraph 72, wherein the second polypeptide of interest is heterologous or homologous to the host cell.

74. The recombinant host cell of paragraph 72 or 73, which is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola* lanugiNOS:a, *Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolour, Trichoderma harzianum, Trichoderma koningii, Trichoderma longibrachiatum, Trichoderma reesei*, or *Trichoderma viride* cell.

75. A method of producing the second polypeptide of interest as defined in any of paragraphs 70-71, comprising cultivating the host cell of any of paragraphs 72-74 under conditions conducive for production of the second polypeptide of interest.

76. The method of paragraph 75, further comprising recovering the second polypeptide of interest.

77. Detergent composition according to any of the preceding composition paragraphs, wherein the detergent adjunct ingredient is a surfactant.

78. Detergent composition according to any of the preceding composition paragraphs, wherein the detergent adjunct ingredient is a builder.

79. Detergent composition according to any of the preceding composition paragraphs, wherein the detergent adjunct ingredient is a clay soil removal/anti-redeposition agents.

80. Detergent composition according to paragraphs 12-26, wherein the composition is a liquid detergent composition, comprising a surfactant and a detergent builder in a total concentration of at least 3% by weight, and a detergent enzyme containing microcapsule, wherein the membrane of the microcapsule is produced by cross-linking of a polybranched polyamine having a molecular weight of more than 1 kDa.

81. Detergent composition according to paragraphs 80, wherein the reactive amino groups of the polybranched polyamine constitute at least 15% of the molecular weight.

82. Detergent composition according to paragraph 80 or 81, wherein the microcapsule is produced by using an acid chloride as crosslinking agent.

83. Detergent composition according to any of paragraphs 80-82, wherein the diameter of the microcapsule is at least, or above, 50 micrometers.

84. Detergent composition according to any of paragraphs 80-83, wherein the microcapsule contains at least 1% by weight of active enzyme.

85. Detergent composition according to any of paragraphs 80-84, which further includes an alcohol, such as a polyol.

86. Detergent composition according to any of paragraphs 80-85, wherein the surfactant is an anionic surfactant.

87. Detergent composition according to any of paragraphs 80-86, which is a liquid laundry composition.

88. Detergent composition according to any of paragraphs 80-87, which contains less than 90% by weight of water.

89. Detergent composition according to any of paragraphs 80-88, wherein the detergent enzyme is a polypeptide having DNase activity, protease, amylase, lipase, cellulase, mannanase, pectinase, or oxidoreductase.

90. Detergent composition according to any of paragraphs 80-89, wherein the protease is a metalloprotease or an alkaline serine protease, such as a subtilisin.

91. Detergent composition according to any of paragraphs 80-90, wherein the polypeptide having DNase activity is the polypeptide according to any of claims 45-50.

92. Detergent composition according to any of paragraphs 80-91, wherein the microcapsule is produced by interfacial polymerization using an acid chloride as crosslinking agent.

93. Detergent composition according to any of paragraphs 80-92, wherein the polybranched polyamine is a polyethyleneimine.

94. Detergent composition according to any of paragraphs 80-93, wherein the microcapsule comprises a source of Mg2+, Ca2+, or Zn2+ ions, such as a poorly soluble salt of Mg2+, Ca2+, or Zn2+.

Assays and Detergent Compositions

Detergent Compositions

The below mentioned detergent composition can be used in combination with the enzyme of the invention.

Biotex Black (Liquid)

5-15% Anionic surfactants, <5% Nonionic surfactants, perfume, enzymes, DMDM and hydantoin.

Composition of Ariel Sensitive White & Colour, Liquid Detergent Composition

Aqua, Alcohol Ethoxy Sulfate, Alcohol Ethoxylate, Amino Oxide, Citrid Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-42485 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w).

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour&Style (Liquid)

Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (Liquid)

Ingredients: 15-30% Anionic surfactants, Non-ionic surfacts, 5-15% Soap, <5% Polycarboxylates, Perfume, Phosphates, Optical Brighteners Persil 2 in1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-amiNOS:tilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium AnilinomorpholinotriazinylamiNOS:tilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin.

Persil Colour Care Biological Powder

Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2in1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-amiNOS:tilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2in1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquarternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes.

Composition of Model Detergent T (Powder)

Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal.

Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance.

Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone.

Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diamiNOS:tilbene, disulfonate, sodium formate, disodium distyrylbiphenyl disulfonate, calcium formate, polyethylene glycol 4000, mannanase, pectinase, Liquitint™ Blue, dimethicone.

Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase.

Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diamiNOS:tilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:
Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:
Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:
Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

hTide Simply Clean & Fresh:
Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:
Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:
Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:
Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:
Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:
Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:
Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:
Sodium bicarbonate, sodium carbonate, sodium percarbonate, alcohol ethoxylate, sodium chloride, maleic/acrylic copolymer, nonanoyloxy benzene sulfonate, sodium sulfate, colour ant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:
Polyvinyl Alcohol pouch film, wherein there is packed a liquid part and a powder part:
Liquid Ingredients: Dipropylene Glycol, diquaternium Ethoxysulfate, Water, Glycerin, Liquitint™ Orange,
Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:
Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:
Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:
Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:
Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

HEY SPORT TEX WASH Detergent

Aqua, dodecylbenzenesulfonsaure, laureth-11, peg-75 lanolin, propylene glycol, alcohol denat., potassium soyate, potassium hydroxide, disodium cocoamphodiacetate, ethylendiamine triacetate cocosalkyl acetamide, parfum, zinc ricinoleate, sodium chloride, benzisothiazolinone, methylisothiazolinone, ci 16255, benzyl alcohol.

The products named Tide, Ariel, Gain and Fairy are commercially available products supplied by Procter & Gamble. The products named Persil are commercially available products supplied by Unilever and Henkel. The products named Hey Sport are commercially available products supplied by Hey Sport.

| Ingredient | Amount (in wt. %) |
| --- | --- |
| Anionic detersive surfactant (such as alkyl benzene sulphonate, alkyl ethoxylated sulphate and mixtures | from 8 wt. % to 15 wt. % thereof) |
| Non-ionic detersive surfactant (such as alkyl ethoxylated alcohol) | from 0.5 wt. % to 4 wt. % |
| Cationic detersive surfactant (such as quaternary ammonium compounds) | from 0 to 4 wt. % |
| Other detersive surfactant (such as zwiterionic detersive surfactants, amphoteric surfactants and mixtures thereof) | from 0 wt. % to 4 wt. % |
| Carboxylate polymer (such as co-polymers of maleic acid and acrylic acid) | from 1 wt. % to 4 wt. % |

| | |
|---|---|
| Polyethylene glycol polymer (such as a polyethylene glycol polymer comprising poly vinyl acetate side chains) | from 0.5 wt. % to 4 wt. % |
| Polyester soil release polymer (such as Repel-o-tex from and/or Texcare polymers) | 0.1 to 2 wt. % |
| Cellulosic polymer (such as carboxymethyl cellulose, methyl cellulose and combinations thereof) | from 0.5 wt. % to 2 wt. % |
| Other polymer (such as amine polymers, dye transfer inhibitor polymers, hexamethylenediamine derivative polymers, and mixtures thereof) | from 0 wt. % to 4 wt. % |
| Zeolite builder and phosphate builder (such as zeolite 4A and/or sodium tripolyphosphate) | from 0 wt. % to 4 wt. % |
| Other builder (such as sodium citrate and/or citric acid) | from 0 wt. % to 3 wt. % |
| Carbonate salt (such as sodium carbonate and/or sodium bicarbonate) | from 15 wt. % to 30 wt. % |
| Silicate salt (such as sodium silicate) | from 0 wt. % to 10 wt. % |
| Filler (such as sodium sulphate and/or bio-fillers) | from 10 wt. % to 40 wt. % |
| Source of available oxygen (such as sodium percarbonate) | from 10 wt. % to 20 wt. % |
| Bleach activator (such as tetraacetylethylene diamine (TAED) and/or nonanoyloxybenzenesulphonate (NOBS) | from 2 wt. % to 8 wt. % |
| Bleach catalyst (such as oxaziridinium-based bleach catalyst and/or transition metal bleach catalyst) | from 0 wt. % to 0.1 wt. % |
| Other bleach (such as reducing bleach and/or pre- formed peracid) | from 0 wt. % to 10 wt. % |
| Chelant (such as ethylenediamine-N'N'-disuccinic acid (EDDS) and/or hydroxyethane diphosphonic acid(HEDP) | from 0.2 wt. % to1 wt. % |
| Photobleach (such as zinc and/or aluminium sulphonated phthalocyanine) | from 0 wt. % to 0.1 wt. % |
| Hueing agent (such as direct violet 99, acid red 52, acid blue 80, direct violet 9, solvent violet 13 and any combination thereof) | from 0 wt. % to 1 wt. % |
| Brightener (such as brightener 15 and/or brightener 49) | from 0.1 wt. % to 0.4 wt. % |
| Protease (such as Savinase, Savinase Ultra, Purafect, FN3, FN4 and any combination thereof) | from 0.1 wt. % to 0.4 wt. % |
| Amylase (such as Termamyl, Termamyl ultra Natalase, Optisize, Stainzyme, Stainzyme Plus, and any combination thereof) | from 0.05 wt. % to 0.2 wt. % |
| Cellulase (such as Carezyme and/or Celluclean) | from 0.05 wt. % to 0.2 wt. % |
| Lipase (such as Lipex, Lipolex, Lipoclean and any combination thereof) | from 0.2 to 1 wt. % |
| Other enzyme (such as xyloglucanase, cutinase, pectate lyase, mannanase, bleaching enzyme) | from 0 wt. % to 2 wt. % |
| Fabric softener (such as montmorillonite clay and/or polydimethylsiloxane (PDMS) | from 0 wt. % to 4 wt. % |
| Flocculant (such as polyethylene oxide) | from 0 wt. % to 1 wt. % |
| Suds suppressor (such as silicone and/or fatty acid) | from 0 wt. % to 0.1 wt. % |
| Perfume (such as perfume microcapsule, spray-on perfume, starch encapsulated perfume accords, perfume loaded zeolite, and any combination thereof) | from 0.1 wt. % to 1 wt. % |
| Aesthetics (such as coloured soap rings and/or coloured speckles/noodles) | from 0 wt. % to 1 wt. % |
| Miscellaneous | Balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO 2014032269. | from about 0.5 wt. % to about 1.5 wt. % |
| Amylase (Stainzyme Plus(R), having an enzyme activity of 14 mg active enzyme/g) | from about 0.1 wt. % to about 0.5 wt. % |
| Anionic detersive surfactant (such as alkyl benzene sulphonate, alkyl ethoxylated sulphate and mixtures thereof) | from about 8 wt. % to about 15 wt. % |
| Non-ionic detersive surfactant (such as alkyl ethoxylated alcohol) | from about 0.5 wt. % to 4 wt. % |
| Cationic detersive surfactant (such as quaternary ammonium compounds) | from about 0 wt. % to about 4 wt. % |
| Other detersive surfactant (such as zwiterionic detersive surfactants, amphoteric surfactants and mixtures thereof) | from about 0 wt. % to 4 wt. % |
| Carboxylate polymer (such as co-polymers of maleic acid and acrylic acid) | from about 1 wt. % to about 4 wt. % |
| Polyethylene glycol polymer (such as a polyethylene glycol polymer comprising poly vinyl acetate side chains) | from about 0 wt. % to about 4 wt. % |
| Polyester soil release polymer (such as Repel-O- Tex(R) and/or Texcare(R) polymers) | from about 0.1 wt. % to about 2 wt. % |
| Cellulosic polymer (such as carboxymethyl cellulose, methyl cellulose and combinations thereof) | from about 0.5 wt. % to about 2 wt. % |
| Other polymer (such as amine polymers, dye transfer inhibitor polymers, hexamethylenediamine derivative polymers, and mixtures thereof) | from about 0 wt. % to about 4 wt. % |
| Zeolite builder and phosphate builder (such as zeolite 4A and/or sodium tripolyphosphate) | from about 0 wt. % to about 4 wt. % |
| Other builder (such as sodium citrate and/or citric acid) | from about 0 wt. % to about 3 wt. % |

| | -continued |
|---|---|
| Carbonate salt (such as sodium carbonate and/or sodium bicarbonate) | from about 15 t % to about 30 wt. % |
| Silicate salt (such as sodium silicate) | from about 0 wt. % to about 10 wt. % |
| Filler (such as sodium sulphate and/or bio-fillers) | from about 10 wt. % to about 40 wt. % |
| Source of available oxygen (such as sodium percarbonate) | from about 10 wt. % to about 20 wt. % |
| Bleach activator (such as tetraacetylethylene diamine (TAED) and/or nonanoyloxybenzenesulphonate (NOBS) | from about 2 wt. % to about 8 wt. % |
| Bleach catalyst (such as oxaziridinium-based bleach catalyst and/or transition metal bleach catalyst) | from about 0 wt. % to about 0.1 wt. % |
| Other bleach (such as reducing bleach and/or pre formed peracid) | from about 0 wt. % to about 10 wt. % |
| Chelant (such as ethylenediamine-N'N'-disuccinic acid (EDDS) and/or hydroxyethane diphosphonic acid (HEDP) | from about 0.2 wt. % to about 1 wt. % |
| Photobleach (such as zinc and/or aluminium sulphonated phthalocyanine) | from about 0 wt. % to about 0.1 wt. % |
| Hueing agent (such as direct violet 99, acid red 52, acid blue 80, direct violet 9, solvent violet 13 and any combination thereof) | from about 0 wt. % to about 0.5 wt. % |
| Brightener (such as brightener 15 and/or brightener 49) | from about 0.1 wt. % to about 0.4 wt. % |
| Protease (such as Savinase, Polarzyme, Purafect, FN3, FN4 and any combination thereof, typically having an enzyme activity of from about 20 mg to about 100 mg active enzyme/g) | from about 0.1 wt. % to about 1.5 wt. % |
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 wt. % to about 0.2 wt. % |
| Cellulase (such as Carezyme(R), Celluzyme(R) and/or Celluclean(R), typically having an enzyme activity of about from 10 to 50 mg active enzyme/g) | from about 0.05 wt. % to 0.5 wt. % |
| Lipase (such as Lipex(R), Lipolex(R), Lipoclean(R) and any combination thereof, typically having an enzyme activity of from about 10 mg to about 50 mg active enzyme/g) | from about 0.2 wt. % to about 1 wt. % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 wt. % to 2 wt. % |
| Fabric softener (such as montmorillonite clay and/or polydimethylsiloxane (PDMS)) | from 0 wt. % to 15 wt. % |
| Flocculant (such as polyethylene oxide) | from 0 wt. % to 1 wt. % |
| Suds suppressor (such as silicone and/or fatty acid) | from 0 wt. % to 0.1 wt. % |
| Perfume (such as perfume microcapsule, spray-on perfume, starch encapsulated perfume accords, perfume loaded zeolite, and any combination thereof) | from 0.1 wt. % to 1 wt. % |
| Aesthetics (such as colour ed soap rings and/or colour ed speckles/noodles) | from 0 wt. % to 1 wt. % |
| Miscellaneous | Balance |

All enzyme levels expressed as rug active enzyme protein per 100 g detergent composition. Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®).

Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Basel, Switzerland. NOBS is sodium nonanoyloxybenzenesulfonate, supplied by Eastman, Batesville, Ark., USA.

TAED is tetraacetylethylenediamine, supplied under the Peractive® brand name by Clariant GmbH, Sulzbach, Germany.

Sodium carbonate and sodium bicarbonate can be obtained from Solvay, Brussels, Belgium.

Polyacrylate, polyacrylate/maleate copolymers can be obtained from BASF, Ludwigshafen, Germany.

Repel-O-Tex® can be obtained from Rhodia, Paris, France.

Texcare® can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK.

Hydroxy ethane di phosphonate (HEDP) was supplied by Dow Chemical, Midland, Mich., USA.

Enzymes Savinase®, Savinase® Ultra, Stainzyme® Plus, Lipex®, Lipolex®, Lipoclean®, Celluclean®, Carezyme®, Natalase®, Stainzyme®, Stainzyme® Plus, Termamyl®, Termamyl® ultra, and Mannaway® can be obtained from Novozymes, Bagsvaerd, Denmark.

Enzymes Purafect®, FN3, FN4 and Optisize can be obtained from Genencor International Inc., Palo Alto, Calif., US.

Direct violet 9 and 99 can be obtained from BASF DE, Ludwigshafen, Germany. Solvent violet 13 can be obtained from Ningbo Lixing Chemical Co., Ltd. Ningbo, Zhejiang, China. Brighteners can be obtained from Ciba Specialty Chemicals, Basel, Switzerland.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Terg-O-Timeter (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.). All beakers shall be clean and without traces of prior test material.

The wash solution with desired amount of detergent, temperature and water hardness is prepared in a bucket. The detergent is allowed to dissolve during magnet stirring for 10 min. Wash solution shall be used within 30 to 60 min after preparation.

800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The solid swatches are separated from the ballast load. The soil swatches are transferred to a 5L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the colour intensity using a Colour Eye as described herein.

Enzyme Assays

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added, and DNase activity are observed as colour less zones around the spotted enzyme solutions.

Assay II

Analysis of E-2-Nonenal on Textile Using an Electronic Nose.

One way of testing for the presence of malodour on textiles is by using E-2-Nonenal as a marker for the malodour, as this compound contributes to the malodour on laundry.

Add a solution of E-2-nonenal to a 5 cm×5 cm textile swatch and place the swatch in a 20 mL glass vial for GC analysis and cap the vial. Analyze 5 mL headspace from the capped vials in a Heracles II Electronic nose from Alpha M. O. S., France (double column gas chromatograph with 2 FIDs, column 1: MXT5 and column 2: MXT1701) after 20 minutes incubation at 40° C.

EXAMPLES

Methods

General methods of PCR, cloning, ligation nucleotides etc. are well-known to a person skilled in the art and may for example be found in in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

Example 1 Cloning and Expression of a DNase from *Vibrissea flavovirens*

The DNase was derived from fruiting body of a fungal strain isolated in Japan by standard microbiological isolation techniques. The strain was identified and taxonomy was assigned based on DNA sequencing of the ribosomal ITS region (Table 1).

TABLE 1

| Organism name | Source |
| --- | --- |
| *Vibrissea flavovirens* FC-2743 | fruiting body, Japan |

Chromosomal DNA isolated from pure cultures of the *Vibrissea flavovirens* strain FC-2743 with the DNeasy Plant Mini Kit from Qiagen (Hilden, Germany) was subjected to full genome sequencing using Illumina technology. Genome sequencing, the subsequent assembly of reads and the gene discovery (i.e., annotation of gene functions) is known to the person skilled in the art and the service can be purchased commercially. The genome sequence was analyzed for putative DNases from the PFAM database family PF07510 (Finn et al., 2014, *Nucleic Acids Research* 42:D222-D230) This analysis identified a gene encoding the putative DNase with the nucleotide sequence and deduced amino acid sequence given in SEQ ID NO: 1 and SEQ ID NO: 2, respectively. The encoded protein is 209 amino acids. Using the SignalP program (Nielsen et al., 1997, *Protein Engineering* 10: 1-6), a signal peptide of 19 residues was determined. The mature protein contains 190 amino acids with a predicted molecular mass of 20 kDa and an isoelectric pH of 5.8.

The gene encoding the *Vibrissea flavovirens* DNase was amplified by PCR and cloned in the expression vector pDau109 (WO 2005/042735) by a IN-FUSION™ Cloning Kit (BD Biosciences, Palo Alto, Calif., USA). Cloning of the *Vibrissea flavovirens* DNase gene into Bam HI-Xho I digested pDau109 resulted in the transcription of the *Vibrissea flavovirens* DNase gene under the control of a NA2-tpi double promoter. NA2-tpi is a mod-ified promoter from the gene encoding the *Aspergillus niger* neutral alpha-amylase in which the untranslated leader has been replaced by an untranslated leader from the gene encoding the *Aspergillus nidulans* triose phosphate isomerase. The *Vibrissea flavovirens* DNase gene containing expression plasmid was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference. Transformants were purified on COVE sucrose selection plates through single conidia prior to sporulating them on PDA plates. Production of the *Vibrissea flavovirens* DNase polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, Calif., USA) by Coomassie staining. Subsequently, a recombinant *Aspergillus oryzae* clone containing the integrated expression construct was grown in liquid culture. The culture broth was collected by filtration through a bottle top MF75 Supor MachV 0.2 µm PES filter (Thermo Fisher Scientific, Roskilde, Denmark) in order to remove the rest of the *Aspergillus oryzae* host cells.

The DNases from *Penicillium reticulisporum* (SEQ ID NO: 4), *Acremonium dichromosporum* (SEQ ID NO: 5), *Preussia aemulans* (SEQ ID NO: 6), *Colletotrichum circinans* (SEQ ID NO: 7), *Clavicipitaceae* (SEQ ID NO: 8), *Preussia aemulans* (SEQ ID NO: 9) or *Trichurus spiralis* (SEQ ID NO: 10) was cloned and expressed in a similar way.

Example 2 MiniLOM Liquid Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at -80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 2

Deep cleaning of biofilm established on polyester by fungal DNases in miniLOM.

| Host name | $L\text{-value}_{Model\ detergent\ A}$ | $\Delta L_{Model\ detergent\ A}$ |
|---|---|---|
| No enzyme | 88.09 | 0 |
| *Vibressea flavovirens* | 83.48 | 4.61 |
| *Penicillium reticulisporum* | 88.00 | 4.41 |
| *Acremonium dichromosporum* | 87.49 | 3.91 |
| *Preussia aemulans* | 87.87 | 4.29 |
| *Colletotrichum circinans* | 86.48 | 2.89 |
| Clavicipitaceae | 89.05 | 5.47 |
| *Preussia aemulans* | 85.69 | 2.10 |
| *Trichurus spiralis* | 87.33 | 3.75 |

Example 3 MiniLOM Wash in Powder Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of powder model detergent T without bleach and powder model detergent T with bleach were prepared by weighing out and dissolving detergents in water with water with hardness 15° dH. Dosing of detergent T without bleach and model detergent T with bleach model detergent was 5.30 g/L. The AEO Biosoft N25-7 (NI) (0.16 g/l) component of model detergent T without bleach and model detergent T with bleach was added separately. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 3

Deep cleaning of biofilm by *Vibressea flavovirens* DNase in miniLOM.

| Detergent | Type of textile | Soil (g/L) | DNase conc. (ppm) | L-value | L-value$_{with\ DNase}$ - L-Value$_{without\ DNase}$ |
|---|---|---|---|---|---|
| Model detergent T w/o bleach | Polyester | 0.7 | 0 | 85.58 | |
| Model detergent T w/o bleach | Polyester | 0.7 | 0.5 | 82.39 | 3.19 |
| Model detergent T w bleach | Polyester | 0.7 | 0 | 85.62 | |
| Model detergent T w bleach | Polyester | 0.7 | 0.5 | 84.95 | 0.67 |

Example 4: Cloning, Expression and Fermentation of DNases

The DNases were cloned from fungal strains obtained from a variety of sources. *Pyrenochaetopsis* sp. was isolated in Denmark and received from the University of Copenhagen and is the source for the mature peptide with SEQ ID NO: 27. *Aspergillus sydowii, Cladosporium cladosporioides, Rhinocladiella* sp., *Pyronema domesticum, Paradendryphiella salina, Purpureocillium lilacinum, Warcupiella spinulosa*, and *Arthrinium arundinis* were isolated from environmental samples by standard microbiological isolation techniques.

| Strain | Origin | Mature peptide SEQ ID: |
|---|---|---|
| *Aspergillus sydowii* | Denmark | 30 |
| *Cladosporium cladosporioides* | Brazil | 33 |
| *Rhinocladiella* sp. | Denmark | 36 |
| *Paradendryphiella salina* | Ireland | 48 |
| *Purpureocillium lilacinum* | Denmark | 54 |
| *Warcupiella spinulosa* | Japan | 57 |
| *Arthrinium arundinis* | Denmark | 69 |

*Pyronema domesticum* was purchased from the University of Oslo and is the source for the mature peptide with SEQ ID NO: 39.

*Phialophora geniculate, Stenocarpella maydis, Acrophialophora fusispora*, and *Chaetomium luteum* were purchased from the CBS Fungal Biodiversity Centre, Utrecht, The Netherlands.

| Strain | CBS strain number | Origin | Mature peptide SEQ ID: |
|---|---|---|---|
| *Phialophora geniculata* | CBS680.94 | Indonesia | 45 and 72 |
| *Stenocarpella maydis* | CBS187.55 | USA | 60 |
| *Acrophialophora fusispora* | CBS380.55 | India | 63 |
| *Chaetomium luteum* | CBS543.83 | Pakistan | 66 |

Genomic DNA was isolated from the strains and the genomic sequences were determined, assembled and annotated by standard methods or by purchasing the services commercially. The annotated genomes were searched for putative DNases with a NUC2_B domain.

The predicted peptides with SEQ ID NO: 26, 29, 32, 35, 38, 41, 44, 59, 62, 65, 68, and 71 were found to have a NUC2_B domain and the corresponding DNA sequences encoding them with SEQ ID NO: 25, 28, 31, 34, 37, 40, 43, 58, 61, 64, 67, and 70 were PCR amplified from genomic DNA isolated from *Pyrenochaetopsis* sp., *Aspergillus sydowii, Cladosporium cladosporioides, Rhinocladiella* sp., *Pyronema domesticum, Aspergillus niger, Phialophora geniculate, Paradendryphiella salina, Purpureocillium lilacinum, Warcupiella spinulosa, Stenocarpella maydis, Acrophialophora fusispora, Chaetomium luteum*, and *Arthrinium arundinis* and cloned into the *Aspergillus* expression vector pMStr57 (WO 04/032648).

The sequences of the NUC2_B encoding genes cloned in the expression vector were confirmed, and the expression constructs were transformed into the *Aspergillus oryzae* strain MT3568 (WO 2011/057140). Transformants were selected on acetamide during regeneration from protoplasts and subsequently re-isolated under selection (Christensen et al., 1988, *Biotechnology* 6: 1419-1422 and WO 2004/032648).

For production of the recombinant DNases, a single *Aspergillus* transformant was selected for each DNase and the transformants were cultured in 500 ml baffled flasks containing 150 ml of DAP-4C-1 medium (WO 2012/103350). The cultures were shaken on a rotary table at 150 RPM at 30° C. for 4 days. The culture broth was subsequently separated from cellular material by passage through a 0.22 um filter.

Example 5: Chromatographic Purification of Recombinant DNases pH of the filtered sample was adjusted to around pH 7.5 and 1.8 M ammonium sulfate was added. The sample was applied to a 5 ml HiTrap™ Phenyl (HS) column on an Äkta Explorer. Prior to loading, the column had been equilibrated in 5 column volumes (CV) of 50 mM HEPES+1.8 M AMS pH 7. In order to remove unbound material, the column was washed with 5 CV of 50 mM HEPES+1.8 M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3 CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Protein concentration in the final sample was estimated by measuring absorption at 280 nm.

Example 6 Cloning, Expression and Fermentation of DNases

Strains

*Escherichia coli* Top-10 strain purchased from TIANGEN (TIANGEN Biotech Co. Ltd., Beijing, China) was used to propagate our expression vector.

*Aspergillus oryzae* MT3568 strain was used for heterologous expression of the gene encoding a polypeptide having homology with polypeptides with phospholipase activity. *A. oryzae* MT3568 is an amdS (acetamidase) disrupted gene derivative of *A. oryzae* JaL355 (WO 02/40694) in which pyrG auxotrophy was restored by disrupting the *A. oryzae* acetamidase (amdS) gene with the pyrG gene.

Media

YPM medium was composed of 10 g yeast extract, 20 g Bacto-peptone, 20 g maltose, and deionised water to 1000 ml.

LB plates were composed of 10 g of Bacto-tryptone, 5 g of yeast extract, 10 g of sodium chloride, 15 g of Bacto-agar, and deionised water to 1000 ml.

LB medium was composed of 1 g of Bacto-tryptone, 5 g of yeast extract, and 10 g of sodium chloride, and deionised water to 1000 ml.

COVE sucrose plates were composed of 342 g of sucrose, 20 g of agar powder, 20 ml of COVE salt solution, and deionized water to 1 liter. The medium was sterilized by autoclaving at 15 psi for 15 minutes. The medium was cooled to 60° C. and 10 mM acetamide, 15 mM CsCl, Triton X-100 (50 µl/500 ml) were added.

COVE-2 plate/tube for isolation: 30 g/L sucrose, 20 ml/L COVE salt solution, 10 mM acetamide, 30 g/L noble agar (Difco, Cat #214220).

COVE salt solution was composed of 26 g of $MgSO_4.7H_2O$, 26 g of KCL, 26 g of $KH_2PO_4$, 50 ml of COVE trace metal solution, and deionised water to 1000 ml.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionised water to 1000 ml.

Methyl green DNA test agar plates was made by suspending 42.05 g "DNase Test Agar Base w/ methyl green" (HiMedia Laboratories Pvt. Ltd., Inida) in 1000 ml distilled water and sterilized by autoclaving.

Example 7: Cloning, Expression and Fermentation of Fungal DNases

The DNases were derived from fungal strains isolated from environmental samples by standard microbiological isolation techniques. Strains were identified and taxonomy was assigned based on DNA sequencing of the internal transcribed spacer, ITS, of the 18S rRNA gene (Table 4).

TABLE 4

| Donor Organism name | source country | SEQ ID NO |
|---|---|---|
| *Aspergillus insuetus* | China | 51 |

Chromosomal DNA from the strain (Table. 4) was isolated by QIAamp DNA Blood Mini Kit (Qiagen, Hilden, Germany). 5 µg of chromosomal DNA were sent for full genome sequencing using Illumina technology. Genome sequencing, and, e.g., annotation of gene functions is known to the person skilled in the art and the service can be purchased commercially.

The genome sequences were analyzed for putative DNases from the PFAM database families NUC2 domain. This analysis identified 3 genes encoding putative DNases which were subsequently cloned and recombinantly expressed in *Aspergillus oryzae*. The gene was amplified by PCR from above isolated fungal genomic DNA. The purified PCR product was cloned into the previously digested expression vector pCaHj505 by ligation with an IN-FUSION™ CF Dry-down Cloning Kit (Clontech Laboratories, Inc., Mountain View, Calif., USA) according to the manufacturer's instructions. The ligation mixture was used to transform *E. coli* TOP10 chemically competent cells (described in Strains). Correct colonies containing the DNase was selected and verified by DNA sequencing (by SinoGenoMax Company Limited, Beijing, China). The DNase comprising colonies were cultivated overnight in 3 ml of LB medium supplemented with 100 µg of ampicillin per ml. Plasmid DNA was purified using a Qiagen Spin Miniprep kit (Cat. 27106) (QIAGEN GmbH, Hilden, Germany) according to the manufacturer's instructions. Using the SignalP program v.3 (Nielsen et al., 1997, *Protein Engineering* 10: 1-6), the signal peptide and accordingly the mature peptide of the DNase was predicted. Protoplasts of *Aspergillus oryzae* MT3568 was prepared according to WO 95/02043. 100 µl of protoplasts were respectively mixed with 2.5-10 µg of each *Aspergillus* expression vector comprising DNases and 250 µl of 60% PEG 4000, 10 mM $CaCl_2$, and 10 mM Tris-HCl pH 7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of YPM medium. After 3 days cultivation at 30° C., the culture broths were analyzed by SDS-PAGE using Novex® 4-20% Tris-Glycine Gel (Invitrogen Corporation, Carlsbad, Calif., USA) to identify the transformants producing the largest amount of recombinant DNAses with respective estimated mature peptide size. The hydrolytic activity of the DNase produced by the *Aspergillus* transformants was investigated using methyl green DNA test agar plates. 20 µl aliquots of the culture broth from the different transformants, or buffer (negative control) were distributed into punched holes with a diameter of 3 mm and incubated for 1 hour at 37° C. The plates were subsequently examined for the presence or absence of a white zone around the holes corresponding to phospholipase activity. Based on those two selection criteria, spores of the best transformant were spread on COVE-2 plates for re-isolation in order to isolate single colonies. Then a single colony was spread on a COVE-2 tube until sporulation. Spores from the best expressed transformant were cultivated in 2400 ml of YPM medium in shake flasks during 3 days at a temperature of 30° C. under 80 rpm agitation. Culture broth was harvested by filtration using a 0.2 µm filter device. The filtered fermentation broth was used for enzyme characterization.

Example 8: Purification of Recombinant DNase by Metal Ion Affinity Chromatography (IMAC)

The culture broth harvested in example 7 was precipitated with ammonium sulfate (80% saturated). Precipitates were re-dissolved in 50 ml of 20 mM PBS pH 7.0, and then filtered through a 0.45 µm filter. The filtered crude protein solution was applied to a 50 ml self-packed Ni sepharose excel affinity column (GE Healthcare, Buckinghamshire, UK) equilibrated with 20 mM PBS pH 7.0 and 300 mM sodium chloride. Proteins were eluted with a linear 0-0.5 M imidazole gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 9

A phylogenetic tree was constructed, of public and proprietary polypeptide sequences containing an Exo_ endo_phos domain, as defined in PFAM (PF03372, Pfam version 30.0 Finn (2016). *Nucleic Acids Research*, Database Issue 44:D279-D285). The phylogenetic tree was constructed from a multiple alignment of mature polypeptide sequences containing at least one Exo_endo_phos domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al. (2010) PloS one, 5(3)) and visualized using iTOL (Letunic & Bork, 2007. *Bioinformatics* 23(1): 127-128). The polypeptides in Exo_endo_phos can be separated into distinct sub-clusters, where we denoted one sub-cluster defined by the motif [G/Y/W/F/A/H]NI[R/Q/D/E/V] (SEQ ID NO: 73), corresponding to positions 396 to 399 in SEQ ID NO: 36.

Creating Phylogenetic Tree for NUC2

Reference SEQ ID: 36 (*Rhinocladiella* sp.)

A phylogenetic tree was constructed, of polypeptide sequences containing a NUC2 domain, as defined above. The phylogenetic tree was constructed from a multiple alignment of mature polypeptide sequences containing at least one NUC2 domain. The sequences were aligned using the MUSCLE algorithm version 3.8.31 (Edgar, R. C. (2004). Nucleic Acids Research, 32(5), 1792-1797). and the tree was constructed using FastTree version 2.1.8 (Price et al., 2010, *PloS one* 5(3)) and visualized using iTOL (Letunic & Bork, 2007, *Bioinformatics* 23(1): 127-128).

Creating Phylogenetic Tree for NUC2_B

A phylogenetic tree was constructed, of polypeptide sequences containing a NUC2 domain, as defined above. The phylogenetic tree was constructed from a multiple alignment of mature polypeptide sequences containing at least one NUC2 domain. The sequences were aligned using the MUSCLE algorithm version 3.8.31 (Edgar, 2004, *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC2 can be separated into at least one distinct sub-clusters, one was denoted sub-clusters NUC2_B defined with motif SDH[D/H/L]P (SEQ ID NO: 74), corresponding to positions 610 to 614 of SEQ ID NO: 36. The polypeptides of this sub-cluster, e.g., domain, e.g., clade may further comprise motif or GGNI[R/Q] corresponding to position 395 to 399 in SEQ ID NO: 36. The polypeptides have NUC2_B catalytic domains, wherein the NUC2_B catalytic domain having a trusted domain cut-off score of at least 100.0, preferably a score of at least 135, preferably a score of at least 150, preferably a score of at least 250 when queried using a Profile Hidden Markov.

Hidden Markov Model (HMM):

The experimentally verified functional NUC2_B endonucleases were analyzed using the HMMER software package (available at http://hmmer.org; the theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., 1994, *J. Mol. Biol.* 235:1501-1531), following the user guide which is available from HMMER (Janelia Farm Research Campus, Ashburn, Va., http://hmmer.org). Hidden Markov models are used in a number of databases that aim at classifying proteins, for review see Bateman and Haft, 2002, *Brief Bioinform* 3: 236-245. The output of the HMMER hmmbuild software program is a profile Hidden Markov Model (profile HMM) that characterizes the input sequences. As stated in the user guide, profile HMMs are statistical descriptions of the consensus of a multiple sequence alignment. They use position-specific scores for amino acids (or nucleotides) and position specific scores for opening and extending an insertion or deletion. Compared to other profile based methods, HMMs have a formal probabilistic basis. Profile HMMs for a large number of protein families are publicly available in the PFAM database (Janelia Farm Research Campus, Ashburn, Va.).

The profile HMM was built as follows:

Step 1. Build a Sequence Alignment

The polypeptides shown in SEQ ID NO: 10, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 6, SEQ ID NO: 60, SEQ ID NO: 63, SEQ ID NO: 66, SEQ ID NO: 69, SEQ ID NO: 7, SEQ ID NO: 72 were aligned using the MUSCLE algorithm version 3.8.31 with default parameters (Edgar, 2004, *Nucleic Acids Research* 32(5): 1792-1797), and from this multiple sequence alignment the HMM was built with the software program hmmbuild version 3.1b2 (available at http://hmmer.org). hmmbuild reads the multiple sequence alignment file created by MUSCLE, builds a new profile HMM, and saves the profile HMM to a HMMER profile file. A profile HMM is completely described in a HMMER profile file, which contains all the probabilities that are used to parameterize the HMM.

Step 2. Test the Specificity and Sensitivity of the Built Profile HMMs

The Profile HMM was evaluated using hmmsearch version 3.1b2 software program with default settings, which reads a Profile HMM file and searches a sequence file for significantly similar sequence matches. The sequence file searched contained all Uniprot sequences annotated with Pfam family Exo_endo_phos (Pfam family PF03372, database version 30.0 UniProt annotated 14852 sequences). During the search, the size of the database (Z parameter) was set to 1 billion. This size setting ensures that significant E-values against the current database will remain significant in the foreseeable future. The hmmsearch trusted domain cut-off domT was set at 150.0.

A hmmer search, using hmmsearch, with the profile HMM generated from the alignment of the NUC2_B experimentally active endo-nucleases, matched 3395 sequences in UniProt above a Trusted domain cut-off of 157.0; all matching pFam domain PF03372 and all comprising NUC2_B motif SDH[DHL]P. This result indicates that members of the NUC2_B family share significant sequence similarity. A hmmer search with a Trusted domain cut-off of 150 was used to separate NUC2_B from other proteins.

SEQUENCE LISTING

```
<160> NUMBER OF SEQ ID NOS: 75

<210> SEQ ID NO 1
<211> LENGTH: 630
<212> TYPE: DNA
```

<213> ORGANISM: Vibrissea flavovirens

<400> SEQUENCE: 1

| | | | | | |
|---|---|---|---|---|---|
| atgtatacct | ccctcctcgt | ctctgtcctc | ctctcctccc | tccctctcgt | cctcaccacc | 60 |
| ccctcccca | tcatcgcgcg | gacaccgccc | aatatcccca | caaccgctac | cgcgaagtcc | 120 |
| cagctcgcgg | ccttgactgt | tgcggccgcg | ggtccgcaga | ccgggtactc | gcgtgacctg | 180 |
| tttccgacct | ggatcacgat | ctctgggacg | tgtaatacga | gggagacggt | gctgaagagg | 240 |
| gatgggacga | atgtggtagt | tgattcggcg | tgtgtggcta | cgagtgggag | ttggtatagt | 300 |
| ccgtatgatg | gggcgacttg | gacggcggct | agtgatgttg | atattgatca | tatggttccg | 360 |
| ttgagtaatg | cttggaagag | tggtgcgagt | gcctggacaa | cagcacagag | acagactttt | 420 |
| gccaatgatc | tgactaatcc | tcaactattg | gccgttacgg | acaatgtcaa | tcaagctaag | 480 |
| ggtgatagtg | gaccggagga | ctggaagcca | tcgttgacct | catactggtg | cacatatgcc | 540 |
| aaaatgtggg | ttaaggtcaa | gactgtttat | gatcttacga | tcacgtcggc | tgagaagact | 600 |
| gctttgacta | ctatgctgaa | cacttgttga | | | | 630 |

<210> SEQ ID NO 2
<211> LENGTH: 209
<212> TYPE: PRT
<213> ORGANISM: Vibrissea flavovirens

<400> SEQUENCE: 2

Met Tyr Thr Ser Leu Leu Val Ser Val Leu Ser Ser Leu Pro Leu
1               5                   10                  15

Val Leu Thr Thr Pro Leu Pro Ile Ile Ala Arg Thr Pro Pro Asn Ile
                20                  25                  30

Pro Thr Thr Ala Thr Ala Lys Ser Gln Leu Ala Ala Leu Thr Val Ala
            35                  40                  45

Ala Ala Gly Pro Gln Thr Gly Tyr Ser Arg Asp Leu Phe Pro Thr Trp
        50                  55                  60

Ile Thr Ile Ser Gly Thr Cys Asn Thr Arg Glu Thr Val Leu Lys Arg
65                  70                  75                  80

Asp Gly Thr Asn Val Val Val Asp Ser Ala Cys Val Ala Thr Ser Gly
                85                  90                  95

Ser Trp Tyr Ser Pro Tyr Asp Gly Ala Thr Trp Thr Ala Ala Ser Asp
            100                 105                 110

Val Asp Ile Asp His Met Val Pro Leu Ser Asn Ala Trp Lys Ser Gly
        115                 120                 125

Ala Ser Ala Trp Thr Thr Ala Gln Arg Gln Thr Phe Ala Asn Asp Leu
    130                 135                 140

Thr Asn Pro Gln Leu Leu Ala Val Thr Asp Asn Val Asn Gln Ala Lys
145                 150                 155                 160

Gly Asp Ser Gly Pro Glu Asp Trp Lys Pro Ser Leu Thr Ser Tyr Trp
                165                 170                 175

Cys Thr Tyr Ala Lys Met Trp Val Lys Val Lys Thr Val Tyr Asp Leu
            180                 185                 190

Thr Ile Thr Ser Ala Glu Lys Thr Ala Leu Thr Thr Met Leu Asn Thr
        195                 200                 205

Cys

<210> SEQ ID NO 3
<211> LENGTH: 190
<212> TYPE: PRT

-continued

<213> ORGANISM: Vibrissea flavovirens

<400> SEQUENCE: 3

```
Thr Pro Leu Pro Ile Ala Arg Thr Pro Asn Ile Pro Thr Thr
1               5                   10                  15

Ala Thr Ala Lys Ser Gln Leu Ala Ala Leu Thr Val Ala Ala Gly
            20                  25                  30

Pro Gln Thr Gly Tyr Ser Arg Asp Leu Phe Pro Thr Trp Ile Thr Ile
            35                  40                  45

Ser Gly Thr Cys Asn Thr Arg Glu Thr Val Leu Lys Arg Asp Gly Thr
    50                  55                  60

Asn Val Val Val Asp Ser Ala Cys Val Ala Thr Ser Gly Ser Trp Tyr
65                  70                  75                  80

Ser Pro Tyr Asp Gly Ala Thr Trp Thr Ala Ala Ser Asp Val Asp Ile
                85                  90                  95

Asp His Met Val Pro Leu Ser Asn Ala Trp Lys Ser Gly Ala Ser Ala
                100                 105                 110

Trp Thr Thr Ala Gln Arg Gln Thr Phe Ala Asn Asp Leu Thr Asn Pro
            115                 120                 125

Gln Leu Leu Ala Val Thr Asp Asn Val Asn Gly Ala Lys Gly Asp Ser
        130                 135                 140

Gly Pro Glu Asp Trp Lys Pro Ser Leu Thr Ser Tyr Trp Cys Thr Tyr
145                 150                 155                 160

Ala Lys Met Trp Val Lys Val Lys Thr Val Tyr Asp Leu Thr Ile Thr
                165                 170                 175

Ser Ala Glu Lys Thr Ala Leu Thr Thr Met Leu Asn Thr Cys
            180                 185                 190
```

<210> SEQ ID NO 4
<211> LENGTH: 191
<212> TYPE: PRT
<213> ORGANISM: Penicillium reticulisporum

<400> SEQUENCE: 4

```
Leu Pro Ala Pro Glu Ala Leu Pro Ala Pro Pro Gly Val Pro Ser Ala
1               5                   10                  15

Ser Thr Ala Gln Ser Glu Leu Ala Ala Leu Thr Val Ala Ala Gln Gly
            20                  25                  30

Ser Gln Asp Gly Tyr Ser Arg Ser Lys Phe Pro His Trp Ile Thr Gln
            35                  40                  45

Ser Gly Ser Cys Asp Thr Arg Asp Val Val Leu Lys Arg Asp Gly Thr
    50                  55                  60

Asn Val Val Gln Ser Ala Ser Gly Cys Thr Ile Thr Ser Gly Lys Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
                100                 105                 110

Gly Trp Thr Thr Ala Ala Arg Gln Ala Phe Ala Asn Asp Leu Thr Asn
            115                 120                 125

Pro Gln Leu Leu Val Val Thr Asp Asn Val Asn Glu Ser Lys Gly Asp
        130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
```

```
                165                 170                 175
Thr Ser Ala Glu Lys Ser Ala Leu Thr Ser Met Leu Ser Thr Cys
            180                 185                 190

<210> SEQ ID NO 5
<211> LENGTH: 182
<212> TYPE: PRT
<213> ORGANISM: Acremonium dichromosporum

<400> SEQUENCE: 5

Ile Pro Pro Gly Ile Pro Ser Glu Ala Thr Ala Arg Ser Leu Leu Ser
1               5                   10                  15

Ser Leu Thr Val Ala Pro Thr Val Asp Asp Gly Thr Tyr Asp Arg Asp
            20                  25                  30

Leu Phe Pro His Trp Ser Ser Val Glu Gly Asn Cys Asn Ala Arg Glu
        35                  40                  45

Phe Val Leu Arg Arg Asp Gly Asp Gly Val Ser Val Gly Asn Asp Cys
    50                  55                  60

Tyr Pro Thr Ala Gly Thr Trp Thr Cys Pro Tyr Asp Gly Lys Arg His
65                  70                  75                  80

Ser Val Pro Ser Asp Val Ser Ile Asp His Met Val Pro Leu His Asn
                85                  90                  95

Ala Trp Met Thr Gly Ala Ser Glu Trp Thr Thr Ala Glu Arg Glu Ala
            100                 105                 110

Phe Ala Asn Asp Ile Asp Gly Pro Gln Leu Trp Ala Val Thr Ser Thr
        115                 120                 125

Thr Asn Ser Gln Lys Gly Ser Asp Ala Pro Asp Glu Trp Gln Pro Pro
    130                 135                 140

Gln Thr Ser Ile His Cys Lys Tyr Ala Ala Trp Ile Gln Val Lys
145                 150                 155                 160

Ser Thr Tyr Asp Leu Thr Val Ser Ser Ala Glu Gln Ala Ala Leu Glu
                165                 170                 175

Glu Met Leu Gly Arg Cys
            180

<210> SEQ ID NO 6
<211> LENGTH: 590
<212> TYPE: PRT
<213> ORGANISM: Preussia aemulans

<400> SEQUENCE: 6

Leu Ser Ile Ser Glu Ile Asn Gly Pro Lys Tyr Leu Ser Pro Tyr Ala
1               5                   10                  15

Gly Gln Thr Val Ser Asn Val Ala Gly Ile Val Thr Ala Lys Gly Pro
            20                  25                  30

Ser Gly Ile Trp Ile Arg Ser Thr Thr Pro Asp Arg Asp Asp Lys Thr
        35                  40                  45

Ser Glu Ser Ile Tyr Val Phe Asn Lys Thr Phe Gly Ala Asn Leu Thr
    50                  55                  60

Val Gly Asp Ser Ile Val Ile Gly Gly Lys Val Glu Glu Tyr Arg Ser
65                  70                  75                  80

Asn Lys Asp Tyr Val Tyr Leu Thr Glu Ile Ser Ser Pro Val Leu Glu
                85                  90                  95

Ser Lys Ile Ser Ser Gly Asn Ala Val Lys Pro Leu Val Ile Gly Lys
            100                 105                 110

Asp Thr Ser Lys Pro Pro Thr Glu Gln Phe Ser Ser Leu Asp Gly Gly
```

```
            115                 120                 125
Asp Val Phe Gly Val Pro Asn Asn Val Ser Leu Val Ser Val Ala Asn
        130                 135                 140
Pro Thr Leu Glu Pro Lys Lys Tyr Gly Met Asp Phe Trp Glu Ser Leu
145                 150                 155                 160
Ser Gly Glu Leu Val Thr Val Lys Lys Pro Thr Ala Leu Ser Lys Pro
                165                 170                 175
Ser Asn Phe Gly Asp Thr Trp Val Gly Asp Trp Lys Val Thr Gly
            180                 185                 190
Asp Asn Lys Arg Gly Gly Leu Thr Gln Thr Asp Lys Asp Ala Asn Pro
            195                 200                 205
Glu Thr Ile Ile Ile Gly Ser Pro Leu Asp Gly Ser Ser Asn Pro Leu
        210                 215                 220
Thr Val Lys Leu Gly Asp Glu Leu Ser Glu Ile Thr Gly Val Val Thr
225                 230                 235                 240
Tyr Ala Phe Gly Phe Tyr Arg Ile Leu Pro Thr Thr Ala Leu Lys Val
                245                 250                 255
Val Lys Ser Gln Gln Gln Glu Leu Pro Ser Ala Thr Ser Leu Ile Ser
            260                 265                 270
Ser Gly Lys Cys Asp Gly Leu Thr Phe Gly Ala Tyr Asn Val Glu Asn
        275                 280                 285
Leu Phe Thr Gly Ser Lys His Met Pro Asn Ile Ser Ala His Ile Val
    290                 295                 300
Thr Tyr Leu Lys Ser Pro Asp Phe Ile Phe Ile Gln Glu Val Gln Asp
305                 310                 315                 320
Asp Asn Gly Pro Thr Asn Asp Gly Val Val Ser Ala Asn Ala Thr Leu
                325                 330                 335
Thr Ala Leu Thr Glu Ala Ile Val Ala Ala Gly Gly Pro Gln Tyr Thr
            340                 345                 350
Phe Thr Asp Ile Ala Pro Ser Ser Asn Gln Asp Gly Gly Ala Pro Gly
        355                 360                 365
Gly Asn Ile Arg Val Ala Tyr Leu Tyr Lys Ala Ser Leu Val Arg Leu
    370                 375                 380
Tyr Lys Pro Asn Pro Gly Thr Ala Leu Asp Ala Asn Glu Val Leu Ala
385                 390                 395                 400
Gly Pro Thr Leu Lys Phe Asn Pro Gly Arg Ile Asp Pro Thr Asn Glu
                405                 410                 415
Ala Trp Thr Ala Ser Arg Lys Pro Leu Val Ala Glu Trp Glu Val Ile
            420                 425                 430
Ser Lys Asn Gly Lys Asp Gly Gly Lys Phe Phe Thr Val Asn Val His
        435                 440                 445
Phe Gly Ser Lys Gly Gly Ser Ser Ile Gln Gly Asp Ala Arg Pro
    450                 455                 460
Pro Val Asn Gly Gly Ile Glu Asp Arg Leu Ala Gln Ala Gln Leu Thr
465                 470                 475                 480
Ala Asn Phe Val Lys Ala Ile Leu Ala Lys Asp Arg Asn Ala Arg Ile
                485                 490                 495
Ile Thr Ala Gly Asp Phe Asn Glu Phe Ala Ser Val Glu Pro Met Glu
            500                 505                 510
Glu Tyr Val Lys Val Ser Gly Leu Lys Asp Leu Asp Glu Val Thr Lys
        515                 520                 525
Ile Lys Asp Val Glu Arg Tyr Thr Tyr Leu Phe Asp Met Asn Ala Gln
    530                 535                 540
```

```
Gln Leu Asp His Met Tyr Ile Ser Pro Ala Leu Glu Lys Lys Ala Lys
545                 550                 555                 560

Tyr Glu His Ile His Ile Asn Thr Trp Val Asp Arg Ala Ala Gln Ile
                565                 570                 575

Ser Asp His Asp Pro Ser Val Ala Lys Leu Asp Val Cys Ser
            580                 585                 590

<210> SEQ ID NO 7
<211> LENGTH: 589
<212> TYPE: PRT
<213> ORGANISM: Colletotrichum circinans

<400> SEQUENCE: 7

Leu Thr Ile Ala Glu Ile Asn Gly Asn Lys Phe Leu Ser Pro Phe Lys
1               5                   10                  15

Asp Gln Ser Val Thr Asn Val Thr Gly Leu Val Leu Ala Lys Gly Pro
            20                  25                  30

Ser Gly Ile Trp Ile Arg Ser Thr Thr Pro Asp Asp Asp Asp Ala Thr
        35                  40                  45

Ser Glu Ala Val Tyr Val Tyr Gly Ser Thr Val Gly Ala Asn Leu Thr
    50                  55                  60

Val Gly Asp Leu Ile Thr Leu Asp Gly Lys Ile Gln Glu Tyr Arg Ser
65                  70                  75                  80

Ala Thr Asn Tyr Ile Tyr Leu Thr Glu Leu Ser Ser Pro Lys Asn Val
                85                  90                  95

Val Val Val Ser Lys Gly Asn Glu Val Val Pro Leu Val Ile Gly Val
            100                 105                 110

Asp Thr Leu Asn Pro Pro Thr Glu Gln Tyr Thr Ser Leu Asp Gly Gly
        115                 120                 125

Asp Ile Tyr Ala Val Pro Asn Ala Val Ala Asn Ile Ser Ala Val Asn
    130                 135                 140

Pro Val Leu Glu Pro Thr Leu Tyr Gly Leu Asp Phe Trp Glu Ser Leu
145                 150                 155                 160

Ser Gly Glu Leu Val Thr Val Lys Asn Pro Val Ser Ile Thr Arg Pro
                165                 170                 175

Asn Gln Tyr Gly Asp Thr Trp Val Leu Gly Asp Trp Pro Thr Thr Gly
            180                 185                 190

Arg Asn Thr His Gly Gly Ile Thr Met Thr Asp Lys Asp Ser Asn Pro
        195                 200                 205

Glu Ala Ile Ile Ile Gly Ser Pro Leu Asp Gly Thr Lys Asn Pro Glu
    210                 215                 220

Ser Lys Met Gly Asp Gln Leu Thr Glu Ile Thr Gly Val Val Thr Tyr
225                 230                 235                 240

Ala Phe Gly Phe Tyr Arg Ile Leu Pro Leu Thr Ala Val Ser Ile Ala
                245                 250                 255

Lys Asn Ala Thr Asn Asp Ala Pro Pro Thr Thr Leu Val Ser Arg Gly
            260                 265                 270

Asp Cys Arg Gly Ile Thr Ile Gly Asp Tyr Asn Val Glu Asn Leu Ala
        275                 280                 285

Pro Asn Ser Ala His Leu Pro Ala Val Ala Ala His Ile Val Asp Tyr
    290                 295                 300

Leu Lys Thr Pro Asp Leu Ile Phe Val Gln Glu Val Gln Asp Asn Thr
305                 310                 315                 320

Gly Ala Thr Asn Asn Gly Val Val Ser Ser Asn Val Thr Leu Ser Thr
```

```
                        325                 330                 335
Leu Ala Ala Ala Ile Glu Ala Lys Ser Gly Val Phe Tyr Asp Phe Val
                340                 345                 350

Val Val Asp Pro Val Asp Gly Lys Asp Gly Ala Pro Gly Gly Asn
            355                 360                 365

Ile Arg Val Ala Tyr Leu Tyr Lys Pro Asp Val Ile Glu Leu Trp Lys
        370                 375                 380

Pro Asn Pro Gly Gly Ser Leu Asp Ala Asn Glu Val Leu Pro Gly Pro
385                 390                 395                 400

Gln Leu Lys Tyr Asn Pro Gly Arg Ile Ala Pro Thr Ser Ser Ala Trp
                405                 410                 415

Asp Ala Ser Arg Lys Pro Leu Val Ala Ala Trp Arg Ala Ile Lys Gly
                420                 425                 430

Pro Gln Asn Lys Ile Phe Phe Thr Val Asn Val His Phe Ala Ser Lys
                435                 440                 445

Gly Gly Ser Ser Ser Leu His Gly Asp Leu Arg Pro Pro Val Asn Gly
            450                 455                 460

Val Val Asn Pro Arg Ile Gln Gln Ala Glu Leu Thr Gly Asn Phe Ile
465                 470                 475                 480

Ala Glu Ile Leu Ala Ala Asp Pro Asn Ala Arg Ile Ile Ala Ala Gly
                485                 490                 495

Asp Phe Asn Glu Phe Ala Phe Val Glu Pro Leu Lys Ala Phe Thr Ala
                500                 505                 510

Lys Ser Gly Leu Ile Asp Leu Asp Glu Ala Val Gly Ile Pro Val Glu
                515                 520                 525

Glu Arg Tyr Thr Tyr Val Tyr Asp Met Asn Ala Gln Glu Leu Asp His
            530                 535                 540

Met Phe Val Ser Pro Ala Leu Ala His Lys Asn Gly Thr Lys Tyr Glu
545                 550                 555                 560

His Ile His Ile Asn Ser Trp Glu Leu Tyr Asp Asp Leu Val Ser Asp
                565                 570                 575

His Asp Pro Ser Val Ala Gln Phe Asn Val Cys Gly Cys
            580                 585

<210> SEQ ID NO 8
<211> LENGTH: 186
<212> TYPE: PRT
<213> ORGANISM: Clavicipitaceae

<400> SEQUENCE: 8

Val Pro Val Pro Ala Pro Pro Gly Ile Pro Ser Thr Ser Thr Ala Lys
1               5                   10                  15

Thr Leu Leu Ala Gly Leu Lys Val Ala Thr Pro Leu Ser Gly Asp Gly
                20                  25                  30

Tyr Ser Arg Asp Lys Phe Pro Thr Trp Glu Thr Ile Gln Gly Thr Cys
            35                  40                  45

Asn Ala Arg Glu Phe Val Ile Lys Arg Asp Gly Thr Asp Val Lys Thr
        50                  55                  60

Asn Ser Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
                100                 105                 110
```

```
Gln Arg Lys Ala Leu Ala Asn Asp Ile Thr Arg Pro Gln Leu Trp Ala
            115                 120                 125

Val Ser Ala His Ala Asn Arg Gly Lys Ser Asp Asp Ser Pro Asp Glu
130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Lys Leu Thr Ile Thr Asp Thr Glu Lys
                165                 170                 175

Gly Ala Leu Ala Gly Met Leu Asp Thr Cys
            180                 185
```

<210> SEQ ID NO 9
<211> LENGTH: 281
<212> TYPE: PRT
<213> ORGANISM: Preussia aemulans

<400> SEQUENCE: 9

```
Leu Ser Val Pro Arg Ala Ala Pro Ala Ser Ile Asp Leu Arg Pro Asn
1               5                   10                  15

Asp Leu Leu Lys Ser Thr Arg Gly Pro Tyr Gly Pro Asn Gly Arg Gly
                20                  25                  30

Arg Thr Gly Ser Thr Ser Ala Thr Ala Phe Asn Glu Leu Gln Leu Asn
            35                  40                  45

Leu Cys Asn Ser Gly Phe Ala Asn Cys Tyr Ala Asn Gly Asp Ser Ile
50                  55                  60

Pro Glu Gly Gly Glu Leu Ile Tyr Ala Thr Gly Pro Asn Val Val Thr
65                  70                  75                  80

Ile Asn Glu Ile Cys Ser Asn Asp Val Ser Thr Leu Gln Ser Tyr Leu
                85                  90                  95

Gly Glu Ala Trp Pro Thr Asp Tyr Thr Tyr Ser Val Phe Met Pro Ala
            100                 105                 110

Ile Asp Arg Arg Thr Asn Gln Gln Tyr Lys Cys Lys Asn Gly Ala Gln
        115                 120                 125

Tyr Gly Ser Val Val Leu Gly Arg Val Pro Ser Ala Thr Trp Ser Gly
    130                 135                 140

Ile Asp Ala Tyr Gly Gly Lys Tyr Ser Thr Gln Asp Asp Ser Asn Glu
145                 150                 155                 160

Leu Arg Ile Phe Val Cys Val Ala Ala Arg Gly Asp His Phe Ala Cys
                165                 170                 175

Thr Thr His Leu Thr Ser Lys Ser Glu Pro Leu Ala Met Thr Gln Cys
            180                 185                 190

Lys Ala Leu Met Ser Asp Ala Ile Pro Tyr Leu Lys Ser Gln Ser Gly
        195                 200                 205

Ser Thr Thr Arg Thr Val Val Ala Gly Asp Phe Asn Leu Glu Tyr Asp
    210                 215                 220

Thr Gly Asp Ala Glu Asn Met Gln Lys Cys Val Pro Ser Gly Trp Thr
225                 230                 235                 240

Arg Lys Gly Asp Gly Ser Val Gln His Thr Ile Phe Asp Asn Thr Leu
                245                 250                 255

Lys Phe Gly Ser Ser Lys Lys Tyr Gly Leu Ser Tyr Thr Asp His Asp
            260                 265                 270

Gly Trp Leu Val Lys Met Thr Val Gly
        275                 280
```

<210> SEQ ID NO 10

```
<211> LENGTH: 585
<212> TYPE: PRT
<213> ORGANISM: Trichurus spiralis

<400> SEQUENCE: 10

Leu Ser Ile Ala Glu Ile Asn Gly Asn Arg Phe Ile Ser Pro Tyr Asn
1               5                   10                  15

Gly Gln Thr Val Thr Asn Val Glu Gly Leu Val Thr Ala Val Ser Ser
            20                  25                  30

Ala Gly Phe Tyr Leu Arg Ser Thr Lys Ala Asp Arg Asp Ala Ala Thr
        35                  40                  45

Ser Glu Gly Leu Tyr Val Tyr Gly Ser Asn Ala Ala Lys Thr Val Thr
    50                  55                  60

Val Gly Asp Ile Ile Thr Val Ser Gly Lys Val Ser Glu Tyr Arg Ser
65                  70                  75                  80

Asn Val Asp Tyr Leu Tyr Leu Thr Glu Leu Thr Ser Pro Gln Asn Ile
                85                  90                  95

Thr Ile Val Ser Ser Gly Ala Lys Val Lys Pro Leu Val Ile Gly Lys
            100                 105                 110

Asp Thr Tyr Ser Pro Pro Thr Ser Lys Phe Ser Ser Leu Asp Glu Gly
        115                 120                 125

Gly Leu Phe Gly Val Pro Asn Asn Val Ser Arg Ile Ser Val Ala Asn
    130                 135                 140

Pro Lys Leu Gln Pro Lys Lys Tyr Gly Leu Asp Phe Trp Glu Ser Ile
145                 150                 155                 160

Val Gly Glu Leu Val Thr Ile Lys Glu Ala Tyr Gly Val Gly Arg Pro
                165                 170                 175

Asn Gln Tyr Gly Asp Val Trp Val Arg Gly Asn Trp Lys Val Thr Gly
            180                 185                 190

Lys Asn Lys Gln Gly Gly Leu Thr Met Thr Asp Gly Asp Ala Asn Pro
        195                 200                 205

Glu Thr Ile Ile Ile Gly Thr Pro Leu Asp Ala Ser Lys Asn Pro Thr
    210                 215                 220

Asp Thr Lys Met Gly Asp Tyr Tyr Gly Asp Ile Thr Gly Val Val Ser
225                 230                 235                 240

Tyr Ala Phe Gly Phe Tyr Arg Val Leu Pro Leu Thr His Ile Thr Pro
                245                 250                 255

Glu Arg Asn Ser Ser Ala Ala His Pro Pro Val Ser Phe Thr Ser Lys
            260                 265                 270

Gly Ser Cys Lys Gly Ile Thr Val Ala Asp Tyr Asn Ala Glu Asn Leu
        275                 280                 285

Ala Pro Thr Ser Thr His Leu Pro Gln Val Val Asp Gln Ile Ile Asn
    290                 295                 300

Met Leu Lys Thr Pro Asp Leu Leu Phe Leu Gln Glu Val Gln Asp Asn
305                 310                 315                 320

Ser Gly Ser Lys Asn Asp Gly Val Val Ser Ala Asn Val Thr Leu Thr
                325                 330                 335

Thr Leu Val Asp Ser Leu Phe Glu Thr Ser Gly Val Gln Tyr Ala Phe
            340                 345                 350

Ala Glu Val Glu Pro Glu Asn Leu Lys Asp Gly Gln Pro Gly Gly
        355                 360                 365

Asn Ile Arg Val Ala Tyr Leu Tyr Arg Pro Asp Val Val Glu Leu Tyr
    370                 375                 380

Lys Pro Asn Gln Gly Gly Ser Asn Asp Ala Asn Glu Val Leu Pro Gly
```

```
                385                 390                 395                 400
Pro Leu Leu Lys Tyr Asn Pro Gly Arg Ile Asp Pro Ala Asn Ala Ala
                    405                 410                 415

Trp Val Asp Ser Arg Lys Pro Leu Val Ala Met Trp Arg Ala Val Lys
                    420                 425                 430

Gly Gly Lys Lys Pro Phe Phe Thr Val Asn Val His Phe Thr Ser Lys
                    435                 440                 445

Gly Gly Ser Thr Ser Leu His Gly Asp Ala Arg Pro Pro Val Asn Leu
                    450                 455                 460

Gly Val Asp Gln Arg Thr Met Gln Ala Glu Val Thr Ala Asp Phe Ile
465                 470                 475                 480

Ala Gln Ile Leu Glu Glu Asp Lys Lys Ala Tyr Val Ile Ala Ala Gly
                    485                 490                 495

Asp Phe Asn Glu Phe Val Gln Val Gln Pro Leu Gln Thr Phe Ala Lys
                    500                 505                 510

Lys Ser Gly Leu Thr Glu Leu Asp Glu Val Ala Lys Ile Ser Met Asn
                    515                 520                 525

Glu Arg Tyr Thr Tyr Leu Phe Asp Met Asn Ser Glu Ala Leu Asp His
                    530                 535                 540

Met Tyr Val Ser Lys Gly Ile Gly Lys Ser Val Lys Tyr Glu His Met
545                 550                 555                 560

Asn Leu Asn Thr Trp Gln Asn Tyr Asp Asp Gln Val Ser Asp His Asp
                    565                 570                 575

Pro Ser Val Ala Arg Phe Asp Leu Cys
                    580                 585

<210> SEQ ID NO 11
<211> LENGTH: 807
<212> TYPE: DNA
<213> ORGANISM: Penicillium reticulisporum
<220> FEATURE:
<221> NAME/KEY: CDS
<222> LOCATION: (1)..(218)
<220> FEATURE:
<221> NAME/KEY: sig_peptide
<222> LOCATION: (1)..(69)
<220> FEATURE:
<221> NAME/KEY: mat_peptide
<222> LOCATION: (70)..(804)
<220> FEATURE:
<221> NAME/KEY: CDS
<222> LOCATION: (272)..(446)
<220> FEATURE:
<221> NAME/KEY: CDS
<222> LOCATION: (503)..(641)
<220> FEATURE:
<221> NAME/KEY: CDS
<222> LOCATION: (695)..(804)

<400> SEQUENCE: 11 atg aga ttt tct caa ctc aca cag acc ttg ata ggt ctt ttg gct ttt      48
Met Arg Phe Ser Gln Leu Thr Gln Thr Leu Ile Gly Leu Leu Ala Phe
            -20                 -15                 -10 cag cct gct ctg atc gca gga ctc ccg gcc ccg gaa gct ctc cca gcc      96
Gln Pro Ala Leu Ile Ala Gly Leu Pro Ala Pro Glu Ala Leu Pro Ala
        -5                  -1   1               5 cct cct ggc gtc cct agt gct tca act gcc cag agc gaa ctg gct gca     144
Pro Pro Gly Val Pro Ser Ala Ser Thr Ala Gln Ser Glu Leu Ala Ala
10                  15                  20                  25 ctg aca gtc gcc gct caa gga tcg caa gat ggt tat tct cga agc aag     192
Leu Thr Val Ala Ala Gln Gly Ser Gln Asp Gly Tyr Ser Arg Ser Lys
                30                  35                  40
```

```
ttc cct cac tgg atc aca caa tct gg  gtaagagaat ttaatttcac         238
Phe Pro His Trp Ile Thr Gln Ser Gly
             45                  50 agttcgtgta tggcgcgctc attatccatg cag g agc tgc gac acc cgg gat    290
                                      Ser Cys Asp Thr Arg Asp
                                                           55 gta gtg ctg aag cgt gac ggg aca aat gtg gta caa agc gcg agt gga  338
Val Val Leu Lys Arg Asp Gly Thr Asn Val Val Gln Ser Ala Ser Gly
                 60                  65                  70 tgt acc att acc agc ggt aaa tgg gtt tca cca tat gac ggt gca acc  386
Cys Thr Ile Thr Ser Gly Lys Trp Val Ser Pro Tyr Asp Gly Ala Thr
             75                  80                  85 tgg act gcc tcg agc gat gtc gac att gac cac ctt gtc ccg ctg tcc  434
Trp Thr Ala Ser Ser Asp Val Asp Ile Asp His Leu Val Pro Leu Ser
         90                  95                 100 aat gcc tgg aag gtaagaatat cccccaagta gtgaaaccgg gtcaagacga       486
Asn Ala Trp Lys
105 ctgatgtgtt tgatag tcg ggt gct tct gga tgg acc acc gca gcg cga cag  538
               Ser Gly Ala Ser Gly Trp Thr Thr Ala Ala Arg Gln
                                110                 115                 120 gcc ttt gcg aat gac ctg acc aat cca caa ctc ctg gtc gtg act gac  586
Ala Phe Ala Asn Asp Leu Thr Asn Pro Gln Leu Leu Val Val Thr Asp
                125                 130                 135 aat gtc aac gag tcc aag ggc gat aaa ggt ccc gag gaa tgg aaa cct  634
Asn Val Asn Glu Ser Lys Gly Asp Lys Gly Pro Glu Glu Trp Lys Pro
            140                 145                 150 cca ctt a gtatgtgtgg ctttttataa cggccattga agatatagct aacctgggaa  691
Pro Leu tag cc  tcg tac tat tgc acc tac gct gag atg tgg gtg aag gtc aag  738
        Ser Tyr Tyr Cys Thr Tyr Ala Glu Met Trp Val Lys Val Lys
            155                 160                 165 tcg gtc tac aaa ctc act atc acg tcc gct gag aaa tcc gcc ctg acg  786
Ser Val Tyr Lys Leu Thr Ile Thr Ser Ala Glu Lys Ser Ala Leu Thr
170                 175                 180                 185 agc atg ctc agt act tgc tag                                       807
Ser Met Leu Ser Thr Cys
                190

<210> SEQ ID NO 12
<211> LENGTH: 214
<212> TYPE: PRT
<213> ORGANISM: Penicillium reticulisporum

<400> SEQUENCE: 12

Met Arg Phe Ser Gln Leu Thr Gln Thr Leu Ile Gly Leu Leu Ala Phe
            -20                 -15                 -10

Gln Pro Ala Leu Ile Ala Gly Leu Pro Ala Pro Glu Ala Leu Pro Ala
         -5                  -1  1                   5

Pro Pro Gly Val Pro Ser Ala Ser Thr Ala Gln Ser Glu Leu Ala Ala
10                  15                  20                  25

Leu Thr Val Ala Ala Gln Gly Ser Gln Asp Gly Tyr Ser Arg Ser Lys
                30                  35                  40

Phe Pro His Trp Ile Thr Gln Ser Gly Ser Cys Asp Thr Arg Asp Val
            45                  50                  55

Val Leu Lys Arg Asp Gly Thr Asn Val Val Gln Ser Ala Ser Gly Cys
        60                  65                  70

Thr Ile Thr Ser Gly Lys Trp Val Ser Pro Tyr Asp Gly Ala Thr Trp
```

```
                    75                  80                  85
Thr Ala Ser Ser Asp Val Asp Ile Asp His Leu Val Pro Leu Ser Asn
 90                  95                 100                 105

Ala Trp Lys Ser Gly Ala Ser Gly Trp Thr Thr Ala Ala Arg Gln Ala
                    110                 115                 120

Phe Ala Asn Asp Leu Thr Asn Pro Gln Leu Leu Val Val Thr Asp Asn
                125                 130                 135

Val Asn Glu Ser Lys Gly Asp Lys Gly Pro Glu Glu Trp Lys Pro Pro
            140                 145                 150

Leu Thr Ser Tyr Tyr Cys Thr Tyr Ala Glu Met Trp Val Lys Val Lys
        155                 160                 165

Ser Val Tyr Lys Leu Thr Ile Thr Ser Ala Glu Lys Ser Ala Leu Thr
170                 175                 180                 185

Ser Met Leu Ser Thr Cys
                190

<210> SEQ ID NO 13
<211> LENGTH: 663
<212> TYPE: DNA
<213> ORGANISM: Acremonium dichromosporum
<220> FEATURE:
<221> NAME/KEY: CDS
<222> LOCATION: (1)..(348)
<220> FEATURE:
<221> NAME/KEY: sig_peptide
<222> LOCATION: (1)..(51)
<220> FEATURE:
<221> NAME/KEY: mat_peptide
<222> LOCATION: (52)..(660)
<220> FEATURE:
<221> NAME/KEY: CDS
<222> LOCATION: (412)..(660)

<400> SEQUENCE: 13 atg agg gct gta ctc gct gcc gtg ctc tac tcc gct gtc gcg gtt gtt      48
Met Arg Ala Val Leu Ala Ala Val Leu Tyr Ser Ala Val Ala Val Val
        -15                 -10                 -5 gcc att cct cct ggt att ccc agt gag gcg act gcg cgc tcg ctt ctc      96
Ala Ile Pro Pro Gly Ile Pro Ser Glu Ala Thr Ala Arg Ser Leu Leu
 -1   1                   5                  10                  15 agc agc ctg act gtg gcg ccc acc gtt gac gat ggc acc tac gat cgc     144
Ser Ser Leu Thr Val Ala Pro Thr Val Asp Asp Gly Thr Tyr Asp Arg
                 20                  25                  30 gac ctg ttc cct cac tgg tct tca gtc gag ggc aac tgc aac gcg cga     192
Asp Leu Phe Pro His Trp Ser Ser Val Glu Gly Asn Cys Asn Ala Arg
             35                  40                  45 gag ttc gtt ctc cgt cgt gat ggt gac ggt gtc tcg gtt gga aat gac     240
Glu Phe Val Leu Arg Arg Asp Gly Asp Gly Val Ser Val Gly Asn Asp
         50                  55                  60 tgc tat ccc acc gct ggc acc tgg acg tgc cca tat gat gga aag aga     288
Cys Tyr Pro Thr Ala Gly Thr Trp Thr Cys Pro Tyr Asp Gly Lys Arg
     65                  70                  75 cac agc gtg ccc agc gat gtc tca atc gac cac atg gtg cct ctg cac     336
His Ser Val Pro Ser Asp Val Ser Ile Asp His Met Val Pro Leu His
 80                  85                  90                  95 aac gcg tgg atg gtacgttgcc tcatcgtaga aacatgcac gattcgcccc          388
Asn Ala Trp Met tgctgacatg attctccaaa aag act ggt gct tct gag tgg acc acg gcg gaa   441
                          Thr Gly Ala Ser Glu Trp Thr Thr Ala Glu
                                            100                 105 cgc gag gcg ttt gcc aat gac att gac ggg ccc cag ctg tgg gct gtc     489
```

-continued

```
                 Arg Glu Ala Phe Ala Asn Asp Ile Asp Gly Pro Gln Leu Trp Ala Val
                 110                 115                 120                 125 act agc acg acc aac tcg caa aag ggg tcg gac gcg cca gat gag tgg          537
Thr Ser Thr Thr Asn Ser Gln Lys Gly Ser Asp Ala Pro Asp Glu Trp
                130                 135                 140 cag cct ccc cag acg agc att cac tgc aag tac gct gct gcg tgg atc         585
Gln Pro Pro Gln Thr Ser Ile His Cys Lys Tyr Ala Ala Ala Trp Ile
            145                 150                 155 cag gtc aag agc acc tac gac ctg act gtg agc tcg gca gag cag gcc         633
Gln Val Lys Ser Thr Tyr Asp Leu Thr Val Ser Ser Ala Glu Gln Ala
        160                 165                 170 gct ctg gag gaa atg ctg ggc agg tgc tga                                 663
Ala Leu Glu Glu Met Leu Gly Arg Cys
    175                 180
```

```
<210> SEQ ID NO 14
<211> LENGTH: 199
<212> TYPE: PRT
<213> ORGANISM: Acremonium dichromosporum

<400> SEQUENCE: 14

Met Arg Ala Val Leu Ala Ala Val Leu Tyr Ser Ala Val Ala Val
            -15                 -10                 -5

Ala Ile Pro Pro Gly Ile Pro Ser Glu Ala Thr Ala Arg Ser Leu Leu
 -1   1               5                  10                  15

Ser Ser Leu Thr Val Ala Pro Thr Val Asp Asp Gly Thr Tyr Asp Arg
                20                  25                  30

Asp Leu Phe Pro His Trp Ser Val Glu Gly Asn Cys Asn Ala Arg
            35                  40                  45

Glu Phe Val Leu Arg Arg Asp Gly Asp Gly Val Ser Val Gly Asn Asp
        50                  55                  60

Cys Tyr Pro Thr Ala Gly Thr Trp Thr Cys Pro Tyr Asp Gly Lys Arg
65                  70                  75

His Ser Val Pro Ser Asp Val Ser Ile Asp His Met Val Pro Leu His
            80                  85                  90                  95

Asn Ala Trp Met Thr Gly Ala Ser Glu Trp Thr Thr Ala Glu Arg Glu
                100                 105                 110

Ala Phe Ala Asn Asp Ile Asp Gly Pro Gln Leu Trp Ala Val Thr Ser
            115                 120                 125

Thr Thr Asn Ser Gln Lys Gly Ser Asp Ala Pro Asp Glu Trp Gln Pro
        130                 135                 140

Pro Gln Thr Ser Ile His Cys Lys Tyr Ala Ala Ala Trp Ile Gln Val
    145                 150                 155

Lys Ser Thr Tyr Asp Leu Thr Val Ser Ser Ala Glu Gln Ala Ala Leu
160                 165                 170                 175

Glu Glu Met Leu Gly Arg Cys
                180
```

```
<210> SEQ ID NO 15
<211> LENGTH: 2297
<212> TYPE: DNA
<213> ORGANISM: Preussia aemulans
<220> FEATURE:
<221> NAME/KEY: CDS
<222> LOCATION: (1)..(661)
<220> FEATURE:
<221> NAME/KEY: sig_peptide
<222> LOCATION: (1)..(48)
<220> FEATURE:
<221> NAME/KEY: mat_peptide
```

```
<222> LOCATION: (49)..(2294)
<220> FEATURE:
<221> NAME/KEY: CDS
<222> LOCATION: (723)..(1094)
<220> FEATURE:
<221> NAME/KEY: CDS
<222> LOCATION: (1150)..(1619)
<220> FEATURE:
<221> NAME/KEY: CDS
<222> LOCATION: (1980)..(2294)

<400> SEQUENCE: 15 atg gca gct ctc ctt cgt ttt gcc gcc ctc acc ggc ctt gcg tcc gcg      48
Met Ala Ala Leu Leu Arg Phe Ala Ala Leu Thr Gly Leu Ala Ser Ala
    -15                 -10                  -5                  -1 ctc tct ata tcc gaa atc aat ggg ccg aaa tac ctc tct ccc tat gcg      96
Leu Ser Ile Ser Glu Ile Asn Gly Pro Lys Tyr Leu Ser Pro Tyr Ala
  1               5                  10                  15 ggc caa acc gtc tcc aat gta gcg gga atc gtc aca gca aag gga ccc     144
Gly Gln Thr Val Ser Asn Val Ala Gly Ile Val Thr Ala Lys Gly Pro
                20                  25                  30 agc gga atc tgg att cga tcc acg acc ccc gac cgc gat gac aag aca     192
Ser Gly Ile Trp Ile Arg Ser Thr Thr Pro Asp Arg Asp Asp Lys Thr
         35                  40                  45 tct gag tcc ata tac gta ttc aac aag acc ttt ggc gcg aac ttg acc     240
Ser Glu Ser Ile Tyr Val Phe Asn Lys Thr Phe Gly Ala Asn Leu Thr
 50                  55                  60 gtt ggt gac tca att gtc att gga ggc aag gtg gag gaa tac cgc tcg     288
Val Gly Asp Ser Ile Val Ile Gly Gly Lys Val Glu Glu Tyr Arg Ser
 65                  70                  75                  80 aac aag gac tat gtg tat ctt acg gag atc tca tcg ccc gtg ttg gag     336
Asn Lys Asp Tyr Val Tyr Leu Thr Glu Ile Ser Ser Pro Val Leu Glu
                 85                  90                  95 agc aag att tcg agc ggg aat gca gtc aag ccg ttg gtt att ggg aag     384
Ser Lys Ile Ser Ser Gly Asn Ala Val Lys Pro Leu Val Ile Gly Lys
            100                 105                 110 gat act tca aag ccg ccg aca gag caa ttc agt tca ttg gat ggg ggc     432
Asp Thr Ser Lys Pro Pro Thr Glu Gln Phe Ser Ser Leu Asp Gly Gly
        115                 120                 125 gac gtg ttt ggc gtc ccg aat aat gtg tca ctt gtg tca gtc gca aat     480
Asp Val Phe Gly Val Pro Asn Asn Val Ser Leu Val Ser Val Ala Asn
    130                 135                 140 ccg acc ctg gag ccg aag aag tat ggc atg gat ttc tgg gag agc ttg     528
Pro Thr Leu Glu Pro Lys Lys Tyr Gly Met Asp Phe Trp Glu Ser Leu
145                 150                 155                 160 agt ggc gag ttg gtc acc gtg aag aag ccc act gcc cta tcg aag ccg     576
Ser Gly Glu Leu Val Thr Val Lys Lys Pro Thr Ala Leu Ser Lys Pro
                165                 170                 175 agc aat ttt ggt gat acc tgg gta gtt gga gat tgg aag gtt acg ggt     624
Ser Asn Phe Gly Asp Thr Trp Val Val Gly Asp Trp Lys Val Thr Gly
            180                 185                 190 gac aac aag cgc ggt ggg tta acg cag acg gac aaa g gtaagtcgaa         671
Asp Asn Lys Arg Gly Gly Leu Thr Gln Thr Asp Lys
        195                 200 tccgaatacc gcagacgagg gaggaggcag gaaggtgttg acgggaaaca g ac  gcg     727
                                                         Asp Ala
                                                             205 aat cct gag acc atc ata att gga tct ccg ctc gac ggt tcc tcc aac     775
Asn Pro Glu Thr Ile Ile Ile Gly Ser Pro Leu Asp Gly Ser Ser Asn
        210                 215                 220 ccg ctc acc gtc aag ctc ggc gac gaa ctc tca gag atc act ggc gtg     823
Pro Leu Thr Val Lys Leu Gly Asp Glu Leu Ser Glu Ile Thr Gly Val
```

```
                    225                 230                 235
gta acg tac gcc ttt ggc ttc tat cgc atc ctg ccc aca acc gct ctc    871
Val Thr Tyr Ala Phe Gly Phe Tyr Arg Ile Leu Pro Thr Thr Ala Leu
240                 245                 250 aaa gtc gtc aag tcc cag cag cag gaa ctt ccg tcc gca acg agc ctc    919
Lys Val Val Lys Ser Gln Gln Gln Glu Leu Pro Ser Ala Thr Ser Leu
255                 260                 265                 270 atc tcg agt ggg aaa tgc gat ggc ctc acc ttt ggt gca tac aat gtc    967
Ile Ser Ser Gly Lys Cys Asp Gly Leu Thr Phe Gly Ala Tyr Asn Val
                275                 280                 285 gag aac ctc ttc act ggt tcc aag cat atg cca aac att tct gca cac   1015
Glu Asn Leu Phe Thr Gly Ser Lys His Met Pro Asn Ile Ser Ala His
            290                 295                 300 atc gtt aca tac ttg aag tct cct gac ttc atc ttc atc caa gaa gtc   1063
Ile Val Thr Tyr Leu Lys Ser Pro Asp Phe Ile Phe Ile Gln Glu Val
        305                 310                 315 cag gac gac aat ggc ccc act aac gac gga g gtaagcttcc accatattca   1114
Gln Asp Asp Asn Gly Pro Thr Asn Asp Gly
320                 325 gccacagaag ccacacagaa gcttacactc acag tc  gta tct gca aat gca    1166
                                          Val Val Ser Ala Asn Ala
                                                  330 acc ctc aca gca tta aca gag gct att gtg gcc gca gga ggc ccg cag   1214
Thr Leu Thr Ala Leu Thr Glu Ala Ile Val Ala Ala Gly Gly Pro Gln
335                 340                 345                 350 tac acc ttc acc gat atc gcg cca tcc agc aat cag gac ggc ggg gcc   1262
Tyr Thr Phe Thr Asp Ile Ala Pro Ser Ser Asn Gln Asp Gly Gly Ala
                355                 360                 365 ccg gga ggg aac atc cgt gtt gct tat ctc tac aaa gct tcg ctc gtc   1310
Pro Gly Gly Asn Ile Arg Val Ala Tyr Leu Tyr Lys Ala Ser Leu Val
            370                 375                 380 cgc cta tac aag ccg aat cca ggc acg gca ctg gat gca aac gaa gtc   1358
Arg Leu Tyr Lys Pro Asn Pro Gly Thr Ala Leu Asp Ala Asn Glu Val
        385                 390                 395 ttg gcg gga cct acg ctg aag ttc aac cca gga cgt atc gac cct acc   1406
Leu Ala Gly Pro Thr Leu Lys Phe Asn Pro Gly Arg Ile Asp Pro Thr
400                 405                 410 aac gag gca tgg acg gca agt cgc aag ccg ctc gtc gca gag tgg gaa   1454
Asn Glu Ala Trp Thr Ala Ser Arg Lys Pro Leu Val Ala Glu Trp Glu
415                 420                 425                 430 gtc att agc aag aac ggc aaa gac ggt ggc aag ttc ttc act gtc aac   1502
Val Ile Ser Lys Asn Gly Lys Asp Gly Gly Lys Phe Phe Thr Val Asn
                435                 440                 445 gtt cat ttt ggc tcc aag ggt ggt agc agc agc atc cag ggc gat gcg   1550
Val His Phe Gly Ser Lys Gly Gly Ser Ser Ser Ile Gln Gly Asp Ala
            450                 455                 460 agg ccg cct gtc aat ggt ggt atc gag gac cgt ctc gca cag gcc cag   1598
Arg Pro Pro Val Asn Gly Gly Ile Glu Asp Arg Leu Ala Gln Ala Gln
        465                 470                 475 ttg act gcg aac ttc gtc aaa gtaagtacca aacttttcct tctttcccca     1649
Leu Thr Ala Asn Phe Val Lys
        480                 485 tgtcaatcct acgatggaca tttgccacgg cttcgttgtg agcttaacaa aaggcttgtt  1709
ttggcaaaac accacaacac agcgtcgcac tgtcgccggc cctctggcgc cgggccagag  1769
tatagcgaac atcacaaggc caccctggac gaagatcgag ctgcgtctcg ggatatggag  1829
ccgacgcagg tgctttcaaa gggtccagtg tgccgctgtt gagccgcaga aagggcatgg  1889
aatcgctgca taggacccta taaatcccag cgagcgagga gagccgtcaa tatagagttc  1949
```

```
aatctcgaaa cagagctgac acgcacttag gcc atc ctt gcc aag gac cga aac         2003
                                 Ala Ile Leu Ala Lys Asp Arg Asn
                                                 490 gcg cgg att ata acc gca ggt gat ttc aac gag ttc gcc tct gtt gag          2051
Ala Arg Ile Ile Thr Ala Gly Asp Phe Asn Glu Phe Ala Ser Val Glu
495                 500                 505 ccc atg gag gaa tac gta aaa gtt tct ggc ctg aag gac ctt gac gaa          2099
Pro Met Glu Glu Tyr Val Lys Val Ser Gly Leu Lys Asp Leu Asp Glu
510                 515                 520                 525 gtg acc aag atc aag gat gtc gag cgc tat aca tac ctc ttt gac atg          2147
Val Thr Lys Ile Lys Asp Val Glu Arg Tyr Thr Tyr Leu Phe Asp Met
                530                 535                 540 aac gcc cag cag ctg gac cac atg tac atc agc ccg gca ctg gag aag          2195
Asn Ala Gln Gln Leu Asp His Met Tyr Ile Ser Pro Ala Leu Glu Lys
            545                 550                 555 aag gcc aag tac gaa cat att cat atc aac acg tgg gtg gat agg gcc          2243
Lys Ala Lys Tyr Glu His Ile His Ile Asn Thr Trp Val Asp Arg Ala
        560                 565                 570 gca caa att agc gac cac gac cca tct gtg gcg aaa ctc gac gtg tgt          2291
Ala Gln Ile Ser Asp His Asp Pro Ser Val Ala Lys Leu Asp Val Cys
575                 580                 585 tcc tga                                                                   2297
Ser
590

<210> SEQ ID NO 16
<211> LENGTH: 606
<212> TYPE: PRT
<213> ORGANISM: Preussia aemulans

<400> SEQUENCE: 16

Met Ala Ala Leu Leu Arg Phe Ala Ala Leu Thr Gly Leu Ala Ser Ala
    -15                 -10                 -5                  -1

Leu Ser Ile Ser Glu Ile Asn Gly Pro Lys Tyr Leu Ser Pro Tyr Ala
1               5                   10                  15

Gly Gln Thr Val Ser Asn Val Ala Gly Ile Val Thr Ala Lys Gly Pro
                20                  25                  30

Ser Gly Ile Trp Ile Arg Ser Thr Thr Pro Asp Arg Asp Lys Thr
            35                  40                  45

Ser Glu Ser Ile Tyr Val Phe Asn Lys Thr Phe Gly Ala Asn Leu Thr
        50                  55                  60

Val Gly Asp Ser Ile Val Ile Gly Gly Lys Val Glu Glu Tyr Arg Ser
65                  70                  75                  80

Asn Lys Asp Tyr Val Tyr Leu Thr Glu Ile Ser Ser Pro Val Leu Glu
                85                  90                  95

Ser Lys Ile Ser Ser Gly Asn Ala Val Lys Pro Leu Val Ile Gly Lys
            100                 105                 110

Asp Thr Ser Lys Pro Pro Thr Glu Gln Phe Ser Leu Asp Gly Gly
        115                 120                 125

Asp Val Phe Gly Val Pro Asn Asn Val Ser Leu Val Ser Val Ala Asn
130                 135                 140

Pro Thr Leu Glu Pro Lys Lys Tyr Gly Met Asp Phe Trp Glu Ser Leu
145                 150                 155                 160

Ser Gly Glu Leu Val Thr Val Lys Lys Pro Thr Ala Leu Ser Lys Pro
                165                 170                 175

Ser Asn Phe Gly Asp Thr Trp Val Val Gly Asp Trp Lys Val Thr Gly
            180                 185                 190
```

```
Asp Asn Lys Arg Gly Gly Leu Thr Gln Thr Asp Lys Asp Ala Asn Pro
            195                 200                 205

Glu Thr Ile Ile Ile Gly Ser Pro Leu Asp Gly Ser Ser Asn Pro Leu
210                 215                 220

Thr Val Lys Leu Gly Asp Glu Leu Ser Glu Ile Thr Gly Val Val Thr
225                 230                 235                 240

Tyr Ala Phe Gly Phe Tyr Arg Ile Leu Pro Thr Thr Ala Leu Lys Val
                245                 250                 255

Val Lys Ser Gln Gln Gln Glu Leu Pro Ser Ala Thr Ser Leu Ile Ser
            260                 265                 270

Ser Gly Lys Cys Asp Gly Leu Thr Phe Gly Ala Tyr Asn Val Glu Asn
            275                 280                 285

Leu Phe Thr Gly Ser Lys His Met Pro Asn Ile Ser Ala His Ile Val
290                 295                 300

Thr Tyr Leu Lys Ser Pro Asp Phe Ile Phe Ile Gln Glu Val Gln Asp
305                 310                 315                 320

Asp Asn Gly Pro Thr Asn Asp Gly Val Val Ser Ala Asn Ala Thr Leu
                325                 330                 335

Thr Ala Leu Thr Glu Ala Ile Val Ala Ala Gly Gly Pro Gln Tyr Thr
            340                 345                 350

Phe Thr Asp Ile Ala Pro Ser Ser Asn Gln Asp Gly Gly Ala Pro Gly
            355                 360                 365

Gly Asn Ile Arg Val Ala Tyr Leu Tyr Lys Ala Ser Leu Val Arg Leu
370                 375                 380

Tyr Lys Pro Asn Pro Gly Thr Ala Leu Asp Ala Asn Glu Val Leu Ala
385                 390                 395                 400

Gly Pro Thr Leu Lys Phe Asn Pro Gly Arg Ile Asp Pro Thr Asn Glu
                405                 410                 415

Ala Trp Thr Ala Ser Arg Lys Pro Leu Val Ala Glu Trp Glu Val Ile
            420                 425                 430

Ser Lys Asn Gly Lys Asp Gly Gly Lys Phe Phe Thr Val Asn Val His
            435                 440                 445

Phe Gly Ser Lys Gly Gly Ser Ser Ile Gln Gly Asp Ala Arg Pro
450                 455                 460

Pro Val Asn Gly Gly Ile Glu Asp Arg Leu Ala Gln Ala Gln Leu Thr
465                 470                 475                 480

Ala Asn Phe Val Lys Ala Ile Leu Ala Lys Asp Arg Asn Ala Arg Ile
                485                 490                 495

Ile Thr Ala Gly Asp Phe Asn Glu Phe Ala Ser Val Glu Pro Met Glu
            500                 505                 510

Glu Tyr Val Lys Val Ser Gly Leu Lys Asp Leu Asp Glu Val Thr Lys
            515                 520                 525

Ile Lys Asp Val Glu Arg Tyr Thr Tyr Leu Phe Asp Met Asn Ala Gln
530                 535                 540

Gln Leu Asp His Met Tyr Ile Ser Pro Ala Leu Glu Lys Lys Ala Lys
545                 550                 555                 560

Tyr Glu His Ile His Ile Asn Thr Trp Val Asp Arg Ala Ala Gln Ile
                565                 570                 575

Ser Asp His Asp Pro Ser Val Ala Lys Leu Asp Val Cys Ser
            580                 585                 590

<210> SEQ ID NO 17
<211> LENGTH: 2011
```

```
<212> TYPE: DNA
<213> ORGANISM: Colletotrichum circinans
<220> FEATURE:
<221> NAME/KEY: CDS
<222> LOCATION: (1)..(284)
<220> FEATURE:
<221> NAME/KEY: sig_peptide
<222> LOCATION: (1)..(48)
<220> FEATURE:
<221> NAME/KEY: mat_peptide
<222> LOCATION: (49)..(2008)
<220> FEATURE:
<221> NAME/KEY: CDS
<222> LOCATION: (344)..(720)
<220> FEATURE:
<221> NAME/KEY: CDS
<222> LOCATION: (779)..(1596)
<220> FEATURE:
<221> NAME/KEY: CDS
<222> LOCATION: (1673)..(2008)

<400> SEQUENCE: 17
```

| | | | | | | | | | | | | | | | | |
|---|---|---|---|---|---|---|---|---|---|---|---|---|---|---|---|---|
| atg | aag | gtc | acc | tct | ctc | ttc | ctc | tcc | acc | gcc | ggc | gcc | gcc | tcg | gcc | 48 |
| Met | Lys | Val | Thr | Ser | Leu | Phe | Leu | Ser | Thr | Ala | Gly | Ala | Ala | Ser | Ala | |
| | -15 | | | | -10 | | | | -5 | | | | -1 | | | |

| | | | | | | | | | | | | | | | | |
|---|---|---|---|---|---|---|---|---|---|---|---|---|---|---|---|---|
| ctg | acc | att | gcc | gag | atc | aac | ggc | aac | aag | ttc | ctc | tcg | ccg | ttc | aag | 96 |
| Leu | Thr | Ile | Ala | Glu | Ile | Asn | Gly | Asn | Lys | Phe | Leu | Ser | Pro | Phe | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | cag | tcc | gtg | acc | aac | gtc | acc | ggt | ctg | gtt | ctg | gcc | aag | gga | ccc | 144 |
| Asp | Gln | Ser | Val | Thr | Asn | Val | Thr | Gly | Leu | Val | Leu | Ala | Lys | Gly | Pro | |
| | | 20 | | | | | 25 | | | | | 30 | | | | |

| | | | | | | | | | | | | | | | | |
|---|---|---|---|---|---|---|---|---|---|---|---|---|---|---|---|---|
| agc | ggc | atc | tgg | att | cgc | tcg | acc | acc | ccc | gac | gat | gac | gat | gcc | acc | 192 |
| Ser | Gly | Ile | Trp | Ile | Arg | Ser | Thr | Thr | Pro | Asp | Asp | Asp | Asp | Ala | Thr | |
| | 35 | | | | | 40 | | | | | 45 | | | | | |

| | | | | | | | | | | | | | | | | |
|---|---|---|---|---|---|---|---|---|---|---|---|---|---|---|---|---|
| tct | gag | gcc | gtc | tac | gtc | tac | ggc | agc | acc | gtc | ggc | gca | aac | ctg | acc | 240 |
| Ser | Glu | Ala | Val | Tyr | Val | Tyr | Gly | Ser | Thr | Val | Gly | Ala | Asn | Leu | Thr | |
| 50 | | | | | 55 | | | | | 60 | | | | | | |

| | | | | | | | | | | | | | | |
|---|---|---|---|---|---|---|---|---|---|---|---|---|---|---|---|
| gtg | ggc | gac | ctc | atc | acc | ctg | gac | ggc | aag | atc | cag | gag | tac | ag | 284 |
| Val | Gly | Asp | Leu | Ile | Thr | Leu | Asp | Gly | Lys | Ile | Gln | Glu | Tyr | Arg | |
| 65 | | | | | 70 | | | | | 75 | | | | | |

| | | | | |
|---|---|---|---|---|
| gtatgagaat | tcggcgcgca | tactcccgtt | caaggtcgct | gttggctaac actgcgcag | 343 |

| | | | | | | | | | | | | | | | | |
|---|---|---|---|---|---|---|---|---|---|---|---|---|---|---|---|---|
| g | tcc | gcg | acg | aac | tac | atc | tac | ctc | acg | gag | ctc | agc | tcc | ccc | aag aac | 392 |
| | Ser | Ala | Thr | Asn | Tyr | Ile | Tyr | Leu | Thr | Glu | Leu | Ser | Ser | Pro | Lys Asn | |
| | 80 | | | | | 85 | | | | | 90 | | | | 95 | |

| | | | | | | | | | | | | | | | | |
|---|---|---|---|---|---|---|---|---|---|---|---|---|---|---|---|---|
| gtc | gtc | gtc | gtg | tcc | aag | ggc | aac | gag | gtt | gtc | cca | ctc | gtc | att | ggc | 440 |
| Val | Val | Val | Val | Ser | Lys | Gly | Asn | Glu | Val | Val | Pro | Leu | Val | Ile | Gly | |
| | | | | 100 | | | | | 105 | | | | | 110 | | |

| | | | | | | | | | | | | | | | | |
|---|---|---|---|---|---|---|---|---|---|---|---|---|---|---|---|---|
| gtc | gac | acc | ctg | aac | ccg | cct | acc | gag | cag | tac | acc | agc | ctc | gac | ggc | 488 |
| Val | Asp | Thr | Leu | Asn | Pro | Pro | Thr | Glu | Gln | Tyr | Thr | Ser | Leu | Asp | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| ggc | gac | atc | tac | gcc | gtg | ccc | aac | gcc | gtc | gcc | aac | atc | tcc | gcc | gtt | 536 |
| Gly | Asp | Ile | Tyr | Ala | Val | Pro | Asn | Ala | Val | Ala | Asn | Ile | Ser | Ala | Val | |
| | | 130 | | | | | 135 | | | | | 140 | | | | |

| | | | | | | | | | | | | | | | | |
|---|---|---|---|---|---|---|---|---|---|---|---|---|---|---|---|---|
| aac | ccc | gtt | ctg | gag | cct | acc | ctg | tac | ggc | ctc | gac | ttc | tgg | gag | agc | 584 |
| Asn | Pro | Val | Leu | Glu | Pro | Thr | Leu | Tyr | Gly | Leu | Asp | Phe | Trp | Glu | Ser | |
| | 145 | | | | | 150 | | | | | 155 | | | | | |

| | | | | | | | | | | | | | | | | |
|---|---|---|---|---|---|---|---|---|---|---|---|---|---|---|---|---|
| ctg | agc | ggc | gag | ctg | gtg | acg | gtc | aag | aac | ccc | gtc | tcc | atc | acc | cgc | 632 |
| Leu | Ser | Gly | Glu | Leu | Val | Thr | Val | Lys | Asn | Pro | Val | Ser | Ile | Thr | Arg | |
| 160 | | | | | 165 | | | | | 170 | | | | | 175 | |

| | | | | | | | | | | | | | | | | |
|---|---|---|---|---|---|---|---|---|---|---|---|---|---|---|---|---|
| ccc | aac | cag | tac | ggt | gac | acc | tgg | gtc | ctt | ggc | gac | tgg | ccc | acc | acc | 680 |
| Pro | Asn | Gln | Tyr | Gly | Asp | Thr | Trp | Val | Leu | Gly | Asp | Trp | Pro | Thr | Thr | |
| | | | 180 | | | | | 185 | | | | | 190 | | | |

| | | | | | | | | | | |
|---|---|---|---|---|---|---|---|---|---|---|---|
| ggc | cgc | aac | act | cac | ggc | ggc | atc | acc | atg | act | gac aag g gtaagtcgcc | 730 |
| Gly | Arg | Asn | Thr | His | Gly | Gly | Ile | Thr | Met | Thr | Asp Lys | |

```
                195                 200
ctcgcgcgct tgacatttac tcgcagagca cccgctgacg cgtccaag ac  tcc aac      786
                                                         Asp Ser Asn
                                                             205 ccc gag gcc atc atc atc ggc tcc ccc ctc gac ggg acc aag aac ccc      834
Pro Glu Ala Ile Ile Ile Gly Ser Pro Leu Asp Gly Thr Lys Asn Pro
            210                 215                 220 gag tcc aag atg ggc gac cag ctc acc gag atc acc ggt gtc gtc acc      882
Glu Ser Lys Met Gly Asp Gln Leu Thr Glu Ile Thr Gly Val Val Thr
225                 230                 235 tac gcc ttc ggc ttc tac cgc atc ctc cct ctt acc gca gtc tcc att      930
Tyr Ala Phe Gly Phe Tyr Arg Ile Leu Pro Leu Thr Ala Val Ser Ile
240                 245                 250                 255 gcc aag aac gcc acc aac gac gcg ccg ccc acc acc ctc gtc agc agg      978
Ala Lys Asn Ala Thr Asn Asp Ala Pro Pro Thr Thr Leu Val Ser Arg
            260                 265                 270 ggt gac tgc cgc ggc atc acc atc ggc gac tac aac gtc gag aac ctt     1026
Gly Asp Cys Arg Gly Ile Thr Ile Gly Asp Tyr Asn Val Glu Asn Leu
                275                 280                 285 gcc ccg aac tct gcc cac ctc ccc gcc gtc gcc gcc cac atc gtc gac     1074
Ala Pro Asn Ser Ala His Leu Pro Ala Val Ala Ala His Ile Val Asp
            290                 295                 300 tac ctc aag acc ccc gac ctc atc ttc gtc cag gag gtc cag gac aac     1122
Tyr Leu Lys Thr Pro Asp Leu Ile Phe Val Gln Glu Val Gln Asp Asn
305                 310                 315 acc ggc gcc acc aac aac ggc gtt gtc tcc tcc aac gtc acc ctc tcc     1170
Thr Gly Ala Thr Asn Asn Gly Val Val Ser Ser Asn Val Thr Leu Ser
320                 325                 330                 335 acc ctc gct gcc gcg atc gag gcc aag agc ggc gtc ttc tac gac ttc     1218
Thr Leu Ala Ala Ala Ile Glu Ala Lys Ser Gly Val Phe Tyr Asp Phe
            340                 345                 350 gtt gtg gtt gac ccc gtc gat ggc aag gac ggc ggt gcc ccc gga ggc     1266
Val Val Val Asp Pro Val Asp Gly Lys Asp Gly Gly Ala Pro Gly Gly
                355                 360                 365 aac atc cgc gtc gcc tac ctc tac aag ccc gac gtc atc gag ctg tgg     1314
Asn Ile Arg Val Ala Tyr Leu Tyr Lys Pro Asp Val Ile Glu Leu Trp
            370                 375                 380 aag ccc aac ccc ggt ggc agc ctg gac gcc aac gag gtc ctg ccc ggc     1362
Lys Pro Asn Pro Gly Gly Ser Leu Asp Ala Asn Glu Val Leu Pro Gly
385                 390                 395 ccg cag ctc aag tat aac ccc ggc cgc atc gcg ccc acc agc agc gcg     1410
Pro Gln Leu Lys Tyr Asn Pro Gly Arg Ile Ala Pro Thr Ser Ser Ala
400                 405                 410                 415 tgg gac gcc agc cgc aag ccc ctc gtc gcc gcg tgg cgc gcc atc aag     1458
Trp Asp Ala Ser Arg Lys Pro Leu Val Ala Ala Trp Arg Ala Ile Lys
            420                 425                 430 ggc ccc cag aac aag atc ttc ttc acc gtc aac gtc cac ttc gcc tcc     1506
Gly Pro Gln Asn Lys Ile Phe Phe Thr Val Asn Val His Phe Ala Ser
                435                 440                 445 aag ggc ggt tct tcc tca ctg cac ggc gac ctc cgc cct ccc gtc aac     1554
Lys Gly Gly Ser Ser Ser Leu His Gly Asp Leu Arg Pro Pro Val Asn
            450                 455                 460 ggc gtc gtg aac ccc cgc atc cag cag gcc gaa ctc acc ggt             1596
Gly Val Val Asn Pro Arg Ile Gln Gln Ala Glu Leu Thr Gly
465                 470                 475 gtaagcctct cacctccccc tcacccgctt cctgaaccct gcaaaatcat gatccgtgac   1656
tgaccaagca taacag aac ttc atc gcc gag atc ctt gct gcg gac ccc aac   1708
               Asn Phe Ile Ala Glu Ile Leu Ala Ala Asp Pro Asn
                                     480                 485
```

```
gcc cgc atc atc gcg gcc ggc gac ttc aac gag ttc gcc ttc gtc gag    1756
Ala Arg Ile Ile Ala Ala Gly Asp Phe Asn Glu Phe Ala Phe Val Glu
490             495                 500                 505 ccc ctc aag gcc ttc acc gcc aag tcc ggc ctg atc gac ctc gac gag    1804
Pro Leu Lys Ala Phe Thr Ala Lys Ser Gly Leu Ile Asp Leu Asp Glu
            510                 515                 520 gcc gtc ggg atc ccc gtc gag gag cgc tac acg tac gtc tac gac atg    1852
Ala Val Gly Ile Pro Val Glu Glu Arg Tyr Thr Tyr Val Tyr Asp Met
                525                 530                 535 aac gcg cag gag ctc gac cac atg ttt gtc agc ccc gcg ctg gcc cac    1900
Asn Ala Gln Glu Leu Asp His Met Phe Val Ser Pro Ala Leu Ala His
        540                 545                 550 aag aac ggc acc aag tac gag cac atc cac atc aac tcg tgg gag ctg    1948
Lys Asn Gly Thr Lys Tyr Glu His Ile His Ile Asn Ser Trp Glu Leu
555             560                 565 tat gac gac ctc gtc agc gac cac gac ccc tcg gtg gcg cag ttc aac    1996
Tyr Asp Asp Leu Val Ser Asp His Asp Pro Ser Val Ala Gln Phe Asn
570             575                 580                 585 gtc tgc gga tgc tag                                                 2011
Val Cys Gly Cys <210> SEQ ID NO 18
<211> LENGTH: 605
<212> TYPE: PRT
<213> ORGANISM: Colletotrichum circinans

<400> SEQUENCE: 18

Met Lys Val Thr Ser Leu Phe Leu Ser Thr Ala Gly Ala Ser Ala
    -15

```
              210                 215                 220
Ser Lys Met Gly Asp Gln Leu Thr Glu Ile Thr Gly Val Val Thr Tyr
225                 230                 235                 240

Ala Phe Gly Phe Tyr Arg Ile Leu Pro Leu Thr Ala Val Ser Ile Ala
                245                 250                 255

Lys Asn Ala Thr Asn Asp Ala Pro Pro Thr Thr Leu Val Ser Arg Gly
                260                 265                 270

Asp Cys Arg Gly Ile Thr Ile Gly Asp Tyr Asn Val Glu Asn Leu Ala
            275                 280                 285

Pro Asn Ser Ala His Leu Pro Ala Val Ala Ala His Ile Val Asp Tyr
        290                 295                 300

Leu Lys Thr Pro Asp Leu Ile Phe Val Gln Glu Val Gln Asp Asn Thr
305                 310                 315                 320

Gly Ala Thr Asn Asn Gly Val Val Ser Ser Asn Val Thr Leu Ser Thr
                325                 330                 335

Leu Ala Ala Ala Ile Glu Ala Lys Ser Gly Val Phe Tyr Asp Phe Val
                340                 345                 350

Val Val Asp Pro Val Asp Gly Lys Asp Gly Ala Pro Gly Gly Asn
                355                 360                 365

Ile Arg Val Ala Tyr Leu Tyr Lys Pro Asp Val Ile Glu Leu Trp Lys
            370                 375                 380

Pro Asn Pro Gly Gly Ser Leu Asp Ala Asn Glu Val Leu Pro Gly Pro
385                 390                 395                 400

Gln Leu Lys Tyr Asn Pro Gly Arg Ile Ala Pro Thr Ser Ser Ala Trp
                405                 410                 415

Asp Ala Ser Arg Lys Pro Leu Val Ala Ala Trp Arg Ala Ile Lys Gly
                420                 425                 430

Pro Gln Asn Lys Ile Phe Phe Thr Val Asn Val His Phe Ala Ser Lys
            435                 440                 445

Gly Gly Ser Ser Ser Leu His Gly Asp Leu Arg Pro Pro Val Asn Gly
        450                 455                 460

Val Val Asn Pro Arg Ile Gln Gln Ala Glu Leu Thr Gly Asn Phe Ile
465                 470                 475                 480

Ala Glu Ile Leu Ala Ala Asp Pro Asn Ala Arg Ile Ile Ala Ala Gly
                485                 490                 495

Asp Phe Asn Glu Phe Ala Phe Val Glu Pro Leu Lys Ala Phe Thr Ala
                500                 505                 510

Lys Ser Gly Leu Ile Asp Leu Asp Glu Ala Val Gly Ile Pro Val Glu
            515                 520                 525

Glu Arg Tyr Thr Tyr Val Tyr Asp Met Asn Ala Gln Glu Leu Asp His
        530                 535                 540

Met Phe Val Ser Pro Ala Leu Ala His Lys Asn Gly Thr Lys Tyr Glu
545                 550                 555                 560

His Ile His Ile Asn Ser Trp Glu Leu Tyr Asp Asp Leu Val Ser Asp
                565                 570                 575

His Asp Pro Ser Val Ala Gln Phe Asn Val Cys Gly Cys
            580                 585

<210> SEQ ID NO 19
<211> LENGTH: 800
<212> TYPE: DNA
<213> ORGANISM: Clavicipitaceae
<220> FEATURE:
<221> NAME/KEY: CDS
<222> LOCATION: (1)..(72)
```

```
<220> FEATURE:
<221> NAME/KEY: sig_peptide
<222> LOCATION: (1)..(54)
<220> FEATURE:
<221> NAME/KEY: mat_peptide
<222> LOCATION: (55)..(797)
<220> FEATURE:
<221> NAME/KEY: CDS
<222> LOCATION: (142)..(275)
<220> FEATURE:
<221> NAME/KEY: CDS
<222> LOCATION: (329)..(485)
<220> FEATURE:
<221> NAME/KEY: CDS
<222> LOCATION: (549)..(797)

<400> SEQUENCE: 19 atg aag ttc tct tcg gca tct ctc gtc gtg tcc gct gct gcg ctt gtc       48
Met Lys Phe Ser Ser Ala Ser Leu Val Val Ser Ala Ala Ala Leu Val
        -15                 -10                 -5 ctc ggt gtg cct gtg cct gcg ccc gtaagcaatc ctactcctga cacgctgtca     102
Leu Gly Val Pro Val Pro Ala Pro
 -1   1               5 tcgtgtaaca aagcctaact cttttttttg ttcttctag ccc ggc atc cca agc        156
                                           Pro Gly Ile Pro Ser
                                                          10 acg tcg aca gcc aag act ctt ctt gct ggc ctc aag gtt gct acc ccg      204
Thr Ser Thr Ala Lys Thr Leu Leu Ala Gly Leu Lys Val Ala Thr Pro
         15                  20                  25 ttg agt ggt gat ggg tac tct cgt gat aag ttc cct act tgg gag acc      252
Leu Ser Gly Asp Gly Tyr Ser Arg Asp Lys Phe Pro Thr Trp Glu Thr
         30                  35                  40 att cag gga act tgc aat gct cg gtgagtttgc ccatctcctt ttgttcttgt     305
Ile Gln Gly Thr Cys Asn Ala Arg
         45                  50 caggttgcta atgcccatgg tag c gag ttt gtc att aag cga gac gga aca      356
                            Glu Phe Val Ile Lys Arg Asp Gly Thr
                                         55                  60 gac gtc aag acc aac agc gca tgc gtc gca gag tcc ggc aac tgg gtc      404
Asp Val Lys Thr Asn Ser Ala Cys Val Ala Glu Ser Gly Asn Trp Val
             65                  70                  75 tct ccg tat gac ggg gtc aag ttc acc gca gca cgc gat ctc gac att      452
Ser Pro Tyr Asp Gly Val Lys Phe Thr Ala Ala Arg Asp Leu Asp Ile
         80                  85                  90 gac cac atg gtt cca ctg aag aat gcc tgg att gtaagacgac tacctaacca   505
Asp His Met Val Pro Leu Lys Asn Ala Trp Ile
         95                 100 tcttgtcctc aattccacgt accttgtcta acttgcttgt cag tcc ggt gcc tca     560
                                             Ser Gly Ala Ser
                                                      105 caa tgg acc acc gag cag cgc aaa gct ctc gcc aac gac att acc cgt      608
Gln Trp Thr Thr Glu Gln Arg Lys Ala Leu Ala Asn Asp Ile Thr Arg
         110                 115                 120 ccc cag ctc tgg gcc gta tca gcc cat gcc aac cgc ggc aag agt gac      656
Pro Gln Leu Trp Ala Val Ser Ala His Ala Asn Arg Gly Lys Ser Asp
         125                 130                 135 gat agc ccc gac gag tgg aag cct cct ctg aag act ttc tgg tgc aca      704
Asp Ser Pro Asp Glu Trp Lys Pro Pro Leu Lys Thr Phe Trp Cys Thr
140                  145                 150                 155 tac gcc aag agt tgg gtg cag gtg aag agc ttc tat aag ttg act att      752
Tyr Ala Lys Ser Trp Val Gln Val Lys Ser Phe Tyr Lys Leu Thr Ile
                 160                 165                 170 acg gat acc gag aaa ggt gct ttg gct ggc atg ctg gat act tgc taa      800
Thr Asp Thr Glu Lys Gly Ala Leu Ala Gly Met Leu Asp Thr Cys
```

```
Thr Asp Thr Glu Lys Gly Ala Leu Ala Gly Met Leu Asp Thr Cys
            175                 180                 185
```

<210> SEQ ID NO 20
<211> LENGTH: 204
<212> TYPE: PRT
<213> ORGANISM: Clavicipitaceae

<400> SEQUENCE: 20

```
Met Lys Phe Ser Ser Ala Ser Leu Val Val Ser Ala Ala Leu Val
                -15                 -10                 -5
Leu Gly Val Pro Val Pro Ala Pro Pro Gly Ile Pro Ser Thr Ser Thr
        -1  1               5                  10
Ala Lys Thr Leu Leu Ala Gly Leu Lys Val Ala Thr Pro Leu Ser Gly
 15                  20                  25                  30
Asp Gly Tyr Ser Arg Asp Lys Phe Pro Thr Trp Glu Thr Ile Gln Gly
                 35                  40                  45
Thr Cys Asn Ala Arg Glu Phe Val Ile Lys Arg Asp Gly Thr Asp Val
             50                  55                  60
Lys Thr Asn Ser Ala Cys Val Ala Glu Ser Gly Asn Trp Val Ser Pro
 65                  70                  75
Tyr Asp Gly Val Lys Phe Thr Ala Ala Arg Asp Leu Asp Ile Asp His
 80                  85                  90
Met Val Pro Leu Lys Asn Ala Trp Ile Ser Gly Ala Ser Gln Trp Thr
 95                 100                 105                 110
Thr Glu Gln Arg Lys Ala Leu Ala Asn Asp Ile Thr Arg Pro Gln Leu
                115                 120                 125
Trp Ala Val Ser Ala His Ala Asn Arg Gly Lys Ser Asp Asp Ser Pro
                130                 135                 140
Asp Glu Trp Lys Pro Pro Leu Lys Thr Phe Trp Cys Thr Tyr Ala Lys
            145                 150                 155
Ser Trp Val Gln Val Lys Ser Phe Tyr Lys Leu Thr Ile Thr Asp Thr
 160                 165                 170
Glu Lys Gly Ala Leu Ala Gly Met Leu Asp Thr Cys
175                 180                 185
```

<210> SEQ ID NO 21
<211> LENGTH: 921
<212> TYPE: DNA
<213> ORGANISM: Preussia aemulans
<220> FEATURE:
<221> NAME/KEY: CDS
<222> LOCATION: (1)..(918)
<220> FEATURE:
<221> NAME/KEY: sig_peptide
<222> LOCATION: (1)..(75)
<220> FEATURE:
<221> NAME/KEY: mat_peptide
<222> LOCATION: (76)..(918)

<400> SEQUENCE: 21

```
atg ttg cta tca aaa acc cac ccg att ctc tgc gca acc ttt gga att      48
Met Leu Leu Ser Lys Thr His Pro Ile Leu Cys Ala Thr Phe Gly Ile
-25                 -20                 -15                 -10 gtc tca ttc tcc acc ctt tcg acc agc ctc agc gtc cca cgc gcc gct      96
Val Ser Phe Ser Thr Leu Ser Thr Ser Leu Ser Val Pro Arg Ala Ala
                 -5                  -1  1               5 ccc gcc tcc att gat ctc cgc ccc aac gat ctc ctc aaa tct acg cgc     144
Pro Ala Ser Ile Asp Leu Arg Pro Asn Asp Leu Leu Lys Ser Thr Arg
            10                  15                  20
```

```
ggc cct tat ggc cca aat ggc cgt ggt cgt acg gga agc aca tcg gca      192
Gly Pro Tyr Gly Pro Asn Gly Arg Gly Arg Thr Gly Ser Thr Ser Ala
     25                  30                  35 acg gca ttc aat gag ctg cag ttg aat ctc tgc aac tcc ggc ttt gcc      240
Thr Ala Phe Asn Glu Leu Gln Leu Asn Leu Cys Asn Ser Gly Phe Ala
 40                  45                  50                  55 aac tgc tat gcc aat ggc gac tcc atc cct gaa ggc ggc gaa ctg atc      288
Asn Cys Tyr Ala Asn Gly Asp Ser Ile Pro Glu Gly Gly Glu Leu Ile
                     60                  65                  70 tac gca act ggg cct aac gtc gta acc atc aac gaa att tgt tcg aac      336
Tyr Ala Thr Gly Pro Asn Val Val Thr Ile Asn Glu Ile Cys Ser Asn
                 75                  80                  85 gat gtc tcg aca ctc cag tcg tac ttg ggt gaa gca tgg cca acg gat      384
Asp Val Ser Thr Leu Gln Ser Tyr Leu Gly Glu Ala Trp Pro Thr Asp
             90                  95                 100 tat acg tat tcg gtt ttc atg ccc gcc atc gat cgt cgc acc aat caa      432
Tyr Thr Tyr Ser Val Phe Met Pro Ala Ile Asp Arg Arg Thr Asn Gln
        105                 110                 115 cag tat aag tgc aag aac ggt gca cag tat ggc agc gtg gtg ctg ggc      480
Gln Tyr Lys Cys Lys Asn Gly Ala Gln Tyr Gly Ser Val Val Leu Gly
120                 125                 130                 135 cgt gtt ccc agt gca act tgg agc gga att gat gcc tat ggt ggg aaa      528
Arg Val Pro Ser Ala Thr Trp Ser Gly Ile Asp Ala Tyr Gly Gly Lys
                140                 145                 150 tac agc aca caa gac gac agc aac gaa ttg agg att ttt gtg tgc gtc      576
Tyr Ser Thr Gln Asp Asp Ser Asn Glu Leu Arg Ile Phe Val Cys Val
            155                 160                 165 gcc gcc cga ggg gac cat ttt gca tgt acc acc cac ttg acc tcc aag      624
Ala Ala Arg Gly Asp His Phe Ala Cys Thr Thr His Leu Thr Ser Lys
        170                 175                 180 tcc gaa ccg ttg gct atg act cag tgc aag gca ctg atg tct gat gcg      672
Ser Glu Pro Leu Ala Met Thr Gln Cys Lys Ala Leu Met Ser Asp Ala
    185                 190                 195 att ccg tat ctg aag agc cag agt gga tct acg act agg aca gtt gtt      720
Ile Pro Tyr Leu Lys Ser Gln Ser Gly Ser Thr Thr Arg Thr Val Val
200                 205                 210                 215 gct ggg gat ttc aat cta gag tat gac act ggg gat gca gaa aat atg      768
Ala Gly Asp Phe Asn Leu Glu Tyr Asp Thr Gly Asp Ala Glu Asn Met
                220                 225                 230 cag aag tgt gta ccg tcg gga tgg act agg aag ggc gat gga agt gtg      816
Gln Lys Cys Val Pro Ser Gly Trp Thr Arg Lys Gly Asp Gly Ser Val
            235                 240                 245 cag cat act atc ttt gac aat act ttg aag ttt ggg agt tcg aag aag      864
Gln His Thr Ile Phe Asp Asn Thr Leu Lys Phe Gly Ser Ser Lys Lys
        250                 255                 260 tat ggg ctt agt tat acg gat cat gat ggg tgg ttg gtg aag atg aca      912
Tyr Gly Leu Ser Tyr Thr Asp His Asp Gly Trp Leu Val Lys Met Thr
    265                 270                 275 gtt ggt taa                                                          921
Val Gly
280

<210> SEQ ID NO 22
<211> LENGTH: 306
<212> TYPE: PRT
<213> ORGANISM: Preussia aemulans

<400> SEQUENCE: 22

Met Leu Leu Ser Lys Thr His Pro Ile Leu Cys Ala Thr Phe Gly Ile
-25                 -20                 -15                 -10
```

```
Val Ser Phe Ser Thr Leu Ser Thr Ser Leu Ser Val Pro Arg Ala Ala
            -5                  -1  1               5
Pro Ala Ser Ile Asp Leu Arg Pro Asn Asp Leu Leu Lys Ser Thr Arg
         10              15                  20
Gly Pro Tyr Gly Pro Asn Gly Arg Gly Arg Thr Gly Ser Thr Ser Ala
     25              30                  35
Thr Ala Phe Asn Glu Leu Gln Leu Asn Leu Cys Asn Ser Gly Phe Ala
 40              45                  50                  55
Asn Cys Tyr Ala Asn Gly Asp Ser Ile Pro Glu Gly Gly Glu Leu Ile
             60                  65                  70
Tyr Ala Thr Gly Pro Asn Val Val Thr Ile Asn Glu Ile Cys Ser Asn
         75                  80                  85
Asp Val Ser Thr Leu Gln Ser Tyr Leu Gly Glu Ala Trp Pro Thr Asp
         90                  95                 100
Tyr Thr Tyr Ser Val Phe Met Pro Ala Ile Asp Arg Arg Thr Asn Gln
        105                 110                 115
Gln Tyr Lys Cys Lys Asn Gly Ala Gln Tyr Gly Ser Val Val Leu Gly
120                 125                 130                 135
Arg Val Pro Ser Ala Thr Trp Ser Gly Ile Asp Ala Tyr Gly Gly Lys
                140                 145                 150
Tyr Ser Thr Gln Asp Asp Ser Asn Glu Leu Arg Ile Phe Val Cys Val
                155                 160                 165
Ala Ala Arg Gly Asp His Phe Ala Cys Thr Thr His Leu Thr Ser Lys
                170                 175                 180
Ser Glu Pro Leu Ala Met Thr Gln Cys Lys Ala Leu Met Ser Asp Ala
185                 190                 195
Ile Pro Tyr Leu Lys Ser Gln Ser Gly Ser Thr Thr Arg Thr Val Val
200                 205                 210                 215
Ala Gly Asp Phe Asn Leu Glu Tyr Asp Thr Gly Asp Ala Glu Asn Met
                220                 225                 230
Gln Lys Cys Val Pro Ser Gly Trp Thr Arg Lys Gly Asp Gly Ser Val
                235                 240                 245
Gln His Thr Ile Phe Asp Asn Thr Leu Lys Phe Gly Ser Ser Lys Lys
                250                 255                 260
Tyr Gly Leu Ser Tyr Thr Asp His Asp Gly Trp Leu Val Lys Met Thr
                265                 270                 275
Val Gly
280

<210> SEQ ID NO 23
<211> LENGTH: 2122
<212> TYPE: DNA
<213> ORGANISM: Trichurus spiralis
<220> FEATURE:
<221> NAME/KEY: CDS
<222> LOCATION: (1)..(284)
<220> FEATURE:
<221> NAME/KEY: sig_peptide
<222> LOCATION: (1)..(48)
<220> FEATURE:
<221> NAME/KEY: mat_peptide
<222> LOCATION: (49)..(2119)
<220> FEATURE:
<221> NAME/KEY: CDS
<222> LOCATION: (365)..(741)
<220> FEATURE:
<221> NAME/KEY: CDS
<222> LOCATION: (834)..(1651)
<220> FEATURE:
<221> NAME/KEY: CDS
```

<222> LOCATION: (1796)..(2119)

<400> SEQUENCE: 23

```
atg aag act ttc gga gct ctg ttt gca gcc atc tcc ggc gct acg gcg      48
Met Lys Thr Phe Gly Ala Leu Phe Ala Ala Ile Ser Gly Ala Thr Ala
    -15                 -10                 -5                  -1 ctg agc atc gcc gag atc aac ggc aat cgc ttc atc tcg ccg tac aat      96
Leu Ser Ile Ala Glu Ile Asn Gly Asn Arg Phe Ile Ser Pro Tyr Asn
 1               5                  10                  15 ggc cag act gtc acc aac gtc gag ggc cta gtc act gcc gtg agc agc     144
Gly Gln Thr Val Thr Asn Val Glu Gly Leu Val Thr Ala Val Ser Ser
                20                  25                  30 gct ggc ttc tac ctc cgg tcg acc aag gcg gat cgc gat gcg gcg acg     192
Ala Gly Phe Tyr Leu Arg Ser Thr Lys Ala Asp Arg Asp Ala Ala Thr
             35                  40                  45 tcc gag ggc ttg tac gtg tac gga agc aac gcg gcg aag acg gtg act     240
Ser Glu Gly Leu Tyr Val Tyr Gly Ser Asn Ala Ala Lys Thr Val Thr
         50                  55                  60 gtg gga gac att att acc gtc agt ggc aag gtc tcg gaa tac cg          284
Val Gly Asp Ile Ile Thr Val Ser Gly Lys Val Ser Glu Tyr Arg
 65                  70                  75 gtaagtggac ttgtgtcccc gcaaggccct gtgcctactg ccgtgtagag cgcgggaatt   344
gactgccgtt gattgtatag a tcc aac gtc gac tac ctc tac ctc acc gag     395
                        Ser Asn Val Asp Tyr Leu Tyr Leu Thr Glu
                         80                  85 ctt acc tcg ccc cag aac att acc att gtc tcg tct ggc gcc aag gtc     443
Leu Thr Ser Pro Gln Asn Ile Thr Ile Val Ser Ser Gly Ala Lys Val
 90                  95                 100                 105 aag ccc ctt gtc atc ggc aag gac acc tac tcc ccg ccg acc agc aag     491
Lys Pro Leu Val Ile Gly Lys Asp Thr Tyr Ser Pro Pro Thr Ser Lys
                110                 115                 120 ttc tcc agc ctg gat gag gga ggt ctc ttt ggc gtg ccc aac aat gtt     539
Phe Ser Ser Leu Asp Glu Gly Gly Leu Phe Gly Val Pro Asn Asn Val
            125                 130                 135 tcg cgc atc tcc gtc gca aac ccg aag ctc cag ccc aag aag tac gga     587
Ser Arg Ile Ser Val Ala Asn Pro Lys Leu Gln Pro Lys Lys Tyr Gly
        140                 145                 150 ttg gac ttc tgg gag agc att gtg ggt gag ctt gtc act atc aag gag     635
Leu Asp Phe Trp Glu Ser Ile Val Gly Glu Leu Val Thr Ile Lys Glu
155                 160                 165 gcg tat gga gtc ggc cga cca aac cag tac ggc gac gtt tgg gtg cgg     683
Ala Tyr Gly Val Gly Arg Pro Asn Gln Tyr Gly Asp Val Trp Val Arg
170                 175                 180                 185 gga aac tgg aag gtc acc ggc aag aac aag cag ggt ggt ttg acc atg     731
Gly Asn Trp Lys Val Thr Gly Lys Asn Lys Gln Gly Gly Leu Thr Met
                190                 195                 200 acc gac ggc g gtatgtattt tccaagttat tcatcacgtc cagttccctc           781
Thr Asp Gly ggtggcggac ggctcagtag aagtgaatgc tgacagtgat tacttgatat ag ac gcc    838
                                                          Asp Ala
                                                           205 aac cct gaa acc atc atc atc ggc acc ccc ctt gat gcc agc aag aac     886
Asn Pro Glu Thr Ile Ile Ile Gly Thr Pro Leu Asp Ala Ser Lys Asn
             210                 215                 220 ccc act gat acc aag atg ggc gac tac tat ggc gat atc acg ggt gta     934
Pro Thr Asp Thr Lys Met Gly Asp Tyr Tyr Gly Asp Ile Thr Gly Val
         225                 230                 235 gtg tct tac gcg ttt gga ttc tat cgc gtc ctc cct ctg act cac atc     982
Val Ser Tyr Ala Phe Gly Phe Tyr Arg Val Leu Pro Leu Thr His Ile
```

```
                240                 245                 250
act ccc gag cgc aac tct tcc gca gcc cac ccc ccc gta agc ttt acc    1030
Thr Pro Glu Arg Asn Ser Ser Ala Ala His Pro Pro Val Ser Phe Thr
255                 260                 265                 270 agc aag ggc agc tgc aag ggc atc acc gtg gcc gac tac aac gcg gag    1078
Ser Lys Gly Ser Cys Lys Gly Ile Thr Val Ala Asp Tyr Asn Ala Glu
                275                 280                 285 aac ctt gcc ccg acc agc acc cac ctc ccc cag gtc gtt gac cag att    1126
Asn Leu Ala Pro Thr Ser Thr His Leu Pro Gln Val Val Asp Gln Ile
            290                 295                 300 atc aac atg ctg aag acc ccc gac ctc ttg ttc ctg cag gag gtc cag    1174
Ile Asn Met Leu Lys Thr Pro Asp Leu Leu Phe Leu Gln Glu Val Gln
        305                 310                 315 gac aac tct ggt tcc aag aat gac ggc gtt gtc agt gcc aac gtc acc    1222
Asp Asn Ser Gly Ser Lys Asn Asp Gly Val Val Ser Ala Asn Val Thr
320                 325                 330 ctg acc acc ctc gtg gac agc cta ttc gag acc agc ggc gtg cag tac    1270
Leu Thr Thr Leu Val Asp Ser Leu Phe Glu Thr Ser Gly Val Gln Tyr
335                 340                 345                 350 gcc ttc gct gag gtg gag ccg gag aac ctg aag gac ggc ggt caa ccc    1318
Ala Phe Ala Glu Val Glu Pro Glu Asn Leu Lys Asp Gly Gly Gln Pro
                355                 360                 365 ggc ggg aac atc cgc gtc gcc tat ctc tac cgc ccc gat gtc gtc gag    1366
Gly Gly Asn Ile Arg Val Ala Tyr Leu Tyr Arg Pro Asp Val Val Glu
            370                 375                 380 ctg tac aag ccc aac cag ggt gga agc aac gac gcc aac gag gtc ctg    1414
Leu Tyr Lys Pro Asn Gln Gly Gly Ser Asn Asp Ala Asn Glu Val Leu
        385                 390                 395 ccc ggg cca ttg ctc aag tac aac ccc ggc cgc atc gac ccc gcc aac    1462
Pro Gly Pro Leu Leu Lys Tyr Asn Pro Gly Arg Ile Asp Pro Ala Asn
400                 405                 410 gcg gcg tgg gtc gat agc cgc aag ccc ctg gtg gcc atg tgg cgc gcc    1510
Ala Ala Trp Val Asp Ser Arg Lys Pro Leu Val Ala Met Trp Arg Ala
415                 420                 425                 430 gtc aag ggt ggg aag aag ccc ttc ttc act gtg aat gtt cac ttc acg    1558
Val Lys Gly Gly Lys Lys Pro Phe Phe Thr Val Asn Val His Phe Thr
                435                 440                 445 agc aag gga gga tct act agc ctg cac ggc gat gct cga ccc cct gtt    1606
Ser Lys Gly Gly Ser Thr Ser Leu His Gly Asp Ala Arg Pro Pro Val
            450                 455                 460 aac ttg gga gtt gac caa cgg acc atg cag gcc gag gtc acg gct        1651
Asn Leu Gly Val Asp Gln Arg Thr Met Gln Ala Glu Val Thr Ala
        465                 470                 475 gtaagttttg tttgtttgat ttaacgccc cccaaccta ctccgtctca gagcttggtg    1711
ttccggcatg ccgaggacga ggaagacgga aaattggctt gaaagaaaaa ttgtgcgatg   1771
aatcgcgact gacattatct ctag gac ttc att gcc cag atc ctc gag gag     1822
                          Asp Phe Ile Ala Gln Ile Leu Glu Glu
                                      480                 485 gac aag aag gcg tac gtc atc gct gcc ggt gac ttc aac gag ttc gtc    1870
Asp Lys Lys Ala Tyr Val Ile Ala Ala Gly Asp Phe Asn Glu Phe Val
                490                 495                 500 cag gtt cag ccg ctg cag acc ttc gcc aag aag tcc ggc ctg acc gag    1918
Gln Val Gln Pro Leu Gln Thr Phe Ala Lys Lys Ser Gly Leu Thr Glu
            505                 510                 515 ctc gat gag gtg gct aag atc tcc atg aat gag cgc tac acg tac ctg    1966
Leu Asp Glu Val Ala Lys Ile Ser Met Asn Glu Arg Tyr Thr Tyr Leu
        520                 525                 530 ttc gat atg aac tcg gag gcc ctc gac cac atg tac gtg agc aag ggt    2014
```

-continued

```
              Phe Asp Met Asn Ser Glu Ala Leu Asp His Met Tyr Val Ser Lys Gly
              535                 540                 545                 550 att ggc aag tca gtc aag tac gag cat atg aac ctc aac acc tgg cag              2062
Ile Gly Lys Ser Val Lys Tyr Glu His Met Asn Leu Asn Thr Trp Gln
                        555                 560                 565 aac tac gac gac cag gtg agc gac cac gac ccg agc gtc gcg agg ttc              2110
Asn Tyr Asp Asp Gln Val Ser Asp His Asp Pro Ser Val Ala Arg Phe
                570                 575                 580 gac ctt tgc tag                                                              2122
Asp Leu Cys
        585

<210> SEQ ID NO 24
<211> LENGTH: 601
<212> TYPE: PRT
<213> ORGANISM: Trichurus spiralis

<400> SEQUENCE: 24

Met Lys Thr Phe Gly Ala Leu Phe Ala Ala Ile Ser Gly Ala Thr Ala
        -15                 -10                  -5                  -1

Leu Ser Ile Ala Glu Ile Asn Gly Asn Arg Phe Ile Ser Pro Tyr Asn
1                5                  10                  15

Gly Gln Thr Val Thr Asn Val Glu Gly Leu Val Thr Ala Val Ser Ser
                20                  25                  30

Ala Gly Phe Tyr Leu Arg Ser Thr Lys Ala Asp Arg Asp Ala Ala Thr
        35                  40                  45

Ser Glu Gly Leu Tyr Val Tyr Gly Ser Asn Ala Ala Lys Thr Val Thr
50                  55                  60

Val Gly Asp Ile Ile Thr Val Ser Gly Lys Val Ser Glu Tyr Arg Ser
65                  70                  75                  80

Asn Val Asp Tyr Leu Tyr Leu Thr Glu Leu Thr Ser Pro Gln Asn Ile
                85                  90                  95

Thr Ile Val Ser Ser Gly Ala Lys Val Lys Pro Leu Val Ile Gly Lys
            100                 105                 110

Asp Thr Tyr Ser Pro Pro Thr Ser Lys Phe Ser Ser Leu Asp Glu Gly
        115                 120                 125

Gly Leu Phe Gly Val Pro Asn Asn Val Ser Arg Ile Ser Val Ala Asn
130                 135                 140

Pro Lys Leu Gln Pro Lys Lys Tyr Gly Leu Asp Phe Trp Glu Ser Ile
145                 150                 155                 160

Val Gly Glu Leu Val Thr Ile Lys Glu Ala Tyr Gly Val Gly Arg Pro
                165                 170                 175

Asn Gln Tyr Gly Asp Val Trp Val Arg Gly Asn Trp Lys Val Thr Gly
            180                 185                 190

Lys Asn Lys Gln Gly Gly Leu Thr Met Thr Asp Gly Asp Ala Asn Pro
        195                 200                 205

Glu Thr Ile Ile Gly Thr Pro Leu Asp Ala Ser Lys Asn Pro Thr
        210                 215                 220

Asp Thr Lys Met Gly Asp Tyr Tyr Gly Asp Ile Thr Gly Val Val Ser
225                 230                 235                 240

Tyr Ala Phe Gly Phe Tyr Arg Val Leu Pro Leu Thr His Ile Thr Pro
                245                 250                 255

Glu Arg Asn Ser Ser Ala Ala His Pro Pro Val Ser Phe Thr Ser Lys
            260                 265                 270

Gly Ser Cys Lys Gly Ile Thr Val Ala Asp Tyr Asn Ala Glu Asn Leu
        275                 280                 285
```

Ala Pro Thr Ser Thr His Leu Pro Gln Val Val Asp Gln Ile Ile Asn
            290                 295                 300

Met Leu Lys Thr Pro Asp Leu Leu Phe Leu Gln Glu Val Gln Asp Asn
305                 310                 315                 320

Ser Gly Ser Lys Asn Asp Gly Val Val Ser Ala Asn Val Thr Leu Thr
                325                 330                 335

Thr Leu Val Asp Ser Leu Phe Glu Thr Ser Gly Val Gln Tyr Ala Phe
            340                 345                 350

Ala Glu Val Glu Pro Glu Asn Leu Lys Asp Gly Gly Gln Pro Gly Gly
        355                 360                 365

Asn Ile Arg Val Ala Tyr Leu Tyr Arg Pro Asp Val Val Glu Leu Tyr
370                 375                 380

Lys Pro Asn Gln Gly Gly Ser Asn Asp Ala Asn Glu Val Leu Pro Gly
385                 390                 395                 400

Pro Leu Leu Lys Tyr Asn Pro Gly Arg Ile Asp Pro Ala Asn Ala Ala
                405                 410                 415

Trp Val Asp Ser Arg Lys Pro Leu Val Ala Met Trp Arg Ala Val Lys
            420                 425                 430

Gly Gly Lys Lys Pro Phe Phe Thr Val Asn Val His Phe Thr Ser Lys
        435                 440                 445

Gly Gly Ser Thr Ser Leu His Gly Asp Ala Arg Pro Pro Val Asn Leu
450                 455                 460

Gly Val Asp Gln Arg Thr Met Gln Ala Glu Val Thr Ala Asp Phe Ile
465                 470                 475                 480

Ala Gln Ile Leu Glu Glu Asp Lys Lys Ala Tyr Val Ile Ala Ala Gly
                485                 490                 495

Asp Phe Asn Glu Phe Val Gln Val Gln Pro Leu Gln Thr Phe Ala Lys
            500                 505                 510

Lys Ser Gly Leu Thr Glu Leu Asp Glu Val Ala Lys Ile Ser Met Asn
        515                 520                 525

Glu Arg Tyr Thr Tyr Leu Phe Asp Met Asn Ser Glu Ala Leu Asp His
530                 535                 540

Met Tyr Val Ser Lys Gly Ile Gly Lys Ser Val Lys Tyr Glu His Met
545                 550                 555                 560

Asn Leu Asn Thr Trp Gln Asn Tyr Asp Asp Gln Val Ser Asp His Asp
                565                 570                 575

Pro Ser Val Ala Arg Phe Asp Leu Cys
            580                 585

```
<210> SEQ ID NO 25
<211> LENGTH: 2088
<212> TYPE: DNA
<213> ORGANISM: Pyrenochaetopsis sp.
<220> FEATURE:
<221> NAME/KEY: sig_peptide
<222> LOCATION: (1)..(60)
<220> FEATURE:
<221> NAME/KEY: CDS
<222> LOCATION: (1)..(1045)
<220> FEATURE:
<221> NAME/KEY: mat_peptide
<222> LOCATION: (61)..(2085)
<220> FEATURE:
<221> NAME/KEY: CDS
<222> LOCATION: (1120)..(1592)
<220> FEATURE:
<221> NAME/KEY: CDS
<222> LOCATION: (1768)..(2085)
```

-continued

```
<400> SEQUENCE: 25 atg gcc cct ctc acc acc ctc ctc acc ctc cta aca tcc ctc acc ctc      48
Met Ala Pro Leu Thr Thr Leu Leu Thr Leu Leu Thr Ser Leu Thr Leu
-20             -15                 -10                 -5 tca gca agc gcc acc aca atc gcc gaa ata aac ggc ccc gcc ttc ctc      96
Ser Ala Ser Ala Thr Thr Ile Ala Glu Ile Asn Gly Pro Ala Phe Leu
        -1  1             5                  10 tcc ccc ttc aaa ggc caa acc gtt gca aac gtc agc gga atc atc acc     144
Ser Pro Phe Lys Gly Gln Thr Val Ala Asn Val Ser Gly Ile Ile Thr
             15                 20                  25 gcc aaa gga ccc gac ggc ctt tgg atc cgg tct aca ctg cca gac cgc     192
Ala Lys Gly Pro Asp Gly Leu Trp Ile Arg Ser Thr Leu Pro Asp Arg
         30                 35                  40 gat gag cgc acc tcg gaa tct ctg tac gtg ttt ggc agt aaa ttc ggc     240
Asp Glu Arg Thr Ser Glu Ser Leu Tyr Val Phe Gly Ser Lys Phe Gly
45                  50                  55                  60 gcc aat ctg act gtc ggc gac tct att atc ctg gga gga aag gtg caa     288
Ala Asn Leu Thr Val Gly Asp Ser Ile Ile Leu Gly Gly Lys Val Gln
                 65                  70                  75 gag tac agg agt agt aag gat tac att tac ctg act gag ctg tca agc     336
Glu Tyr Arg Ser Ser Lys Asp Tyr Ile Tyr Leu Thr Glu Leu Ser Ser
             80                  85                  90 ccg gtg ctg gcg aaa aag gtc agc agt ggg aat aaa gtc gac gca ctc     384
Pro Val Leu Ala Lys Lys Val Ser Ser Gly Asn Lys Val Asp Ala Leu
         95                 100                 105 gtc att ggc aag gat acg cgt gac ccc ccg acc gag cag tat agt agt     432
Val Ile Gly Lys Asp Thr Arg Asp Pro Pro Thr Glu Gln Tyr Ser Ser
110                 115                 120 ttg gac ggc ggc gat gtc ttc gcc gta ccg aac aac gtc tcg cag atc     480
Leu Asp Gly Gly Asp Val Phe Ala Val Pro Asn Asn Val Ser Gln Ile
125                 130                 135                 140 agc gtt gcg aac ccc gaa ttg cag ccg aag aag tac ggc ctc gac ttc     528
Ser Val Ala Asn Pro Glu Leu Gln Pro Lys Lys Tyr Gly Leu Asp Phe
                145                 150                 155 tgg gag agt ctg agc ggc gaa ctg gtg acg gtg aag aag cct act gcg     576
Trp Glu Ser Leu Ser Gly Glu Leu Val Thr Val Lys Lys Pro Thr Ala
            160                 165                 170 ctc acc aag ccg aat cag tac ggt gat acg tgg gtt gtt ggt aac tgg     624
Leu Thr Lys Pro Asn Gln Tyr Gly Asp Thr Trp Val Val Gly Asn Trp
        175                 180                 185 aag gtt acg ggc cgc aat gac cgc gat ggc ctg acg ttg acg gac aaa     672
Lys Val Thr Gly Arg Asn Asp Arg Asp Gly Leu Thr Leu Thr Asp Lys
    190                 195                 200 gat gcg aat cct gaa gcc atc atc att ggc acg ccg ctt gat gga acg     720
Asp Ala Asn Pro Glu Ala Ile Ile Ile Gly Thr Pro Leu Asp Gly Thr
205                 210                 215                 220 aag aac ccc act gat act cgc atg ggt gac tcg gtt gat gag att acc     768
Lys Asn Pro Thr Asp Thr Arg Met Gly Asp Ser Val Asp Glu Ile Thr
                225                 230                 235 ggt gtc atc acg tac gcg ttt ggg tac tac cgt atc ttg cct ttg acg     816
Gly Val Ile Thr Tyr Ala Phe Gly Tyr Tyr Arg Ile Leu Pro Leu Thr
            240                 245                 250 gct atc aag gtt acc aag tcg cag aag cca gct ctt ccc aag ccg act     864
Ala Ile Lys Val Thr Lys Ser Gln Lys Pro Ala Leu Pro Lys Pro Thr
        255                 260                 265 aag ctc gag tcg aag gga aag tgc gat gga atc acc ttt gga gat tat     912
Lys Leu Glu Ser Lys Gly Lys Cys Asp Gly Ile Thr Phe Gly Asp Tyr
    270                 275                 280 aat gtc gag aat ctg gcg gcc aac tcc tcg cat ctc cct tct ata gct     960
```

```
                Asn Val Glu Asn Leu Ala Ala Asn Ser Ser His Leu Pro Ser Ile Ala
                285                 290                 295                 300 gcg cat att gtc aat tac atg aag agc ccg gat gtt ctc ttc gtt cag        1008
Ala His Ile Val Asn Tyr Met Lys Ser Pro Asp Val Leu Phe Val Gln
            305                 310                 315 gag att cag gac gat gat ggt cct aca aac gac gca g gtaagtactt           1055
Glu Ile Gln Asp Asp Asp Gly Pro Thr Asn Asp Ala
320                 325 cctaaccttt aaagcaaaac atcaacttct taccgcgttg tgatcttata ctgagatctg      1115 ccag tc gta tcc gcc aac ctt acc ctc tcc aca ctc gtc gca gcc atc       1163
      Val Val Ser Ala Asn Leu Thr Leu Ser Thr Leu Val Ala Ala Ile
          330                 335                 340 tcc tca gcc ggc ggc cca acc tac gcc ttc gca gac atc gat ccc gtg        1211
Ser Ser Ala Gly Gly Pro Thr Tyr Ala Phe Ala Asp Ile Asp Pro Val
    345                 350                 355 gac gac caa gac ggc ggc gaa ccc ggc ggc aat atc cgc gtc gcc tac        1259
Asp Asp Gln Asp Gly Gly Glu Pro Gly Gly Asn Ile Arg Val Ala Tyr
360                 365                 370                 375 ctc tac aag ccc tcg cta atc cgc ctc tac aag ccc aac cca ggt ggc        1307
Leu Tyr Lys Pro Ser Leu Ile Arg Leu Tyr Lys Pro Asn Pro Gly Gly
            380                 385                 390 tct ctc gat gcc aac gca gtc aac gat gga ccc acg ctc aag tac aac        1355
Ser Leu Asp Ala Asn Ala Val Asn Asp Gly Pro Thr Leu Lys Tyr Asn
        395                 400                 405 ccc ggc cgt att gac cct acc aac ccg gct tgg act gcg agc cgc aag        1403
Pro Gly Arg Ile Asp Pro Thr Asn Pro Ala Trp Thr Ala Ser Arg Lys
    410                 415                 420 ccc ctc gtg gcg cag tgg gag gtc att ggt aag agt aat gcg aag aag        1451
Pro Leu Val Ala Gln Trp Glu Val Ile Gly Lys Ser Asn Ala Lys Lys
425                 430                 435 ttg gat acg ttc ttt acg gtg aat gtg cac ttt ggg tcc aag ggt gga       1499
Leu Asp Thr Phe Phe Thr Val Asn Val His Phe Gly Ser Lys Gly Gly
440                 445                 450                 455 agc agc agc ttg cac ggt gat gct cga ccg cct gtc aat ggc ggg gtg       1547
Ser Ser Ser Leu His Gly Asp Ala Arg Pro Pro Val Asn Gly Gly Val
            460                 465                 470 gag gat agg ctc gcg cag gca cag ctt acg gcg aac ttt gtc aag            1592
Glu Asp Arg Leu Ala Gln Ala Gln Leu Thr Ala Asn Phe Val Lys
        475                 480                 485 gtacgttttg aagtctcttt tggtcctgtc cagatgagcg tgaaatggat gtaggctgct     1652
actaaagcag cttatatcgg actgtaccat gtggtgcgaa aagcgccacg ttcacgcaca     1712
ataggacttc ccactcgcac aactcggcga gagcacaaag ctgacagcgc cctag gac     1770
                                                              Asp att ctc tcc aaa gac aag gac gcc cgc atc atc aca tca ggc gac atg       1818
Ile Leu Ser Lys Asp Lys Asp Ala Arg Ile Ile Thr Ser Gly Asp Met
        490                 495                 500 aac gag ttc gcc ttc gtc gag cct ctg gag cag ctc aaa gac atc tca       1866
Asn Glu Phe Ala Phe Val Glu Pro Leu Glu Gln Leu Lys Asp Ile Ser
    505                 510                 515 ggc ctc aag gac cta gat gtt gaa gcc ggc atc gac aag ctc gaa agg       1914
Gly Leu Lys Asp Leu Asp Val Glu Ala Gly Ile Asp Lys Leu Glu Arg
520                 525                 530                 535 tac acc tac ctc ttc gac atg aat gct cag cag ctt gac cac aca ttc       1962
Tyr Thr Tyr Leu Phe Asp Met Asn Ala Gln Gln Leu Asp His Thr Phe
            540                 545                 550 gtg tcg aag gcg att gcg aag gag gat ccc aag tac gag cat ata cat       2010
Val Ser Lys Ala Ile Ala Lys Glu Asp Pro Lys Tyr Glu His Ile His
        555                 560                 565
```

```
atc aat acc tgg gtg gac tat gcg gac cag atc agc gac cac gat ccg    2058
Ile Asn Thr Trp Val Asp Tyr Ala Asp Gln Ile Ser Asp His Asp Pro
    570                 575                 580 tcg gtg gct aga ctg agt gta tgc gcg taa                            2088
Ser Val Ala Arg Leu Ser Val Cys Ala
    585                 590
```

<210> SEQ ID NO 26
<211> LENGTH: 612
<212> TYPE: PRT
<213> ORGANISM: Pyrenochaetopsis sp.

<400> SEQUENCE: 26

```
Met Ala Pro Leu Thr Thr Leu Leu Thr Leu Leu Thr Ser Leu Thr Leu
-20             -15                 -10                 -5

Ser Ala Ser Ala Thr Thr Ile Ala Glu Ile Asn Gly Pro Ala Phe Leu
            -1  1               5                   10

Ser Pro Phe Lys Gly Gln Thr Val Ala Asn Val Ser Gly Ile Ile Thr
        15                  20                  25

Ala Lys Gly Pro Asp Gly Leu Trp Ile Arg Ser Thr Leu Pro Asp Arg
    30                  35                  40

Asp Glu Arg Thr Ser Glu Ser Leu Tyr Val Phe Gly Ser Lys Phe Gly
45                  50                  55                  60

Ala Asn Leu Thr Val Gly Asp Ser Ile Ile Leu Gly Gly Lys Val Gln
                65                  70                  75

Glu Tyr Arg Ser Ser Lys Asp Tyr Ile Tyr Leu Thr Glu Leu Ser Ser
                80                  85                  90

Pro Val Leu Ala Lys Lys Val Ser Ser Gly Asn Lys Val Asp Ala Leu
            95                  100                 105

Val Ile Gly Lys Asp Thr Arg Asp Pro Pro Thr Glu Gln Tyr Ser Ser
    110                 115                 120

Leu Asp Gly Gly Asp Val Phe Ala Val Pro Asn Asn Val Ser Gln Ile
125                 130                 135                 140

Ser Val Ala Asn Pro Glu Leu Gln Pro Lys Lys Tyr Gly Leu Asp Phe
                145                 150                 155

Trp Glu Ser Leu Ser Gly Glu Leu Val Thr Val Lys Lys Pro Thr Ala
                160                 165                 170

Leu Thr Lys Pro Asn Gln Tyr Gly Asp Thr Trp Val Val Gly Asn Trp
            175                 180                 185

Lys Val Thr Gly Arg Asn Asp Arg Asp Gly Leu Thr Leu Thr Asp Lys
    190                 195                 200

Asp Ala Asn Pro Glu Ala Ile Ile Ile Gly Thr Pro Leu Asp Gly Thr
205                 210                 215                 220

Lys Asn Pro Thr Asp Thr Arg Met Gly Asp Ser Val Asp Glu Ile Thr
                225                 230                 235

Gly Val Ile Thr Tyr Ala Phe Gly Tyr Tyr Arg Ile Leu Pro Leu Thr
                240                 245                 250

Ala Ile Lys Val Thr Lys Ser Gln Lys Pro Ala Leu Pro Lys Pro Thr
            255                 260                 265

Lys Leu Glu Ser Lys Gly Lys Cys Asp Gly Ile Thr Phe Gly Asp Tyr
    270                 275                 280

Asn Val Glu Asn Leu Ala Ala Asn Ser Ser His Leu Pro Ser Ile Ala
285                 290                 295                 300

Ala His Ile Val Asn Tyr Met Lys Ser Pro Asp Val Leu Phe Val Gln
                305                 310                 315
```

```
Glu Ile Gln Asp Asp Asp Gly Pro Thr Asn Asp Ala Val Val Ser Ala
            320                 325                 330

Asn Leu Thr Leu Ser Thr Leu Val Ala Ala Ile Ser Ala Gly Gly
        335                 340                 345

Pro Thr Tyr Ala Phe Ala Asp Ile Asp Pro Val Asp Asp Gln Asp Gly
    350                 355                 360

Gly Glu Pro Gly Gly Asn Ile Arg Val Ala Tyr Leu Tyr Lys Pro Ser
365                 370                 375                 380

Leu Ile Arg Leu Tyr Lys Pro Asn Pro Gly Gly Ser Leu Asp Ala Asn
            385                 390                 395

Ala Val Asn Asp Gly Pro Thr Leu Lys Tyr Asn Pro Gly Arg Ile Asp
            400                 405                 410

Pro Thr Asn Pro Ala Trp Thr Ala Ser Arg Lys Pro Leu Val Ala Gln
            415                 420                 425

Trp Glu Val Ile Gly Lys Ser Asn Ala Lys Lys Leu Asp Thr Phe Phe
    430                 435                 440

Thr Val Asn Val His Phe Gly Ser Lys Gly Gly Ser Ser Ser Leu His
445                 450                 455                 460

Gly Asp Ala Arg Pro Pro Val Asn Gly Gly Val Glu Asp Arg Leu Ala
            465                 470                 475

Gln Ala Gln Leu Thr Ala Asn Phe Val Lys Asp Ile Leu Ser Lys Asp
            480                 485                 490

Lys Asp Ala Arg Ile Ile Thr Ser Gly Asp Met Asn Glu Phe Ala Phe
            495                 500                 505

Val Glu Pro Leu Glu Gln Leu Lys Asp Ile Ser Gly Leu Lys Asp Leu
    510                 515                 520

Asp Val Glu Ala Gly Ile Asp Lys Leu Glu Arg Tyr Thr Tyr Leu Phe
525                 530                 535                 540

Asp Met Asn Ala Gln Gln Leu Asp His Thr Phe Val Ser Lys Ala Ile
            545                 550                 555

Ala Lys Glu Asp Pro Lys Tyr Glu His Ile His Ile Asn Thr Trp Val
            560                 565                 570

Asp Tyr Ala Asp Gln Ile Ser Asp His Asp Pro Ser Val Ala Arg Leu
            575                 580                 585

Ser Val Cys Ala
    590

<210> SEQ ID NO 27
<211> LENGTH: 592
<212> TYPE: PRT
<213> ORGANISM: Pyrenochaetopsis sp.

<400> SEQUENCE: 27

Thr Thr Ile Ala Glu Ile Asn Gly Pro Ala Phe Leu Ser Pro Phe Lys
1               5                   10                  15

Gly Gln Thr Val Ala Asn Val Ser Gly Ile Ile Thr Ala Lys Gly Pro
            20                  25                  30

Asp Gly Leu Trp Ile Arg Ser Thr Leu Pro Asp Arg Asp Glu Arg Thr
        35                  40                  45

Ser Glu Ser Leu Tyr Val Phe Gly Ser Lys Phe Gly Ala Asn Leu Thr
    50                  55                  60

Val Gly Asp Ser Ile Ile Leu Gly Gly Lys Val Gln Glu Tyr Arg Ser
65                  70                  75                  80

Ser Lys Asp Tyr Ile Tyr Leu Thr Glu Leu Ser Ser Pro Val Leu Ala
```

```
                    85                  90                  95
Lys Lys Val Ser Ser Gly Asn Lys Val Asp Ala Leu Val Ile Gly Lys
                100                 105                 110

Asp Thr Arg Asp Pro Pro Thr Glu Gln Tyr Ser Ser Leu Asp Gly Gly
                115                 120                 125

Asp Val Phe Ala Val Pro Asn Asn Val Ser Gln Ile Ser Val Ala Asn
            130                 135                 140

Pro Glu Leu Gln Pro Lys Lys Tyr Gly Leu Asp Phe Trp Glu Ser Leu
145                 150                 155                 160

Ser Gly Glu Leu Val Thr Val Lys Lys Pro Thr Ala Leu Thr Lys Pro
                165                 170                 175

Asn Gln Tyr Gly Asp Thr Trp Val Val Gly Asn Trp Lys Val Thr Gly
                180                 185                 190

Arg Asn Asp Arg Asp Gly Leu Thr Leu Thr Asp Lys Asp Ala Asn Pro
                195                 200                 205

Glu Ala Ile Ile Ile Gly Thr Pro Leu Asp Gly Thr Lys Asn Pro Thr
            210                 215                 220

Asp Thr Arg Met Gly Asp Ser Val Asp Glu Ile Thr Gly Val Ile Thr
225                 230                 235                 240

Tyr Ala Phe Gly Tyr Tyr Arg Ile Leu Pro Leu Thr Ala Ile Lys Val
                245                 250                 255

Thr Lys Ser Gln Lys Pro Ala Leu Pro Lys Pro Thr Lys Leu Glu Ser
                260                 265                 270

Lys Gly Lys Cys Asp Gly Ile Thr Phe Gly Asp Tyr Asn Val Glu Asn
                275                 280                 285

Leu Ala Ala Asn Ser Ser His Leu Pro Ser Ile Ala Ala His Ile Val
            290                 295                 300

Asn Tyr Met Lys Ser Pro Asp Val Leu Phe Val Gln Glu Ile Gln Asp
305                 310                 315                 320

Asp Asp Gly Pro Thr Asn Asp Ala Val Val Ser Ala Asn Leu Thr Leu
                325                 330                 335

Ser Thr Leu Val Ala Ala Ile Ser Ser Ala Gly Gly Pro Thr Tyr Ala
            340                 345                 350

Phe Ala Asp Ile Asp Pro Val Asp Asp Gln Asp Gly Gly Glu Pro Gly
                355                 360                 365

Gly Asn Ile Arg Val Ala Tyr Leu Tyr Lys Pro Ser Leu Ile Arg Leu
            370                 375                 380

Tyr Lys Pro Asn Pro Gly Gly Ser Leu Asp Ala Asn Ala Val Asn Asp
385                 390                 395                 400

Gly Pro Thr Leu Lys Tyr Asn Pro Gly Arg Ile Asp Pro Thr Asn Pro
                405                 410                 415

Ala Trp Thr Ala Ser Arg Lys Pro Leu Val Ala Gln Trp Glu Val Ile
                420                 425                 430

Gly Lys Ser Asn Ala Lys Lys Leu Asp Thr Phe Phe Thr Val Asn Val
            435                 440                 445

His Phe Gly Ser Lys Gly Gly Ser Ser Leu His Gly Asp Ala Arg
450                 455                 460

Pro Pro Val Asn Gly Gly Val Glu Asp Arg Leu Ala Gln Ala Gln Leu
465                 470                 475                 480

Thr Ala Asn Phe Val Lys Asp Ile Leu Ser Lys Asp Lys Asp Ala Arg
            485                 490                 495

Ile Ile Thr Ser Gly Asp Met Asn Glu Phe Ala Phe Val Glu Pro Leu
                500                 505                 510
```

```
Glu Gln Leu Lys Asp Ile Ser Gly Leu Lys Asp Leu Asp Val Glu Ala
        515                 520                 525

Gly Ile Asp Lys Leu Glu Arg Tyr Thr Tyr Leu Phe Asp Met Asn Ala
    530                 535                 540

Gln Gln Leu Asp His Thr Phe Val Ser Lys Ala Ile Ala Lys Glu Asp
545                 550                 555                 560

Pro Lys Tyr Glu His Ile His Ile Asn Thr Trp Val Asp Tyr Ala Asp
                565                 570                 575

Gln Ile Ser Asp His Asp Pro Ser Val Ala Arg Leu Ser Val Cys Ala
                580                 585                 590

<210> SEQ ID NO 28
<211> LENGTH: 1930
<212> TYPE: DNA
<213> ORGANISM: Aspergillus sydowii
<220> FEATURE:
<221> NAME/KEY: CDS
<222> LOCATION: (1)..(670)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1927)
<220> FEATURE:
<221> NAME/KEY: CDS
<222> LOCATION: (717)..(1537)
<220> FEATURE:
<221> NAME/KEY: CDS
<222> LOCATION: (1598)..(1927)

<400> SEQUENCE: 28 atg aga tcc ttc gct acc ctg aca gcg tta tcc tgg gtc ctg ccc gcg      48
Met Arg Ser Phe Ala Thr Leu Thr Ala Leu Ser Trp Val Leu Pro Ala
        -15                 -10                  -5 gtg gca gtg acg atc agc gag atc aat ggg aat act tac ctt tcg ccg      96
Val Ala Val Thr Ile Ser Glu Ile Asn Gly Asn Thr Tyr Leu Ser Pro
    -1   1               5                  10 ttt aaa gga gag agt gtt tct gat gtg gag ggt ctt gta aca gca ata     144
Phe Lys Gly Glu Ser Val Ser Asp Val Glu Gly Leu Val Thr Ala Ile
 15                  20                  25                  30 gga gag gac ggg ttt tat ctc cgg tcg acc act ccg gac tct gac gat     192
Gly Glu Asp Gly Phe Tyr Leu Arg Ser Thr Thr Pro Asp Ser Asp Asp
                 35                  40                  45 gcg aca tct gag tcg atc tac gtc tac gga agc agt gcc gtt tca gag     240
Ala Thr Ser Glu Ser Ile Tyr Val Tyr Gly Ser Ser Ala Val Ser Glu
             50                  55                  60 gtc act gtc gga gac att atc gct ctt agt ggc gaa gtg tct gag tat     288
Val Thr Val Gly Asp Ile Ile Ala Leu Ser Gly Glu Val Ser Glu Tyr
         65                  70                  75 cgc tcc cag gca gcc tat ttg tac cta acg gaa atc acc tcg ccg tcg     336
Arg Ser Gln Ala Ala Tyr Leu Tyr Leu Thr Glu Ile Thr Ser Pro Ser
     80                  85                  90 agc atc gtc gtc aag tca agt gga aat gag gtc gca cct gtc gtc att     384
Ser Ile Val Val Lys Ser Ser Gly Asn Glu Val Ala Pro Val Val Ile
 95                 100                 105                 110 ggc aag gat cgc tcg ccc ccg aca gag gta tac tct ggt ctc gat ggt     432
Gly Lys Asp Arg Ser Pro Pro Thr Glu Val Tyr Ser Gly Leu Asp Gly
                115                 120                 125 gcc gac ggt gat gtc tat gcg ctg ccg aac aac gcc agc caa atc tct     480
Ala Asp Gly Asp Val Tyr Ala Leu Pro Asn Asn Ala Ser Gln Ile Ser
            130                 135                 140
```

| | | |
|---|---|---|
| gcc gag aat cct gtt ctg aaa cct gag ctc tac ggg atg gac ttc tgg<br>Ala Glu Asn Pro Val Leu Lys Pro Glu Leu Tyr Gly Met Asp Phe Trp<br>     145                  150                 155 | | 528 |
| gag agt ctc agc ggc gag ctc gtt tcc ctc acc gga ttg act atc atc<br>Glu Ser Leu Ser Gly Glu Leu Val Ser Leu Thr Gly Leu Thr Ile Ile<br>  160                    165                  170 | | 576 |
| acc aaa ccc aac cag tac ggc gac gtc ttt gtg cga ggg gac tgg gct<br>Thr Lys Pro Asn Gln Tyr Gly Asp Val Phe Val Arg Gly Asp Trp Ala<br>175                   180                 185                 190 | | 624 |
| gtc tcg ggc ctg aac gag aac ggt ggg ctg acc atg agc gca aat g<br>Val Ser Gly Leu Asn Glu Asn Gly Gly Leu Thr Met Ser Ala Asn<br>                195                  200                205 | | 670 |
| gtatgcacct cctgttactg agataaagcc tactgaccac gtcaag at tca aat<br>                                                                   Asp Ser Asn | | 724 |
| ccc gag gcc atc aag atc gga act cct ctc gac ggg acc aac aac agc<br>Pro Glu Ala Ile Lys Ile Gly Thr Pro Leu Asp Gly Thr Asn Asn Ser<br>     210                  215                  220 | | 772 |
| gac tcc tcc aag gtc ggg gac acc gtc gag gac gtc aca ggc gtc gtc<br>Asp Ser Ser Lys Val Gly Asp Thr Val Glu Asp Val Thr Gly Val Val<br>225                   230                 235                 240 | | 820 |
| cag tgg aag ttc ggc cag tac atg gtt ctc cca cta aca gct tta acc<br>Gln Trp Lys Phe Gly Gln Tyr Met Val Leu Pro Leu Thr Ala Leu Thr<br>                     245                  250                255 | | 868 |
| gtg acg ggc tca aac gac aca gtc gcc ggc ccc tcc acc ctg act ggc<br>Val Thr Gly Ser Asn Asp Thr Val Ala Gly Pro Ser Thr Leu Thr Gly<br>  260                    265                  270 | | 916 |
| gac gga acc tgc aag tcc cta agc atc ggc gct tac aac gtc gaa aac<br>Asp Gly Thr Cys Lys Ser Leu Ser Ile Gly Ala Tyr Asn Val Glu Asn<br>275                   280                 285 | | 964 |
| cta acg cca acc tca acc cac atc tcc aaa atc gcc gac cac ata gcc<br>Leu Thr Pro Thr Ser Thr His Ile Ser Lys Ile Ala Asp His Ile Ala<br>     290                  295                  300 | | 1012 |
| aac tac ctc aac ggg ccg gca atc atg tgc cta cag gaa atc caa gac<br>Asn Tyr Leu Asn Gly Pro Ala Ile Met Cys Leu Gln Glu Ile Gln Asp<br>305                   310                 315                 320 | | 1060 |
| aac aac ggc gca aca gac gac ggc acc gtc act gca aac ctc acc ttg<br>Asn Asn Gly Ala Thr Asp Asp Gly Thr Val Thr Ala Asn Leu Thr Leu<br>                     325                  330                335 | | 1108 |
| acc aaa ctc acg ggc ctg atc tcc gcc gcc ggt ggg cca gac tac aac<br>Thr Lys Leu Thr Gly Leu Ile Ser Ala Ala Gly Gly Pro Asp Tyr Asn<br>  340                    345                  350 | | 1156 |
| ttc acc gaa atc ccc cca gtc aac aac gct gac ggc gga gag cca ggc<br>Phe Thr Glu Ile Pro Pro Val Asn Asn Ala Asp Gly Gly Glu Pro Gly<br>     355                  360                  365 | | 1204 |
| ggg aac atc cgc gtg gca tac ttg tac aac ccg agc atc gta cgc ctg<br>Gly Asn Ile Arg Val Ala Tyr Leu Tyr Asn Pro Ser Ile Val Arg Leu<br>370                   375                 380 | | 1252 |
| cac aat gca aac ccc ggc aca tcc gcc gac gcg aac gag gtg ctg gtc<br>His Asn Ala Asn Pro Gly Thr Ser Ala Asp Ala Asn Glu Val Leu Val<br>385                   390                 395                 400 | | 1300 |
| tcg cat ggc cca gag ctg aaa ttc aat cct ggc ctt att gac ccg gat<br>Ser His Gly Pro Glu Leu Lys Phe Asn Pro Gly Leu Ile Asp Pro Asp<br>                     405                  410                415 | | 1348 |
| agc gag gct tgg gat gcg tcg cgc aaa ccg ctt gcc gct gcg tgg gag<br>Ser Glu Ala Trp Asp Ala Ser Arg Lys Pro Leu Ala Ala Ala Trp Glu<br>  420                    425                  430 | | 1396 |
| acg gtc gat ggg gag aat aag ttc ttc act gtt aat gtg cac ctg tcg<br>Thr Val Asp Gly Glu Asn Lys Phe Phe Thr Val Asn Val His Leu Ser<br>435                   440                 445 | | 1444 |

| | | | | | | | | | | | | | | |
|---|---|---|---|---|---|---|---|---|---|---|---|---|---|---|
| agt | aag | ggt | ggt | ggt | tcg | gct | ata | cag | ggt | gat | gcc | aga | cca | ccc | gtt | 1492
| Ser | Lys | Gly | Gly | Gly | Ser | Ala | Ile | Gln | Gly | Asp | Ala | Arg | Pro | Pro | Val |
| | 450 | | | | 455 | | | | | 460 | | | | | |

| aac | ggt | ggt | gtt | gag | cag | cgt | act | gcg | cag | gcg | gaa | gtc | atc | gct | | 1537
|---|---|---|---|---|---|---|---|---|---|---|---|---|---|---|---|---|
| Asn | Gly | Gly | Val | Glu | Gln | Arg | Thr | Ala | Gln | Ala | Glu | Val | Ile | Ala |
| 465 | | | | | 470 | | | | | 475 | | | | | gtatgtccta gtccccagct ccaacacctg atctgcggaa acaaatctaa ttgaatatag    1597

| tcc | ttc | gta | tct | gac | atc | ctg | gcc | gcc | gat | gca | aac | gca | aag | att | ctc | 1645
|---|---|---|---|---|---|---|---|---|---|---|---|---|---|---|---|---|
| Ser | Phe | Val | Ser | Asp | Ile | Leu | Ala | Ala | Asp | Ala | Asn | Ala | Lys | Ile | Leu |
| 480 | | | | | 485 | | | | | 490 | | | | | 495 |

| aca | acg | ggc | gac | ttc | aat | gaa | ttc | tcc | ttc | gtt | tcg | ccg | ctg | gag | acc | 1693
|---|---|---|---|---|---|---|---|---|---|---|---|---|---|---|---|---|
| Thr | Thr | Gly | Asp | Phe | Asn | Glu | Phe | Ser | Phe | Val | Ser | Pro | Leu | Glu | Thr |
| | | | | | 500 | | | | | 505 | | | | | 510 |

| ttc | gtg | gag | aag | tct | ggg | ctc | cgc | gag | ctg | gac | gat | gtc | gtt | ggg | atc | 1741
|---|---|---|---|---|---|---|---|---|---|---|---|---|---|---|---|---|
| Phe | Val | Glu | Lys | Ser | Gly | Leu | Arg | Glu | Leu | Asp | Asp | Val | Val | Gly | Ile |
| | | | 515 | | | | | 520 | | | | | 525 | | |

| ccg | gcg | aca | gag | cgc | tat | acg | tac | ata | tac | gac | tcg | aac | cac | cag | cag | 1789
|---|---|---|---|---|---|---|---|---|---|---|---|---|---|---|---|---|
| Pro | Ala | Thr | Glu | Arg | Tyr | Thr | Tyr | Ile | Tyr | Asp | Ser | Asn | His | Gln | Gln |
| | | 530 | | | | | 535 | | | | | 540 | | | |

| ctg | gac | cac | atg | ttt | gtg | tca | gat | ggg | ctc | gca | aag | aat | gcc | cag | ctg | 1837
|---|---|---|---|---|---|---|---|---|---|---|---|---|---|---|---|---|
| Leu | Asp | His | Met | Phe | Val | Ser | Asp | Gly | Leu | Ala | Lys | Asn | Ala | Gln | Leu |
| 545 | | | | | 550 | | | | | 555 | | | | | |

| gag | cat | gtc | cat | gtg | aac | act | tgg | ttg | aat | tat | gat | gat | gcg | gcg | tcg | 1885
|---|---|---|---|---|---|---|---|---|---|---|---|---|---|---|---|---|
| Glu | His | Val | His | Val | Asn | Thr | Trp | Leu | Asn | Tyr | Asp | Asp | Ala | Ala | Ser |
| 560 | | | | | 565 | | | | | 570 | | | | | 575 |

| gac | cat | gat | ccg | tct | gtt | gcg | tta | ttt | gac | gtt | tgt | gag | ctg | tga | | 1930
|---|---|---|---|---|---|---|---|---|---|---|---|---|---|---|---|---|
| Asp | His | Asp | Pro | Ser | Val | Ala | Leu | Phe | Asp | Val | Cys | Glu | Leu |
| | | | 580 | | | | | 585 | | | | | |

<210> SEQ ID NO 29
<211> LENGTH: 607
<212> TYPE: PRT
<213> ORGANISM: Aspergillus sydowii

<400> SEQUENCE: 29

Met Arg Ser Phe Ala Thr Leu Thr Ala Leu Ser Trp Val Leu Pro Ala
                -15                 -10                  -5

Val Ala Val Thr Ile Ser Glu Ile Asn Gly Asn Thr Tyr Leu Ser Pro
 -1   1               5                  10

Phe Lys Gly Glu Ser Val Ser Asp Val Glu Gly Leu Val Thr Ala Ile
 15                  20                  25                  30

Gly Glu Asp Gly Phe Tyr Leu Arg Ser Thr Thr Pro Asp Ser Asp Asp
                 35                  40                  45

Ala Thr Ser Glu Ser Ile Tyr Val Tyr Gly Ser Ser Ala Val Ser Glu
             50                  55                  60

Val Thr Val Gly Asp Ile Ala Leu Ser Gly Glu Val Ser Glu Tyr
         65                  70                  75

Arg Ser Gln Ala Ala Tyr Leu Tyr Leu Thr Glu Ile Thr Ser Pro Ser
 80                  85                  90

Ser Ile Val Val Lys Ser Ser Gly Asn Glu Val Ala Pro Val Val Ile
 95                 100                 105                 110

Gly Lys Asp Arg Ser Pro Thr Glu Val Tyr Ser Gly Leu Asp Gly
                115                 120                 125

Ala Asp Gly Asp Val Tyr Ala Leu Pro Asn Asn Ala Ser Gln Ile Ser
                130                 135                 140

Ala Glu Asn Pro Val Leu Lys Pro Glu Leu Tyr Gly Met Asp Phe Trp
145                 150                 155

```
Glu Ser Leu Ser Gly Glu Leu Val Ser Leu Thr Gly Leu Thr Ile Ile
160                 165                 170

Thr Lys Pro Asn Gln Tyr Gly Asp Val Phe Val Arg Gly Asp Trp Ala
175                 180                 185                 190

Val Ser Gly Leu Asn Glu Asn Gly Gly Leu Thr Met Ser Ala Asn Asp
            195                 200                 205

Ser Asn Pro Glu Ala Ile Lys Ile Gly Thr Pro Leu Asp Gly Thr Asn
        210                 215                 220

Asn Ser Asp Ser Ser Lys Val Gly Asp Thr Val Glu Asp Val Thr Gly
        225                 230                 235

Val Val Gln Trp Lys Phe Gly Gln Tyr Met Val Leu Pro Leu Thr Ala
240                 245                 250

Leu Thr Val Thr Gly Ser Asn Asp Thr Val Ala Gly Pro Ser Thr Leu
255                 260                 265                 270

Thr Gly Asp Gly Thr Cys Lys Ser Leu Ser Ile Gly Ala Tyr Asn Val
                275                 280                 285

Glu Asn Leu Thr Pro Thr Ser Thr His Ile Ser Lys Ile Ala Asp His
            290                 295                 300

Ile Ala Asn Tyr Leu Asn Gly Pro Ala Ile Met Cys Leu Gln Glu Ile
        305                 310                 315

Gln Asp Asn Asn Gly Ala Thr Asp Asp Gly Thr Val Thr Ala Asn Leu
320                 325                 330

Thr Leu Thr Lys Leu Thr Gly Leu Ile Ser Ala Ala Gly Gly Pro Asp
335                 340                 345                 350

Tyr Asn Phe Thr Glu Ile Pro Pro Val Asn Asn Ala Asp Gly Gly Glu
                355                 360                 365

Pro Gly Gly Asn Ile Arg Val Ala Tyr Leu Tyr Asn Pro Ser Ile Val
            370                 375                 380

Arg Leu His Asn Ala Asn Pro Gly Thr Ser Ala Asp Ala Asn Glu Val
        385                 390                 395

Leu Val Ser His Gly Pro Glu Leu Lys Phe Asn Pro Gly Leu Ile Asp
400                 405                 410

Pro Asp Ser Glu Ala Trp Asp Ala Ser Arg Lys Pro Leu Ala Ala Ala
415                 420                 425                 430

Trp Glu Thr Val Asp Gly Glu Asn Lys Phe Thr Val Asn Val His
                435                 440                 445

Leu Ser Ser Lys Gly Gly Ser Ala Ile Gln Gly Asp Ala Arg Pro
            450                 455                 460

Pro Val Asn Gly Gly Val Glu Gln Arg Thr Ala Gln Ala Glu Val Ile
        465                 470                 475

Ala Ser Phe Val Ser Asp Ile Leu Ala Ala Asp Ala Asn Ala Lys Ile
480                 485                 490

Leu Thr Thr Gly Asp Phe Asn Glu Phe Ser Phe Val Ser Pro Leu Glu
495                 500                 505                 510

Thr Phe Val Glu Lys Ser Gly Leu Arg Glu Leu Asp Asp Val Val Gly
                515                 520                 525

Ile Pro Ala Thr Glu Arg Tyr Thr Tyr Ile Tyr Asp Ser Asn His Gln
            530                 535                 540

Gln Leu Asp His Met Phe Val Ser Asp Gly Leu Ala Lys Asn Ala Gln
        545                 550                 555

Leu Glu His Val His Val Asn Thr Trp Leu Asn Tyr Asp Asp Ala Ala
560                 565                 570

Ser Asp His Asp Pro Ser Val Ala Leu Phe Asp Val Cys Glu Leu
```

```
575             580             585
```

<210> SEQ ID NO 30
<211> LENGTH: 589
<212> TYPE: PRT
<213> ORGANISM: Aspergillus sydowii

<400> SEQUENCE: 30

```
Val Thr Ile Ser Glu Ile Asn Gly Asn Thr Tyr Leu Ser Pro Phe Lys
1               5                   10                  15

Gly Glu Ser Val Ser Asp Val Glu Gly Leu Val Thr Ala Ile Gly Glu
            20                  25                  30

Asp Gly Phe Tyr Leu Arg Ser Thr Pro Asp Ser Asp Asp Ala Thr
        35                  40                  45

Ser Glu Ser Ile Tyr Val Tyr Gly Ser Ala Val Ser Glu Val Thr
    50                  55                  60

Val Gly Asp Ile Ile Ala Leu Ser Gly Glu Val Ser Glu Tyr Arg Ser
65                  70                  75                  80

Gln Ala Ala Tyr Leu Tyr Leu Thr Glu Ile Thr Ser Pro Ser Ser Ile
                85                  90                  95

Val Val Lys Ser Ser Gly Asn Glu Val Ala Pro Val Val Ile Gly Lys
            100                 105                 110

Asp Arg Ser Pro Pro Thr Glu Val Tyr Ser Gly Leu Asp Gly Ala Asp
        115                 120                 125

Gly Asp Val Tyr Ala Leu Pro Asn Asn Ala Ser Gln Ile Ser Ala Glu
    130                 135                 140

Asn Pro Val Leu Lys Pro Glu Leu Tyr Gly Met Asp Phe Trp Glu Ser
145                 150                 155                 160

Leu Ser Gly Glu Leu Val Ser Leu Thr Gly Leu Thr Ile Ile Thr Lys
                165                 170                 175

Pro Asn Gln Tyr Gly Asp Val Phe Val Arg Gly Asp Trp Ala Val Ser
            180                 185                 190

Gly Leu Asn Glu Asn Gly Gly Leu Thr Met Ser Ala Asn Asp Ser Asn
        195                 200                 205

Pro Glu Ala Ile Lys Ile Gly Thr Pro Leu Asp Gly Thr Asn Asn Ser
    210                 215                 220

Asp Ser Ser Lys Val Gly Asp Thr Val Glu Asp Val Thr Gly Val Val
225                 230                 235                 240

Gln Trp Lys Phe Gly Gln Tyr Met Val Leu Pro Leu Thr Ala Leu Thr
                245                 250                 255

Val Thr Gly Ser Asn Asp Thr Val Ala Gly Pro Ser Thr Leu Thr Gly
            260                 265                 270

Asp Gly Thr Cys Lys Ser Leu Ser Ile Gly Ala Tyr Asn Val Glu Asn
        275                 280                 285

Leu Thr Pro Thr Ser Thr His Ile Ser Lys Ile Ala Asp His Ile Ala
    290                 295                 300

Asn Tyr Leu Asn Gly Pro Ala Ile Met Cys Leu Gln Glu Ile Gln Asp
305                 310                 315                 320

Asn Asn Gly Ala Thr Asp Asp Gly Thr Val Thr Ala Asn Leu Thr Leu
                325                 330                 335

Thr Lys Leu Thr Gly Leu Ile Ser Ala Ala Gly Gly Pro Asp Tyr Asn
            340                 345                 350

Phe Thr Glu Ile Pro Pro Val Asn Asn Ala Asp Gly Gly Glu Pro Gly
        355                 360                 365
```

```
Gly Asn Ile Arg Val Ala Tyr Leu Tyr Asn Pro Ser Ile Val Arg Leu
    370                 375                 380

His Asn Ala Asn Pro Gly Thr Ser Ala Asp Ala Asn Glu Val Leu Val
385                 390                 395                 400

Ser His Gly Pro Glu Leu Lys Phe Asn Pro Gly Leu Ile Asp Pro Asp
                405                 410                 415

Ser Glu Ala Trp Asp Ala Ser Arg Lys Pro Leu Ala Ala Trp Glu
                420                 425                 430

Thr Val Asp Gly Glu Asn Lys Phe Phe Thr Val Asn His Leu Ser
                435                 440                 445

Ser Lys Gly Gly Gly Ser Ala Ile Gln Gly Asp Ala Arg Pro Pro Val
    450                 455                 460

Asn Gly Gly Val Glu Gln Arg Thr Ala Gln Ala Glu Val Ile Ala Ser
465                 470                 475                 480

Phe Val Ser Asp Ile Leu Ala Ala Asp Ala Asn Ala Lys Ile Leu Thr
                485                 490                 495

Thr Gly Asp Phe Asn Glu Phe Ser Phe Val Ser Pro Leu Glu Thr Phe
                500                 505                 510

Val Glu Lys Ser Gly Leu Arg Glu Leu Asp Asp Val Val Gly Ile Pro
                515                 520                 525

Ala Thr Glu Arg Tyr Thr Tyr Ile Tyr Asp Ser Asn His Gln Gln Leu
                530                 535                 540

Asp His Met Phe Val Ser Asp Gly Leu Ala Lys Asn Ala Gln Leu Glu
545                 550                 555                 560

His Val His Val Asn Thr Trp Leu Asn Tyr Asp Asp Ala Ala Ser Asp
                565                 570                 575

His Asp Pro Ser Val Ala Leu Phe Asp Val Cys Glu Leu
                580                 585

<210> SEQ ID NO 31
<211> LENGTH: 1960
<212> TYPE: DNA
<213> ORGANISM: Cladosporium cladosporioides
<220> FEATURE:
<221> NAME/KEY: CDS
<222> LOCATION: (1)..(109)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1957)
<220> FEATURE:
<221> NAME/KEY: CDS
<222> LOCATION: (166)..(262)
<220> FEATURE:
<221> NAME/KEY: CDS
<222> LOCATION: (319)..(1957)

<400> SEQUENCE: 31 atg acg ctc ctg aag acg ctt ctc aca gct ttg gcc cct tct ggt gca      48
Met Thr Leu Leu Lys Thr Leu Leu Thr Ala Leu Ala Pro Ser Gly Ala
            -15                 -10                 -5 gcc gca gtc acc att gcg gcc atc aat ggc gat agg ttc ttg tca cct      96
Ala Ala Val Thr Ile Ala Ala Ile Asn Gly Asp Arg Phe Leu Ser Pro
    -1  1               5                   10 ctg aac gga act g gtaagtgaat tgctgttgat aaatggctgt gtaaatact         149
Leu Asn Gly Thr
15 gaactctcga attcag gc  gtc cag gat gtt gcc ggt ctt gtc aca gcc aag    200
                     Gly Val Gln Asp Val Ala Gly Leu Val Thr Ala Lys
```

-continued

```
                      20                  25                  30
ggc ccc aac ggc ttc tgg atc cgc tct ccg gaa ccc gat acc cac gac    248
Gly Pro Asn Gly Phe Trp Ile Arg Ser Pro Glu Pro Asp Thr His Asp
             35                  40                  45 cgc act tcg gag ag gtatgcttgc gtctttggaa cctttgttca aactttacat    302
Arg Thr Ser Glu Ser
             50 tgactgacgg ccacag t gtc tat gtt ttc ggc cgc aat gct ctt gga aac    352
                    Val Tyr Val Phe Gly Arg Asn Ala Leu Gly Asn
                                 55                  60 gtg act gtt ggt gac ctt att tcc gtc gat ggc aac gtc acc gag tac    400
Val Thr Val Gly Asp Leu Ile Ser Val Asp Gly Asn Val Thr Glu Tyr
             65                  70                  75 cgc tcc agc aag gac tac gcc tat ctc acc gag atc atc aac ccc aga    448
Arg Ser Ser Lys Asp Tyr Ala Tyr Leu Thr Glu Ile Ile Asn Pro Arg
         80                  85                  90 aac atc cgt gtt gtg tcc agt ggc aac gaa gtc aag cct gtt gtg atc    496
Asn Ile Arg Val Val Ser Ser Gly Asn Glu Val Lys Pro Val Val Ile
95                  100                 105                 110 ggc agc aag aca tct ggc att atc ggc aag aga gat gtc cag cct cct    544
Gly Ser Lys Thr Ser Gly Ile Ile Gly Lys Arg Asp Val Gln Pro Pro
                 115                 120                 125 agg gag cag ttc agt ggc ctc gac aat ggc gat gtc ttt gcc gtt ccc    592
Arg Glu Gln Phe Ser Gly Leu Asp Asn Gly Asp Val Phe Ala Val Pro
             130                 135                 140 aac aac cag tcc ttg atc tct cag gcc aac ccg cgt ctt gag ccg aac    640
Asn Asn Gln Ser Leu Ile Ser Gln Ala Asn Pro Arg Leu Glu Pro Asn
         145                 150                 155 ttg tac ggc atg gac ttc tgg gag tct cta tct ggc gag ctt gtg act    688
Leu Tyr Gly Met Asp Phe Trp Glu Ser Leu Ser Gly Glu Leu Val Thr
160                 165                 170 atc aag ggc gtc act gct cta ggt cgt cag gct aac acc ttt ggc gac    736
Ile Lys Gly Val Thr Ala Leu Gly Arg Gln Ala Asn Thr Phe Gly Asp
175                 180                 185                 190 caa tgg gta cga gga gac tgg aag tct tcc gga aag aac tct cgt ggc    784
Gln Trp Val Arg Gly Asp Trp Lys Ser Ser Gly Lys Asn Ser Arg Gly
                 195                 200                 205 ggt ctc acc gtg act gac cgc gac tcc aac cca gag tcc atc atc att    832
Gly Leu Thr Val Thr Asp Arg Asp Ser Asn Pro Glu Ser Ile Ile Ile
             210                 215                 220 ggt gcg ccc ttg gac gga agc agc aac agt aaa gag acc aag ctt ggc    880
Gly Ala Pro Leu Asp Gly Ser Ser Asn Ser Lys Glu Thr Lys Leu Gly
         225                 230                 235 gac gag ctc gaa gac atc act ggc att gtc aca tac gtc ttc ggc ttc    928
Asp Glu Leu Glu Asp Ile Thr Gly Ile Val Thr Tyr Val Phe Gly Phe
240                 245                 250 tac gcc atc ttc cct caa acc ggt acc aaa gtg aag cgc tct att gat    976
Tyr Ala Ile Phe Pro Gln Thr Gly Thr Lys Val Lys Arg Ser Ile Asp
255                 260                 265                 270 gca ttc ccg cct cct tcg tcc atc gtc tcc aat ggc aag tgc agc gga   1024
Ala Phe Pro Pro Pro Ser Ser Ile Val Ser Asn Gly Lys Cys Ser Gly
                 275                 280                 285 ctc aca ttc ggc caa tat aac atc gaa aac ttc gca ccc aac aac tcg   1072
Leu Thr Phe Gly Gln Tyr Asn Ile Glu Asn Phe Ala Pro Asn Asn Ser
             290                 295                 300 cgc gtt ccg ctc att gct gag cac atc gtc gac tac ctc aac acg cca   1120
Arg Val Pro Leu Ile Ala Glu His Ile Val Asp Tyr Leu Asn Thr Pro
         305                 310                 315 tcc gtc atg ttc ctg caa gag gtt caa gac aac tcg ggt gag gcg aac   1168
```

```
              Ser Val Met Phe Leu Gln Glu Val Gln Asp Asn Ser Gly Glu Ala Asn
                  320                 325                 330 gac ggc gtt gtc aac tcc aac ctt acc ctc gct tct ctc tcc caa gcc       1216
Asp Gly Val Val Asn Ser Asn Leu Thr Leu Ala Ser Leu Ser Gln Ala
335                 340                 345                 350 atc agc gag atc tcc ggc gta gac tac ctc tgg gtc aac gtc gac ccc       1264
Ile Ser Glu Ile Ser Gly Val Asp Tyr Leu Trp Val Asn Val Asp Pro
                355                 360                 365 gtc aac aac cag gac ggc gga gct ccc ggc ggt aac atc cag act ccc       1312
Val Asn Asn Gln Asp Gly Gly Ala Pro Gly Gly Asn Ile Gln Thr Pro
                    370                 375                 380 tac ctc tac aac cca ctt caa gtc cgc cta ctc aac gcc aac cca ggt       1360
Tyr Leu Tyr Asn Pro Leu Gln Val Arg Leu Leu Asn Ala Asn Pro Gly
                385                 390                 395 ggc cct aac gac agg aac gag gtc ctc ccc ggt ccc acc ctc cgc ttc       1408
Gly Pro Asn Asp Arg Asn Glu Val Leu Pro Gly Pro Thr Leu Arg Phe
400                 405                 410 aac ccc ggc cgc atc gac gac ggc gtg acc ttc agc aac tcc cgc aag       1456
Asn Pro Gly Arg Ile Asp Asp Gly Val Thr Phe Ser Asn Ser Arg Lys
415                 420                 425                 430 ccc atc gtc gca cac tgg gaa atg gtt gac ggc agc ggc act ttc ttc       1504
Pro Ile Val Ala His Trp Glu Met Val Asp Gly Ser Gly Thr Phe Phe
                435                 440                 445 acc gtc aac aac cac tgg acc tcc aaa ggc ggc tca acc tcc ctc caa       1552
Thr Val Asn Asn His Trp Thr Ser Lys Gly Gly Ser Thr Ser Leu Gln
                450                 455                 460 ggc gat gcc cga cct ccc gtc aac ggc ggc gtc gac cgc cgt atc cgt       1600
Gly Asp Ala Arg Pro Pro Val Asn Gly Gly Val Asp Arg Arg Ile Arg
            465                 470                 475 cag gct gaa gtc act ggc agc ttc atc gcc gag atc ctg aag cag gac       1648
Gln Ala Glu Val Thr Gly Ser Phe Ile Ala Glu Ile Leu Lys Gln Asp
            480                 485                 490 aag aac gcc gcg atc atc gtt gcc ggc gac ttg aac gag ttc gct act       1696
Lys Asn Ala Ala Ile Ile Val Ala Gly Asp Leu Asn Glu Phe Ala Thr
495                 500                 505                 510 gtg gcg cct ttg cgc agg ttc gtt gag gtt tct gga ctc aag gac ttg       1744
Val Ala Pro Leu Arg Arg Phe Val Glu Val Ser Gly Leu Lys Asp Leu
                515                 520                 525 gat gtt gtt gcg aaa atc cct gag ctc gag cga tac tct tac act ttc       1792
Asp Val Val Ala Lys Ile Pro Glu Leu Glu Arg Tyr Ser Tyr Thr Phe
                530                 535                 540 ggc gcg agc cag cag cag ctg gat cat gtt tat gct agt gcg tgg gca       1840
Gly Ala Ser Gln Gln Gln Leu Asp His Val Tyr Ala Ser Ala Trp Ala
            545                 550                 555 tcc aga aag gtg ggc aag ggg gac ttt gag cat gta cat gtt aat act       1888
Ser Arg Lys Val Gly Lys Gly Asp Phe Glu His Val His Val Asn Thr
            560                 565                 570 tgg gtt gca gag gag gat gtg ggg agt gat cac gat cct gct gtt gcc       1936
Trp Val Ala Glu Glu Asp Val Gly Ser Asp His Asp Pro Ala Val Ala
575                 580                 585                 590 cgg ctt aac gtg tgc agc acg taa                                        1960
Arg Leu Asn Val Cys Ser Thr
                595

<210> SEQ ID NO 32
<211> LENGTH: 615
<212> TYPE: PRT
<213> ORGANISM: Cladosporium cladosporioides

<400> SEQUENCE: 32
```

```
Met Thr Leu Leu Lys Thr Leu Leu Thr Ala Leu Ala Pro Ser Gly Ala
        -15                 -10                 -5

Ala Ala Val Thr Ile Ala Ala Ile Asn Gly Asp Arg Phe Leu Ser Pro
 -1   1              5                  10

Leu Asn Gly Thr Gly Val Gln Asp Val Ala Gly Leu Val Thr Ala Lys
 15              20                  25                  30

Gly Pro Asn Gly Phe Trp Ile Arg Ser Pro Glu Pro Asp Thr His Asp
             35                  40                  45

Arg Thr Ser Glu Ser Val Tyr Val Phe Gly Arg Asn Ala Leu Gly Asn
             50                  55                  60

Val Thr Val Gly Asp Leu Ile Ser Val Asp Gly Asn Val Thr Glu Tyr
             65                  70                  75

Arg Ser Ser Lys Asp Tyr Ala Tyr Leu Thr Glu Ile Ile Asn Pro Arg
 80                  85                  90

Asn Ile Arg Val Val Ser Ser Gly Asn Glu Val Lys Pro Val Val Ile
 95                 100                 105                 110

Gly Ser Lys Thr Ser Gly Ile Ile Gly Lys Arg Asp Val Gln Pro Pro
                115                 120                 125

Arg Glu Gln Phe Ser Gly Leu Asp Asn Gly Asp Val Phe Ala Val Pro
             130                 135                 140

Asn Asn Gln Ser Leu Ile Ser Gln Ala Asn Pro Arg Leu Glu Pro Asn
             145                 150                 155

Leu Tyr Gly Met Asp Phe Trp Glu Ser Leu Ser Gly Glu Leu Val Thr
             160                 165                 170

Ile Lys Gly Val Thr Ala Leu Gly Arg Gln Ala Asn Thr Phe Gly Asp
175                 180                 185                 190

Gln Trp Val Arg Gly Asp Trp Lys Ser Ser Gly Lys Asn Ser Arg Gly
                195                 200                 205

Gly Leu Thr Val Thr Asp Arg Asp Ser Asn Pro Glu Ser Ile Ile Ile
                210                 215                 220

Gly Ala Pro Leu Asp Gly Ser Ser Asn Ser Lys Glu Thr Lys Leu Gly
                225                 230                 235

Asp Glu Leu Glu Asp Ile Thr Gly Ile Val Thr Tyr Val Phe Gly Phe
240                 245                 250

Tyr Ala Ile Phe Pro Gln Thr Gly Thr Lys Val Lys Arg Ser Ile Asp
255                 260                 265                 270

Ala Phe Pro Pro Ser Ser Ile Val Ser Asn Gly Lys Cys Ser Gly
                275                 280                 285

Leu Thr Phe Gly Gln Tyr Asn Ile Glu Asn Phe Ala Pro Asn Asn Ser
                290                 295                 300

Arg Val Pro Leu Ile Ala Glu His Ile Val Asp Tyr Leu Asn Thr Pro
                305                 310                 315

Ser Val Met Phe Leu Gln Glu Val Gln Asp Asn Ser Gly Glu Ala Asn
                320                 325                 330

Asp Gly Val Val Asn Ser Asn Leu Thr Leu Ala Ser Leu Ser Gln Ala
335                 340                 345                 350

Ile Ser Glu Ile Ser Gly Val Asp Tyr Leu Trp Val Asn Val Asp Pro
                355                 360                 365

Val Asn Asn Gln Asp Gly Gly Ala Pro Gly Asn Ile Gln Thr Pro
                370                 375                 380

Tyr Leu Tyr Asn Pro Leu Gln Val Arg Leu Leu Asn Ala Asn Pro Gly
                385                 390                 395

Gly Pro Asn Asp Arg Asn Glu Val Leu Pro Gly Pro Thr Leu Arg Phe
```

```
                400             405             410
Asn Pro Gly Arg Ile Asp Asp Gly Val Thr Phe Ser Asn Ser Arg Lys
415                 420                 425                 430

Pro Ile Val Ala His Trp Glu Met Val Asp Gly Ser Gly Thr Phe Phe
                435                 440                 445

Thr Val Asn Asn His Trp Thr Ser Lys Gly Gly Ser Thr Ser Leu Gln
                450                 455                 460

Gly Asp Ala Arg Pro Pro Val Asn Gly Gly Val Asp Arg Arg Ile Arg
                465                 470                 475

Gln Ala Glu Val Thr Gly Ser Phe Ile Ala Glu Ile Leu Lys Gln Asp
                480                 485                 490

Lys Asn Ala Ala Ile Ile Val Ala Gly Asp Leu Asn Glu Phe Ala Thr
495                 500                 505                 510

Val Ala Pro Leu Arg Arg Phe Val Glu Val Ser Gly Leu Lys Asp Leu
                515                 520                 525

Asp Val Val Ala Lys Ile Pro Glu Leu Glu Arg Tyr Ser Tyr Thr Phe
                530                 535                 540

Gly Ala Ser Gln Gln Gln Leu Asp His Val Tyr Ala Ser Ala Trp Ala
                545                 550                 555

Ser Arg Lys Val Gly Lys Gly Asp Phe Glu His Val His Val Asn Thr
560                 565                 570

Trp Val Ala Glu Glu Asp Val Gly Ser Asp His Asp Pro Ala Val Ala
575                 580                 585                 590

Arg Leu Asn Val Cys Ser Thr
                595

<210> SEQ ID NO 33
<211> LENGTH: 597
<212> TYPE: PRT
<213> ORGANISM: Cladosporium cladosporioides

<400> SEQUENCE: 33

Val Thr Ile Ala Ala Ile Asn Gly Asp Arg Phe Leu Ser Pro Leu Asn
1               5                   10                  15

Gly Thr Gly Val Gln Asp Val Ala Gly Leu Val Thr Ala Lys Gly Pro
                20                  25                  30

Asn Gly Phe Trp Ile Arg Ser Pro Glu Pro Asp Thr His Asp Arg Thr
                35                  40                  45

Ser Glu Ser Val Tyr Val Phe Gly Arg Asn Ala Leu Gly Asn Val Thr
            50                  55                  60

Val Gly Asp Leu Ile Ser Val Asp Gly Asn Val Thr Glu Tyr Arg Ser
65                  70                  75                  80

Ser Lys Asp Tyr Ala Tyr Leu Thr Glu Ile Ile Asn Pro Arg Asn Ile
                85                  90                  95

Arg Val Val Ser Ser Gly Asn Glu Val Lys Pro Val Val Ile Gly Ser
                100                 105                 110

Lys Thr Ser Gly Ile Ile Gly Lys Arg Asp Val Gln Pro Pro Arg Glu
            115                 120                 125

Gln Phe Ser Gly Leu Asp Asn Gly Asp Val Phe Ala Val Pro Asn Asn
130                 135                 140

Gln Ser Leu Ile Ser Gln Ala Asn Pro Arg Leu Glu Pro Asn Leu Tyr
145                 150                 155                 160

Gly Met Asp Phe Trp Glu Ser Leu Ser Gly Glu Leu Val Thr Ile Lys
                165                 170                 175
```

-continued

Gly Val Thr Ala Leu Gly Arg Gln Ala Asn Thr Phe Gly Asp Gln Trp
            180                 185                 190

Val Arg Gly Asp Trp Lys Ser Ser Gly Lys Asn Ser Arg Gly Gly Leu
        195                 200                 205

Thr Val Thr Asp Arg Asp Ser Asn Pro Glu Ser Ile Ile Gly Ala
    210                 215                 220

Pro Leu Asp Gly Ser Ser Asn Ser Lys Glu Thr Lys Leu Gly Asp Glu
225                 230                 235                 240

Leu Glu Asp Ile Thr Gly Ile Val Thr Tyr Val Phe Gly Phe Tyr Ala
                245                 250                 255

Ile Phe Pro Gln Thr Gly Thr Lys Val Lys Arg Ser Ile Asp Ala Phe
            260                 265                 270

Pro Pro Pro Ser Ser Ile Val Ser Asn Gly Lys Cys Ser Gly Leu Thr
        275                 280                 285

Phe Gly Gln Tyr Asn Ile Glu Asn Phe Ala Pro Asn Asn Ser Arg Val
    290                 295                 300

Pro Leu Ile Ala Glu His Ile Val Asp Tyr Leu Asn Thr Pro Ser Val
305                 310                 315                 320

Met Phe Leu Gln Glu Val Gln Asp Asn Ser Gly Glu Ala Asn Asp Gly
                325                 330                 335

Val Val Asn Ser Asn Leu Thr Leu Ala Ser Leu Ser Gln Ala Ile Ser
            340                 345                 350

Glu Ile Ser Gly Val Asp Tyr Leu Trp Val Asn Val Asp Pro Val Asn
        355                 360                 365

Asn Gln Asp Gly Gly Ala Pro Gly Gly Asn Ile Gln Thr Pro Tyr Leu
    370                 375                 380

Tyr Asn Pro Leu Gln Val Arg Leu Leu Asn Ala Asn Pro Gly Gly Pro
385                 390                 395                 400

Asn Asp Arg Asn Glu Val Leu Pro Gly Pro Thr Leu Arg Phe Asn Pro
                405                 410                 415

Gly Arg Ile Asp Asp Gly Val Thr Phe Ser Asn Ser Arg Lys Pro Ile
            420                 425                 430

Val Ala His Trp Glu Met Val Asp Gly Ser Gly Thr Phe Phe Thr Val
        435                 440                 445

Asn Asn His Trp Thr Ser Lys Gly Gly Ser Thr Ser Leu Gln Gly Asp
    450                 455                 460

Ala Arg Pro Pro Val Asn Gly Gly Val Asp Arg Arg Ile Arg Gln Ala
465                 470                 475                 480

Glu Val Thr Gly Ser Phe Ile Ala Glu Ile Leu Lys Gln Asp Lys Asn
                485                 490                 495

Ala Ala Ile Ile Val Ala Gly Asp Leu Asn Glu Phe Ala Thr Val Ala
            500                 505                 510

Pro Leu Arg Arg Phe Val Glu Val Ser Gly Leu Lys Asp Leu Asp Val
        515                 520                 525

Val Ala Lys Ile Pro Glu Leu Glu Arg Tyr Ser Tyr Thr Phe Gly Ala
    530                 535                 540

Ser Gln Gln Gln Leu Asp His Val Tyr Ala Ser Ala Trp Ala Ser Arg
545                 550                 555                 560

Lys Val Gly Lys Gly Asp Phe Glu His Val His Val Asn Thr Trp Val
                565                 570                 575

Ala Glu Glu Asp Val Gly Ser Asp His Asp Pro Ala Val Ala Arg Leu
            580                 585                 590

Asn Val Cys Ser Thr

<210> SEQ ID NO 34
<211> LENGTH: 1928
<212> TYPE: DNA
<213> ORGANISM: Rhinocladiella sp.
<220> FEATURE:
<221> NAME/KEY: CDS
<222> LOCATION: (1)..(694)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1925)
<220> FEATURE:
<221> NAME/KEY: CDS
<222> LOCATION: (745)..(1925)

<400> SEQUENCE: 34

| | | | | | | | | | | | | | | | | |
|---|---|---|---|---|---|---|---|---|---|---|---|---|---|---|---|---|
| atg | cct | ttt | cct | aac | aag | gtt | ggc | acg | ata | gct | gca | ttg | gct | ctg | agc | 48 |
| Met | Pro | Phe | Pro | Asn | Lys | Val | Gly | Thr | Ile | Ala | Ala | Leu | Ala | Leu | Ser | |
| -25 | | | | -20 | | | | | -15 | | | | | -10 | | |

| | | | | | | | | | | | | | | | | |
|---|---|---|---|---|---|---|---|---|---|---|---|---|---|---|---|---|
| aac | ctg | tat | tgc | cag | ttc | gct | tcg | gca | ctg | aca | att | gca | gag | atc | aat | 96 |
| Asn | Leu | Tyr | Cys | Gln | Phe | Ala | Ser | Ala | Leu | Thr | Ile | Ala | Glu | Ile | Asn | |
| | | | -5 | | | | -1 | 1 | | | | 5 | | | | |

| | | | | | | | | | | | | | | | | |
|---|---|---|---|---|---|---|---|---|---|---|---|---|---|---|---|---|
| ggc | aac | aaa | tac | ttg | tcg | ccc | tac | gcc | ggc | cag | gct | gtt | acc | aat | ata | 144 |
| Gly | Asn | Lys | Tyr | Leu | Ser | Pro | Tyr | Ala | Gly | Gln | Ala | Val | Thr | Asn | Ile | |
| | | 10 | | | | | 15 | | | | | 20 | | | | |

| | | | | | | | | | | | | | | | | |
|---|---|---|---|---|---|---|---|---|---|---|---|---|---|---|---|---|
| tcc | ggg | ctt | gtc | act | gcc | aaa | ggg | ccg | agc | ggc | atc | ttc | atc | cgc | tcg | 192 |
| Ser | Gly | Leu | Val | Thr | Ala | Lys | Gly | Pro | Ser | Gly | Ile | Phe | Ile | Arg | Ser | |
| | 25 | | | | | 30 | | | | | 35 | | | | | |

| | | | | | | | | | | | | | | | | |
|---|---|---|---|---|---|---|---|---|---|---|---|---|---|---|---|---|
| acg | acg | cct | gac | agt | gat | cca | gca | aca | tct | gaa | tcg | gtc | tat | gta | ttt | 240 |
| Thr | Thr | Pro | Asp | Ser | Asp | Pro | Ala | Thr | Ser | Glu | Ser | Val | Tyr | Val | Phe | |
| 40 | | | | | 45 | | | | | 50 | | | | | 55 | |

| | | | | | | | | | | | | | | | | |
|---|---|---|---|---|---|---|---|---|---|---|---|---|---|---|---|---|
| ggg | agc | aat | gcg | ggg | cgc | aat | gtg | acc | gtg | ggg | gat | gtt | atc | act | ctt | 288 |
| Gly | Ser | Asn | Ala | Gly | Arg | Asn | Val | Thr | Val | Gly | Asp | Val | Ile | Thr | Leu | |
| | | | 60 | | | | | 65 | | | | | 70 | | | |

| | | | | | | | | | | | | | | | | |
|---|---|---|---|---|---|---|---|---|---|---|---|---|---|---|---|---|
| gat | ggc | acc | gtt | acg | gaa | ttc | aga | tcc | acg | tca | aac | ccc | acc | tat | ctc | 336 |
| Asp | Gly | Thr | Val | Thr | Glu | Phe | Arg | Ser | Thr | Ser | Asn | Pro | Thr | Tyr | Leu | |
| | | 75 | | | | | 80 | | | | | 85 | | | | |

| | | | | | | | | | | | | | | | | |
|---|---|---|---|---|---|---|---|---|---|---|---|---|---|---|---|---|
| ttc | ctc | acc | gag | atc | act | agt | ccc | cgc | aat | gtt | aag | act | gta | tcc | agc | 384 |
| Phe | Leu | Thr | Glu | Ile | Thr | Ser | Pro | Arg | Asn | Val | Lys | Thr | Val | Ser | Ser | |
| | 90 | | | | | 95 | | | | | 100 | | | | | |

| | | | | | | | | | | | | | | | | |
|---|---|---|---|---|---|---|---|---|---|---|---|---|---|---|---|---|
| gga | aat | cac | gta | gcg | cct | ctc | gtc | att | gga | aag | gac | acc | agt | gcc | cct | 432 |
| Gly | Asn | His | Val | Ala | Pro | Leu | Val | Ile | Gly | Lys | Asp | Thr | Ser | Ala | Pro | |
| | 105 | | | | | 110 | | | | | 115 | | | | | |

| | | | | | | | | | | | | | | | | |
|---|---|---|---|---|---|---|---|---|---|---|---|---|---|---|---|---|
| ccc | act | cag | caa | ttc | tcc | ggg | ctc | gac | gac | gga | gat | gcg | ctt | ggt | gtg | 480 |
| Pro | Thr | Gln | Gln | Phe | Ser | Gly | Leu | Asp | Asp | Gly | Asp | Ala | Leu | Gly | Val | |
| 120 | | | | | 125 | | | | | 130 | | | | | 135 | |

| | | | | | | | | | | | | | | | | |
|---|---|---|---|---|---|---|---|---|---|---|---|---|---|---|---|---|
| ccc | aac | aac | gca | agc | ctg | att | tcg | gtc | acc | aac | ccg | gag | cta | aag | ccc | 528 |
| Pro | Asn | Asn | Ala | Ser | Leu | Ile | Ser | Val | Thr | Asn | Pro | Glu | Leu | Lys | Pro | |
| | | | 140 | | | | | 145 | | | | | 150 | | | |

| | | | | | | | | | | | | | | | | |
|---|---|---|---|---|---|---|---|---|---|---|---|---|---|---|---|---|
| tca | gaa | ttt | ggt | atg | gac | ttc | tgg | gag | agt | ttg | tcc | ggg | gaa | ctt | gtg | 576 |
| Ser | Glu | Phe | Gly | Met | Asp | Phe | Trp | Glu | Ser | Leu | Ser | Gly | Glu | Leu | Val | |
| | | | 155 | | | | | 160 | | | | | 165 | | | |

| | | | | | | | | | | | | | | | | |
|---|---|---|---|---|---|---|---|---|---|---|---|---|---|---|---|---|
| acc | att | aag | ggc | gcg | aag | gcc | atc | agt | aaa | ccc | aac | aac | ttt | ggg | gat | 624 |
| Thr | Ile | Lys | Gly | Ala | Lys | Ala | Ile | Ser | Lys | Pro | Asn | Asn | Phe | Gly | Asp | |
| | | 170 | | | | | 175 | | | | | 180 | | | | |

| | | | | | | | | | | | | | | | | |
|---|---|---|---|---|---|---|---|---|---|---|---|---|---|---|---|---|
| act | tgg | gtc | act | gga | gac | tgg | aag | gtc | aca | ggc | cgc | aat | gct | cgc | ggc | 672 |
| Thr | Trp | Val | Thr | Gly | Asp | Trp | Lys | Val | Thr | Gly | Arg | Asn | Ala | Arg | Gly | |
| | 185 | | | | | 190 | | | | | 195 | | | | | |

| | | | | | | | |
|---|---|---|---|---|---|---|---|
| ggc | ctt | acc | atg | acc | aag | aat | g gtaagagatg ttaaacaatg atatggaatt | 724 |

```
Gly Leu Thr Met Thr Lys Asn
200                 205 tgcagaagct catataacag at  tcg aat cct gag gcc atc atc att ggt act       776
                          Asp Ser Asn Pro Glu Ala Ile Ile Ile Gly Thr
                                      210                 215 cct ctg gac ggc acg cgc aat gcc aat gga acc aag ctt ggt gac tca         824
Pro Leu Asp Gly Thr Arg Asn Ala Asn Gly Thr Lys Leu Gly Asp Ser
            220                 225                 230 ctc gaa gac atc acc ggt gtc att acg tac ggc ttt ggc ttt tat cgc         872
Leu Glu Asp Ile Thr Gly Val Ile Thr Tyr Gly Phe Gly Phe Tyr Arg
        235                 240                 245 ata tta cca gtg act ggc atc aag gtc aca ggg tct gcc cag cct gcg         920
Ile Leu Pro Val Thr Gly Ile Lys Val Thr Gly Ser Ala Gln Pro Ala
250                 255                 260                 265 ttg cct ccc tca acc act ctg aag gct gga aag tct tgc cga gac ttg         968
Leu Pro Pro Ser Thr Thr Leu Lys Ala Gly Lys Ser Cys Arg Asp Leu
                270                 275                 280 acc ttc ggc tcc tac aac gtc gaa aac ctg agt cct aca aag tca atc        1016
Thr Phe Gly Ser Tyr Asn Val Glu Asn Leu Ser Pro Thr Lys Ser Ile
            285                 290                 295 ttg cct agc att gcc tcg cac atc gcc aac gtc atg aag gcc cca tct        1064
Leu Pro Ser Ile Ala Ser His Ile Ala Asn Val Met Lys Ala Pro Ser
        300                 305                 310 ctt gtc ttc ctt cag gag atc cag gat aac aat ggc gct gtc aac gac        1112
Leu Val Phe Leu Gln Glu Ile Gln Asp Asn Asn Gly Ala Val Asn Asp
315                 320                 325 gca gtt gtt gat gcg aac ctc acc ctc tcg act ctt gca gcc gaa gtc        1160
Ala Val Val Asp Ala Asn Leu Thr Leu Ser Thr Leu Ala Ala Glu Val
330                 335                 340                 345 aat cgc ctt tct ggc gtt aat tat gcc tac gta gac gtc gac cct gtt        1208
Asn Arg Leu Ser Gly Val Asn Tyr Ala Tyr Val Asp Val Asp Pro Val
                350                 355                 360 gac gac caa gac ggt ggt gag cct ggc ggc aac atc cgc aca gcc tac        1256
Asp Asp Gln Asp Gly Gly Glu Pro Gly Gly Asn Ile Arg Thr Ala Tyr
            365                 370                 375 ttc tac gat ccc act gtt ctc cgc ctt cgt aac cca aac cct ggc agc        1304
Phe Tyr Asp Pro Thr Val Leu Arg Leu Arg Asn Pro Asn Pro Gly Ser
        380                 385                 390 ccc act gac gcc aac gag gtc ctg caa ggc gat gtt ctt cgt ggc cct        1352
Pro Thr Asp Ala Asn Glu Val Leu Gln Gly Asp Val Leu Arg Gly Pro
395                 400                 405 gag ctc aag tac aat ccc ggg cgc atc gac ccg acc aat gcc gcc tgg        1400
Glu Leu Lys Tyr Asn Pro Gly Arg Ile Asp Pro Thr Asn Ala Ala Trp
410                 415                 420                 425 gaa aga tct cgc aag cct tta acc gct gtc tgg gaa acc ctc gat gga        1448
Glu Arg Ser Arg Lys Pro Leu Thr Ala Val Trp Glu Thr Leu Asp Gly
                430                 435                 440 cgc aac aag ttt ttt acc atc aac gtc cat ttt gcc tcc aaa ggt ggt        1496
Arg Asn Lys Phe Phe Thr Ile Asn Val His Phe Ala Ser Lys Gly Gly
            445                 450                 455 tct tca tcc gtt cag ggt gac ccc cgt cct ccg atc aac ggt gtc att        1544
Ser Ser Ser Val Gln Gly Asp Pro Arg Pro Pro Ile Asn Gly Val Ile
        460                 465                 470 gat gtt cgc acg cag caa gca cag atc acc gcc gag ttc atc cgc gac        1592
Asp Val Arg Thr Gln Gln Ala Gln Ile Thr Ala Glu Phe Ile Arg Asp
475                 480                 485 atc ctc cgt aaa gac cct acc tcg tcc gtc atc atc gct ggt gac ttc        1640
Ile Leu Arg Lys Asp Pro Thr Ser Ser Val Ile Ile Ala Gly Asp Phe
490                 495                 500                 505
```

| | | | | | | | | | | | | | | | | |
|---|---|---|---|---|---|---|---|---|---|---|---|---|---|---|---|---|
| aac | gaa | ttc | gcc | ttc | gtc | cag | ccg | ctg | gaa | ggg | ttc | tcc | aag | acg | tct | 1688 |
| Asn | Glu | Phe | Ala | Phe | Val | Gln | Pro | Leu | Glu | Gly | Phe | Ser | Lys | Thr | Ser | |
| | | | | 510 | | | | | 515 | | | | | 520 | | |
| tgg | atg | cag | gac | ctt | gat | gca | gtt | gct | ggc | att | aaa | ccc | gaa | gag | aga | 1736 |
| Trp | Met | Gln | Asp | Leu | Asp | Ala | Val | Ala | Gly | Ile | Lys | Pro | Glu | Glu | Arg | |
| | | 525 | | | | | 530 | | | | | 535 | | | | |
| tac | acc | tac | ctc | ttt | gac | atg | aac | tgt | cag | cag | cta | gat | cac | atg | tac | 1784 |
| Tyr | Thr | Tyr | Leu | Phe | Asp | Met | Asn | Cys | Gln | Gln | Leu | Asp | His | Met | Tyr | |
| 540 | | | | | | 545 | | | | | 550 | | | | | |
| gtg | agc | cca | gta | ctc | gcc | gcc | aag | aag | tat | att | ggg | cgc | gtg | aaa | tat | 1832 |
| Val | Ser | Pro | Val | Leu | Ala | Ala | Lys | Lys | Tyr | Ile | Gly | Arg | Val | Lys | Tyr | |
| 555 | | | | | 560 | | | | | 565 | | | | | | |
| gag | cac | atc | cac | atc | aac | aca | tgg | gag | aca | agg | gct | gga | caa | att | agt | 1880 |
| Glu | His | Ile | His | Ile | Asn | Thr | Trp | Glu | Thr | Arg | Ala | Gly | Gln | Ile | Ser | |
| 570 | | | | | 575 | | | | | 580 | | | | | 585 | |
| gac | cac | gat | ccg | agc | gtg | gca | caa | cta | gat | gta | tgc | cgg | ctt | ttt | tag | 1928 |
| Asp | His | Asp | Pro | Ser | Val | Ala | Gln | Leu | Asp | Val | Cys | Arg | Leu | Phe | | |
| | | | | 590 | | | | | 595 | | | | | 600 | | |

<210> SEQ ID NO 35
<211> LENGTH: 625
<212> TYPE: PRT
<213> ORGANISM: Rhinocladiella sp.

<400> SEQUENCE: 35

Met Pro Phe Pro Asn Lys Val Gly Thr Ile Ala Ala Leu Ala Leu Ser
-25                 -20                 -15                 -10

Asn Leu Tyr Cys Gln Phe Ala Ser Ala Leu Thr Ile Ala Glu Ile Asn
            -5                  -1  1               5

Gly Asn Lys Tyr Leu Ser Pro Tyr Ala Gly Gln Ala Val Thr Asn Ile
            10                  15                  20

Ser Gly Leu Val Thr Ala Lys Gly Pro Ser Gly Ile Phe Ile Arg Ser
        25                  30                  35

Thr Thr Pro Asp Ser Asp Pro Ala Thr Ser Glu Ser Val Tyr Val Phe
40                  45                  50                  55

Gly Ser Asn Ala Gly Arg Asn Val Thr Val Gly Asp Val Ile Thr Leu
                60                  65                  70

Asp Gly Thr Val Thr Glu Phe Arg Ser Thr Ser Asn Pro Thr Tyr Leu
            75                  80                  85

Phe Leu Thr Glu Ile Thr Ser Pro Arg Asn Val Lys Thr Val Ser Ser
        90                  95                  100

Gly Asn His Val Ala Pro Leu Val Ile Gly Lys Asp Thr Ser Ala Pro
105                 110                 115

Pro Thr Gln Gln Phe Ser Gly Leu Asp Asp Gly Asp Ala Leu Gly Val
120                 125                 130                 135

Pro Asn Asn Ala Ser Leu Ile Ser Val Thr Asn Pro Glu Leu Lys Pro
                140                 145                 150

Ser Glu Phe Gly Met Asp Phe Trp Glu Ser Leu Ser Gly Glu Leu Val
            155                 160                 165

Thr Ile Lys Gly Ala Lys Ala Ile Ser Lys Pro Asn Asn Phe Gly Asp
        170                 175                 180

Thr Trp Val Thr Gly Asp Trp Lys Val Thr Gly Arg Asn Ala Arg Gly
        185                 190                 195

Gly Leu Thr Met Thr Lys Asn Asp Ser Asn Pro Glu Ala Ile Ile Ile
200                 205                 210                 215

Gly Thr Pro Leu Asp Gly Thr Arg Asn Ala Asn Gly Thr Lys Leu Gly
                220                 225                 230

```
Asp Ser Leu Glu Asp Ile Thr Gly Val Ile Thr Tyr Gly Phe Gly Phe
            235                 240                 245

Tyr Arg Ile Leu Pro Val Thr Gly Ile Lys Val Thr Gly Ser Ala Gln
            250                 255                 260

Pro Ala Leu Pro Pro Ser Thr Thr Leu Lys Ala Gly Lys Ser Cys Arg
265                 270                 275

Asp Leu Thr Phe Gly Ser Tyr Asn Val Glu Asn Leu Ser Pro Thr Lys
280                 285                 290                 295

Ser Ile Leu Pro Ser Ile Ala Ser His Ile Ala Asn Val Met Lys Ala
                300                 305                 310

Pro Ser Leu Val Phe Leu Gln Glu Ile Gln Asp Asn Asn Gly Ala Val
            315                 320                 325

Asn Asp Ala Val Val Asp Ala Asn Leu Thr Leu Ser Thr Leu Ala Ala
            330                 335                 340

Glu Val Asn Arg Leu Ser Gly Val Asn Tyr Ala Tyr Val Asp Val Asp
            345                 350                 355

Pro Val Asp Asp Gln Asp Gly Gly Glu Pro Gly Gly Asn Ile Arg Thr
360                 365                 370                 375

Ala Tyr Phe Tyr Asp Pro Thr Val Leu Arg Leu Arg Asn Pro Asn Pro
            380                 385                 390

Gly Ser Pro Thr Asp Ala Asn Glu Val Leu Gln Gly Asp Val Leu Arg
            395                 400                 405

Gly Pro Glu Leu Lys Tyr Asn Pro Gly Arg Ile Asp Pro Thr Asn Ala
            410                 415                 420

Ala Trp Glu Arg Ser Arg Lys Pro Leu Thr Ala Val Trp Glu Thr Leu
            425                 430                 435

Asp Gly Arg Asn Lys Phe Phe Thr Ile Asn Val His Phe Ala Ser Lys
440                 445                 450                 455

Gly Gly Ser Ser Ser Val Gln Gly Asp Pro Arg Pro Pro Ile Asn Gly
            460                 465                 470

Val Ile Asp Val Arg Thr Gln Gln Ala Gln Ile Thr Ala Glu Phe Ile
            475                 480                 485

Arg Asp Ile Leu Arg Lys Asp Pro Thr Ser Ser Val Ile Ile Ala Gly
            490                 495                 500

Asp Phe Asn Glu Phe Ala Phe Val Gln Pro Leu Glu Gly Phe Ser Lys
505                 510                 515

Thr Ser Trp Met Gln Asp Leu Asp Ala Val Ala Gly Ile Lys Pro Glu
520                 525                 530                 535

Glu Arg Tyr Thr Tyr Leu Phe Asp Met Asn Cys Gln Gln Leu Asp His
            540                 545                 550

Met Tyr Val Ser Pro Val Leu Ala Ala Lys Lys Tyr Ile Gly Arg Val
            555                 560                 565

Lys Tyr Glu His Ile His Ile Asn Thr Trp Glu Thr Arg Ala Gly Gln
            570                 575                 580

Ile Ser Asp His Asp Pro Ser Val Ala Gln Leu Asp Val Cys Arg Leu
            585                 590                 595

Phe
600

<210> SEQ ID NO 36
<211> LENGTH: 600
<212> TYPE: PRT
<213> ORGANISM: Rhinocladiella sp.
```

```
<400> SEQUENCE: 36

Leu Thr Ile Ala Glu Ile Asn Gly Asn Lys Tyr Leu Ser Pro Tyr Ala
  1               5                  10                  15

Gly Gln Ala Val Thr Asn Ile Ser Gly Leu Val Thr Ala Lys Gly Pro
             20                  25                  30

Ser Gly Ile Phe Ile Arg Ser Thr Pro Asp Ser Asp Pro Ala Thr
         35                  40                  45

Ser Glu Ser Val Tyr Val Phe Gly Ser Asn Ala Gly Arg Asn Val Thr
 50                  55                  60

Val Gly Asp Val Ile Thr Leu Asp Gly Thr Val Thr Glu Phe Arg Ser
 65                  70                  75                  80

Thr Ser Asn Pro Thr Tyr Leu Phe Leu Thr Glu Ile Thr Ser Pro Arg
                 85                  90                  95

Asn Val Lys Thr Val Ser Ser Gly Asn His Val Ala Pro Leu Val Ile
            100                 105                 110

Gly Lys Asp Thr Ser Ala Pro Pro Thr Gln Gln Phe Ser Gly Leu Asp
            115                 120                 125

Asp Gly Asp Ala Leu Gly Val Pro Asn Asn Ala Ser Leu Ile Ser Val
        130                 135                 140

Thr Asn Pro Glu Leu Lys Pro Ser Glu Phe Gly Met Asp Phe Trp Glu
145                 150                 155                 160

Ser Leu Ser Gly Glu Leu Val Thr Ile Lys Gly Ala Lys Ala Ile Ser
                165                 170                 175

Lys Pro Asn Asn Phe Gly Asp Thr Trp Val Thr Gly Asp Trp Lys Val
            180                 185                 190

Thr Gly Arg Asn Ala Arg Gly Gly Leu Thr Met Thr Lys Asn Asp Ser
        195                 200                 205

Asn Pro Glu Ala Ile Ile Ile Gly Thr Pro Leu Asp Gly Thr Arg Asn
210                 215                 220

Ala Asn Gly Thr Lys Leu Gly Asp Ser Leu Glu Asp Ile Thr Gly Val
225                 230                 235                 240

Ile Thr Tyr Gly Phe Gly Phe Tyr Arg Ile Leu Pro Val Thr Gly Ile
                245                 250                 255

Lys Val Thr Gly Ser Ala Gln Pro Ala Leu Pro Pro Ser Thr Thr Leu
            260                 265                 270

Lys Ala Gly Lys Ser Cys Arg Asp Leu Thr Phe Gly Ser Tyr Asn Val
        275                 280                 285

Glu Asn Leu Ser Pro Thr Lys Ser Ile Leu Pro Ser Ile Ala Ser His
290                 295                 300

Ile Ala Asn Val Met Lys Ala Pro Ser Leu Val Phe Leu Gln Glu Ile
305                 310                 315                 320

Gln Asp Asn Asn Gly Ala Val Asn Asp Ala Val Asp Ala Asn Leu
                325                 330                 335

Thr Leu Ser Thr Leu Ala Ala Glu Val Asn Arg Leu Ser Gly Val Asn
            340                 345                 350

Tyr Ala Tyr Val Asp Val Asp Pro Val Asp Asp Gln Asp Gly Gly Glu
        355                 360                 365

Pro Gly Gly Asn Ile Arg Thr Ala Tyr Phe Tyr Asp Pro Thr Val Leu
370                 375                 380

Arg Leu Arg Asn Pro Asn Pro Gly Ser Pro Thr Asp Ala Asn Glu Val
385                 390                 395                 400

Leu Gln Gly Asp Val Leu Arg Gly Pro Glu Leu Lys Tyr Asn Pro Gly
                405                 410                 415
```

```
Arg Ile Asp Pro Thr Asn Ala Ala Trp Glu Arg Ser Arg Lys Pro Leu
            420                 425                 430

Thr Ala Val Trp Glu Thr Leu Asp Gly Arg Asn Lys Phe Phe Thr Ile
            435                 440                 445

Asn Val His Phe Ala Ser Lys Gly Gly Ser Ser Val Gln Gly Asp
450                 455                 460

Pro Arg Pro Pro Ile Asn Gly Val Ile Asp Val Arg Thr Gln Gln Ala
465                 470                 475                 480

Gln Ile Thr Ala Glu Phe Ile Arg Asp Ile Leu Arg Lys Asp Pro Thr
            485                 490                 495

Ser Ser Val Ile Ile Ala Gly Asp Phe Asn Glu Phe Ala Phe Val Gln
            500                 505                 510

Pro Leu Glu Gly Phe Ser Lys Thr Ser Trp Met Gln Asp Leu Asp Ala
            515                 520                 525

Val Ala Gly Ile Lys Pro Glu Glu Arg Tyr Thr Tyr Leu Phe Asp Met
            530                 535                 540

Asn Cys Gln Gln Leu Asp His Met Tyr Val Ser Pro Val Leu Ala Ala
545                 550                 555                 560

Lys Lys Tyr Ile Gly Arg Val Lys Tyr Glu His Ile His Ile Asn Thr
            565                 570                 575

Trp Glu Thr Arg Ala Gly Gln Ile Ser Asp His Asp Pro Ser Val Ala
            580                 585                 590

Gln Leu Asp Val Cys Arg Leu Phe
            595                 600

<210> SEQ ID NO 37
<211> LENGTH: 1821
<212> TYPE: DNA
<213> ORGANISM: Pyronema domesticum
<220> FEATURE:
<221> NAME/KEY: CDS
<222> LOCATION: (1)..(1818)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1818)

<400> SEQUENCE: 37 atg aga tcc tac gtt ctt acc acg ctt gtt tcc tac ctg ggt gtt gcc      48
Met Arg Ser Tyr Val Leu Thr Thr Leu Val Ser Tyr Leu Gly Val Ala
            -15                 -10                 -5 tcc gca gtt tcc att gcg gaa atc aac ggc ccc gca ttt ctt tca ccc      96
Ser Ala Val Ser Ile Ala Glu Ile Asn Gly Pro Ala Phe Leu Ser Pro
 -1   1               5                  10 tac gcc gga aaa tca gtc acc gac atc act ggc ctc gtc aca gcg gtt     144
Tyr Ala Gly Lys Ser Val Thr Asp Ile Thr Gly Leu Val Thr Ala Val
15              20                  25                  30 gga cca tcc ggt ttt ttc ctc cga gat gtt gca tct aca tca tcc cgt     192
Gly Pro Ser Gly Phe Phe Leu Arg Asp Val Ala Ser Thr Ser Ser Arg
                35                  40                  45 ctc cgc cgc aat cag tcc gga tcg caa gct gtc tac gtt ttt aat tcc     240
Leu Arg Arg Asn Gln Ser Gly Ser Gln Ala Val Tyr Val Phe Asn Ser
            50                  55                  60 gcc gcc gca aag aat gtc acc gcc ggg gac atc ata aac atc aac tct     288
Ala Ala Ala Lys Asn Val Thr Ala Gly Asp Ile Ile Asn Ile Asn Ser
        65                  70                  75 gcc tcc gtc gtc gaa tac caa aac aac caa gcc tac att cct ttg aca     336
```

```
                Ala Ser Val Val Glu Tyr Gln Asn Asn Gln Ala Tyr Ile Pro Leu Thr
                    80                  85                  90 gag atc acc aac cca tcc gcc atc caa att gtc tcc aag ggc cat gaa       384
Glu Ile Thr Asn Pro Ser Ala Ile Gln Ile Val Ser Lys Gly His Glu
 95                 100                 105                 110 gtc att ccc att cct ctt gga cgc aac ggt ctg cag cct cct act ggt       432
Val Ile Pro Ile Pro Leu Gly Arg Asn Gly Leu Gln Pro Pro Thr Gly
                    115                 120                 125 cag ttt tct gct ctc gac aac ggc gac att ttt ggc ctc ccc aat gga       480
Gln Phe Ser Ala Leu Asp Asn Gly Asp Ile Phe Gly Leu Pro Asn Gly
            130                 135                 140 gct tcc aaa atc tca agc acc aac gca act ctt gta cca act aaa ttt       528
Ala Ser Lys Ile Ser Ser Thr Asn Ala Thr Leu Val Pro Thr Lys Phe
            145                 150                 155 ggt ctc gac ttc tgg gag tct tta agc gga gaa ttc gtt ggc atc tca       576
Gly Leu Asp Phe Trp Glu Ser Leu Ser Gly Glu Phe Val Gly Ile Ser
        160                 165                 170 tct ccc act gcc ctc ggt cca act agt cga tac ggg gac atc tgg atc       624
Ser Pro Thr Ala Leu Gly Pro Thr Ser Arg Tyr Gly Asp Ile Trp Ile
175                 180                 185                 190 cgc ggc gac tgg gaa gtt acg ggc ttg aac tcc gcc ggt ggt ctc acc       672
Arg Gly Asp Trp Glu Val Thr Gly Leu Asn Ser Ala Gly Gly Leu Thr
                    195                 200                 205 atc act act ggt act tcc tca gac gcc aac ccg gaa acc atc atc atc       720
Ile Thr Thr Gly Thr Ser Ser Asp Ala Asn Pro Glu Thr Ile Ile Ile
                210                 215                 220 ggt tca cct ctt gat gga acc aaa aac ccc tcc gtc aag ctc gga gac       768
Gly Ser Pro Leu Asp Gly Thr Lys Asn Pro Ser Val Lys Leu Gly Asp
            225                 230                 235 att ctc aac cct att caa gga gtc atc acc tac ggc ttt ggt ttc tac       816
Ile Leu Asn Pro Ile Gln Gly Val Ile Thr Tyr Gly Phe Gly Phe Tyr
        240                 245                 250 cgt ctc ctc ccc acc aca gcc att tcc atc aag agc gca cgt aat gca       864
Arg Leu Leu Pro Thr Thr Ala Ile Ser Ile Lys Ser Ala Arg Asn Ala
255                 260                 265                 270 acc act cca gtc acc act tta aaa tca gag aaa tcc tgt aaa gct gta       912
Thr Thr Pro Val Thr Thr Leu Lys Ser Glu Lys Ser Cys Lys Ala Val
                    275                 280                 285 act atc ggc caa tac aat gtc gaa aat ctc tcc cct tcc tca agc cat       960
Thr Ile Gly Gln Tyr Asn Val Glu Asn Leu Ser Pro Ser Ser Ser His
                290                 295                 300 ctt aac gcc att gcc gat cat att ggt tac aac atg ggc tct ccg gat      1008
Leu Asn Ala Ile Ala Asp His Ile Gly Tyr Asn Met Gly Ser Pro Asp
            305                 310                 315 tta atc tac gtt caa gaa ctc caa gac aac tct gga gcc acc aac gac      1056
Leu Ile Tyr Val Gln Glu Leu Gln Asp Asn Ser Gly Ala Thr Asn Asp
        320                 325                 330 ggc ata act agc ggt aac atg aca ctc gcc gct tta gcc tac gcc att      1104
Gly Ile Thr Ser Gly Asn Met Thr Leu Ala Ala Leu Ala Tyr Ala Ile
335                 340                 345                 350 gaa gga atc tcc ggt att caa tac cac tgg gcg gaa gta gat cct gag      1152
Glu Gly Ile Ser Gly Ile Gln Tyr His Trp Ala Glu Val Asp Pro Glu
                    355                 360                 365 gat aac ctg gac gga gga caa ccc ggt ggc aac atc cgt gtt gca tat      1200
Asp Asn Leu Asp Gly Gly Gln Pro Gly Gly Asn Ile Arg Val Ala Tyr
                370                 375                 380 ctc tac aac ccc tct gta ttt tcc atc tcc ggc acg ccc ggt acc gca      1248
Leu Tyr Asn Pro Ser Val Phe Ser Ile Ser Gly Thr Pro Gly Thr Ala
            385                 390                 395
```

| | | | | | | | | | | | | | | |
|---|---|---|---|---|---|---|---|---|---|---|---|---|---|---|
| tcc | gaa | gca | acc | act | gta | caa | ccc | ggt | cca | tcc | ctc | tcg | ctg | aac | cct | 1296 |
| Ser | Glu | Ala | Thr | Thr | Val | Gln | Pro | Gly | Pro | Ser | Leu | Ser | Leu | Asn | Pro |
| | 400 | | | | 405 | | | | | 410 | | | | | |

| ggg | aga | atc | gat | cct | caa | aac | gtg | gct | ttc | act | aac | tcc | cgt | aag | ccg | 1344 |
|---|---|---|---|---|---|---|---|---|---|---|---|---|---|---|---|---|
| Gly | Arg | Ile | Asp | Pro | Gln | Asn | Val | Ala | Phe | Thr | Asn | Ser | Arg | Lys | Pro |
| 415 | | | | | 420 | | | | | 425 | | | | | 430 |

| ttg | gtg | gcc | cag | ttc | tct | gtt | gag | gga | acc | cag | aaa | ccg | ttt | ttt | gct | 1392 |
|---|---|---|---|---|---|---|---|---|---|---|---|---|---|---|---|---|
| Leu | Val | Ala | Gln | Phe | Ser | Val | Glu | Gly | Thr | Gln | Lys | Pro | Phe | Phe | Ala |
| | | | | 435 | | | | | 440 | | | | | 445 | |

| atc | aat | gtc | cat | agt | gga | tcc | aaa | ggt | ggt | tct | tct | tct | ttg | cat | ggg | 1440 |
|---|---|---|---|---|---|---|---|---|---|---|---|---|---|---|---|---|
| Ile | Asn | Val | His | Ser | Gly | Ser | Lys | Gly | Gly | Ser | Ser | Ser | Leu | His | Gly |
| | | | 450 | | | | 455 | | | | | 460 | | | |

| gat | gca | aga | cca | ccc | atg | aat | gga | gga | att | gaa | gac | cgt | att | gcg | cag | 1488 |
|---|---|---|---|---|---|---|---|---|---|---|---|---|---|---|---|---|
| Asp | Ala | Arg | Pro | Pro | Met | Asn | Gly | Gly | Ile | Glu | Asp | Arg | Ile | Ala | Gln |
| | | 465 | | | | | 470 | | | | | 475 | | | |

| cat | gaa | gct | att | gcg | agc | ttt | atc | cag | gca | ctt | aag | aag | gag | gat | gaa | 1536 |
|---|---|---|---|---|---|---|---|---|---|---|---|---|---|---|---|---|
| His | Glu | Ala | Ile | Ala | Ser | Phe | Ile | Gln | Ala | Leu | Lys | Lys | Glu | Asp | Glu |
| | 480 | | | | | 485 | | | | | 490 | | | | |

| aat | gtt | aat | atc | cta | gcc | gcg | ggg | gat | ttt | aat | gag | ttt | tcg | gga | gtg | 1584 |
|---|---|---|---|---|---|---|---|---|---|---|---|---|---|---|---|---|
| Asn | Val | Asn | Ile | Leu | Ala | Ala | Gly | Asp | Phe | Asn | Glu | Phe | Ser | Gly | Val |
| 495 | | | | | 500 | | | | | 505 | | | | | 510 |

| gcg | cca | atg | gag | gtt | ttt | agg | gat | ttg | atg | tgg | gac | gtg | gat | gag | gtt | 1632 |
|---|---|---|---|---|---|---|---|---|---|---|---|---|---|---|---|---|
| Ala | Pro | Met | Glu | Val | Phe | Arg | Asp | Leu | Met | Trp | Asp | Val | Asp | Glu | Val |
| | | | | 515 | | | | | 520 | | | | | 525 | |

| gtg | gat | gtt | agc | aag | gag | gag | agg | tat | act | tat | aat | tat | gat | atg | aat | 1680 |
|---|---|---|---|---|---|---|---|---|---|---|---|---|---|---|---|---|
| Val | Asp | Val | Ser | Lys | Glu | Glu | Arg | Tyr | Thr | Tyr | Asn | Tyr | Asp | Met | Asn |
| | | | 530 | | | | 535 | | | | | 540 | | | |

| tgc | cag | cag | ctt | gat | cat | acg | ttg | att | tcg | gct | ggg | ttg | aag | gag | aag | 1728 |
|---|---|---|---|---|---|---|---|---|---|---|---|---|---|---|---|---|
| Cys | Gln | Gln | Leu | Asp | His | Thr | Leu | Ile | Ser | Ala | Gly | Leu | Lys | Glu | Lys |
| | | 545 | | | | | 550 | | | | | 555 | | | |

| gtg | agc | ggt | tat | cag | cat | ttg | cat | gtt | aat | act | tgg | agc | gag | gtc | gag | 1776 |
|---|---|---|---|---|---|---|---|---|---|---|---|---|---|---|---|---|
| Val | Ser | Gly | Tyr | Gln | His | Leu | His | Val | Asn | Thr | Trp | Ser | Glu | Val | Glu |
| | 560 | | | | | 565 | | | | | 570 | | | | |

| act | agt | gat | cat | gat | cct | agt | gtg | ggg | gtt | tat | gat | ctt | tgt | tag | | 1821 |
|---|---|---|---|---|---|---|---|---|---|---|---|---|---|---|---|---|
| Thr | Ser | Asp | His | Asp | Pro | Ser | Val | Gly | Val | Tyr | Asp | Leu | Cys | | |
| 575 | | | | | 580 | | | | | 585 | | | | | |

<210> SEQ ID NO 38
<211> LENGTH: 606
<212> TYPE: PRT
<213> ORGANISM: Pyronema domesticum

<400> SEQUENCE: 38

Met Arg Ser Tyr Val Leu Thr Thr Leu Val Ser Tyr Leu Gly Val Ala
            -15                 -10                  -5

Ser Ala Val Ser Ile Ala Glu Ile Asn Gly Pro Ala Phe Leu Ser Pro
 -1  1               5                   10

Tyr Ala Gly Lys Ser Val Thr Asp Ile Thr Gly Leu Val Thr Ala Val
 15               20                25                30

Gly Pro Ser Gly Phe Phe Leu Arg Asp Val Ala Ser Thr Ser Ser Arg
             35                 40                45

Leu Arg Arg Asn Gln Ser Gly Ser Gln Ala Val Tyr Val Phe Asn Ser
          50                55                60

Ala Ala Ala Lys Asn Val Thr Ala Gly Asp Ile Asn Ile Asn Ser
       65                70                75

Ala Ser Val Val Glu Tyr Gln Asn Asn Gln Ala Tyr Ile Pro Leu Thr
 80               85                90

Glu Ile Thr Asn Pro Ser Ala Ile Gln Ile Val Ser Lys Gly His Glu
 95              100              105            110

```
Val Ile Pro Ile Pro Leu Gly Arg Asn Gly Leu Gln Pro Pro Thr Gly
            115                 120                 125

Gln Phe Ser Ala Leu Asp Asn Gly Asp Ile Phe Gly Leu Pro Asn Gly
            130                 135                 140

Ala Ser Lys Ile Ser Ser Thr Asn Ala Thr Leu Val Pro Thr Lys Phe
            145                 150                 155

Gly Leu Asp Phe Trp Glu Ser Leu Ser Gly Glu Phe Val Gly Ile Ser
            160                 165                 170

Ser Pro Thr Ala Leu Gly Pro Thr Ser Arg Tyr Gly Asp Ile Trp Ile
175                 180                 185                 190

Arg Gly Asp Trp Glu Val Thr Gly Leu Asn Ser Ala Gly Gly Leu Thr
                195                 200                 205

Ile Thr Thr Gly Thr Ser Ser Asp Ala Asn Pro Glu Thr Ile Ile Ile
            210                 215                 220

Gly Ser Pro Leu Asp Gly Thr Lys Asn Pro Ser Val Lys Leu Gly Asp
            225                 230                 235

Ile Leu Asn Pro Ile Gln Gly Val Ile Thr Tyr Gly Phe Gly Phe Tyr
240                 245                 250

Arg Leu Leu Pro Thr Thr Ala Ile Ser Ile Lys Ser Ala Arg Asn Ala
255                 260                 265                 270

Thr Thr Pro Val Thr Thr Leu Lys Ser Glu Lys Ser Cys Lys Ala Val
            275                 280                 285

Thr Ile Gly Gln Tyr Asn Val Glu Asn Leu Ser Pro Ser Ser Ser His
            290                 295                 300

Leu Asn Ala Ile Ala Asp His Ile Gly Tyr Asn Met Gly Ser Pro Asp
            305                 310                 315

Leu Ile Tyr Val Gln Glu Leu Gln Asp Asn Ser Gly Ala Thr Asn Asp
320                 325                 330

Gly Ile Thr Ser Gly Asn Met Thr Leu Ala Ala Leu Ala Tyr Ala Ile
335                 340                 345                 350

Glu Gly Ile Ser Gly Ile Gln Tyr His Trp Ala Glu Val Asp Pro Glu
                355                 360                 365

Asp Asn Leu Asp Gly Gly Gln Pro Gly Gly Asn Ile Arg Val Ala Tyr
            370                 375                 380

Leu Tyr Asn Pro Ser Val Phe Ser Ile Ser Gly Thr Pro Gly Thr Ala
            385                 390                 395

Ser Glu Ala Thr Thr Val Gln Pro Gly Pro Ser Leu Ser Leu Asn Pro
400                 405                 410

Gly Arg Ile Asp Pro Gln Asn Val Ala Phe Thr Asn Ser Arg Lys Pro
415                 420                 425                 430

Leu Val Ala Gln Phe Ser Val Glu Gly Thr Gln Lys Pro Phe Phe Ala
            435                 440                 445

Ile Asn Val His Ser Gly Ser Lys Gly Gly Ser Ser Leu His Gly
            450                 455                 460

Asp Ala Arg Pro Pro Met Asn Gly Ile Glu Asp Arg Ile Ala Gln
            465                 470                 475

His Glu Ala Ile Ala Ser Phe Ile Gln Ala Leu Lys Lys Glu Asp Glu
            480                 485                 490

Asn Val Asn Ile Leu Ala Ala Gly Asp Phe Asn Glu Phe Ser Gly Val
495                 500                 505                 510

Ala Pro Met Glu Val Phe Arg Asp Leu Met Trp Asp Val Asp Glu Val
            515                 520                 525
```

Val Asp Val Ser Lys Glu Glu Arg Tyr Thr Tyr Asn Tyr Asp Met Asn
            530                 535                 540

Cys Gln Gln Leu Asp His Thr Leu Ile Ser Ala Gly Leu Lys Glu Lys
            545                 550                 555

Val Ser Gly Tyr Gln His Leu His Val Asn Thr Trp Ser Glu Val Glu
            560                 565                 570

Thr Ser Asp His Asp Pro Ser Val Gly Val Tyr Asp Leu Cys
575                 580                 585

<210> SEQ ID NO 39
<211> LENGTH: 588
<212> TYPE: PRT
<213> ORGANISM: Pyronema domesticum

<400> SEQUENCE: 39

Val Ser Ile Ala Glu Ile Asn Gly Pro Ala Phe Leu Ser Pro Tyr Ala
1               5                   10                  15

Gly Lys Ser Val Thr Asp Ile Thr Gly Leu Val Thr Ala Val Gly Pro
            20                  25                  30

Ser Gly Phe Phe Leu Arg Asp Val Ala Ser Thr Ser Arg Leu Arg
            35                  40                  45

Arg Asn Gln Ser Gly Ser Gln Ala Val Tyr Val Phe Asn Ser Ala Ala
            50                  55                  60

Ala Lys Asn Val Thr Ala Gly Asp Ile Ile Asn Ile Asn Ser Ala Ser
65                  70                  75                  80

Val Val Glu Tyr Gln Asn Asn Gln Ala Tyr Ile Pro Leu Thr Glu Ile
                85                  90                  95

Thr Asn Pro Ser Ala Ile Gln Ile Val Ser Lys Gly His Glu Val Ile
            100                 105                 110

Pro Ile Pro Leu Gly Arg Asn Gly Leu Gln Pro Thr Gly Gln Phe
            115                 120                 125

Ser Ala Leu Asp Asn Gly Asp Ile Phe Gly Leu Pro Asn Gly Ala Ser
            130                 135                 140

Lys Ile Ser Ser Thr Asn Ala Thr Leu Val Pro Thr Lys Phe Gly Leu
145                 150                 155                 160

Asp Phe Trp Glu Ser Leu Ser Gly Glu Phe Val Gly Ile Ser Ser Pro
                165                 170                 175

Thr Ala Leu Gly Pro Thr Ser Arg Tyr Gly Asp Ile Trp Ile Arg Gly
            180                 185                 190

Asp Trp Glu Val Thr Gly Leu Asn Ser Ala Gly Gly Leu Thr Ile Thr
            195                 200                 205

Thr Gly Thr Ser Ser Asp Ala Asn Pro Glu Thr Ile Ile Gly Ser
            210                 215                 220

Pro Leu Asp Gly Thr Lys Asn Pro Ser Val Lys Leu Gly Asp Ile Leu
225                 230                 235                 240

Asn Pro Ile Gln Gly Val Ile Thr Tyr Gly Phe Gly Phe Tyr Arg Leu
                245                 250                 255

Leu Pro Thr Thr Ala Ile Ser Ile Lys Ser Ala Arg Asn Ala Thr Thr
            260                 265                 270

Pro Val Thr Thr Leu Lys Ser Glu Lys Ser Cys Lys Ala Val Thr Ile
            275                 280                 285

Gly Gln Tyr Asn Val Glu Asn Leu Ser Pro Ser Ser His Leu Asn
            290                 295                 300

Ala Ile Ala Asp His Ile Gly Tyr Asn Met Gly Ser Pro Asp Leu Ile
305                 310                 315                 320

Tyr Val Gln Glu Leu Gln Asp Asn Ser Gly Ala Thr Asn Asp Gly Ile
            325                 330                 335

Thr Ser Gly Asn Met Thr Leu Ala Ala Leu Ala Tyr Ala Ile Glu Gly
            340                 345                 350

Ile Ser Gly Ile Gln Tyr His Trp Ala Glu Val Asp Pro Glu Asp Asn
            355                 360                 365

Leu Asp Gly Gly Gln Pro Gly Gly Asn Ile Arg Val Ala Tyr Leu Tyr
370                 375                 380

Asn Pro Ser Val Phe Ser Ile Ser Gly Thr Pro Gly Thr Ala Ser Glu
385                 390                 395                 400

Ala Thr Thr Val Gln Pro Gly Pro Ser Leu Ser Leu Asn Pro Gly Arg
            405                 410                 415

Ile Asp Pro Gln Asn Val Ala Phe Thr Asn Ser Arg Lys Pro Leu Val
            420                 425                 430

Ala Gln Phe Ser Val Glu Gly Thr Gln Lys Pro Phe Phe Ala Ile Asn
            435                 440                 445

Val His Ser Gly Ser Lys Gly Ser Ser Ser Leu His Gly Asp Ala
    450                 455                 460

Arg Pro Pro Met Asn Gly Gly Ile Glu Asp Arg Ile Ala Gln His Glu
465                 470                 475                 480

Ala Ile Ala Ser Phe Ile Gln Ala Leu Lys Lys Glu Asp Glu Asn Val
            485                 490                 495

Asn Ile Leu Ala Ala Gly Asp Phe Asn Glu Phe Ser Gly Val Ala Pro
            500                 505                 510

Met Glu Val Phe Arg Asp Leu Met Trp Asp Val Asp Glu Val Val Asp
            515                 520                 525

Val Ser Lys Glu Glu Arg Tyr Thr Tyr Asn Tyr Asp Met Asn Cys Gln
            530                 535                 540

Gln Leu Asp His Thr Leu Ile Ser Ala Gly Leu Lys Glu Lys Val Ser
545                 550                 555                 560

Gly Tyr Gln His Leu His Val Asn Thr Trp Ser Glu Val Glu Thr Ser
            565                 570                 575

Asp His Asp Pro Ser Val Gly Val Tyr Asp Leu Cys
            580                 585

```
<210> SEQ ID NO 40
<211> LENGTH: 2027
<212> TYPE: DNA
<213> ORGANISM: Aspergillus niger
<220> FEATURE:
<221> NAME/KEY: CDS
<222> LOCATION: (1)..(670)
<220> FEATURE:
<221> NAME/KEY: sig_peptide
<222> LOCATION: (1)..(57)
<220> FEATURE:
<221> NAME/KEY: mat_peptide
<222> LOCATION: (58)..(2024)
<220> FEATURE:
<221> NAME/KEY: CDS
<222> LOCATION: (727)..(1095)
<220> FEATURE:
<221> NAME/KEY: CDS
<222> LOCATION: (1160)..(1605)
<220> FEATURE:
<221> NAME/KEY: CDS
<222> LOCATION: (1698)..(2024)

<400> SEQUENCE: 40 atg cgc atg atc ccc tcg ctg tgt gcg gca gca ctg ctc ttc cgc agc         48
```

-continued

```
                    Met Arg Met Ile Pro Ser Leu Cys Ala Ala Ala Leu Leu Phe Arg Ser
                            -15                 -10                  -5 gcg ctg gcc gtg acc atc ccc gag atc aat ggc gac cga tac gtt tct     96
Ala Leu Ala Val Thr Ile Pro Glu Ile Asn Gly Asp Arg Tyr Val Ser
         -1   1               5                       10 tcc tac caa ggc aaa cga gtc tcc ggt ctc aag ggc ctc gtc aca gcc     144
Ser Tyr Gln Gly Lys Arg Val Ser Gly Leu Lys Gly Leu Val Thr Ala
 15                  20                  25 aaa ggt tcc agc ggg ttc tat att cgc gcc acg gat gcc gat tcg gac     192
Lys Gly Ser Ser Gly Phe Tyr Ile Arg Ala Thr Asp Ala Asp Ser Asp
 30                      35                  40                  45 tcc cgc acc tcc aac tcc atc tac gtg tat gga agc agt gga gtg tct     240
Ser Arg Thr Ser Asn Ser Ile Tyr Val Tyr Gly Ser Ser Gly Val Ser
                     50                  55                  60 caa gtc acg gtc ggc gat att gtc act cta agt ggc aag gtc aca gaa     288
Gln Val Thr Val Gly Asp Ile Val Thr Leu Ser Gly Lys Val Thr Glu
                 65                  70                  75 tac cga tcc tcc tcc agc tac gtc tat agt act gag atc gag tcg cca     336
Tyr Arg Ser Ser Ser Ser Tyr Val Tyr Ser Thr Glu Ile Glu Ser Pro
             80                  85                  90 tcc gac atc cag gtg ctg tcc agc gat aat att gta acc ccc gtc gtc     384
Ser Asp Ile Gln Val Leu Ser Ser Asp Asn Ile Val Thr Pro Val Val
 95                     100                 105 att gga aag gat aat ctg gat cct cct acc gag cag tac tct tcc ctg     432
Ile Gly Lys Asp Asn Leu Asp Pro Pro Thr Glu Gln Tyr Ser Ser Leu
110                 115                 120                 125 gac aat ggc gat gtc ttc agc ctg ccc ggc aac tcc agt cgg ctc tcc     480
Asp Asn Gly Asp Val Phe Ser Leu Pro Gly Asn Ser Ser Arg Leu Ser
                    130                 135                 140 act gcg aat ccg gtt ttg gag ccg acc gag tat ggc atg gac ttc tgg     528
Thr Ala Asn Pro Val Leu Glu Pro Thr Glu Tyr Gly Met Asp Phe Trp
                145                 150                 155 cag agc ctg agt ggt gaa ctg gcg acc ttg act gga ctc aca gcc atc     576
Gln Ser Leu Ser Gly Glu Leu Ala Thr Leu Thr Gly Leu Thr Ala Ile
            160                 165                 170 agc aag gcc aat tca tac ggg gat acc tgg gtg att ggt gac tgg cca     624
Ser Lys Ala Asn Ser Tyr Gly Asp Thr Trp Val Ile Gly Asp Trp Pro
175                 180                 185 gtg acg ggg aag aat gac cgg ggc ggg ctg acc atg cgt gca aat g       670
Val Thr Gly Lys Asn Asp Arg Gly Gly Leu Thr Met Arg Ala Asn
190                 195                 200 gtttgattgc ctgactctgt tgtcgcgcca acaactgact tggcattcga ttgcag ac   728
                                                                Asp
                                                                205 tca aac ccg gaa tcc atc gtc atc ggc tct ccg ttg gat ggg act aaa     776
Ser Asn Pro Glu Ser Ile Val Ile Gly Ser Pro Leu Asp Gly Thr Lys
                    210                 215                 220 aac cca act gac act aaa ctg ggt gat acc ctc gag gat ata act gga     824
Asn Pro Thr Asp Thr Lys Leu Gly Asp Thr Leu Glu Asp Ile Thr Gly
            225                 230                 235 atc atc acg cag gca tat gga ttc tac acg ctg ctg cct ctg acg gcc     872
Ile Ile Thr Gln Ala Tyr Gly Phe Tyr Thr Leu Leu Pro Leu Thr Ala
        240                 245                 250 ttg acg aag acc ggg tcc aac acc acg gag gcg aca gca aca acc ctc     920
Leu Thr Lys Thr Gly Ser Asn Thr Thr Glu Ala Thr Ala Thr Thr Leu
    255                 260                 265 cag gca gat gga acc tgt agt tca atc acc atc gga gat tac aat gtt     968
Gln Ala Asp Gly Thr Cys Ser Ser Ile Thr Ile Gly Asp Tyr Asn Val
270                 275                 280                 285
```

```
gac aat ttt tct cca cag tcg agc acc atg agc ggg att ggg gag cac       1016
Asp Asn Phe Ser Pro Gln Ser Ser Thr Met Ser Gly Ile Gly Glu His
            290                 295                 300 atc gcc aag tat ttg aac agt ccg acc gtc ttg ttc ttg cag gag atc       1064
Ile Ala Lys Tyr Leu Asn Ser Pro Thr Val Leu Phe Leu Gln Glu Ile
            305                 310                 315 cag gac aac agc gga gca acc gac gac ggt g gtaatttcaa ccctctcccc       1115
Gln Asp Asn Ser Gly Ala Thr Asp Asp Gly
            320                 325 acaacatcat gataagatca tgtcactgac atccttgaca ccag tc  gtc tcc gcc      1170
                                                    Val Val Ser Ala
                                                                330 aac gag aca ctg tcc aag ctc gct agc gca gtc aaa gag cac ggc gga       1218
Asn Glu Thr Leu Ser Lys Leu Ala Ser Ala Val Lys Glu His Gly Gly
            335                 340                 345 gtc gcg tac aac tac act gac atc gat ccg gag aat gac acg aac ggc       1266
Val Ala Tyr Asn Tyr Thr Asp Ile Asp Pro Glu Asn Asp Thr Asn Gly
            350                 355                 360 gga gaa cgc ggc ggt aat atc cgg cca gcc tac ctc ttc gac cca tcg       1314
Gly Glu Arg Gly Gly Asn Ile Arg Pro Ala Tyr Leu Phe Asp Pro Ser
365                 370                 375 gtg gtc cga ctg cga aac tac aat ccc ggg tcc agc acc gac tcc acc       1362
Val Val Arg Leu Arg Asn Tyr Asn Pro Gly Ser Ser Thr Asp Ser Thr
380                 385                 390                 395 tcc gtc ctc tcc gac ggc agt cta agc tac aac cca ggt ctg att gat       1410
Ser Val Leu Ser Asp Gly Ser Leu Ser Tyr Asn Pro Gly Leu Ile Asp
                400                 405                 410 ccc tct aac gag gcc tgg gat gac agt cgc aag cca ttg gta gcc cag       1458
Pro Ser Asn Glu Ala Trp Asp Asp Ser Arg Lys Pro Leu Val Ala Gln
            415                 420                 425 tgg gag acc ctg gac ggc aag aac aca ttc tac acg atc aac gtg cac       1506
Trp Glu Thr Leu Asp Gly Lys Asn Thr Phe Tyr Thr Ile Asn Val His
            430                 435                 440 ttc acc tcc aaa tat gac agc act tcg ctg gag ggc gat ccg cga ccc       1554
Phe Thr Ser Lys Tyr Asp Ser Thr Ser Leu Glu Gly Asp Pro Arg Pro
            445                 450                 455 ccc gta aac gga tgg gtg gag aac cgc gtg gac cag gct aaa gtg gtt       1602
Pro Val Asn Gly Trp Val Glu Asn Arg Val Asp Gln Ala Lys Val Val
460                 465                 470                 475 gct gtgagtgttt ttttttttt tttccgcgct aacgttctct ctcatcttgg             1655
Ala ttgtgtctgg aaccgaacaa tgtctgaccg tggttggtat ag aaa ttt gtt acc        1709
                                               Lys Phe Val Thr
                                                            480 tcc att ctg gat gtc aat tcc gac gcg aag att att act gcc ggt gac       1757
Ser Ile Leu Asp Val Asn Ser Asp Ala Lys Ile Ile Thr Ala Gly Asp
                485                 490                 495 ttt aac gag tat gca ttt gtc gag cct cta gag gtg ttt gtc tcc gag       1805
Phe Asn Glu Tyr Ala Phe Val Glu Pro Leu Glu Val Phe Val Ser Glu
            500                 505                 510 tcc aag ctg cag gac ctt gag gag gtc act ggc atc cct gcg acc gag       1853
Ser Lys Leu Gln Asp Leu Glu Glu Val Thr Gly Ile Pro Ala Thr Glu
            515                 520                 525 agg tat acc tat ctg tat aac cag aac tgc gaa tca ctg gac cac atg       1901
Arg Tyr Thr Tyr Leu Tyr Asn Gln Asn Cys Glu Ser Leu Asp His Met
            530                 535                 540 tat gtg agt tct gcg ttg acg tcc ggg gcc aag atg gag cat att cat       1949
Tyr Val Ser Ser Ala Leu Thr Ser Gly Ala Lys Met Glu His Ile His
545                 550                 555                 560
```

```
gtc aac tcg tgg gtg tcg acg gat gat gag ttg tcg gat cat gac cct    1997
Val Asn Ser Trp Val Ser Thr Asp Asp Glu Leu Ser Asp His Asp Pro
            565                 570                 575 aca gtc gcg ttg ttc aat atg tgc gag taa                             2027
Thr Val Ala Leu Phe Asn Met Cys Glu
            580             585
```

<210> SEQ ID NO 41
<211> LENGTH: 604
<212> TYPE: PRT
<213> ORGANISM: Aspergillus niger

<400> SEQUENCE: 41

```
Met Arg Met Ile Pro Ser Leu Cys Ala Ala Leu Leu Phe Arg Ser
                -15                 -10                  -5

Ala Leu Ala Val Thr Ile Pro Glu Ile Asn Gly Asp Arg Tyr Val Ser
         -1   1               5                  10

Ser Tyr Gln Gly Lys Arg Val Ser Gly Leu Lys Gly Leu Val Thr Ala
             15                  20                  25

Lys Gly Ser Ser Gly Phe Tyr Ile Arg Ala Thr Asp Ala Asp Ser Asp
 30              35                  40                  45

Ser Arg Thr Ser Asn Ser Ile Tyr Val Tyr Gly Ser Ser Gly Val Ser
                 50                  55                  60

Gln Val Thr Val Gly Asp Ile Val Thr Leu Ser Gly Lys Val Thr Glu
                 65                  70                  75

Tyr Arg Ser Ser Ser Tyr Val Tyr Ser Thr Glu Ile Glu Ser Pro
             80                  85                  90

Ser Asp Ile Gln Val Leu Ser Ser Asn Ile Val Thr Pro Val Val
     95                 100                 105

Ile Gly Lys Asp Asn Leu Asp Pro Pro Thr Glu Gln Tyr Ser Ser Leu
110                 115                 120                 125

Asp Asn Gly Asp Val Phe Ser Leu Pro Gly Asn Ser Ser Arg Leu Ser
                130                 135                 140

Thr Ala Asn Pro Val Leu Glu Pro Thr Glu Tyr Gly Met Asp Phe Trp
                145                 150                 155

Gln Ser Leu Ser Gly Glu Leu Ala Thr Leu Thr Gly Leu Thr Ala Ile
                160                 165                 170

Ser Lys Ala Asn Ser Tyr Gly Asp Thr Trp Val Ile Gly Asp Trp Pro
    175                 180                 185

Val Thr Gly Lys Asn Asp Arg Gly Gly Leu Thr Met Arg Ala Asn Asp
190                 195                 200                 205

Ser Asn Pro Glu Ser Ile Val Ile Gly Ser Pro Leu Asp Gly Thr Lys
                210                 215                 220

Asn Pro Thr Asp Thr Lys Leu Gly Asp Thr Leu Glu Asp Ile Thr Gly
                225                 230                 235

Ile Ile Thr Gln Ala Tyr Gly Phe Tyr Thr Leu Leu Pro Leu Thr Ala
                240                 245                 250

Leu Thr Lys Thr Gly Ser Asn Thr Thr Glu Ala Thr Ala Thr Thr Leu
                255                 260                 265

Gln Ala Asp Gly Thr Cys Ser Ser Ile Thr Ile Gly Asp Tyr Asn Val
270                 275                 280                 285

Asp Asn Phe Ser Pro Gln Ser Ser Thr Met Ser Gly Ile Gly Glu His
                290                 295                 300

Ile Ala Lys Tyr Leu Asn Ser Pro Thr Val Leu Phe Leu Gln Glu Ile
                305                 310                 315
```

```
Gln Asp Asn Ser Gly Ala Thr Asp Gly Val Val Ser Ala Asn Glu
    320                 325                 330
Thr Leu Ser Lys Leu Ala Ser Ala Val Lys Glu His Gly Gly Val Ala
335                 340                 345
Tyr Asn Tyr Thr Asp Ile Asp Pro Glu Asn Asp Thr Asn Gly Gly Glu
350                 355                 360                 365
Arg Gly Gly Asn Ile Arg Pro Ala Tyr Leu Phe Asp Pro Ser Val Val
                370                 375                 380
Arg Leu Arg Asn Tyr Asn Pro Gly Ser Ser Thr Asp Ser Thr Ser Val
                385                 390                 395
Leu Ser Asp Gly Ser Leu Ser Tyr Asn Pro Gly Leu Ile Asp Pro Ser
                400                 405                 410
Asn Glu Ala Trp Asp Asp Ser Arg Lys Pro Leu Val Ala Gln Trp Glu
                415                 420                 425
Thr Leu Asp Gly Lys Asn Thr Phe Tyr Thr Ile Asn Val His Phe Thr
430                 435                 440                 445
Ser Lys Tyr Asp Ser Thr Ser Leu Glu Gly Asp Pro Arg Pro Val
                450                 455                 460
Asn Gly Trp Val Glu Asn Arg Val Asp Gln Ala Lys Val Val Ala Lys
                465                 470                 475
Phe Val Thr Ser Ile Leu Asp Val Asn Ser Asp Ala Lys Ile Ile Thr
                480                 485                 490
Ala Gly Asp Phe Asn Glu Tyr Ala Phe Val Glu Pro Leu Glu Val Phe
                495                 500                 505
Val Ser Glu Ser Lys Leu Gln Asp Leu Glu Glu Val Thr Gly Ile Pro
510                 515                 520                 525
Ala Thr Glu Arg Tyr Thr Tyr Leu Tyr Asn Gln Asn Cys Glu Ser Leu
                530                 535                 540
Asp His Met Tyr Val Ser Ser Ala Leu Thr Ser Gly Ala Lys Met Glu
                545                 550                 555
His Ile His Val Asn Ser Trp Val Ser Thr Asp Glu Leu Ser Asp
                560                 565                 570
His Asp Pro Thr Val Ala Leu Phe Asn Met Cys Glu
575                 580                 585

<210> SEQ ID NO 42
<211> LENGTH: 585
<212> TYPE: PRT
<213> ORGANISM: Aspergillus niger

<400> SEQUENCE: 42

Val Thr Ile Pro Glu Ile Asn Gly Asp Arg Tyr Val Ser Ser Tyr Gln
1               5                   10                  15
Gly Lys Arg Val Ser Gly Leu Lys Gly Leu Val Thr Ala Lys Gly Ser
                20                  25                  30
Ser Gly Phe Tyr Ile Arg Ala Thr Asp Ala Asp Ser Asp Ser Arg Thr
            35                  40                  45
Ser Asn Ser Ile Tyr Val Tyr Gly Ser Ser Gly Val Ser Gln Val Thr
        50                  55                  60
Val Gly Asp Ile Val Thr Leu Ser Gly Lys Val Thr Glu Tyr Arg Ser
65                  70                  75                  80
Ser Ser Ser Tyr Val Tyr Ser Thr Glu Ile Glu Ser Pro Ser Asp Ile
                85                  90                  95
Gln Val Leu Ser Ser Asp Asn Ile Val Thr Pro Val Val Ile Gly Lys
                100                 105                 110
```

```
Asp Asn Leu Asp Pro Pro Thr Glu Gln Tyr Ser Ser Leu Asp Asn Gly
        115                 120                 125

Asp Val Phe Ser Leu Pro Gly Asn Ser Ser Arg Leu Ser Thr Ala Asn
130                 135                 140

Pro Val Leu Glu Pro Thr Glu Tyr Gly Met Asp Phe Trp Gln Ser Leu
145                 150                 155                 160

Ser Gly Glu Leu Ala Thr Leu Thr Gly Leu Thr Ala Ile Ser Lys Ala
                165                 170                 175

Asn Ser Tyr Gly Asp Thr Trp Val Ile Gly Asp Trp Pro Val Thr Gly
            180                 185                 190

Lys Asn Asp Arg Gly Gly Leu Thr Met Arg Ala Asn Asp Ser Asn Pro
        195                 200                 205

Glu Ser Ile Val Ile Gly Ser Pro Leu Asp Gly Thr Lys Asn Pro Thr
        210                 215                 220

Asp Thr Lys Leu Gly Asp Thr Leu Glu Asp Ile Thr Gly Ile Ile Thr
225                 230                 235                 240

Gln Ala Tyr Gly Phe Tyr Thr Leu Leu Pro Leu Thr Ala Leu Thr Lys
                245                 250                 255

Thr Gly Ser Asn Thr Thr Glu Ala Thr Ala Thr Thr Leu Gln Ala Asp
            260                 265                 270

Gly Thr Cys Ser Ser Ile Thr Ile Gly Asp Tyr Asn Val Asp Asn Phe
        275                 280                 285

Ser Pro Gln Ser Ser Thr Met Ser Gly Ile Gly Glu His Ile Ala Lys
        290                 295                 300

Tyr Leu Asn Ser Pro Thr Val Leu Phe Leu Gln Glu Ile Gln Asp Asn
305                 310                 315                 320

Ser Gly Ala Thr Asp Asp Gly Val Val Ser Ala Asn Glu Thr Leu Ser
                325                 330                 335

Lys Leu Ala Ser Ala Val Lys Glu His Gly Gly Val Ala Tyr Asn Tyr
            340                 345                 350

Thr Asp Ile Asp Pro Glu Asn Asp Thr Asn Gly Gly Glu Arg Gly Gly
        355                 360                 365

Asn Ile Arg Pro Ala Tyr Leu Phe Asp Pro Ser Val Val Arg Leu Arg
        370                 375                 380

Asn Tyr Asn Pro Gly Ser Ser Thr Asp Ser Thr Ser Val Leu Ser Asp
385                 390                 395                 400

Gly Ser Leu Ser Tyr Asn Pro Gly Leu Ile Asp Pro Ser Asn Glu Ala
                405                 410                 415

Trp Asp Asp Ser Arg Lys Pro Leu Val Ala Gln Trp Glu Thr Leu Asp
            420                 425                 430

Gly Lys Asn Thr Phe Tyr Thr Ile Asn Val His Phe Thr Ser Lys Tyr
        435                 440                 445

Asp Ser Thr Ser Leu Glu Gly Asp Pro Arg Pro Pro Val Asn Gly Trp
450                 455                 460

Val Glu Asn Arg Val Asp Gln Ala Lys Val Ala Lys Phe Val Thr
465                 470                 475                 480

Ser Ile Leu Asp Val Asn Ser Asp Ala Lys Ile Ile Thr Ala Gly Asp
                485                 490                 495

Phe Asn Glu Tyr Ala Phe Val Glu Pro Leu Glu Val Phe Val Ser Glu
            500                 505                 510

Ser Lys Leu Gln Asp Leu Glu Glu Val Thr Gly Ile Pro Ala Thr Glu
        515                 520                 525
```

```
Arg Tyr Thr Tyr Leu Tyr Asn Gln Asn Cys Glu Ser Leu Asp His Met
            530                 535                 540

Tyr Val Ser Ser Ala Leu Thr Ser Gly Ala Lys Met Glu His Ile His
545                 550                 555                 560

Val Asn Ser Trp Val Ser Thr Asp Asp Glu Leu Ser Asp His Asp Pro
                565                 570                 575

Thr Val Ala Leu Phe Asn Met Cys Glu
            580                 585

<210> SEQ ID NO 43
<211> LENGTH: 1985
<212> TYPE: DNA
<213> ORGANISM: Phialophora geniculata
<220> FEATURE:
<221> NAME/KEY: CDS
<222> LOCATION: (1)..(284)
<220> FEATURE:
<221> NAME/KEY: sig_peptide
<222> LOCATION: (1)..(48)
<220> FEATURE:
<221> NAME/KEY: mat_peptide
<222> LOCATION: (49)..(1982)
<220> FEATURE:
<221> NAME/KEY: CDS
<222> LOCATION: (379)..(755)
<220> FEATURE:
<221> NAME/KEY: CDS
<222> LOCATION: (835)..(1982)

<400> SEQUENCE: 43 atg aag gtc cct gct gcc ctc ctt tcc gtc gtt ggc gcc gcc tcg gct      48
Met Lys Val Pro Ala Ala Leu Leu Ser Val Val Gly Ala Ala Ser Ala
        -15                 -10                  -5                  -1 gcc acc att gcc gag atc aac ggc aac agg ttc atg tct ccc ctt cag      96
Ala Thr Ile Ala Glu Ile Asn Gly Asn Arg Phe Met Ser Pro Leu Gln
  1               5                  10                  15 ggc gag gta gtg acc ggt gtc gag ggt ctg gtg ctc gcc aag ggc ccc     144
Gly Glu Val Val Thr Gly Val Glu Gly Leu Val Leu Ala Lys Gly Pro
            20                  25                  30 aat ggc att tgg ctg cgc tcg acc gtc ccc gac gat gac gac ctc acc     192
Asn Gly Ile Trp Leu Arg Ser Thr Val Pro Asp Asp Asp Asp Leu Thr
        35                  40                  45 tcc gag gcc gtc tac gtc ttc gac cgc aac atc atc gct cgc ctc agc     240
Ser Glu Ala Val Tyr Val Phe Asp Arg Asn Ile Ile Ala Arg Leu Ser
 50                  55                  60 gtc ggc gac att gtc aag ctt gat gga acc atc ctc gag tac ag          284
Val Gly Asp Ile Val Lys Leu Asp Gly Thr Ile Leu Glu Tyr Arg
65                  70                  75 gtacgggcag acttccctcg cctcggcaac acaccgcaga ccataattca gtcctcttgc   344
ccgtgtttac ccaactaacg gagcattgtt gcag g gca caa gct gct cac atg    397
                                     Ala Gln Ala Ala His Met
                                      80                  85 tac ttg acc gag atc acg gcc acc agc aac ctc gag atc ctc tcc agc     445
Tyr Leu Thr Glu Ile Thr Ala Thr Ser Asn Leu Glu Ile Leu Ser Ser
                90                  95                 100 aac aac acc gtc acc gcc tac gtc att gga gag gac acc ggt gct cct     493
Asn Asn Thr Val Thr Ala Tyr Val Ile Gly Glu Asp Thr Gly Ala Pro
            105                 110                 115 ccc acc gag cag tac agc tct ctg gac gag ggc gac atc ttc gcc gtt     541
Pro Thr Glu Gln Tyr Ser Ser Leu Asp Glu Gly Asp Ile Phe Ala Val
        120                 125                 130 ccc aac aac gtc tac cgc gtc tcc gag gag aac ccc gtc ctt gag ccc     589
Pro Asn Asn Val Tyr Arg Val Ser Glu Glu Asn Pro Val Leu Glu Pro
```

```
                135                 140                 145
tcc aag tat ggc atg gac tac tgg cgt gcc atc aac ggc gag ctc gtc     637
Ser Lys Tyr Gly Met Asp Tyr Trp Arg Ala Ile Asn Gly Glu Leu Val
150                 155                 160                 165 acc atc aag acc ccc gtc ggt gtc agc cgc ccc aac cag ttt ggc gac     685
Thr Ile Lys Thr Pro Val Gly Val Ser Arg Pro Asn Gln Phe Gly Asp
            170                 175                 180 acc tgg gtc gtt ggt acc tgg ccc acc acc ggc cgc aac agc cag ggc     733
Thr Trp Val Val Gly Thr Trp Pro Thr Thr Gly Arg Asn Ser Gln Gly
                185                 190                 195 gga ctc acc ctg cgc gac aag g gtaagtgaaa actggcgagc aaggagcagt     785
Gly Leu Thr Leu Arg Asp Lys
                200 ctcgcgtaca tgtcccagca gtgcggctca aatattgaca tcttgacag at  gcc aac    842
                                                         Asp Ala Asn
                                                             205 cct gag gcc atc att att ggc tcc ccc ctt gat ggg act cgc aac ccc     890
Pro Glu Ala Ile Ile Ile Gly Ser Pro Leu Asp Gly Thr Arg Asn Pro
            210                 215                 220 gag aca aag atg ggt gac aag ttc gcc gag atc acc ggc gtc gtc acc     938
Glu Thr Lys Met Gly Asp Lys Phe Ala Glu Ile Thr Gly Val Val Thr
225                 230                 235 tat gcg ttc ggc ttc tac cgc atc ctg ccc ctg acg gcc atc gaa gtc     986
Tyr Ala Phe Gly Phe Tyr Arg Ile Leu Pro Leu Thr Ala Ile Glu Val
240                 245                 250                 255 gag gag gag gcc acc att gag gtc tcg ccc act acc ctc gag agc cgt    1034
Glu Glu Glu Ala Thr Ile Glu Val Ser Pro Thr Thr Leu Glu Ser Arg
                260                 265                 270 ggc gat tgc cgt ggc ctc acc ttt gcc tcc tac aac atc gag aac ttg    1082
Gly Asp Cys Arg Gly Leu Thr Phe Ala Ser Tyr Asn Ile Glu Asn Leu
                275                 280                 285 tgg gcc gag tct gag cac ctt ccc gag gtc gca gct cac att gtc gag    1130
Trp Ala Glu Ser Glu His Leu Pro Glu Val Ala Ala His Ile Val Glu
                290                 295                 300 tac ctg aag acc ccc gac ttc ctc ttc ctc cag gaa gtc cag gac aac    1178
Tyr Leu Lys Thr Pro Asp Phe Leu Phe Leu Gln Glu Val Gln Asp Asn
                305                 310                 315 aac ggc ccg acc aac aac ggc gtc gtc agc gcc aac atc acc ctc agc    1226
Asn Gly Pro Thr Asn Asn Gly Val Val Ser Ala Asn Ile Thr Leu Ser
320                 325                 330                 335 aac ctg gct gcc gag atc gag gcc cag agc ggc atc gtc tac gag ttc    1274
Asn Leu Ala Ala Glu Ile Glu Ala Gln Ser Gly Ile Val Tyr Glu Phe
                340                 345                 350 gcc gag gtt gag ccc gtc aac aac cag gat ggt ggc cag ccc ggc ggc    1322
Ala Glu Val Glu Pro Val Asn Asn Gln Asp Gly Gly Gln Pro Gly Gly
                355                 360                 365 aac atc cgc aac gcc tac ctc tac cgc ccg gac gtc atc gag ctc tac    1370
Asn Ile Arg Asn Ala Tyr Leu Tyr Arg Pro Asp Val Ile Glu Leu Tyr
                370                 375                 380 gag ccc aac caa ggc ggc agc acc gac cag gcc gaa gtc gtc gac gga    1418
Glu Pro Asn Gln Gly Gly Ser Thr Asp Gln Ala Glu Val Val Asp Gly
385                 390                 395 ccc gcc ctc tcc ttc aac ccg ggc cgc atc gac atc tcc aac tcg gcc    1466
Pro Ala Leu Ser Phe Asn Pro Gly Arg Ile Asp Ile Ser Asn Ser Ala
400                 405                 410                 415 tgg gat gcc agc cgc aag ccc ctc gtc gcc cag tgg cgc gcc gtc cgc    1514
Trp Asp Ala Ser Arg Lys Pro Leu Val Ala Gln Trp Arg Ala Val Arg
                420                 425                 430 ggc ccc cgc agc aag acc ttc ttc acc gtc aac gtc cac aac ggc tcc    1562
```

```
Gly Pro Arg Ser Lys Thr Phe Phe Thr Val Asn Val His Asn Gly Ser
            435                 440                 445 aag ggc ggc tcc tcg acc ctc cac ggc gac ttc cgc cct ccc gtc aac      1610
Lys Gly Gly Ser Ser Thr Leu His Gly Asp Phe Arg Pro Pro Val Asn
            450                 455                 460 aac ggc gtc gag aag cgc acc cag cag acc gag agc gtc ggc gcc ttt      1658
Asn Gly Val Glu Lys Arg Thr Gln Gln Thr Glu Ser Val Gly Ala Phe
465                 470                 475 gtc gat gcc atc ctg gcc cag gac ccc aag gcc cgc atc atc gcc gcc      1706
Val Asp Ala Ile Leu Ala Gln Asp Pro Lys Ala Arg Ile Ile Ala Ala
480                 485                 490                 495 ggc gac tgg aac gag ttc cag ttt gtc cag ccc cag cgc gtc atc gcc      1754
Gly Asp Trp Asn Glu Phe Gln Phe Val Gln Pro Gln Arg Val Ile Ala
                500                 505                 510 gag aag cac aac atg acg gac ctc agt gtc ctc gcc ctc gat gag att      1802
Glu Lys His Asn Met Thr Asp Leu Ser Val Leu Ala Leu Asp Glu Ile
            515                 520                 525 gag cag tac aac tat gtc ttc gac atg aat gcc cag cag ctc gat cac      1850
Glu Gln Tyr Asn Tyr Val Phe Asp Met Asn Ala Gln Gln Leu Asp His
        530                 535                 540 atc ctc gtc tcg ccc gcg ctt gcc act gat gct gcc aag att gag cat      1898
Ile Leu Val Ser Pro Ala Leu Ala Thr Asp Ala Ala Lys Ile Glu His
545                 550                 555 ctt cac ctt gcc gca tgg ttg aga tat ccc gac ctc acg agc gac cac      1946
Leu His Leu Ala Ala Trp Leu Arg Tyr Pro Asp Leu Thr Ser Asp His
560                 565                 570                 575 gac ccg ctt gtt tcg tac ctc aat gtt tgt ggt tgc taa                  1985
Asp Pro Leu Val Ser Tyr Leu Asn Val Cys Gly Cys
                580                 585

<210> SEQ ID NO 44
<211> LENGTH: 603
<212> TYPE: PRT
<213> ORGANISM: Phialophora geniculata

<400> SEQUENCE: 44

Met Lys Val Pro Ala Ala Leu Leu Ser Val Val Gly Ala Ala Ser Ala
        -15                 -10                  -5              -1

Ala Thr Ile Ala Glu Ile Asn Gly Asn Arg Phe Met Ser Pro Leu Gln
1                5                  10                  15

Gly Glu Val Val Thr Gly Val Glu Gly Leu Val Leu Ala Lys Gly Pro
            20                  25                  30

Asn Gly Ile Trp Leu Arg Ser Thr Val Pro Asp Asp Asp Leu Thr
            35                  40                  45

Ser Glu Ala Val Tyr Val Phe Asp Arg Asn Ile Ile Ala Arg Leu Ser
50                  55                  60

Val Gly Asp Ile Val Lys Leu Asp Gly Thr Ile Leu Glu Tyr Arg Ala
65                  70                  75                  80

Gln Ala Ala His Met Tyr Leu Thr Glu Ile Thr Ala Thr Ser Asn Leu
                85                  90                  95

Glu Ile Leu Ser Ser Asn Asn Thr Val Thr Ala Tyr Val Ile Gly Glu
            100                 105                 110

Asp Thr Gly Ala Pro Pro Thr Glu Gln Tyr Ser Ser Leu Asp Glu Gly
        115                 120                 125

Asp Ile Phe Ala Val Pro Asn Asn Val Tyr Arg Val Ser Glu Glu Asn
    130                 135                 140

Pro Val Leu Glu Pro Ser Lys Tyr Gly Met Asp Tyr Trp Arg Ala Ile
145                 150                 155                 160
```

```
Asn Gly Glu Leu Val Thr Ile Lys Thr Pro Val Ser Arg Pro
                165                 170                 175

Asn Gln Phe Gly Asp Thr Trp Val Gly Thr Trp Pro Thr Gly
            180                 185                 190

Arg Asn Ser Gln Gly Gly Leu Thr Leu Arg Asp Lys Asp Ala Asn Pro
        195                 200                 205

Glu Ala Ile Ile Ile Gly Ser Pro Leu Asp Gly Thr Arg Asn Pro Glu
210                 215                 220

Thr Lys Met Gly Asp Lys Phe Ala Glu Ile Thr Gly Val Val Thr Tyr
225                 230                 235                 240

Ala Phe Gly Phe Tyr Arg Ile Leu Pro Leu Thr Ala Ile Glu Val Glu
                245                 250                 255

Glu Glu Ala Thr Ile Glu Val Ser Pro Thr Thr Leu Glu Ser Arg Gly
            260                 265                 270

Asp Cys Arg Gly Leu Thr Phe Ala Ser Tyr Asn Ile Glu Asn Leu Trp
        275                 280                 285

Ala Glu Ser Glu His Leu Pro Glu Val Ala Ala His Ile Val Glu Tyr
290                 295                 300

Leu Lys Thr Pro Asp Phe Leu Phe Leu Gln Glu Val Gln Asp Asn Asn
305                 310                 315                 320

Gly Pro Thr Asn Asn Gly Val Val Ser Ala Asn Ile Thr Leu Ser Asn
                325                 330                 335

Leu Ala Ala Glu Ile Glu Ala Gln Ser Gly Ile Val Tyr Glu Phe Ala
            340                 345                 350

Glu Val Glu Pro Val Asn Asn Gln Asp Gly Gly Gln Pro Gly Gly Asn
        355                 360                 365

Ile Arg Asn Ala Tyr Leu Tyr Arg Pro Asp Val Ile Glu Leu Tyr Glu
370                 375                 380

Pro Asn Gln Gly Gly Ser Thr Asp Gln Ala Glu Val Val Asp Gly Pro
385                 390                 395                 400

Ala Leu Ser Phe Asn Pro Gly Arg Ile Asp Ile Ser Asn Ser Ala Trp
                405                 410                 415

Asp Ala Ser Arg Lys Pro Leu Val Ala Gln Trp Arg Ala Val Arg Gly
            420                 425                 430

Pro Arg Ser Lys Thr Phe Phe Thr Val Asn Val His Asn Gly Ser Lys
        435                 440                 445

Gly Gly Ser Ser Thr Leu His Gly Asp Phe Arg Pro Pro Val Asn Asn
450                 455                 460

Gly Val Glu Lys Arg Thr Gln Gln Thr Glu Ser Val Gly Ala Phe Val
465                 470                 475                 480

Asp Ala Ile Leu Ala Gln Asp Pro Lys Ala Arg Ile Ile Ala Ala Gly
                485                 490                 495

Asp Trp Asn Glu Phe Gln Phe Val Gln Pro Gln Arg Val Ile Ala Glu
            500                 505                 510

Lys His Asn Met Thr Asp Leu Ser Val Leu Ala Leu Asp Glu Ile Glu
        515                 520                 525

Gln Tyr Asn Tyr Val Phe Asp Met Asn Ala Gln Gln Leu Asp His Ile
530                 535                 540

Leu Val Ser Pro Ala Leu Ala Thr Asp Ala Ala Lys Ile Glu His Leu
545                 550                 555                 560

His Leu Ala Ala Trp Leu Arg Tyr Pro Asp Leu Thr Ser Asp His Asp
                565                 570                 575
```

```
Pro Leu Val Ser Tyr Leu Asn Val Cys Gly Cys
            580                 585
```

<210> SEQ ID NO 45
<211> LENGTH: 587
<212> TYPE: PRT
<213> ORGANISM: Phialophora geniculata

<400> SEQUENCE: 45

```
Ala Thr Ile Ala Glu Ile Asn Gly Asn Arg Phe Met Ser Pro Leu Gln
1               5                   10                  15

Gly Glu Val Val Thr Gly Val Glu Gly Leu Val Leu Ala Lys Gly Pro
            20                  25                  30

Asn Gly Ile Trp Leu Arg Ser Thr Val Pro Asp Asp Asp Leu Thr
        35                  40                  45

Ser Glu Ala Val Tyr Val Phe Asp Arg Asn Ile Ile Ala Arg Leu Ser
    50                  55                  60

Val Gly Asp Ile Val Lys Leu Asp Gly Thr Ile Leu Glu Tyr Arg Ala
65                  70                  75                  80

Gln Ala Ala His Met Tyr Leu Thr Glu Ile Thr Ala Thr Ser Asn Leu
                85                  90                  95

Glu Ile Leu Ser Ser Asn Asn Thr Val Thr Ala Tyr Val Ile Gly Glu
            100                 105                 110

Asp Thr Gly Ala Pro Pro Thr Glu Gln Tyr Ser Ser Leu Asp Glu Gly
            115                 120                 125

Asp Ile Phe Ala Val Pro Asn Asn Val Tyr Arg Val Ser Glu Glu Asn
        130                 135                 140

Pro Val Leu Glu Pro Ser Lys Tyr Gly Met Asp Tyr Trp Arg Ala Ile
145                 150                 155                 160

Asn Gly Glu Leu Val Thr Ile Lys Thr Pro Val Gly Val Ser Arg Pro
                165                 170                 175

Asn Gln Phe Gly Asp Thr Trp Val Val Gly Thr Trp Pro Thr Thr Gly
            180                 185                 190

Arg Asn Ser Gln Gly Gly Leu Thr Leu Arg Asp Lys Asp Ala Asn Pro
        195                 200                 205

Glu Ala Ile Ile Ile Gly Ser Pro Leu Asp Gly Thr Arg Asn Pro Glu
    210                 215                 220

Thr Lys Met Gly Asp Lys Phe Ala Glu Ile Thr Gly Val Val Thr Tyr
225                 230                 235                 240

Ala Phe Gly Phe Tyr Arg Ile Leu Pro Leu Thr Ala Ile Glu Val Glu
                245                 250                 255

Glu Glu Ala Thr Ile Glu Val Ser Pro Thr Thr Leu Glu Ser Arg Gly
            260                 265                 270

Asp Cys Arg Gly Leu Thr Phe Ser Tyr Asn Ile Glu Asn Leu Trp
        275                 280                 285

Ala Glu Ser Glu His Leu Pro Glu Val Ala Ala His Ile Val Glu Tyr
    290                 295                 300

Leu Lys Thr Pro Asp Phe Leu Phe Leu Gln Glu Val Gln Asp Asn Asn
305                 310                 315                 320

Gly Pro Thr Asn Asn Gly Val Val Ser Ala Asn Ile Thr Leu Ser Asn
                325                 330                 335

Leu Ala Ala Glu Ile Glu Ala Gln Ser Gly Ile Val Tyr Glu Phe Ala
            340                 345                 350

Glu Val Glu Pro Val Asn Asn Gln Asp Gly Gly Gln Pro Gly Gly Asn
        355                 360                 365
```

```
Ile Arg Asn Ala Tyr Leu Tyr Arg Pro Asp Val Ile Glu Leu Tyr Glu
    370                 375                 380

Pro Asn Gln Gly Gly Ser Thr Asp Gln Ala Glu Val Val Asp Gly Pro
385                 390                 395                 400

Ala Leu Ser Phe Asn Pro Gly Arg Ile Asp Ile Ser Asn Ser Ala Trp
                405                 410                 415

Asp Ala Ser Arg Lys Pro Leu Val Ala Gln Trp Arg Ala Val Arg Gly
            420                 425                 430

Pro Arg Ser Lys Thr Phe Phe Thr Val Asn Val His Asn Gly Ser Lys
        435                 440                 445

Gly Gly Ser Ser Thr Leu His Gly Asp Phe Arg Pro Pro Val Asn Asn
    450                 455                 460

Gly Val Glu Lys Arg Thr Gln Gln Thr Glu Ser Val Gly Ala Phe Val
465                 470                 475                 480

Asp Ala Ile Leu Ala Gln Asp Pro Lys Ala Arg Ile Ile Ala Ala Gly
                485                 490                 495

Asp Trp Asn Glu Phe Gln Phe Val Gln Pro Gln Arg Val Ile Ala Glu
            500                 505                 510

Lys His Asn Met Thr Asp Leu Ser Val Leu Ala Leu Asp Glu Ile Glu
        515                 520                 525

Gln Tyr Asn Tyr Val Phe Asp Met Asn Ala Gln Gln Leu Asp His Ile
    530                 535                 540

Leu Val Ser Pro Ala Leu Ala Thr Asp Ala Ala Lys Ile Glu His Leu
545                 550                 555                 560

His Leu Ala Ala Trp Leu Arg Tyr Pro Asp Leu Thr Ser Asp His Asp
                565                 570                 575

Pro Leu Val Ser Tyr Leu Asn Val Cys Gly Cys
            580                 585

<210> SEQ ID NO 46
<211> LENGTH: 2236
<212> TYPE: DNA
<213> ORGANISM: Paradendryphiella salina
<220> FEATURE:
<221> NAME/KEY: CDS
<222> LOCATION: (1)..(1042)
<220> FEATURE:
<221> NAME/KEY: sig_peptide
<222> LOCATION: (1)..(57)
<220> FEATURE:
<221> NAME/KEY: mat_peptide
<222> LOCATION: (58)..(2233)
<220> FEATURE:
<221> NAME/KEY: CDS
<222> LOCATION: (1197)..(1625)
<220> FEATURE:
<221> NAME/KEY: CDS
<222> LOCATION: (1681)..(1724)
<220> FEATURE:
<221> NAME/KEY: CDS
<222> LOCATION: (1916)..(2233)

<400> SEQUENCE: 46 atg gcg cct tta act cgt ctc ctt gct ctt tcg gca tcc gtg gct act     48
Met Ala Pro Leu Thr Arg Leu Leu Ala Leu Ser Ala Ser Val Ala Thr
                -15                 -10                 -5 tcc aca gcc ctc agc att gct gag atc aac ggt ccc aag ttt ctc tca     96
Ser Thr Ala Leu Ser Ile Ala Glu Ile Asn Gly Pro Lys Phe Leu Ser
        -1  1                   5                   10 ccc tac cgc gat cag acc gtc tcc aac att tct ggt atc gtt act gcc    144
Pro Tyr Arg Asp Gln Thr Val Ser Asn Ile Ser Gly Ile Val Thr Ala
```

```
              15                  20                  25
aag ggc ccc aat ggt ctt tgg ttg cgc tcc ccg aca ccc gac aga gac    192
Lys Gly Pro Asn Gly Leu Trp Leu Arg Ser Pro Thr Pro Asp Arg Asp
 30                  35                  40                  45 gag cgc aca tcc gag tcc ttg tat gtc tac ggc agc acg ttc ggc gcg    240
Glu Arg Thr Ser Glu Ser Leu Tyr Val Tyr Gly Ser Thr Phe Gly Ala
                 50                  55                  60 aac ctg act gtc ggc gat atc att gtc gtt ggt ggg cga gtt acc gag    288
Asn Leu Thr Val Gly Asp Ile Ile Val Val Gly Gly Arg Val Thr Glu
             65                  70                  75 tac cag tcc agc aag gat tac att ccc ttg act gaa ttg tcg gcg cca    336
Tyr Gln Ser Ser Lys Asp Tyr Ile Pro Leu Thr Glu Leu Ser Ala Pro
         80                  85                  90 gtg ctg gag aag aag ttg agt tca gga gcc aac gtg cag cct ttg gtg    384
Val Leu Glu Lys Lys Leu Ser Ser Gly Ala Asn Val Gln Pro Leu Val
     95                 100                 105 att gga gtt gac acg cgg gac cca ccg aac aag cag tat agc agt ttg    432
Ile Gly Val Asp Thr Arg Asp Pro Pro Asn Lys Gln Tyr Ser Ser Leu
110                 115                 120                 125 gat ggc ggt gac gtt ttc gcc gta ccg aac aat gtg agc cag att agc    480
Asp Gly Gly Asp Val Phe Ala Val Pro Asn Asn Val Ser Gln Ile Ser
                130                 135                 140 gtt gcg aat ccg gcg ctt cag ccc aag gag ttt ggt ctc gac ttt tgg    528
Val Ala Asn Pro Ala Leu Gln Pro Lys Glu Phe Gly Leu Asp Phe Trp
            145                 150                 155 gag agc ctg atg gga gag ctg gta acg gtg aag aac cca act gcg ctc    576
Glu Ser Leu Met Gly Glu Leu Val Thr Val Lys Asn Pro Thr Ala Leu
        160                 165                 170 acc aag ccg aac cag tat ggc gac acg tgg gtt gcg ggc gat tgg aag    624
Thr Lys Pro Asn Gln Tyr Gly Asp Thr Trp Val Ala Gly Asp Trp Lys
    175                 180                 185 gtt tct ggt cgc aac aag cgc ggt ggt ttg acc atg acg gat aaa gat    672
Val Ser Gly Arg Asn Lys Arg Gly Gly Leu Thr Met Thr Asp Lys Asp
190                 195                 200                 205 gcc aac cca gag gcc atc atc atc ggt tcg cct ctt gat ggg acc agg    720
Ala Asn Pro Glu Ala Ile Ile Ile Gly Ser Pro Leu Asp Gly Thr Arg
                210                 215                 220 aat cct act gac acc agg atg ggc gac tcg gtc gag gag att act ggt    768
Asn Pro Thr Asp Thr Arg Met Gly Asp Ser Val Glu Glu Ile Thr Gly
            225                 230                 235 gtt gtc acc tac gct ttc gga ttc tat cgc att ttg ccc acg acc gcc    816
Val Val Thr Tyr Ala Phe Gly Phe Tyr Arg Ile Leu Pro Thr Thr Ala
        240                 245                 250 atc acg gtc acc aag tca caa acg cct gat ctt ccc cct gcg tcc aca    864
Ile Thr Val Thr Lys Ser Gln Thr Pro Asp Leu Pro Pro Ala Ser Thr
    255                 260                 265 ctt gtg tcg agc ggg aca tgt gac ggc att acc ttt ggc gta tac aac    912
Leu Val Ser Ser Gly Thr Cys Asp Gly Ile Thr Phe Gly Val Tyr Asn
270                 275                 280                 285 gtc gag aac ctc gca ccc agc tct gac cac cat ccc gac cta gcg aat    960
Val Glu Asn Leu Ala Pro Ser Ser Asp His His Pro Asp Leu Ala Asn
                290                 295                 300 cac att gtc aac tac atg aac agc ccg gac atc att ttc gta cag gaa   1008
His Ile Val Asn Tyr Met Asn Ser Pro Asp Ile Ile Phe Val Gln Glu
            305                 310                 315 gtc cag gac gac aat ggt cct acc aat gac caa g gtaagtttcc           1052
Val Gln Asp Asp Asn Gly Pro Thr Asn Asp Gln
        320                 325 aggaagttta cacaacatcc tcgttgccat ggtccgaatg ctatactagg tatcggacct   1112
```

```
cacacgagct gtcttacctt gcaccggtgt tacacacctc acgctacatg ccgcttatcc    1172
cgtcgtcata ctgaccccat gtag tt  gtt tct gca aac ctc acg ttg agc      1222
                            Val Val Ser Ala Asn Leu Thr Leu Ser
                                330                 335 acg ctc agc gca gcc att gct aca gcc ggc ggt cct aac tat gcc ttc      1270
Thr Leu Ser Ala Ala Ile Ala Thr Ala Gly Gly Pro Asn Tyr Ala Phe
            340                 345                 350 act gag att gta cca gtc gat gat cag gat ggc ggc cag cca ggt ggt      1318
Thr Glu Ile Val Pro Val Asp Asp Gln Asp Gly Gly Gln Pro Gly Gly
355                 360                 365 aac atc cgc aac gca tac ctg tac aag ccc aat gtt ctc cgc ctg tac      1366
Asn Ile Arg Asn Ala Tyr Leu Tyr Lys Pro Asn Val Leu Arg Leu Tyr
370                 375                 380                 385 aag ccg aac ctc ggt ggc tct ctg gat gcg aca gaa gtg gtt gct ggc      1414
Lys Pro Asn Leu Gly Gly Ser Leu Asp Ala Thr Glu Val Val Ala Gly
                390                 395                 400 cca acg ctc tca tac aat ccc gga cgt atc gag ccg gaa aac gaa gcg      1462
Pro Thr Leu Ser Tyr Asn Pro Gly Arg Ile Glu Pro Glu Asn Glu Ala
            405                 410                 415 tgg acg aat agc cga aag ccg cta gct gcg cag tgg gag gtc atc gga      1510
Trp Thr Asn Ser Arg Lys Pro Leu Ala Ala Gln Trp Glu Val Ile Gly
            420                 425                 430 aag cga ggc gca aag aag ccc aat gta ttc ttc acg gtt aat gtg cac      1558
Lys Arg Gly Ala Lys Lys Pro Asn Val Phe Phe Thr Val Asn Val His
        435                 440                 445 ttt gga tct aag gga gga agc agc agc ctg cat ggc gat gcg cga ccg      1606
Phe Gly Ser Lys Gly Gly Ser Ser Ser Leu His Gly Asp Ala Arg Pro
450                 455                 460                 465 ccg gtg aat ggt ggt gtt g gtacgtttat ccagatgcac aattatgtgc           1655
Pro Val Asn Gly Gly Val
                470 ggcagtcgct aatgttgcca tgtag ac  gat cgc ctt gag caa gcc ctt ctc      1706
                                Asp Asp Arg Leu Glu Gln Ala Leu Leu
                                                475             480 acc gcg aac ttc gta aag gtacgttttg agatgatttg cggctgtatg             1754
Thr Ala Asn Phe Val Lys
                485 cgacaaggtg gcacggaggg ggtggctgca gcttgcttct atcttcatga ctcggtggta    1814
catagaacgt ctctctcgca cgaaaggggt gccctttttt tgcctctgag gagaacgatt    1874
ctagacgaag agaccagggc gaagctaaca aaacccaaca g gac atc ctt tct cag    1930
                                              Asp Ile Leu Ser Gln
                                                              490 gac aaa aac gca cgc att gtg act gca ggc gat ttc aac gaa ttc gct      1978
Asp Lys Asn Ala Arg Ile Val Thr Ala Gly Asp Phe Asn Glu Phe Ala
            495                 500                 505 ttc gtg caa cca ctg gag gaa tat acc aaa atc tct gga ctc aag gac      2026
Phe Val Gln Pro Leu Glu Glu Tyr Thr Lys Ile Ser Gly Leu Lys Asp
            510                 515                 520 ctt gac gaa gtt gtc aag ctt gac aag ctc gaa cga tac acc tat ctc      2074
Leu Asp Glu Val Val Lys Leu Asp Lys Leu Glu Arg Tyr Thr Tyr Leu
525                 530                 535 tac gat atg aat act cag gag ctc gac cac atg ttt gtg tcg ccg tca      2122
Tyr Asp Met Asn Thr Gln Glu Leu Asp His Met Phe Val Ser Pro Ser
540                 545                 550                 555 ttg gcg aag agc aga gct aaa ttc gag cac atc cac gtc aat acg tgg      2170
Leu Ala Lys Ser Arg Ala Lys Phe Glu His Ile His Val Asn Thr Trp
            560                 565                 570
```

```
cca gag tac gat gcg caa gtc agc gac cat gac cct tcg gta gcg aga           2218
Pro Glu Tyr Asp Ala Gln Val Ser Asp His Asp Pro Ser Val Ala Arg
            575                 580                 585 ctg gac gtt tgc gct tag                                                   2236
Leu Asp Val Cys Ala
        590
```

<210> SEQ ID NO 47
<211> LENGTH: 611
<212> TYPE: PRT
<213> ORGANISM: Paradendryphiella salina

<400> SEQUENCE: 47

```
Met Ala Pro Leu Thr Arg Leu Leu Ala Leu Ser Ala Ser Val Ala Thr
            -15                 -10                  -5

Ser Thr Ala Leu Ser Ile Ala Glu Ile Asn Gly Pro Lys Phe Leu Ser
         -1  1               5                  10

Pro Tyr Arg Asp Gln Thr Val Ser Asn Ile Ser Gly Ile Val Thr Ala
             15                  20                  25

Lys Gly Pro Asn Gly Leu Trp Leu Arg Ser Pro Thr Pro Asp Arg Asp
 30                  35                  40                  45

Glu Arg Thr Ser Glu Ser Leu Tyr Val Tyr Gly Ser Thr Phe Gly Ala
                 50                  55                  60

Asn Leu Thr Val Gly Asp Ile Ile Val Gly Gly Arg Val Thr Glu
                 65                  70                  75

Tyr Gln Ser Ser Lys Asp Tyr Ile Pro Leu Thr Glu Leu Ser Ala Pro
                 80                  85                  90

Val Leu Glu Lys Lys Leu Ser Ser Gly Ala Asn Val Gln Pro Leu Val
         95                 100                 105

Ile Gly Val Asp Thr Arg Asp Pro Pro Asn Lys Gln Tyr Ser Ser Leu
110                 115                 120                 125

Asp Gly Gly Asp Val Phe Ala Val Pro Asn Asn Val Ser Gln Ile Ser
                130                 135                 140

Val Ala Asn Pro Ala Leu Gln Pro Lys Glu Phe Gly Leu Asp Phe Trp
                145                 150                 155

Glu Ser Leu Met Gly Glu Leu Val Thr Val Lys Asn Pro Thr Ala Leu
                160                 165                 170

Thr Lys Pro Asn Gln Tyr Gly Asp Thr Trp Val Ala Gly Asp Trp Lys
        175                 180                 185

Val Ser Gly Arg Asn Lys Arg Gly Gly Leu Thr Met Thr Asp Lys Asp
190                 195                 200                 205

Ala Asn Pro Glu Ala Ile Ile Ile Gly Ser Pro Leu Asp Gly Thr Arg
                210                 215                 220

Asn Pro Thr Asp Thr Arg Met Gly Asp Ser Val Glu Glu Ile Thr Gly
                225                 230                 235

Val Val Thr Tyr Ala Phe Gly Phe Tyr Arg Ile Leu Pro Thr Thr Ala
        240                 245                 250

Ile Thr Val Thr Lys Ser Gln Thr Pro Asp Leu Pro Pro Ala Ser Thr
        255                 260                 265

Leu Val Ser Ser Gly Thr Cys Asp Gly Ile Thr Phe Gly Val Tyr Asn
270                 275                 280                 285

Val Glu Asn Leu Ala Pro Ser Ser Asp His His Pro Asp Leu Ala Asn
                290                 295                 300

His Ile Val Asn Tyr Met Asn Ser Pro Asp Ile Ile Phe Val Gln Glu
                305                 310                 315
```

```
Val Gln Asp Asp Asn Gly Pro Thr Asn Asp Gln Val Ser Ala Asn
            320                 325                 330

Leu Thr Leu Ser Thr Leu Ser Ala Ala Ile Ala Thr Ala Gly Gly Pro
    335                 340                 345

Asn Tyr Ala Phe Thr Glu Ile Val Pro Val Asp Asp Gln Asp Gly Gly
350                 355                 360                 365

Gln Pro Gly Gly Asn Ile Arg Asn Ala Tyr Leu Tyr Lys Pro Asn Val
                370                 375                 380

Leu Arg Leu Tyr Lys Pro Asn Leu Gly Ser Leu Asp Ala Thr Glu
            385                 390                 395

Val Val Ala Gly Pro Thr Leu Ser Tyr Asn Pro Gly Arg Ile Glu Pro
    400                 405                 410

Glu Asn Glu Ala Trp Thr Asn Ser Arg Lys Pro Leu Ala Ala Gln Trp
    415                 420                 425

Glu Val Ile Gly Lys Arg Gly Ala Lys Lys Pro Asn Val Phe Phe Thr
430                 435                 440                 445

Val Asn Val His Phe Gly Ser Lys Gly Gly Ser Ser Leu His Gly
                450                 455                 460

Asp Ala Arg Pro Pro Val Asn Gly Gly Val Asp Asp Arg Leu Glu Gln
            465                 470                 475

Ala Leu Leu Thr Ala Asn Phe Val Lys Asp Ile Leu Ser Gln Asp Lys
    480                 485                 490

Asn Ala Arg Ile Val Thr Ala Gly Asp Phe Asn Glu Phe Ala Phe Val
    495                 500                 505

Gln Pro Leu Glu Glu Tyr Thr Lys Ile Ser Gly Leu Lys Asp Leu Asp
510                 515                 520                 525

Glu Val Val Lys Leu Asp Lys Leu Glu Arg Tyr Thr Tyr Leu Tyr Asp
            530                 535                 540

Met Asn Thr Gln Glu Leu Asp His Met Phe Val Ser Pro Ser Leu Ala
                545                 550                 555

Lys Ser Arg Ala Lys Phe Glu His Ile His Val Asn Thr Trp Pro Glu
            560                 565                 570

Tyr Asp Ala Gln Val Ser Asp His Asp Pro Ser Val Ala Arg Leu Asp
    575                 580                 585

Val Cys Ala
590

<210> SEQ ID NO 48
<211> LENGTH: 592
<212> TYPE: PRT
<213> ORGANISM: Paradendryphiella salina

<400> SEQUENCE: 48

Leu Ser Ile Ala Glu Ile Asn Gly Pro Lys Phe Leu Ser Pro Tyr Arg
1               5                   10                  15

Asp Gln Thr Val Ser Asn Ile Ser Gly Ile Val Thr Ala Lys Gly Pro
            20                  25                  30

Asn Gly Leu Trp Leu Arg Ser Pro Thr Pro Asp Arg Asp Glu Arg Thr
        35                  40                  45

Ser Glu Ser Leu Tyr Val Tyr Gly Ser Thr Phe Gly Ala Asn Leu Thr
    50                  55                  60

Val Gly Asp Ile Ile Val Val Gly Gly Arg Val Thr Glu Tyr Gln Ser
65                  70                  75                  80

Ser Lys Asp Tyr Ile Pro Leu Thr Glu Leu Ser Ala Pro Val Leu Glu
                85                  90                  95
```

```
Lys Lys Leu Ser Ser Gly Ala Asn Val Gln Pro Leu Val Ile Gly Val
            100                 105                 110

Asp Thr Arg Asp Pro Pro Asn Lys Gln Tyr Ser Ser Leu Asp Gly Gly
            115                 120                 125

Asp Val Phe Ala Val Pro Asn Asn Val Ser Gln Ile Ser Val Ala Asn
            130                 135                 140

Pro Ala Leu Gln Pro Lys Glu Phe Gly Leu Asp Phe Trp Glu Ser Leu
145                 150                 155                 160

Met Gly Glu Leu Val Thr Val Lys Asn Pro Thr Ala Leu Thr Lys Pro
                165                 170                 175

Asn Gln Tyr Gly Asp Thr Trp Val Ala Gly Asp Trp Lys Val Ser Gly
            180                 185                 190

Arg Asn Lys Arg Gly Gly Leu Thr Met Thr Asp Lys Asp Ala Asn Pro
            195                 200                 205

Glu Ala Ile Ile Ile Gly Ser Pro Leu Asp Gly Thr Arg Asn Pro Thr
            210                 215                 220

Asp Thr Arg Met Gly Asp Ser Val Glu Glu Ile Thr Gly Val Val Thr
225                 230                 235                 240

Tyr Ala Phe Gly Phe Tyr Arg Ile Leu Pro Thr Thr Ala Ile Thr Val
            245                 250                 255

Thr Lys Ser Gln Thr Pro Asp Leu Pro Pro Ala Ser Thr Leu Val Ser
            260                 265                 270

Ser Gly Thr Cys Asp Gly Ile Thr Phe Gly Val Tyr Asn Val Glu Asn
            275                 280                 285

Leu Ala Pro Ser Ser Asp His His Pro Asp Leu Ala Asn His Ile Val
            290                 295                 300

Asn Tyr Met Asn Ser Pro Asp Ile Ile Phe Val Gln Glu Val Gln Asp
305                 310                 315                 320

Asp Asn Gly Pro Thr Asn Asp Gln Val Val Ser Ala Asn Leu Thr Leu
            325                 330                 335

Ser Thr Leu Ser Ala Ala Ile Ala Thr Ala Gly Gly Pro Asn Tyr Ala
            340                 345                 350

Phe Thr Glu Ile Val Pro Val Asp Asp Gln Asp Gly Gly Gln Pro Gly
            355                 360                 365

Gly Asn Ile Arg Asn Ala Tyr Leu Tyr Lys Pro Asn Val Leu Arg Leu
            370                 375                 380

Tyr Lys Pro Asn Leu Gly Gly Ser Leu Asp Ala Thr Glu Val Val Ala
385                 390                 395                 400

Gly Pro Thr Leu Ser Tyr Asn Pro Gly Arg Ile Glu Pro Glu Asn Glu
            405                 410                 415

Ala Trp Thr Asn Ser Arg Lys Pro Leu Ala Ala Gln Trp Glu Val Ile
            420                 425                 430

Gly Lys Arg Gly Ala Lys Lys Pro Asn Val Phe Phe Thr Val Asn Val
            435                 440                 445

His Phe Gly Ser Lys Gly Gly Ser Ser Ser Leu His Gly Asp Ala Arg
            450                 455                 460

Pro Pro Val Asn Gly Gly Val Asp Asp Arg Leu Glu Gln Ala Leu Leu
465                 470                 475                 480

Thr Ala Asn Phe Val Lys Asp Ile Leu Ser Gln Asp Lys Asn Ala Arg
            485                 490                 495

Ile Val Thr Ala Gly Asp Phe Asn Glu Phe Ala Phe Val Gln Pro Leu
            500                 505                 510
```

```
Glu Glu Tyr Thr Lys Ile Ser Gly Leu Lys Asp Leu Asp Glu Val Val
            515                 520                 525

Lys Leu Asp Lys Leu Glu Arg Tyr Thr Tyr Leu Tyr Asp Met Asn Thr
530                 535                 540

Gln Glu Leu Asp His Met Phe Val Ser Pro Ser Leu Ala Lys Ser Arg
545                 550                 555                 560

Ala Lys Phe Glu His Ile His Val Asn Thr Trp Pro Glu Tyr Asp Ala
                565                 570                 575

Gln Val Ser Asp His Asp Pro Ser Val Ala Arg Leu Asp Val Cys Ala
            580                 585                 590

<210> SEQ ID NO 49
<211> LENGTH: 1891
<212> TYPE: DNA
<213> ORGANISM: Aspergillus insuetus
<220> FEATURE:
<221> NAME/KEY: CDS
<222> LOCATION: (1)..(670)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1888)
<220> FEATURE:
<221> NAME/KEY: CDS
<222> LOCATION: (720)..(1888)

<400> SEQUENCE: 49
```

| | | | | | | | | | | | | | | | | |
|---|---|---|---|---|---|---|---|---|---|---|---|---|---|---|---|---|
| atg | agg | ttc | ctc | gtg | tct | ctt | tct | gcc | ctc | tcc | tgg | gtc | ctg | ccc | tct | 48 |
| Met | Arg | Phe | Leu | Val | Ser | Leu | Ser | Ala | Leu | Ser | Trp | Val | Leu | Pro | Ser | |
| | | | -15 | | | | | -10 | | | | | -5 | | | |

```
gca gca gcg gca gtg aca att gct gag atc aat gga aat gcg tac ctt      96
Ala Ala Ala Ala Val Thr Ile Ala Glu Ile Asn Gly Asn Ala Tyr Leu
    -1   1               5                   10 tcc ccg ctg aag gga gag agc gtc tct ggc gtc gaa gga ctc gtc act     144
Ser Pro Leu Lys Gly Glu Ser Val Ser Gly Val Glu Gly Leu Val Thr
 15                  20                  25 gct att ggc gag agc ggc ttc ttc ctt cgg tcg act act cca gac tcg     192
Ala Ile Gly Glu Ser Gly Phe Phe Leu Arg Ser Thr Thr Pro Asp Ser
 30                  35                  40                  45 gac gat gcc act tcg gag tcc atc tac gtc tac ggg agc agt tcc gtc     240
Asp Asp Ala Thr Ser Glu Ser Ile Tyr Val Tyr Gly Ser Ser Ser Val
                 50                  55                  60 tcc aaa gtg act gtt gga gac atc atc acg ctc agc gga aag gtt tct     288
Ser Lys Val Thr Val Gly Asp Ile Ile Thr Leu Ser Gly Lys Val Ser
                 65                  70                  75 gaa tac cgg tct cag gat aca tac ctc cac ctg acg gaa atc aca tcc     336
Glu Tyr Arg Ser Gln Asp Thr Tyr Leu His Leu Thr Glu Ile Thr Ser
         80                  85                  90 ccg tct agc atc gtc gtc aag agc agc ggc aac gag gtc act cct gtg     384
Pro Ser Ser Ile Val Val Lys Ser Ser Gly Asn Glu Val Thr Pro Val
 95                 100                 105 gtg att ggc aag gac cgc tct ccc ccg acg gag gtg tac tct tcc ctc     432
Val Ile Gly Lys Asp Arg Ser Pro Pro Thr Glu Val Tyr Ser Ser Leu
110                 115                 120                 125 gac att ggc gac atc tat gcg ctg cca aac aat atc agc cgg atc tct     480
Asp Ile Gly Asp Ile Tyr Ala Leu Pro Asn Asn Ile Ser Arg Ile Ser
                130                 135                 140 gag gag aac agc gcg ctg aag ccc gat gtc aat ggt ctc gac ttt tgg     528
Glu Glu Asn Ser Ala Leu Lys Pro Asp Val Asn Gly Leu Asp Phe Trp
            145                 150                 155
```

```
gag agt ctc agc ggt gag ctc gtc tcg ttg act gat ttg acc atc atc    576
Glu Ser Leu Ser Gly Glu Leu Val Ser Leu Thr Asp Leu Thr Ile Ile
        160                 165                 170 acc aag ccg aac cag tac ggc gat gtc ttt gtt cga ggc aac tgg gct    624
Thr Lys Pro Asn Gln Tyr Gly Asp Val Phe Val Arg Gly Asn Trp Ala
    175                 180                 185 gtt tct ggc ctg aat gag cac ggt ggt ctg acc atg act gcc aag g      670
Val Ser Gly Leu Asn Glu His Gly Gly Leu Thr Met Thr Ala Lys
190                 195                 200 gtacgtctgc tccaataacct tgaggctgga attggactaa caatggtag ac tcc aac   727
                                                       Asp Ser Asn
                                                           205 cca gaa gcc atc aaa atc ggc aca ccc ctt gac ggc acg cgt aac cgc    775
Pro Glu Ala Ile Lys Ile Gly Thr Pro Leu Asp Gly Thr Arg Asn Arg
            210             215                 220 gat gac tcg aag gtc ggg gac atc gtc gaa gat gtc acc ggc gtc gtg    823
Asp Asp Ser Lys Val Gly Asp Ile Val Glu Asp Val Thr Gly Val Val
            225             230                 235 caa tgg gtc ttt ggc cag tac atg gtc ctc ccc acc aca gcg ctc aaa    871
Gln Trp Val Phe Gly Gln Tyr Met Val Leu Pro Thr Thr Ala Leu Lys
240                 245             250                 255 gta acc gcc tcg aac gac acc gcc gcg cca gcc tca acg ctc gtc ggc    919
Val Thr Ala Ser Asn Asp Thr Ala Ala Pro Ala Ser Thr Leu Val Gly
                260             265                 270 gat ggc acc tgc aaa tcc ctc agc atc ggc tcg tac aac gtt gaa aac    967
Asp Gly Thr Cys Lys Ser Leu Ser Ile Gly Ser Tyr Asn Val Glu Asn
            275             280                 285 ctc acc ccc acc gct tcc aac att gag ggc atc gcg aac cac att gca   1015
Leu Thr Pro Thr Ala Ser Asn Ile Glu Gly Ile Ala Asn His Ile Ala
        290                 295                 300 aac tac ctc aac ggt ccc gcc ctc gtc gcc ctt cag gag atc caa gat   1063
Asn Tyr Leu Asn Gly Pro Ala Leu Val Ala Leu Gln Glu Ile Gln Asp
305                 310                 315 aat tcc ggc gca acc gac gac ggt gtc gtc tcc gcc aac gtg acc cta   1111
Asn Ser Gly Ala Thr Asp Asp Gly Val Val Ser Ala Asn Val Thr Leu
320                 325                 330                 335 tcc aca ctc gca aac ctt att gct gct gcc ggc gga cca gac tac gag   1159
Ser Thr Leu Ala Asn Leu Ile Ala Ala Ala Gly Gly Pro Asp Tyr Glu
            340                 345                 350 ttc acc gaa att gtc cca gtg aat aac gct gac ggc ggc cag cct ggc   1207
Phe Thr Glu Ile Val Pro Val Asn Asn Ala Asp Gly Gly Gln Pro Gly
        355                 360                 365 gga aac atc cgc gtc gca tac ctg tac gat cct acc atc atc cgc ctc   1255
Gly Asn Ile Arg Val Ala Tyr Leu Tyr Asp Pro Thr Ile Ile Arg Leu
    370                 375                 380 cgc aat gag aac att ggg tca tcc aca gac gca aac gag gtt ctc gcg   1303
Arg Asn Glu Asn Ile Gly Ser Ser Thr Asp Ala Asn Glu Val Leu Ala
385                 390                 395 ggt gct gag ctg aaa tac aac cca ggc ctc atc gac ccg tcc aac gcc   1351
Gly Ala Glu Leu Lys Tyr Asn Pro Gly Leu Ile Asp Pro Ser Asn Ala
400                 405                 410                 415 gcc tgg gac gca tcc cgc aag ccc ctc gca gca gcc tgg gag acc ctc   1399
Ala Trp Asp Ala Ser Arg Lys Pro Leu Ala Ala Ala Trp Glu Thr Leu
            420                 425                 430 gac ggg aag aac aaa ttc ttc aca gta aac gtc cac ttc tca agt aaa   1447
Asp Gly Lys Asn Lys Phe Phe Thr Val Asn Val His Phe Ser Ser Lys
        435                 440                 445 ggc ggc ggc aca aca ctc cag ggt gac gtc cgc ccc ccg gta aac ggc   1495
Gly Gly Gly Thr Thr Leu Gln Gly Asp Val Arg Pro Pro Val Asn Gly
    450                 455                 460
```

```
gcc gtc gac caa cgc atc gca caa gcc gaa gtc gtc gcg tct ttc atc   1543
Ala Val Asp Gln Arg Ile Ala Gln Ala Glu Val Val Ala Ser Phe Ile
465                 470                 475 gca tct atc ctc gaa aaa gat ccc aag gcc aag atc ctc gca aca ggc   1591
Ala Ser Ile Leu Glu Lys Asp Pro Lys Ala Lys Ile Leu Ala Thr Gly
480                 485                 490                 495 gac ttc aac gaa ttc gcc ttc gtc gaa cca ctg aca acc ttc gtc gca   1639
Asp Phe Asn Glu Phe Ala Phe Val Glu Pro Leu Thr Thr Phe Val Ala
                500                 505                 510 aag tca agc ctc gtc gac ctc gac gag gtc gtg ggt atc ccc gag acg   1687
Lys Ser Ser Leu Val Asp Leu Asp Glu Val Val Gly Ile Pro Glu Thr
            515                 520                 525 gaa cgc tac acg tac atc tac gac tcg aac cat cag cag ctc gac cac   1735
Glu Arg Tyr Thr Tyr Ile Tyr Asp Ser Asn His Gln Gln Leu Asp His
        530                 535                 540 atg ttt gtg tct gag gcg ttg ggg aag ggt gca aag atg gag cat gtc   1783
Met Phe Val Ser Glu Ala Leu Gly Lys Gly Ala Lys Met Glu His Val
    545                 550                 555 cat gtg aat acg tgg ttg aat tat gat gat gcg agc agt gat cat gat   1831
His Val Asn Thr Trp Leu Asn Tyr Asp Asp Ala Ser Ser Asp His Asp
560                 565                 570                 575 ccg tct gtt gcg gtg ttt aat gtt tgt ggg aag aag tcg act tgt aag   1879
Pro Ser Val Ala Val Phe Asn Val Cys Gly Lys Lys Ser Thr Cys Lys
                580                 585                 590 ccc aag tat tag                                                    1891
Pro Lys Tyr <210> SEQ ID NO 50
<211> LENGTH: 613
<212> TYPE: PRT
<213> ORGANISM: Aspergillus insuetus

<400> SEQUENCE: 50

Met Arg Phe Leu Val Ser Leu Ser Ala Leu Ser Trp Val Leu Pro Ser
            -15                 -10                 -5

Ala Ala Ala Ala Val Thr Ile Ala Glu Ile Asn Gly Asn Ala Tyr Leu
        -1  1               5                   10

Ser Pro Leu Lys Gly Glu Ser Val Ser Gly Val Glu Gly Leu Val Thr
        15                  20                  25

Ala Ile Gly Glu Ser Gly Phe Phe Leu Arg Ser Thr Thr Pro Asp Ser
30                  35                  40                  45

Asp Asp Ala Thr Ser Glu Ser Ile Tyr Val Tyr Gly Ser Ser Ser Val
                50                  55                  60

Ser Lys Val Thr Val Gly Asp Ile Ile Thr Leu Ser Gly Lys Val Ser
            65                  70                  75

Glu Tyr Arg Ser Gln Asp Thr Tyr Leu His Leu Thr Glu Ile Thr Ser
        80                  85                  90

Pro Ser Ser Ile Val Val Lys Ser Ser Gly Asn Glu Val Thr Pro Val
        95                  100                 105

Val Ile Gly Lys Asp Arg Ser Pro Pro Thr Glu Val Tyr Ser Ser Leu
110                 115                 120                 125

Asp Ile Gly Asp Ile Tyr Ala Leu Pro Asn Asn Ile Ser Arg Ile Ser
                130                 135                 140

Glu Glu Asn Ser Ala Leu Lys Pro Asp Val Asn Gly Leu Asp Phe Trp
            145                 150                 155

Glu Ser Leu Ser Gly Glu Leu Val Ser Leu Thr Asp Leu Thr Ile Ile
        160                 165                 170
```

-continued

Thr Lys Pro Asn Gln Tyr Gly Asp Val Phe Val Arg Gly Asn Trp Ala
175                 180                 185

Val Ser Gly Leu Asn Glu His Gly Gly Leu Thr Met Thr Ala Lys Asp
190                 195                 200                 205

Ser Asn Pro Glu Ala Ile Lys Ile Gly Thr Pro Leu Asp Gly Thr Arg
            210                 215                 220

Asn Arg Asp Asp Ser Lys Val Gly Asp Ile Val Glu Asp Val Thr Gly
                225                 230                 235

Val Val Gln Trp Val Phe Gly Gln Tyr Met Val Leu Pro Thr Thr Ala
        240                 245                 250

Leu Lys Val Thr Ala Ser Asn Asp Thr Ala Ala Pro Ala Ser Thr Leu
255                 260                 265

Val Gly Asp Gly Thr Cys Lys Ser Leu Ser Ile Gly Ser Tyr Asn Val
270                 275                 280                 285

Glu Asn Leu Thr Pro Thr Ala Ser Asn Ile Glu Gly Ile Ala Asn His
            290                 295                 300

Ile Ala Asn Tyr Leu Asn Gly Pro Ala Leu Val Ala Leu Gln Glu Ile
                305                 310                 315

Gln Asp Asn Ser Gly Ala Thr Asp Asp Gly Val Val Ser Ala Asn Val
        320                 325                 330

Thr Leu Ser Thr Leu Ala Asn Leu Ile Ala Ala Gly Gly Pro Asp
335                 340                 345

Tyr Glu Phe Thr Glu Ile Val Pro Val Asn Asn Ala Asp Gly Gly Gln
350                 355                 360                 365

Pro Gly Gly Asn Ile Arg Val Ala Tyr Leu Tyr Asp Pro Thr Ile Ile
                370                 375                 380

Arg Leu Arg Asn Glu Asn Ile Gly Ser Ser Thr Asp Ala Asn Glu Val
        385                 390                 395

Leu Ala Gly Ala Glu Leu Lys Tyr Asn Pro Gly Leu Ile Asp Pro Ser
                400                 405                 410

Asn Ala Ala Trp Asp Ala Ser Arg Lys Pro Leu Ala Ala Ala Trp Glu
        415                 420                 425

Thr Leu Asp Gly Lys Asn Lys Phe Phe Thr Val Asn Val His Phe Ser
430                 435                 440                 445

Ser Lys Gly Gly Gly Thr Thr Leu Gln Gly Asp Val Arg Pro Pro Val
                450                 455                 460

Asn Gly Ala Val Asp Gln Arg Ile Ala Gln Ala Glu Val Val Ala Ser
                465                 470                 475

Phe Ile Ala Ser Ile Leu Glu Lys Asp Pro Lys Ala Lys Ile Leu Ala
        480                 485                 490

Thr Gly Asp Phe Asn Glu Phe Ala Phe Val Glu Pro Leu Thr Thr Phe
495                 500                 505

Val Ala Lys Ser Ser Leu Val Asp Leu Asp Glu Val Val Gly Ile Pro
510                 515                 520                 525

Glu Thr Glu Arg Tyr Thr Tyr Ile Tyr Asp Ser Asn His Gln Gln Leu
                530                 535                 540

Asp His Met Phe Val Ser Glu Ala Leu Gly Lys Gly Ala Lys Met Glu
            545                 550                 555

His Val His Val Asn Thr Trp Leu Asn Tyr Asp Asp Ala Ser Ser Asp
        560                 565                 570

His Asp Pro Ser Val Ala Val Phe Asn Val Cys Gly Lys Lys Ser Thr
575                 580                 585

```
Cys Lys Pro Lys Tyr
590

<210> SEQ ID NO 51
<211> LENGTH: 594
<212> TYPE: PRT
<213> ORGANISM: Aspergillus insuetus

<400> SEQUENCE: 51

Ala Val Thr Ile Ala Glu Ile Asn Gly Asn Ala Tyr Leu Ser Pro Leu
1               5                   10                  15

Lys Gly Glu Ser Val Ser Gly Val Glu Gly Leu Val Thr Ala Ile Gly
            20                  25                  30

Glu Ser Gly Phe Phe Leu Arg Ser Thr Thr Pro Asp Ser Asp Asp Ala
        35                  40                  45

Thr Ser Glu Ser Ile Tyr Val Tyr Gly Ser Ser Val Ser Lys Val
50                  55                  60

Thr Val Gly Asp Ile Ile Thr Leu Ser Gly Lys Val Ser Glu Tyr Arg
65                  70                  75                  80

Ser Gln Asp Thr Tyr Leu His Leu Thr Glu Ile Thr Ser Pro Ser Ser
                85                  90                  95

Ile Val Val Lys Ser Ser Gly Asn Glu Val Thr Pro Val Val Ile Gly
            100                 105                 110

Lys Asp Arg Ser Pro Pro Thr Glu Val Tyr Ser Ser Leu Asp Ile Gly
        115                 120                 125

Asp Ile Tyr Ala Leu Pro Asn Asn Ile Ser Arg Ile Ser Glu Glu Asn
130                 135                 140

Ser Ala Leu Lys Pro Asp Val Asn Gly Leu Asp Phe Trp Glu Ser Leu
145                 150                 155                 160

Ser Gly Glu Leu Val Ser Leu Thr Asp Leu Thr Ile Ile Thr Lys Pro
                165                 170                 175

Asn Gln Tyr Gly Asp Val Phe Val Arg Gly Asn Trp Ala Val Ser Gly
            180                 185                 190

Leu Asn Glu His Gly Gly Leu Thr Met Thr Ala Lys Asp Ser Asn Pro
        195                 200                 205

Glu Ala Ile Lys Ile Gly Thr Pro Leu Asp Gly Thr Arg Asn Arg Asp
210                 215                 220

Asp Ser Lys Val Gly Asp Ile Val Glu Asp Val Thr Gly Val Val Gln
225                 230                 235                 240

Trp Val Phe Gly Gln Tyr Met Val Leu Pro Thr Thr Ala Leu Lys Val
                245                 250                 255

Thr Ala Ser Asn Asp Thr Ala Ala Pro Ala Ser Thr Leu Val Gly Asp
            260                 265                 270

Gly Thr Cys Lys Ser Leu Ser Ile Gly Ser Tyr Asn Val Glu Asn Leu
        275                 280                 285

Thr Pro Thr Ala Ser Asn Ile Glu Gly Ile Ala Asn His Ile Ala Asn
290                 295                 300

Tyr Leu Asn Gly Pro Ala Leu Val Ala Leu Gln Glu Ile Gln Asp Asn
305                 310                 315                 320

Ser Gly Ala Thr Asp Asp Gly Val Val Ser Ala Asn Val Thr Leu Ser
                325                 330                 335

Thr Leu Ala Asn Leu Ile Ala Ala Gly Gly Pro Asp Tyr Glu Phe
            340                 345                 350

Thr Glu Ile Val Pro Val Asn Asn Ala Asp Gly Gly Gln Pro Gly Gly
        355                 360                 365
```

```
Asn Ile Arg Val Ala Tyr Leu Tyr Asp Pro Thr Ile Ile Arg Leu Arg
    370                 375                 380
Asn Glu Asn Ile Gly Ser Ser Thr Asp Ala Asn Glu Val Leu Ala Gly
385                 390                 395                 400
Ala Glu Leu Lys Tyr Asn Pro Gly Leu Ile Asp Pro Ser Asn Ala Ala
                405                 410                 415
Trp Asp Ala Ser Arg Lys Pro Leu Ala Ala Trp Glu Thr Leu Asp
            420                 425                 430
Gly Lys Asn Lys Phe Phe Thr Val Asn Val His Phe Ser Lys Gly
        435                 440                 445
Gly Gly Thr Thr Leu Gln Gly Asp Val Arg Pro Pro Val Asn Gly Ala
    450                 455                 460
Val Asp Gln Arg Ile Ala Gln Ala Glu Val Val Ala Ser Phe Ile Ala
465                 470                 475                 480
Ser Ile Leu Glu Lys Asp Pro Lys Ala Lys Ile Leu Ala Thr Gly Asp
                485                 490                 495
Phe Asn Glu Phe Ala Phe Val Glu Pro Leu Thr Thr Phe Val Ala Lys
            500                 505                 510
Ser Ser Leu Val Asp Leu Asp Glu Val Val Gly Ile Pro Glu Thr Glu
        515                 520                 525
Arg Tyr Thr Tyr Ile Tyr Asp Ser Asn His Gln Gln Leu Asp His Met
    530                 535                 540
Phe Val Ser Glu Ala Leu Gly Lys Gly Ala Lys Met Glu His Val His
545                 550                 555                 560
Val Asn Thr Trp Leu Asn Tyr Asp Asp Ala Ser Ser Asp His Asp Pro
                565                 570                 575
Ser Val Ala Val Phe Asn Val Cys Gly Lys Lys Ser Thr Cys Lys Pro
            580                 585                 590
Lys Tyr
```

<210> SEQ ID NO 52
<211> LENGTH: 2106
<212> TYPE: DNA
<213> ORGANISM: Purpureocillium lilacinum
<220> FEATURE:
<221> NAME/KEY: CDS
<222> LOCATION: (1)..(293)
<220> FEATURE:
<221> NAME/KEY: sig_peptide
<222> LOCATION: (1)..(57)
<220> FEATURE:
<221> NAME/KEY: mat_peptide
<222> LOCATION: (58)..(2103)
<220> FEATURE:
<221> NAME/KEY: CDS
<222> LOCATION: (373)..(749)
<220> FEATURE:
<221> NAME/KEY: CDS
<222> LOCATION: (892)..(1709)
<220> FEATURE:
<221> NAME/KEY: CDS
<222> LOCATION: (1771)..(2103)

<400> SEQUENCE: 52

```
atg aag tcg ccc atg ctc gcc ctc gcg gcc ctc gcg gcc ccc gct gcc      48
Met Lys Ser Pro Met Leu Ala Leu Ala Ala Leu Ala Ala Pro Ala Ala
                -15                 -10                 -5 gtc gcc gcc gtc gcc att gcc gag atc aac ggc gac cgc ttc ctc tcg      96
Val Ala Ala Val Ala Ile Ala Glu Ile Asn Gly Asp Arg Phe Leu Ser
        -1   1               5                  10
```

| | | | | | | | | | | | | | | | | |
|---|---|---|---|---|---|---|---|---|---|---|---|---|---|---|---|---|
| ccc | ttt | cag | gac | aag | gac | gtg | gcc | aac | gtg | acg | ggc | ctg | gtg | acg | gcc | 144 |
| Pro | Phe | Gln | Asp | Lys | Asp | Val | Ala | Asn | Val | Thr | Gly | Leu | Val | Thr | Ala | |
| | 15 | | | | 20 | | | | | 25 | | | | | | |

| | | | | | | | | | | | | | | | | |
|---|---|---|---|---|---|---|---|---|---|---|---|---|---|---|---|---|
| acc | tcc | aag | acg | ggc | atc | tac | ctg | cgc | agc | acc | gcc | ccg | gac | gac | agc | 192 |
| Thr | Ser | Lys | Thr | Gly | Ile | Tyr | Leu | Arg | Ser | Thr | Ala | Pro | Asp | Asp | Ser | |
| 30 | | | | | 35 | | | | | 40 | | | | | 45 | |

| | | | | | | | | | | | | | | | | |
|---|---|---|---|---|---|---|---|---|---|---|---|---|---|---|---|---|
| cca | gcc | acc | tcg | gag | ggg | ctg | ttt | gtg | ttt | agc | agc | tcc | ctc | gtc | aag | 240 |
| Pro | Ala | Thr | Ser | Glu | Gly | Leu | Phe | Val | Phe | Ser | Ser | Ser | Leu | Val | Lys | |
| | | | | 50 | | | | | 55 | | | | | 60 | | |

| | | | | | | | | | | | | | | | | |
|---|---|---|---|---|---|---|---|---|---|---|---|---|---|---|---|---|
| acg | gcc | aag | gtc | ggc | gac | gtg | gtg | acg | ctc | agc | ggg | ctc | gtc | aag | gag | 288 |
| Thr | Ala | Lys | Val | Gly | Asp | Val | Val | Thr | Leu | Ser | Gly | Leu | Val | Lys | Glu | |
| | | 65 | | | | | 70 | | | | | 75 | | | | |

| | | | | | |
|---|---|---|---|---|---|
| tac | ag | gtgcgtggcc | ctacacacgg | gcgggcattt | tgtctcttgg atcacacggc | 343 |
| Tyr | Arg | | | | | |

| | | | | | | | | |
|---|---|---|---|---|---|---|---|---|
| caggcacact | tcagctgaca | ctcatccag | g | tcc | aac | aag | gac | tac | atc | tac | ctc | 397 |
| | | | | Ser | Asn | Lys | Asp | Tyr | Ile | Tyr | Leu | |
| | | | | | | 80 | | | | 85 | | |

| | | | | | | | | | | | | | | | | |
|---|---|---|---|---|---|---|---|---|---|---|---|---|---|---|---|---|
| acc | gag | ctc | acc | aac | ccg | acc | aac | gtc | gtc | gtc | gtc | tcg | tcg | ggc | aac | 445 |
| Thr | Glu | Leu | Thr | Asn | Pro | Thr | Asn | Val | Val | Val | Val | Ser | Ser | Gly | Asn | |
| | | 90 | | | | | 95 | | | | | 100 | | | | |

| | | | | | | | | | | | | | | | | |
|---|---|---|---|---|---|---|---|---|---|---|---|---|---|---|---|---|
| gcc | gtc | gcg | ccg | ctc | gtc | gtc | ggc | aag | gac | acg | ctg | ccg | ccg | ccg | acg | 493 |
| Ala | Val | Ala | Pro | Leu | Val | Val | Gly | Lys | Asp | Thr | Leu | Pro | Pro | Pro | Thr | |
| 105 | | | | | 110 | | | | | 115 | | | | | | |

| | | | | | | | | | | | | | | | | |
|---|---|---|---|---|---|---|---|---|---|---|---|---|---|---|---|---|
| cgc | gac | ttc | tcg | agc | ctc | gac | gcg | ggc | ggc | gtc | ttt | ggc | gtc | ccc | aac | 541 |
| Arg | Asp | Phe | Ser | Ser | Leu | Asp | Ala | Gly | Gly | Val | Phe | Gly | Val | Pro | Asn | |
| 120 | | | | | 125 | | | | | 130 | | | | | 135 | |

| | | | | | | | | | | | | | | | | |
|---|---|---|---|---|---|---|---|---|---|---|---|---|---|---|---|---|
| gcc | gcg | ggc | acc | gtc | tcg | ggc | gcc | aac | ccc | aag | ctc | gac | ccg | acc | gcc | 589 |
| Ala | Ala | Gly | Thr | Val | Ser | Gly | Ala | Asn | Pro | Lys | Leu | Asp | Pro | Thr | Ala | |
| | | | | 140 | | | | | 145 | | | | | 150 | | |

| | | | | | | | | | | | | | | | | |
|---|---|---|---|---|---|---|---|---|---|---|---|---|---|---|---|---|
| tac | ggg | ctc | gac | ttt | tgg | gag | agc | ctc | gtc | ggc | gag | ctc | gtt | acc | gtg | 637 |
| Tyr | Gly | Leu | Asp | Phe | Trp | Glu | Ser | Leu | Val | Gly | Glu | Leu | Val | Thr | Val | |
| | | | | 155 | | | | | 160 | | | | | 165 | | |

| | | | | | | | | | | | | | | | | |
|---|---|---|---|---|---|---|---|---|---|---|---|---|---|---|---|---|
| aag | gat | gcc | tac | ctt | acc | agc | cgc | ccg | aac | cag | tac | ggc | gac | gtc | tgg | 685 |
| Lys | Asp | Ala | Tyr | Leu | Thr | Ser | Arg | Pro | Asn | Gln | Tyr | Gly | Asp | Val | Trp | |
| | | 170 | | | | | 175 | | | | | 180 | | | | |

| | | | | | | | | | | | | | | | | |
|---|---|---|---|---|---|---|---|---|---|---|---|---|---|---|---|---|
| gtg | cgc | ggc | gac | tgg | gcc | gtc | acg | ggc | gtc | aac | ggc | cac | ggc | ggc | gtc | 733 |
| Val | Arg | Gly | Asp | Trp | Ala | Val | Thr | Gly | Val | Asn | Gly | His | Gly | Gly | Val | |
| 185 | | | | | 190 | | | | | 195 | | | | | | |

| | | | | | | |
|---|---|---|---|---|---|---|
| aca | atg | ctc | gat | ggc | g | gtgagttttt ttgtcttgtc ggcctttgt tgcaggcttg | 789 |
| Thr | Met | Leu | Asp | Gly | | | |
| 200 | | | | | | | |

| | | |
|---|---|---|
| gctatccgag | ctgctgccgg | caaagcgagg aagcgcttga agtcgagcat tgaagccctc | 849 |

| | | | | | |
|---|---|---|---|---|---|
| tcggcccgag | catcaacagc | tgacgagccg | cccaacgcgc | ag ac | gcc aac cct | 902 |
| | | | | | Asp Ala Asn Pro | |
| | | | | | 205 | |

| | | | | | | | | | | | | | | | | |
|---|---|---|---|---|---|---|---|---|---|---|---|---|---|---|---|---|
| gag | acc | att | gtc | gtc | ggc | acg | ccg | ctc | gac | ggc | tcc | gcc | aac | ccg | acg | 950 |
| Glu | Thr | Ile | Val | Val | Gly | Thr | Pro | Leu | Asp | Gly | Ser | Ala | Asn | Pro | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | acc | aag | atg | ggc | gac | ttc | gtc | ggc | gac | gtg | acg | ggc | gtc | gtg | tcc | 998 |
| Asp | Thr | Lys | Met | Gly | Asp | Phe | Val | Gly | Asp | Val | Thr | Gly | Val | Val | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aac | gcg | ttt | ggc | ttc | tac | cgc | atc | ctg | ccg | ctg | acg | cgc | ctc | gtc | ccc | 1046 |
| Asn | Ala | Phe | Gly | Phe | Tyr | Arg | Ile | Leu | Pro | Leu | Thr | Arg | Leu | Val | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | cgc | aac | gcc | tcg | gcc | gag | ttc | ccc | gcc | acg | tcg | ctc | gcc | agc | cgc | 1094 |
| Gln | Arg | Asn | Ala | Ser | Ala | Glu | Phe | Pro | Ala | Thr | Ser | Leu | Ala | Ser | Arg | |
| | | | 260 | | | | | 265 | | | | | 270 | | | |

| | | | | | | | | | | | | | | | | |
|---|---|---|---|---|---|---|---|---|---|---|---|---|---|---|---|---|
| ggc | tcc | tgc | agg | ggc | atc | acc | gtc | gcc | gac | tac | aac | gcc | gag | aac | ctg | 1142 |
| Gly | Ser | Cys | Arg | Gly | Ile | Thr | Val | Ala | Asp | Tyr | Asn | Ala | Glu | Asn | Leu | |

```
            275                 280                 285
gcg ccg gac tcg gcg cac ctg ccc cgc gtc gtc gac cag atc gtc aac    1190
Ala Pro Asp Ser Ala His Leu Pro Arg Val Val Asp Gln Ile Val Asn
290                 295                 300 gag ctg cgc ctc ccg gac ctc gtc ttc ctg cag gag gtg cag gac aac    1238
Glu Leu Arg Leu Pro Asp Leu Val Phe Leu Gln Glu Val Gln Asp Asn
305                 310                 315                 320 tcg ggc gcc gcc aac gac ggc gtc gtc tcg gcc aac ctg acg ctc tcg    1286
Ser Gly Ala Ala Asn Asp Gly Val Val Ser Ala Asn Leu Thr Leu Ser
                325                 330                 335 acc ctc acc cgc ggc atc gag gcc gcc tcg ggc gtc gcc tac gcc ttt    1334
Thr Leu Thr Arg Gly Ile Glu Ala Ala Ser Gly Val Ala Tyr Ala Phe
            340                 345                 350 gca gag gtc gag ccc cag gac ggc aag gac ggc ggc cag ccc ggc ggc    1382
Ala Glu Val Glu Pro Gln Asp Gly Lys Asp Gly Gly Gln Pro Gly Gly
        355                 360                 365 aac atc cgc tgc gcc tac ctc tac cgc ccg gac gtc gtc gag ctg cac    1430
Asn Ile Arg Cys Ala Tyr Leu Tyr Arg Pro Asp Val Val Glu Leu His
370                 375                 380 gag ccg cgc cag ggc ggc agc ctc gac gcc aac gag gtg ctg ccc ggg    1478
Glu Pro Arg Gln Gly Gly Ser Leu Asp Ala Asn Glu Val Leu Pro Gly
385                 390                 395                 400 ccc gcc ctc aag ttc aac ccg ggc cgc atc cag ccc gcc aac gcc gcc    1526
Pro Ala Leu Lys Phe Asn Pro Gly Arg Ile Gln Pro Ala Asn Ala Ala
                405                 410                 415 ttt gac gac agc cgc aag ccc gtc gcc gcc gcc tgg cgc acc gtc aag    1574
Phe Asp Asp Ser Arg Lys Pro Val Ala Ala Ala Trp Arg Thr Val Lys
            420                 425                 430 ggc acc cac aag acc ttc ttc acc gtc aac gtg cac ttc ggc agc aag    1622
Gly Thr His Lys Thr Phe Phe Thr Val Asn Val His Phe Gly Ser Lys
        435                 440                 445 ggc ggg tcc acg acg ctg cac ggc gac gcc cgc ccg ccc gtc aac aag    1670
Gly Gly Ser Thr Thr Leu His Gly Asp Ala Arg Pro Pro Val Asn Lys
    450                 455                 460 ggc gtc gag aag cgc acc gag cag gcg acc att acc gcg gtgagaacac    1719
Gly Val Glu Lys Arg Thr Glu Gln Ala Thr Ile Thr Ala
465                 470                 475 ccacttggct gactctgtct ggcagccgac cacgcagcta acacggcgca g gac ttc    1776
                                                        Asp Phe atc gcc gcc atc ctc aag cag gac ccg cgc gcc cgg gtc atc gcc gcc    1824
Ile Ala Ala Ile Leu Lys Gln Asp Pro Arg Ala Arg Val Ile Ala Ala
480                 485                 490                 495 ggc gac ttc aac gag ttc acg cag gtg cag ccc atg cgc gtc ttc gcc    1872
Gly Asp Phe Asn Glu Phe Thr Gln Val Gln Pro Met Arg Val Phe Ala
                500                 505                 510 gag cgc tcc ggg ctg cgc gac ctc gac gag ctg gcc ggc ctg gcc ccc    1920
Glu Arg Ser Gly Leu Arg Asp Leu Asp Glu Leu Ala Gly Leu Ala Pro
            515                 520                 525 gag gag cgc tac acc tac ctc ttt gac atg aac agc cag gcc ctc gac    1968
Glu Glu Arg Tyr Thr Tyr Leu Phe Asp Met Asn Ser Gln Ala Leu Asp
        530                 535                 540 cac atg tac gtg agc ccc gcg ctc ggc cgc ggc gcc cgc gtc gag cac    2016
His Met Tyr Val Ser Pro Ala Leu Gly Arg Gly Ala Arg Val Glu His
    545                 550                 555 ctg cac gtc aac act tgg cag aac ttc aag ggg cag acg agc gac cac    2064
Leu His Val Asn Thr Trp Gln Asn Phe Lys Gly Gln Thr Ser Asp His
560                 565                 570                 575 gac ccg agc gtg gcg ctg ctg aat gtg tgc ggc tgt gcg tag            2106
Asp Pro Ser Val Ala Leu Leu Asn Val Cys Gly Cys Ala
```

<210> SEQ ID NO 53
<211> LENGTH: 607
<212> TYPE: PRT
<213> ORGANISM: Purpureocillium lilacinum

<400> SEQUENCE: 53

```
Met Lys Ser Pro Met Leu Ala Leu Ala Ala Leu Ala Ala Pro Ala Ala
                -15                 -10                  -5
Val Ala Val Ala Ile Ala Glu Ile Asn Gly Asp Arg Phe Leu Ser
     -1   1               5                  10
Pro Phe Gln Asp Lys Asp Val Ala Asn Val Thr Gly Leu Val Thr Ala
         15                  20                  25
Thr Ser Lys Thr Gly Ile Tyr Leu Arg Ser Thr Ala Pro Asp Asp Ser
 30                  35                  40                  45
Pro Ala Thr Ser Glu Gly Leu Phe Val Phe Ser Ser Leu Val Lys
                 50                  55                  60
Thr Ala Lys Val Gly Asp Val Val Thr Leu Ser Gly Leu Val Lys Glu
                 65                  70                  75
Tyr Arg Ser Asn Lys Asp Tyr Ile Tyr Leu Thr Glu Leu Thr Asn Pro
         80                  85                  90
Thr Asn Val Val Val Ser Ser Gly Asn Ala Val Ala Pro Leu Val
 95                 100                 105
Val Gly Lys Asp Thr Leu Pro Pro Thr Arg Asp Phe Ser Ser Leu
110             115                 120                 125
Asp Ala Gly Gly Val Phe Gly Val Pro Asn Ala Ala Gly Thr Val Ser
                130                 135                 140
Gly Ala Asn Pro Lys Leu Asp Pro Thr Ala Tyr Gly Leu Asp Phe Trp
            145                 150                 155
Glu Ser Leu Val Gly Glu Leu Val Thr Val Lys Asp Ala Tyr Leu Thr
        160                 165                 170
Ser Arg Pro Asn Gln Tyr Gly Asp Val Trp Val Arg Gly Asp Trp Ala
    175                 180                 185
Val Thr Gly Val Asn Gly His Gly Gly Val Thr Met Leu Asp Gly Asp
190                 195                 200                 205
Ala Asn Pro Glu Thr Ile Val Val Gly Thr Pro Leu Asp Gly Ser Ala
                210                 215                 220
Asn Pro Thr Asp Thr Lys Met Gly Asp Phe Val Gly Asp Val Thr Gly
            225                 230                 235
Val Val Ser Asn Ala Phe Gly Phe Tyr Arg Ile Leu Pro Leu Thr Arg
        240                 245                 250
Leu Val Pro Gln Arg Asn Ala Ser Ala Glu Phe Pro Ala Thr Ser Leu
    255                 260                 265
Ala Ser Arg Gly Ser Cys Arg Gly Ile Thr Val Ala Asp Tyr Asn Ala
270                 275                 280                 285
Glu Asn Leu Ala Pro Asp Ser Ala His Leu Pro Arg Val Val Asp Gln
                290                 295                 300
Ile Val Asn Glu Leu Arg Leu Pro Asp Leu Val Phe Leu Gln Glu Val
            305                 310                 315
Gln Asp Asn Ser Gly Ala Ala Asn Asp Gly Val Val Ser Ala Asn Leu
        320                 325                 330
Thr Leu Ser Thr Leu Thr Arg Gly Ile Glu Ala Ala Ser Gly Val Ala
    335                 340                 345
```

```
Tyr Ala Phe Ala Glu Val Glu Pro Gln Asp Gly Lys Asp Gly Gly Gln
350                 355                 360                 365

Pro Gly Gly Asn Ile Arg Cys Ala Tyr Leu Tyr Arg Pro Asp Val Val
            370                 375                 380

Glu Leu His Glu Pro Arg Gln Gly Gly Ser Leu Asp Ala Asn Glu Val
        385                 390                 395

Leu Pro Gly Pro Ala Leu Lys Phe Asn Pro Gly Arg Ile Gln Pro Ala
    400                 405                 410

Asn Ala Ala Phe Asp Asp Ser Arg Lys Pro Val Ala Ala Trp Arg
415                 420                 425

Thr Val Lys Gly Thr His Lys Thr Phe Phe Thr Val Asn Val His Phe
430                 435                 440                 445

Gly Ser Lys Gly Gly Ser Thr Thr Leu His Gly Asp Ala Arg Pro Pro
            450                 455                 460

Val Asn Lys Gly Val Glu Lys Arg Thr Glu Gln Ala Thr Ile Thr Ala
        465                 470                 475

Asp Phe Ile Ala Ala Ile Leu Lys Gln Asp Pro Arg Ala Arg Val Ile
    480                 485                 490

Ala Ala Gly Asp Phe Asn Glu Phe Thr Gln Val Gln Pro Met Arg Val
495                 500                 505

Phe Ala Glu Arg Ser Gly Leu Arg Asp Leu Asp Glu Leu Ala Gly Leu
510                 515                 520                 525

Ala Pro Glu Glu Arg Tyr Thr Tyr Leu Phe Asp Met Asn Ser Gln Ala
            530                 535                 540

Leu Asp His Met Tyr Val Ser Pro Ala Leu Gly Arg Gly Ala Arg Val
        545                 550                 555

Glu His Leu His Val Asn Thr Trp Gln Asn Phe Lys Gly Gln Thr Ser
    560                 565                 570

Asp His Asp Pro Ser Val Ala Leu Leu Asn Val Cys Gly Cys Ala
575                 580                 585

<210> SEQ ID NO 54
<211> LENGTH: 588
<212> TYPE: PRT
<213> ORGANISM: Purpureocillium lilacinum

<400> SEQUENCE: 54

Val Ala Ile Ala Glu Ile Asn Gly Asp Arg Phe Leu Ser Pro Phe Gln
1               5                   10                  15

Asp Lys Asp Val Ala Asn Val Thr Gly Leu Val Thr Ala Thr Ser Lys
            20                  25                  30

Thr Gly Ile Tyr Leu Arg Ser Thr Ala Pro Asp Asp Ser Pro Ala Thr
        35                  40                  45

Ser Glu Gly Leu Phe Val Phe Ser Ser Ser Leu Val Lys Thr Ala Lys
    50                  55                  60

Val Gly Asp Val Val Thr Leu Ser Gly Leu Val Lys Glu Tyr Arg Ser
65                  70                  75                  80

Asn Lys Asp Tyr Ile Tyr Leu Thr Glu Leu Thr Asn Pro Thr Asn Val
                85                  90                  95

Val Val Val Ser Ser Gly Asn Ala Val Ala Pro Leu Val Gly Lys
            100                 105                 110

Asp Thr Leu Pro Pro Pro Thr Arg Asp Phe Ser Ser Leu Asp Ala Gly
        115                 120                 125

Gly Val Phe Gly Val Pro Asn Ala Ala Gly Thr Val Ser Gly Ala Asn
    130                 135                 140
```

```
Pro Lys Leu Asp Pro Thr Ala Tyr Gly Leu Asp Phe Trp Glu Ser Leu
145                 150                 155                 160

Val Gly Glu Leu Val Thr Val Lys Asp Ala Tyr Leu Thr Ser Arg Pro
            165                 170                 175

Asn Gln Tyr Gly Asp Val Trp Val Arg Gly Asp Trp Ala Val Thr Gly
            180                 185                 190

Val Asn Gly His Gly Val Thr Met Leu Asp Gly Asp Ala Asn Pro
        195                 200                 205

Glu Thr Ile Val Val Gly Thr Pro Leu Asp Gly Ser Ala Asn Pro Thr
    210                 215                 220

Asp Thr Lys Met Gly Asp Phe Val Gly Asp Val Thr Gly Val Val Ser
225                 230                 235                 240

Asn Ala Phe Gly Phe Tyr Arg Ile Leu Pro Leu Thr Arg Leu Val Pro
                245                 250                 255

Gln Arg Asn Ala Ser Ala Glu Phe Pro Ala Thr Ser Leu Ala Ser Arg
            260                 265                 270

Gly Ser Cys Arg Gly Ile Thr Val Ala Asp Tyr Asn Ala Glu Asn Leu
        275                 280                 285

Ala Pro Asp Ser Ala His Leu Pro Arg Val Val Asp Gln Ile Val Asn
    290                 295                 300

Glu Leu Arg Leu Pro Asp Leu Val Phe Leu Gln Glu Val Gln Asp Asn
305                 310                 315                 320

Ser Gly Ala Ala Asn Asp Gly Val Val Ser Ala Asn Leu Thr Leu Ser
                325                 330                 335

Thr Leu Thr Arg Gly Ile Glu Ala Ala Ser Gly Val Ala Tyr Ala Phe
            340                 345                 350

Ala Glu Val Glu Pro Gln Asp Gly Lys Asp Gly Gly Gln Pro Gly Gly
            355                 360                 365

Asn Ile Arg Cys Ala Tyr Leu Tyr Arg Pro Asp Val Val Glu Leu His
370                 375                 380

Glu Pro Arg Gln Gly Gly Ser Leu Asp Ala Asn Glu Val Leu Pro Gly
385                 390                 395                 400

Pro Ala Leu Lys Phe Asn Pro Gly Arg Ile Gln Pro Ala Asn Ala Ala
                405                 410                 415

Phe Asp Asp Ser Arg Lys Pro Val Ala Ala Trp Arg Thr Val Lys
            420                 425                 430

Gly Thr His Lys Thr Phe Phe Thr Val Asn Val His Phe Gly Ser Lys
            435                 440                 445

Gly Gly Ser Thr Thr Leu His Gly Asp Ala Arg Pro Pro Val Asn Lys
        450                 455                 460

Gly Val Glu Lys Arg Thr Glu Gln Ala Thr Ile Thr Ala Asp Phe Ile
465                 470                 475                 480

Ala Ala Ile Leu Lys Gln Asp Pro Arg Ala Arg Val Ile Ala Ala Gly
                485                 490                 495

Asp Phe Asn Glu Phe Thr Gln Val Gln Pro Met Arg Val Phe Ala Glu
            500                 505                 510

Arg Ser Gly Leu Arg Asp Leu Asp Glu Leu Ala Gly Leu Ala Pro Glu
            515                 520                 525

Glu Arg Tyr Thr Tyr Leu Phe Asp Met Asn Ser Gln Ala Leu Asp His
            530                 535                 540

Met Tyr Val Ser Pro Ala Leu Gly Arg Gly Ala Arg Val Glu His Leu
545                 550                 555                 560
```

```
His Val Asn Thr Trp Gln Asn Phe Lys Gly Gln Thr Ser Asp His Asp
            565                 570                 575
Pro Ser Val Ala Leu Leu Asn Val Cys Gly Cys Ala
        580                 585

<210> SEQ ID NO 55
<211> LENGTH: 2045
<212> TYPE: DNA
<213> ORGANISM: Warcupiella spinulosa
<220> FEATURE:
<221> NAME/KEY: CDS
<222> LOCATION: (1)..(673)
<220> FEATURE:
<221> NAME/KEY: sig_peptide
<222> LOCATION: (1)..(57)
<220> FEATURE:
<221> NAME/KEY: mat_peptide
<222> LOCATION: (58)..(2042)
<220> FEATURE:
<221> NAME/KEY: CDS
<222> LOCATION: (747)..(1115)
<220> FEATURE:
<221> NAME/KEY: CDS
<222> LOCATION: (1180)..(1625)
<220> FEATURE:
<221> NAME/KEY: CDS
<222> LOCATION: (1716)..(2042)

<400> SEQUENCE: 55 atg agg ctc ccc tct cgc ctc tgc gct gcg gcg ctc ctt gtc ccc tcc     48
Met Arg Leu Pro Ser Arg Leu Cys Ala Ala Ala Leu Leu Val Pro Ser
            -15                 -10                 -5 gcc ctg gcc atc acc atc gcc gag atc aac agc aac aag tac ctc tct     96
Ala Leu Ala Ile Thr Ile Ala Glu Ile Asn Ser Asn Lys Tyr Leu Ser
        -1   1               5                  10 cca tac aag ggc caa acc atc tcc ggt atc gag ggt ctc gtc act gcc    144
Pro Tyr Lys Gly Gln Thr Ile Ser Gly Ile Glu Gly Leu Val Thr Ala
         15                  20                  25 aag ggt tct gca ggt ttc tac ctc cgc tct acc acc ccc gat gat gac    192
Lys Gly Ser Ala Gly Phe Tyr Leu Arg Ser Thr Thr Pro Asp Asp Asp
 30                  35                  40                  45 gat gcc act tcc gag tcg att tac gtc tac ggc agc agt gcc gtc tcc    240
Asp Ala Thr Ser Glu Ser Ile Tyr Val Tyr Gly Ser Ser Ala Val Ser
                 50                  55                  60 aaa gtc gcc gtc ggc gat atc atc acg ttg acc ggg aaa gtg gca gag    288
Lys Val Ala Val Gly Asp Ile Ile Thr Leu Thr Gly Lys Val Ala Glu
             65                  70                  75 tat cgt tcg tct tct tcg tcg tat gtc tac ctg acc gag ttg acc tcc    336
Tyr Arg Ser Ser Ser Ser Ser Tyr Val Tyr Leu Thr Glu Leu Thr Ser
         80                  85                  90 ccc tcc aac att gtc gtc tcc tcc agc gga aac acc gtc act ccc gta    384
Pro Ser Asn Ile Val Val Ser Ser Ser Gly Asn Thr Val Thr Pro Val
 95                 100                 105 gtc att ggc cag cgc ggc ttg att cct ccc act gag cag ttc tct gcg    432
Val Ile Gly Gln Arg Gly Leu Ile Pro Pro Thr Glu Gln Phe Ser Ala
110                 115                 120                 125 ctg gat ggc ggg gat gtt ttc ggc gtt ccg aac aat gac agc cag att    480
Leu Asp Gly Gly Asp Val Phe Gly Val Pro Asn Asn Asp Ser Gln Ile
                130                 135                 140 tct ctt gta aac cct acc ctt aaa ccg gaa aag tac ggt atg gac ttt    528
Ser Leu Val Asn Pro Thr Leu Lys Pro Glu Lys Tyr Gly Met Asp Phe
            145                 150                 155 tgg gag agt ctg agc gga gag ctg gcc act gtc aaa ggt gtc aga gca    576
Trp Glu Ser Leu Ser Gly Glu Leu Ala Thr Val Lys Gly Val Arg Ala
        160                 165                 170
```

```
gtg agc aag ccc aac cga tat ggc gat act tgg gtg gtt ggc gat tgg        624
Val Ser Lys Pro Asn Arg Tyr Gly Asp Thr Trp Val Val Gly Asp Trp
    175                 180                 185 aag agt acg ggg atg aat gag agg ggt gga ttg acc atg act gat aag g      673
Lys Ser Thr Gly Met Asn Glu Arg Gly Gly Leu Thr Met Thr Asp Lys
190                 195                 200                 205 gtgcgttctc cgattttttgt cagaatacac ttatgaagtg tctccaaagg cagcaagcta     733
aagagaaaat cag ac  ggc aac cct gaa gcc att gtt att ggt tct ccc         781
                Asp Gly Asn Pro Glu Ala Ile Val Ile Gly Ser Pro
                    210                 215 ctc gat gga agc agc aat ccc gac aac acc aag ctc ggc gac tat ctc        829
Leu Asp Gly Ser Ser Asn Pro Asp Asn Thr Lys Leu Gly Asp Tyr Leu
    220                 225                 230 gac gac att acc ggt gtc atc acc cag gct tac ggc tac tat gcc ctg        877
Asp Asp Ile Thr Gly Val Ile Thr Gln Ala Tyr Gly Tyr Tyr Ala Leu
235                 240                 245 ctc cct ttg acc gcg ttg acc gtg cgg gag agc aac tcg aca aat gca        925
Leu Pro Leu Thr Ala Leu Thr Val Arg Glu Ser Asn Ser Thr Asn Ala
250                 255                 260                 265 acg gcc acc cgg ttg gcg gcc gat gga aac tgc agt gct atc act gtc        973
Thr Ala Thr Arg Leu Ala Ala Asp Gly Asn Cys Ser Ala Ile Thr Val
        270                 275                 280 gga gac tac aac gtg aac aac ctc tcg cct agc tcg acc acg ttg agt        1021
Gly Asp Tyr Asn Val Asn Asn Leu Ser Pro Ser Ser Thr Thr Leu Ser
            285                 290                 295 cac att gcc aac cac atc gcc aac tac ctc aag agc ccc aca gtg atg        1069
His Ile Ala Asn His Ile Ala Asn Tyr Leu Lys Ser Pro Thr Val Met
                300                 305                 310 ttc gtg cag gag atc cag gat gac aat ggc gct acc aac gat gga g          1115
Phe Val Gln Glu Ile Gln Asp Asp Asn Gly Ala Thr Asn Asp Gly
    315                 320                 325 gtacagttct agccatatcc tgtaccctcc cgcacgataa ccatactaaa taggatcact       1175 acag tc  gtc tcc gca aac ctc act ctc tcg acg cta gtc cgc gag atc       1223
     Val Val Ser Ala Asn Leu Thr Leu Ser Thr Leu Val Arg Glu Ile
         330                 335                 340 aaa tct gcc ggc ggc atc gcc tac tct ttc gtc gac atc gac ccc atc        1271
Lys Ser Ala Gly Gly Ile Ala Tyr Ser Phe Val Asp Ile Asp Pro Ile
    345                 350                 355 gac gac cag gac ggc ggc cag ccc ggc ggc aac atc cgc aac gcc tac        1319
Asp Asp Gln Asp Gly Gly Gln Pro Gly Gly Asn Ile Arg Asn Ala Tyr
360                 365                 370                 375 ctg tac gac tcc tcg atc gtc cgc ctc cgc aac ctc aac ccg ggc tcc        1367
Leu Tyr Asp Ser Ser Ile Val Arg Leu Arg Asn Leu Asn Pro Gly Ser
                380                 385                 390 agc tcc caa gcc cag gat gtc ttc ccg ggc gct gag cta aag tac aac        1415
Ser Ser Gln Ala Gln Asp Val Phe Pro Gly Ala Glu Leu Lys Tyr Asn
            395                 400                 405 ccc ggg ctg atc gac ccg acc cac ccg gcc tgg gac tcc agc cgc aag        1463
Pro Gly Leu Ile Asp Pro Thr His Pro Ala Trp Asp Ser Ser Arg Lys
        410                 415                 420 ccc atc tcc gca gtc tgg gag acg ctc gac ggc aag aac aag ttc ttc        1511
Pro Ile Ser Ala Val Trp Glu Thr Leu Asp Gly Lys Asn Lys Phe Phe
425                 430                 435 acc gtc aac gtg cac ttc acg agc aag ggc ggc ggc agc tcg att gag        1559
Thr Val Asn Val His Phe Thr Ser Lys Gly Gly Gly Ser Ser Ile Glu
440                 445                 450                 455 ggg gac ctc cgg ccg cct gcg aac ggg ggg att gag aag cgt acc gag        1607
Gly Asp Leu Arg Pro Pro Ala Asn Gly Gly Ile Glu Lys Arg Thr Glu
```

-continued

```
                460                 465                 470
cag gcg agc att gtt gct gtatgtattc ctctcctcca ttccttcttt              1655
Gln Ala Ser Ile Val Ala
            475 ccccgcccac tttgtctgag ttgcaaatct gatattgaca cgatacgacc tgtcaaatag    1715 aac ttc acc agc acc ctc ctc aac act gac ccc tcc gcc aag atc atc     1763
Asn Phe Thr Ser Thr Leu Leu Asn Thr Asp Pro Ser Ala Lys Ile Ile
            480                 485                 490 gtg tct ggc gac ttc aac gag ttc acc ttc gtg cag ccc tta gag gtc     1811
Val Ser Gly Asp Phe Asn Glu Phe Thr Phe Val Gln Pro Leu Glu Val
        495                 500                 505 ttt gcc gca gag tcc gga ctt acg gat ctc gat gat gtg gtg ggt acc     1859
Phe Ala Ala Glu Ser Gly Leu Thr Asp Leu Asp Asp Val Val Gly Thr
510                 515                 520                 525 aaa ggc gag gag cgc tat acg tat atc tac gac atg aac tgc cag gcg     1907
Lys Gly Glu Glu Arg Tyr Thr Tyr Ile Tyr Asp Met Asn Cys Gln Ala
                530                 535                 540 ctg gat cat atg ttt gtc agt ggg ggg ttg aag att ggt gcg caa ttt     1955
Leu Asp His Met Phe Val Ser Gly Gly Leu Lys Ile Gly Ala Gln Phe
            545                 550                 555 gag cat gtg cat ctg aat acg tgg gta tcg tat gat gag cag gcg tcg     2003
Glu His Val His Leu Asn Thr Trp Val Ser Tyr Asp Glu Gln Ala Ser
        560                 565                 570 gat cat gat cct agt gtt gcg agg ttt gat gtg tgc gag tga             2045
Asp His Asp Pro Ser Val Ala Arg Phe Asp Val Cys Glu
    575                 580                 585

<210> SEQ ID NO 56
<211> LENGTH: 605
<212> TYPE: PRT
<213> ORGANISM: Warcupiella spinulosa

<400> SEQUENCE: 56

Met Arg Leu Pro Ser Arg Leu Cys Ala Ala Ala Leu Leu Val Pro Ser
                -15                 -10                 -5

Ala Leu Ala Ile Thr Ile Ala Glu Ile Asn Ser Asn Lys Tyr Leu Ser
         -1  1              5                  10

Pro Tyr Lys Gly Gln Thr Ile Ser Gly Ile Glu Gly Leu Val Thr Ala
            15                  20                  25

Lys Gly Ser Ala Gly Phe Tyr Leu Arg Ser Thr Thr Pro Asp Asp Asp
30                  35                  40                  45

Asp Ala Thr Ser Glu Ser Ile Tyr Val Tyr Gly Ser Ser Ala Val Ser
                50                  55                  60

Lys Val Ala Val Gly Asp Ile Ile Thr Leu Thr Gly Lys Val Ala Glu
            65                  70                  75

Tyr Arg Ser Ser Ser Ser Tyr Val Tyr Leu Thr Glu Leu Thr Ser
                80                  85                  90

Pro Ser Asn Ile Val Val Ser Ser Gly Asn Thr Val Thr Pro Val
            95                  100                 105

Val Ile Gly Gln Arg Gly Leu Ile Pro Pro Thr Glu Gln Phe Ser Ala
110                 115                 120                 125

Leu Asp Gly Gly Asp Val Phe Gly Val Pro Asn Asn Asp Ser Gln Ile
                130                 135                 140

Ser Leu Val Asn Pro Thr Leu Lys Pro Glu Lys Tyr Gly Met Asp Phe
            145                 150                 155

Trp Glu Ser Leu Ser Gly Glu Leu Ala Thr Val Lys Gly Val Arg Ala
                160                 165                 170
```

```
Val Ser Lys Pro Asn Arg Tyr Gly Asp Thr Trp Val Gly Asp Trp
    175                 180                 185

Lys Ser Thr Gly Met Asn Glu Arg Gly Gly Leu Thr Met Thr Asp Lys
190                 195                 200                 205

Asp Gly Asn Pro Glu Ala Ile Val Ile Gly Ser Pro Leu Asp Gly Ser
                210                 215                 220

Ser Asn Pro Asp Asn Thr Lys Leu Gly Asp Tyr Leu Asp Asp Ile Thr
            225                 230                 235

Gly Val Ile Thr Gln Ala Tyr Gly Tyr Tyr Ala Leu Leu Pro Leu Thr
        240                 245                 250

Ala Leu Thr Val Arg Glu Ser Asn Ser Thr Asn Ala Thr Ala Thr Arg
255                 260                 265

Leu Ala Ala Asp Gly Asn Cys Ser Ala Ile Thr Val Gly Asp Tyr Asn
270                 275                 280                 285

Val Asn Asn Leu Ser Pro Ser Thr Thr Leu Ser His Ile Ala Asn
                290                 295                 300

His Ile Ala Asn Tyr Leu Lys Ser Pro Thr Val Met Phe Val Gln Glu
            305                 310                 315

Ile Gln Asp Asp Asn Gly Ala Thr Asn Asp Gly Val Val Ser Ala Asn
        320                 325                 330

Leu Thr Leu Ser Thr Leu Val Arg Glu Ile Lys Ser Ala Gly Gly Ile
335                 340                 345

Ala Tyr Ser Phe Val Asp Ile Asp Pro Ile Asp Asp Gln Asp Gly Gly
350                 355                 360                 365

Gln Pro Gly Gly Asn Ile Arg Asn Ala Tyr Leu Tyr Asp Ser Ser Ile
                370                 375                 380

Val Arg Leu Arg Asn Leu Asn Pro Gly Ser Ser Ser Gln Ala Gln Asp
            385                 390                 395

Val Phe Pro Gly Ala Glu Leu Lys Tyr Asn Pro Gly Leu Ile Asp Pro
        400                 405                 410

Thr His Pro Ala Trp Asp Ser Ser Arg Lys Pro Ile Ser Ala Val Trp
    415                 420                 425

Glu Thr Leu Asp Gly Lys Asn Lys Phe Thr Val Asn Val His Phe
430                 435                 440                 445

Thr Ser Lys Gly Gly Gly Ser Ser Ile Glu Gly Asp Leu Arg Pro Pro
                450                 455                 460

Ala Asn Gly Gly Ile Glu Lys Arg Thr Glu Gln Ala Ser Ile Val Ala
            465                 470                 475

Asn Phe Thr Ser Thr Leu Leu Asn Thr Asp Pro Ser Ala Lys Ile Ile
        480                 485                 490

Val Ser Gly Asp Phe Asn Glu Phe Thr Phe Val Gln Pro Leu Glu Val
    495                 500                 505

Phe Ala Ala Glu Ser Gly Leu Thr Asp Leu Asp Val Val Gly Thr
510                 515                 520                 525

Lys Gly Glu Glu Arg Tyr Thr Tyr Ile Tyr Asp Met Asn Cys Gln Ala
                530                 535                 540

Leu Asp His Met Phe Val Ser Gly Gly Leu Lys Ile Gly Ala Gln Phe
            545                 550                 555

Glu His Val His Leu Asn Thr Trp Val Ser Tyr Asp Glu Gln Ala Ser
        560                 565                 570

Asp His Asp Pro Ser Val Ala Arg Phe Asp Val Cys Glu
    575                 580                 585
```

<210> SEQ ID NO 57
<211> LENGTH: 586
<212> TYPE: PRT
<213> ORGANISM: Warcupiella spinulosa

<400> SEQUENCE: 57

```
Ile Thr Ile Ala Glu Ile Asn Ser Asn Lys Tyr Leu Ser Pro Tyr Lys
1               5                   10                  15

Gly Gln Thr Ile Ser Gly Ile Glu Gly Leu Val Thr Ala Lys Gly Ser
            20                  25                  30

Ala Gly Phe Tyr Leu Arg Ser Thr Pro Asp Asp Asp Ala Thr
        35                  40                  45

Ser Glu Ser Ile Tyr Val Tyr Gly Ser Ser Ala Val Ser Lys Val Ala
50                  55                  60

Val Gly Asp Ile Ile Thr Leu Thr Gly Lys Val Ala Glu Tyr Arg Ser
65                  70                  75                  80

Ser Ser Ser Ser Tyr Val Tyr Leu Thr Glu Leu Thr Ser Pro Ser Asn
                85                  90                  95

Ile Val Val Ser Ser Ser Gly Asn Thr Val Thr Pro Val Val Ile Gly
            100                 105                 110

Gln Arg Gly Leu Ile Pro Pro Thr Glu Gln Phe Ser Ala Leu Asp Gly
        115                 120                 125

Gly Asp Val Phe Gly Val Pro Asn Asn Asp Ser Gln Ile Ser Leu Val
    130                 135                 140

Asn Pro Thr Leu Lys Pro Glu Lys Tyr Gly Met Asp Phe Trp Glu Ser
145                 150                 155                 160

Leu Ser Gly Glu Leu Ala Thr Val Lys Gly Val Arg Ala Val Ser Lys
                165                 170                 175

Pro Asn Arg Tyr Gly Asp Thr Trp Val Val Gly Asp Trp Lys Ser Thr
            180                 185                 190

Gly Met Asn Glu Arg Gly Gly Leu Thr Met Thr Asp Lys Asp Gly Asn
        195                 200                 205

Pro Glu Ala Ile Val Ile Gly Ser Pro Leu Asp Gly Ser Ser Asn Pro
    210                 215                 220

Asp Asn Thr Lys Leu Gly Asp Tyr Leu Asp Ile Thr Gly Val Ile
225                 230                 235                 240

Thr Gln Ala Tyr Gly Tyr Tyr Ala Leu Leu Pro Leu Thr Ala Leu Thr
                245                 250                 255

Val Arg Glu Ser Asn Ser Thr Asn Ala Thr Ala Thr Arg Leu Ala Ala
            260                 265                 270

Asp Gly Asn Cys Ser Ala Ile Thr Val Gly Asp Tyr Asn Val Asn Asn
        275                 280                 285

Leu Ser Pro Ser Ser Thr Thr Leu Ser His Ile Ala Asn His Ile Ala
    290                 295                 300

Asn Tyr Leu Lys Ser Pro Thr Val Met Phe Val Gln Glu Ile Gln Asp
305                 310                 315                 320

Asp Asn Gly Ala Thr Asn Asp Gly Val Val Ser Ala Asn Leu Thr Leu
                325                 330                 335

Ser Thr Leu Val Arg Glu Ile Lys Ser Ala Gly Gly Ile Ala Tyr Ser
            340                 345                 350

Phe Val Asp Ile Asp Pro Ile Asp Asp Gln Asp Gly Gly Gln Pro Gly
        355                 360                 365

Gly Asn Ile Arg Asn Ala Tyr Leu Tyr Asp Ser Ser Ile Val Arg Leu
    370                 375                 380
```

```
Arg Asn Leu Asn Pro Gly Ser Ser Gln Ala Gln Asp Val Phe Pro
385                 390                 395                 400

Gly Ala Glu Leu Lys Tyr Asn Pro Gly Leu Ile Asp Pro Thr His Pro
            405                 410                 415

Ala Trp Asp Ser Ser Arg Lys Pro Ile Ser Ala Val Trp Glu Thr Leu
        420                 425                 430

Asp Gly Lys Asn Lys Phe Phe Thr Val Asn Val His Phe Thr Ser Lys
            435                 440                 445

Gly Gly Gly Ser Ser Ile Glu Gly Asp Leu Arg Pro Pro Ala Asn Gly
        450                 455                 460

Gly Ile Glu Lys Arg Thr Glu Gln Ala Ser Ile Val Ala Asn Phe Thr
465                 470                 475                 480

Ser Thr Leu Leu Asn Thr Asp Pro Ser Ala Lys Ile Ile Val Ser Gly
            485                 490                 495

Asp Phe Asn Glu Phe Thr Phe Val Gln Pro Leu Glu Val Phe Ala Ala
            500                 505                 510

Glu Ser Gly Leu Thr Asp Leu Asp Asp Val Val Gly Thr Lys Gly Glu
        515                 520                 525

Glu Arg Tyr Thr Tyr Ile Tyr Asp Met Asn Cys Gln Ala Leu Asp His
        530                 535                 540

Met Phe Val Ser Gly Gly Leu Lys Ile Gly Ala Gln Phe Glu His Val
545                 550                 555                 560

His Leu Asn Thr Trp Val Ser Tyr Asp Glu Gln Ala Ser Asp His Asp
            565                 570                 575

Pro Ser Val Ala Arg Phe Asp Val Cys Glu
            580                 585

<210> SEQ ID NO 58
<211> LENGTH: 1894
<212> TYPE: DNA
<213> ORGANISM: Stenocarpella maydis
<220> FEATURE:
<221> NAME/KEY: CDS
<222> LOCATION: (1)..(1497)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1891)
<220> FEATURE:
<221> NAME/KEY: CDS
<222> LOCATION: (1562)..(1891)

<400> SEQUENCE: 58 atg aag ggc ctc ctc tgc agc gtc gtc ggc gcc ttg ctc act cgc tct    48
Met Lys Gly Leu Leu Cys Ser Val Val Gly Ala Leu Leu Thr Arg Ser
            -15                 -10                 -5 gct gca gcg ctg agc atc tcg cag atc aat ggc aac agg ttc ctg tcg    96
Ala Ala Ala Leu Ser Ile Ser Gln Ile Asn Gly Asn Arg Phe Leu Ser
        -1  1               5                   10 cca tac gac ggc cag acg ctg acc aac atc agc ggg ctg gtc act gcc   144
Pro Tyr Asp Gly Gln Thr Leu Thr Asn Ile Ser Gly Leu Val Thr Ala
    15                  20                  25 aaa ggt ccc act ggc gtc ttt gtc cga tcc acg gcc ccg gac aac gac   192
Lys Gly Pro Thr Gly Val Phe Val Arg Ser Thr Ala Pro Asp Asn Asp
30                  35                  40                  45 acg gcc acc tca gac tcg gcc ttc atc tac agc agc agc gtc ggc agc   240
Thr Ala Thr Ser Asp Ser Ala Phe Ile Tyr Ser Ser Ser Val Gly Ser
            50                  55                  60
```

-continued

```
tcg ctc aat gtc ggg gac atc gtc act ttc agc gcc aag gtg gcc gag      288
Ser Leu Asn Val Gly Asp Ile Val Thr Phe Ser Ala Lys Val Ala Glu
        65                  70                  75 ttc agg tcc agg ggc tct acg tac ctg tac ctg acc gag ctc acc tcg      336
Phe Arg Ser Arg Gly Ser Thr Tyr Leu Tyr Leu Thr Glu Leu Thr Ser
    80                  85                  90 cca gca gac gtc gtt gtc gtc tcc cgc aat aac acc gtc gct ccc ctg      384
Pro Ala Asp Val Val Val Val Ser Arg Asn Asn Thr Val Ala Pro Leu
95                  100                 105 gtg gtt ggc gag gac acg ccg tac cca ccg acc gag aag ttc tcc agc      432
Val Val Gly Glu Asp Thr Pro Tyr Pro Pro Thr Glu Lys Phe Ser Ser
110                 115                 120                 125 ctc gac ggt ggc gac gtc tac cgc atc ccc aac gcc gtt gca aac atc      480
Leu Asp Gly Gly Asp Val Tyr Arg Ile Pro Asn Ala Val Ala Asn Ile
            130                 135                 140 tcc gcg gtg aac ccc gtc ctg gac ccg gca aac tat ggt ctt gac ttt      528
Ser Ala Val Asn Pro Val Leu Asp Pro Ala Asn Tyr Gly Leu Asp Phe
        145                 150                 155 tgg gag agc ctc agt gct gag ctc gtg acc atc agg aac gtg acc gtc      576
Trp Glu Ser Leu Ser Ala Glu Leu Val Thr Ile Arg Asn Val Thr Val
    160                 165                 170 atc tcg cgc cca aac tcg tat ggc gag acg tgg gtg aca ggt gga tgg      624
Ile Ser Arg Pro Asn Ser Tyr Gly Glu Thr Trp Val Thr Gly Gly Trp
175                 180                 185 ccc gtg acg ggc cgc agc gcc cgg gga agt ctg acc atg acc gcc ctg      672
Pro Val Thr Gly Arg Ser Ala Arg Gly Ser Leu Thr Met Thr Ala Leu
190                 195                 200                 205 gac tca aac ccg gag gtc atc aag atc gac gag ccc ctc gat ggc acg      720
Asp Ser Asn Pro Glu Val Ile Lys Ile Asp Glu Pro Leu Asp Gly Thr
            210                 215                 220 agc aac ccg gcc tcg ccc aag atc ggt gac aag gcg acc gac atc acg      768
Ser Asn Pro Ala Ser Pro Lys Ile Gly Asp Lys Ala Thr Asp Ile Thr
        225                 230                 235 ggc gtc gtc tac cag cag ttc ggc ttc tac tac atc ata ccc ctg acc      816
Gly Val Val Tyr Gln Gln Phe Gly Phe Tyr Tyr Ile Ile Pro Leu Thr
    240                 245                 250 gcg tac gag ctg acc acc ctc gcc gac ggc acg gcc cca ccg acg acg      864
Ala Tyr Glu Leu Thr Thr Leu Ala Asp Gly Thr Ala Pro Pro Thr Thr
255                 260                 265 ctg gag agc acg cgg tcc tgc gag ggc atc acc gtc ggc gac tac aac      912
Leu Glu Ser Thr Arg Ser Cys Glu Gly Ile Thr Val Gly Asp Tyr Asn
270                 275                 280                 285 gtc gag aac ctg tcc ccg gcg tcg gcc aac atc gag ggc agg gcg gac      960
Val Glu Asn Leu Ser Pro Ala Ser Ala Asn Ile Glu Gly Arg Ala Asp
            290                 295                 300 cac atc gtc aat tac ctc ggc gcc ccc gac ctc gtg ttc gtc cag gag     1008
His Ile Val Asn Tyr Leu Gly Ala Pro Asp Leu Val Phe Val Gln Glu
        305                 310                 315 atc cag gac ggc agc ggg ccg gcc aac gac ggc gtg gtc gac gcc agc     1056
Ile Gln Asp Gly Ser Gly Pro Ala Asn Asp Gly Val Val Asp Ala Ser
    320                 325                 330 gcc acc ctg acc gcc ctc gtg gac gcc atc gcg gcc gcc ggc aac gtc     1104
Ala Thr Leu Thr Ala Leu Val Asp Ala Ile Ala Ala Ala Gly Asn Val
335                 340                 345 acc tac tcg ttc gtc gag atc gcg ccc gag gac ggc aag gac ggc ggc     1152
Thr Tyr Ser Phe Val Glu Ile Ala Pro Glu Asp Gly Lys Asp Gly Gly
350                 355                 360                 365 cag ccc ggc ggc aac atc cgc gtg gcg tac ctc tac cgc ccc gag gtc     1200
Gln Pro Gly Gly Asn Ile Arg Val Ala Tyr Leu Tyr Arg Pro Glu Val
```

```
                    370                 375                 380
gtc agc ctg tac aag ccc agc ccg ggc gac agc acg acg gcc acc cgc       1248
Val Ser Leu Tyr Lys Pro Ser Pro Gly Asp Ser Thr Thr Ala Thr Arg
            385                 390                 395 gtc gtg gcc ggg gag tcc ggc cca gag ctc acg ctg aac cca ggc cgc       1296
Val Val Ala Gly Glu Ser Gly Pro Glu Leu Thr Leu Asn Pro Gly Arg
        400                 405                 410 atc gac ccg gcc aac ccg tgc tgg gtt gcc acc cgc aag ccg ctg gtc       1344
Ile Asp Pro Ala Asn Pro Cys Trp Val Ala Thr Arg Lys Pro Leu Val
    415                 420                 425 gcc gcc tgg ctc gca gag ggc gcg acg aag ccc ttc ttc acc gtc aac       1392
Ala Ala Trp Leu Ala Glu Gly Ala Thr Lys Pro Phe Phe Thr Val Asn
430                 435                 440                 445 gtg cac tgg agc tcc aag ggc ggc agc tcc agc ctg cag ggt gac atg       1440
Val His Trp Ser Ser Lys Gly Gly Ser Ser Ser Leu Gln Gly Asp Met
                450                 455                 460 cgg ccg ccc gtc aac ggc gtc gtc ggc aac agg ctg gcc cag gcg aac       1488
Arg Pro Pro Val Asn Gly Val Val Gly Asn Arg Leu Ala Gln Ala Asn
            465                 470                 475 gtc aca ggc gtaagctctc cccctcccgc cttcctcttc cagctctccg              1537
Val Thr Gly
        480 ggttgtaatg ctaacacggg gcag caa ttc atc tcc gag atc ctc gcc att        1588
                        Gln Phe Ile Ser Glu Ile Leu Ala Ile
                                            485 gac ccc tcg gcg gca gtc att gcc gcg ggt gac ttc aac gag ttt gcc       1636
Asp Pro Ser Ala Ala Val Ile Ala Ala Gly Asp Phe Asn Glu Phe Ala
490                 495                 500                 505 ttt gtg gag cct ctc acg gcc ttt gcc gat atc tct ggc ctg acg gag       1684
Phe Val Glu Pro Leu Thr Ala Phe Ala Asp Ile Ser Gly Leu Thr Glu
                510                 515                 520 ctg gac gag gtc gtc ggg atc cct ccc gag gag cgc tac aca tac act       1732
Leu Asp Glu Val Val Gly Ile Pro Pro Glu Glu Arg Tyr Thr Tyr Thr
            525                 530                 535 ttt gat atg aac acc cag gcc ctg gac cac atg tac gtc agc ccg gtg       1780
Phe Asp Met Asn Thr Gln Ala Leu Asp His Met Tyr Val Ser Pro Val
        540                 545                 550 ctc gag gag ggt gct ggt tac gag cac atc cac gtc aac acc tgg gcg       1828
Leu Glu Glu Gly Ala Gly Tyr Glu His Ile His Val Asn Thr Trp Ala
    555                 560                 565 gct gag gag gac gtc gtg tcg gac cat gac ccc agc gtt gcg ctt ttc       1876
Ala Glu Glu Asp Val Val Ser Asp His Asp Pro Ser Val Ala Leu Phe
570                 575                 580                 585 ggc gtg tgt ggt gcg tga                                               1894
Gly Val Cys Gly Ala
            590

<210> SEQ ID NO 59
<211> LENGTH: 609
<212> TYPE: PRT
<213> ORGANISM: Stenocarpella maydis

<400> SEQUENCE: 59

Met Lys Gly Leu Leu Cys Ser Val Val Gly Ala Leu Leu Thr Arg Ser
                -15                 -10                  -5

Ala Ala Ala Leu Ser Ile Ser Gln Ile Asn Gly Asn Arg Phe Leu Ser
         -1   1               5                  10

Pro Tyr Asp Gly Gln Thr Leu Thr Asn Ile Ser Gly Leu Val Thr Ala
         15                  20                  25
```

```
Lys Gly Pro Thr Gly Val Phe Val Arg Ser Thr Ala Pro Asp Asn Asp
 30                  35                  40                  45

Thr Ala Thr Ser Asp Ser Ala Phe Ile Tyr Ser Ser Val Gly Ser
             50                  55                  60

Ser Leu Asn Val Gly Asp Ile Val Thr Phe Ser Ala Lys Val Ala Glu
             65                  70                  75

Phe Arg Ser Arg Gly Ser Thr Tyr Leu Tyr Leu Thr Glu Leu Thr Ser
             80                  85                  90

Pro Ala Asp Val Val Val Ser Arg Asn Asn Thr Val Ala Pro Leu
 95                 100                 105

Val Val Gly Glu Asp Thr Pro Tyr Pro Thr Glu Lys Phe Ser Ser
110                 115                 120                 125

Leu Asp Gly Gly Asp Val Tyr Arg Ile Pro Asn Ala Val Ala Asn Ile
                130                 135                 140

Ser Ala Val Asn Pro Val Leu Asp Pro Ala Asn Tyr Gly Leu Asp Phe
                145                 150                 155

Trp Glu Ser Leu Ser Ala Glu Leu Val Thr Ile Arg Asn Val Thr Val
                160                 165                 170

Ile Ser Arg Pro Asn Ser Tyr Gly Glu Thr Trp Val Thr Gly Gly Trp
                175                 180                 185

Pro Val Thr Gly Arg Ser Ala Arg Gly Ser Leu Thr Met Thr Ala Leu
190                 195                 200                 205

Asp Ser Asn Pro Glu Val Ile Lys Ile Asp Glu Pro Leu Asp Gly Thr
                210                 215                 220

Ser Asn Pro Ala Ser Pro Lys Ile Gly Asp Lys Ala Thr Asp Ile Thr
                225                 230                 235

Gly Val Val Tyr Gln Gln Phe Gly Phe Tyr Ile Ile Pro Leu Thr
                240                 245                 250

Ala Tyr Glu Leu Thr Thr Leu Ala Asp Gly Thr Ala Pro Pro Thr Thr
255                 260                 265

Leu Glu Ser Thr Arg Ser Cys Glu Gly Ile Thr Val Gly Asp Tyr Asn
270                 275                 280                 285

Val Glu Asn Leu Ser Pro Ala Ser Ala Asn Ile Glu Gly Arg Ala Asp
                290                 295                 300

His Ile Val Asn Tyr Leu Gly Ala Pro Asp Leu Val Phe Val Gln Glu
                305                 310                 315

Ile Gln Asp Gly Ser Gly Pro Ala Asn Asp Gly Val Asp Ala Ser
                320                 325                 330

Ala Thr Leu Thr Ala Leu Val Asp Ala Ile Ala Ala Gly Asn Val
335                 340                 345

Thr Tyr Ser Phe Val Glu Ile Ala Pro Glu Asp Gly Lys Asp Gly Gly
350                 355                 360                 365

Gln Pro Gly Gly Asn Ile Arg Val Ala Tyr Leu Tyr Arg Pro Glu Val
                370                 375                 380

Val Ser Leu Tyr Lys Pro Ser Pro Gly Asp Ser Thr Thr Ala Thr Arg
                385                 390                 395

Val Val Ala Gly Glu Ser Gly Pro Glu Leu Thr Leu Asn Pro Gly Arg
                400                 405                 410

Ile Asp Pro Ala Asn Pro Cys Trp Val Ala Thr Arg Lys Pro Leu Val
                415                 420                 425

Ala Ala Trp Leu Ala Glu Gly Ala Thr Lys Pro Phe Phe Thr Val Asn
430                 435                 440                 445

Val His Trp Ser Ser Lys Gly Gly Ser Ser Leu Gln Gly Asp Met
```

```
                       450                 455                 460
Arg Pro Pro Val Asn Gly Val Gly Asn Arg Leu Ala Gln Ala Asn
            465                 470                 475
Val Thr Gly Gln Phe Ile Ser Glu Ile Leu Ala Ile Asp Pro Ser Ala
                480                 485                 490
Ala Val Ile Ala Ala Gly Asp Phe Asn Glu Phe Ala Phe Val Glu Pro
            495                 500                 505
Leu Thr Ala Phe Ala Asp Ile Ser Gly Leu Thr Glu Leu Asp Glu Val
510                 515                 520                 525
Val Gly Ile Pro Pro Glu Glu Arg Tyr Thr Tyr Thr Phe Asp Met Asn
                530                 535                 540
Thr Gln Ala Leu Asp His Met Tyr Val Ser Pro Val Leu Glu Glu Gly
            545                 550                 555
Ala Gly Tyr Glu His Ile His Val Asn Thr Trp Ala Ala Glu Glu Asp
                560                 565                 570
Val Val Ser Asp His Asp Pro Ser Val Ala Leu Phe Gly Val Cys Gly
            575                 580                 585
Ala
590

<210> SEQ ID NO 60
<211> LENGTH: 590
<212> TYPE: PRT
<213> ORGANISM: Stenocarpella maydis

<400> SEQUENCE: 60

Leu Ser Ile Ser Gln Ile Asn Gly Asn Arg Phe Leu Ser Pro Tyr Asp
1               5                   10                  15
Gly Gln Thr Leu Thr Asn Ile Ser Gly Leu Val Thr Ala Lys Gly Pro
            20                  25                  30
Thr Gly Val Phe Val Arg Ser Thr Ala Pro Asp Asn Asp Thr Ala Thr
        35                  40                  45
Ser Asp Ser Ala Phe Ile Tyr Ser Ser Ser Val Gly Ser Ser Leu Asn
50                  55                  60
Val Gly Asp Ile Val Thr Phe Ser Ala Lys Val Ala Glu Phe Arg Ser
65                  70                  75                  80
Arg Gly Ser Thr Tyr Leu Tyr Leu Thr Glu Leu Thr Ser Pro Ala Asp
                85                  90                  95
Val Val Val Val Ser Arg Asn Asn Thr Val Ala Pro Leu Val Val Gly
            100                 105                 110
Glu Asp Thr Pro Tyr Pro Pro Thr Glu Lys Phe Ser Ser Leu Asp Gly
        115                 120                 125
Gly Asp Val Tyr Arg Ile Pro Asn Ala Val Ala Asn Ile Ser Ala Val
    130                 135                 140
Asn Pro Val Leu Asp Pro Ala Asn Tyr Gly Leu Asp Phe Trp Glu Ser
145                 150                 155                 160
Leu Ser Ala Glu Leu Val Thr Ile Arg Asn Val Thr Val Ile Ser Arg
                165                 170                 175
Pro Asn Ser Tyr Gly Glu Thr Trp Val Thr Gly Gly Trp Pro Val Thr
            180                 185                 190
Gly Arg Ser Ala Arg Gly Ser Leu Thr Met Thr Ala Leu Asp Ser Asn
        195                 200                 205
Pro Glu Val Ile Lys Ile Asp Glu Pro Leu Asp Gly Thr Ser Asn Pro
    210                 215                 220
```

Ala Ser Pro Lys Ile Gly Asp Lys Ala Thr Asp Ile Thr Gly Val Val
225                 230                 235                 240

Tyr Gln Gln Phe Gly Phe Tyr Tyr Ile Ile Pro Leu Thr Ala Tyr Glu
            245                 250                 255

Leu Thr Thr Leu Ala Asp Gly Thr Ala Pro Pro Thr Thr Leu Glu Ser
        260                 265                 270

Thr Arg Ser Cys Glu Gly Ile Thr Val Gly Asp Tyr Asn Val Glu Asn
    275                 280                 285

Leu Ser Pro Ala Ser Ala Asn Ile Glu Gly Arg Ala Asp His Ile Val
290                 295                 300

Asn Tyr Leu Gly Ala Pro Asp Leu Val Phe Val Gln Glu Ile Gln Asp
305                 310                 315                 320

Gly Ser Gly Pro Ala Asn Asp Gly Val Val Asp Ala Ser Ala Thr Leu
            325                 330                 335

Thr Ala Leu Val Asp Ala Ile Ala Ala Gly Asn Val Thr Tyr Ser
        340                 345                 350

Phe Val Glu Ile Ala Pro Glu Asp Gly Lys Asp Gly Gly Gln Pro Gly
            355                 360                 365

Gly Asn Ile Arg Val Ala Tyr Leu Tyr Arg Pro Glu Val Val Ser Leu
370                 375                 380

Tyr Lys Pro Ser Pro Gly Asp Ser Thr Thr Ala Thr Arg Val Val Ala
385                 390                 395                 400

Gly Glu Ser Gly Pro Glu Leu Thr Leu Asn Pro Gly Arg Ile Asp Pro
            405                 410                 415

Ala Asn Pro Cys Trp Val Ala Thr Arg Lys Pro Leu Val Ala Ala Trp
            420                 425                 430

Leu Ala Glu Gly Ala Thr Lys Pro Phe Phe Thr Val Asn Val His Trp
        435                 440                 445

Ser Ser Lys Gly Gly Ser Ser Leu Gln Gly Asp Met Arg Pro Pro
    450                 455                 460

Val Asn Gly Val Val Gly Asn Arg Leu Ala Gln Ala Asn Val Thr Gly
465                 470                 475                 480

Gln Phe Ile Ser Glu Ile Leu Ala Ile Asp Pro Ser Ala Ala Val Ile
            485                 490                 495

Ala Ala Gly Asp Phe Asn Glu Phe Ala Phe Val Glu Pro Leu Thr Ala
        500                 505                 510

Phe Ala Asp Ile Ser Gly Leu Thr Glu Leu Asp Glu Val Val Gly Ile
        515                 520                 525

Pro Pro Glu Glu Arg Tyr Thr Tyr Thr Phe Asp Met Asn Thr Gln Ala
530                 535                 540

Leu Asp His Met Tyr Val Ser Pro Val Leu Glu Glu Gly Ala Gly Tyr
545                 550                 555                 560

Glu His Ile His Val Asn Thr Trp Ala Ala Glu Glu Asp Val Val Ser
            565                 570                 575

Asp His Asp Pro Ser Val Ala Leu Phe Gly Val Cys Gly Ala
        580                 585                 590

<210> SEQ ID NO 61
<211> LENGTH: 1999
<212> TYPE: DNA
<213> ORGANISM: Acrophialophora fusispora
<220> FEATURE:
<221> NAME/KEY: CDS
<222> LOCATION: (1)..(673)
<220> FEATURE:
<221> NAME/KEY: sig_peptide

```
<222> LOCATION: (1)..(60)
<220> FEATURE:
<221> NAME/KEY: mat_peptide
<222> LOCATION: (61)..(1996)
<220> FEATURE:
<221> NAME/KEY: CDS
<222> LOCATION: (721)..(1559)
<220> FEATURE:
<221> NAME/KEY: CDS
<222> LOCATION: (1611)..(1777)
<220> FEATURE:
<221> NAME/KEY: CDS
<222> LOCATION: (1828)..(1996)

<400> SEQUENCE: 61 atg aag cca tcg ccg ctg ttc tgc tgc gct ttc gcc ggc ctg cag tcg     48
Met Lys Pro Ser Pro Leu Phe Cys Cys Ala Phe Ala Gly Leu Gln Ser
-20             -15                 -10                 -5 ctg gcg gcc gcc ctg act atc gcc gag atc aac ggt aac aag ttc atc     96
Leu Ala Ala Ala Leu Thr Ile Ala Glu Ile Asn Gly Asn Lys Phe Ile
        -1  1               5                  10 tcg tcc tac aat ggt cag gcc gtc acc aat att acc ggc ttg ctg atc    144
Ser Ser Tyr Asn Gly Gln Ala Val Thr Asn Ile Thr Gly Leu Leu Ile
            15                  20                  25 gcc aag ggg ccc aac ggt gtc tgg atc cgc tcg acc acg ccc gac gac    192
Ala Lys Gly Pro Asn Gly Val Trp Ile Arg Ser Thr Thr Pro Asp Asp
        30                  35                  40 gac cag gca acg tct gag gcc atc tac gtc ttc agc agc agc gtg ggc    240
Asp Gln Ala Thr Ser Glu Ala Ile Tyr Val Phe Ser Ser Ser Val Gly
45                  50                  55                  60 gcc aat ctg acc gtc ggc gac atc atc tcg ctg gat ggc aag gtg tcc    288
Ala Asn Leu Thr Val Gly Asp Ile Ile Ser Leu Asp Gly Lys Val Ser
                65                  70                  75 gag tat cgg tcc agc tcc aac tac atg tac ctg acc gag atc acc tcc    336
Glu Tyr Arg Ser Ser Ser Asn Tyr Met Tyr Leu Thr Glu Ile Thr Ser
            80                  85                  90 ccg aag aac gtc aag gtc gtc tca tcc ggg aac acg gtc acc ccg cta    384
Pro Lys Asn Val Lys Val Val Ser Ser Gly Asn Thr Val Thr Pro Leu
        95                 100                 105 gtt atc ggc cag gac acg ctg tcg cct cca acg gtg cag tac agc agc    432
Val Ile Gly Gln Asp Thr Leu Ser Pro Pro Thr Val Gln Tyr Ser Ser
    110                 115                 120 ctg gat aac ggt gac atc tac aac ctg ccc aat ggc gtg gca aac gtc    480
Leu Asp Asn Gly Asp Ile Tyr Asn Leu Pro Asn Gly Val Ala Asn Val
125                 130                 135                 140 tcc gcg gcg aat ccc gtg ctg gat ccc acc aag tac ggc ctg gat ttc    528
Ser Ala Ala Asn Pro Val Leu Asp Pro Thr Lys Tyr Gly Leu Asp Phe
                145                 150                 155 tgg gag agc ctc agc ggt gag ctg gtc acg gtg aaa aag ccg acc gcc    576
Trp Glu Ser Leu Ser Gly Glu Leu Val Thr Val Lys Lys Pro Thr Ala
            160                 165                 170 atc aag acg ccg aat cag tac ggc gat acc tgg gtt att ggc gac tgg    624
Ile Lys Thr Pro Asn Gln Tyr Gly Asp Thr Trp Val Ile Gly Asp Trp
        175                 180                 185 gct gta act ggg agg aac cat cac ggc ggc gtg acc atg tcc gac aag g  673
Ala Val Thr Gly Arg Asn His His Gly Gly Val Thr Met Ser Asp Lys
    190                 195                 200 gtcagtgaag cgtccatcca ccgtgatcac acactcacac attgcag ac tcc aac      728
                                               Asp Ser Asn
                                                   205 cct gaa gcc atc atc atc ggc tcg cct ctg gac cgc act aag aac cca    776
Pro Glu Ala Ile Ile Ile Gly Ser Pro Leu Asp Arg Thr Lys Asn Pro
        210                 215                 220
```

```
acc acc tcc aag atg ggc gac cag ttc gag gac atc act ggc gtc gtt       824
Thr Thr Ser Lys Met Gly Asp Gln Phe Glu Asp Ile Thr Gly Val Val
        225                 230                 235 cag cac gcc ttt ggc ttc tac tcc atc ctc ccc ctg acc gcc atc aag       872
Gln His Ala Phe Gly Phe Tyr Ser Ile Leu Pro Leu Thr Ala Ile Lys
240                 245                 250                 255 acc acc acc gca gcc tcc gcc gcc gcc cct ccc act acc ctc ctc agc       920
Thr Thr Thr Ala Ala Ser Ala Ala Ala Pro Pro Thr Thr Leu Leu Ser
                260                 265                 270 cag ggc aag tgc aag gcc atc act gtc ggc agc tac aac gtc gag aac       968
Gln Gly Lys Cys Lys Ala Ile Thr Val Gly Ser Tyr Asn Val Glu Asn
                275                 280                 285 ctg gcc ccc aac tca acc cac ctc ccc aag gtc gct gcc cac atc gtc      1016
Leu Ala Pro Asn Ser Thr His Leu Pro Lys Val Ala Ala His Ile Val
        290                 295                 300 gac tac ctc aag acc ccg gac ctg atc ttc gtc caa gaa gtc cag gac      1064
Asp Tyr Leu Lys Thr Pro Asp Leu Ile Phe Val Gln Glu Val Gln Asp
        305                 310                 315 aac agc ggc ccc acc gac gac ggc gtg gtc tcc gcc aac acg acc ctc      1112
Asn Ser Gly Pro Thr Asp Asp Gly Val Val Ser Ala Asn Thr Thr Leu
320                 325                 330                 335 acc acc ctc gtc gac gcc atc cac tcc ctc agc gga gtg acc tac gcc      1160
Thr Thr Leu Val Asp Ala Ile His Ser Leu Ser Gly Val Thr Tyr Ala
                340                 345                 350 ttt gcc gac gtc gac cca gtc tcc aac gcc gac ggc ggc cag cca ggc      1208
Phe Ala Asp Val Asp Pro Val Ser Asn Ala Asp Gly Gly Gln Pro Gly
                355                 360                 365 ggc aac atc cgc cag gcc tac ctg tac cgc ccc gag gtg gtc agc ctg      1256
Gly Asn Ile Arg Gln Ala Tyr Leu Tyr Arg Pro Glu Val Val Ser Leu
        370                 375                 380 tac aag cca aac caa ggc ggc tcc aac gac gcg acc gag gtc gtg ccc      1304
Tyr Lys Pro Asn Gln Gly Gly Ser Asn Asp Ala Thr Glu Val Val Pro
        385                 390                 395 ggc aag ggt aac ggt ctt gcc ggc gtg ccg acg ctg tcg ttc aac ccg      1352
Gly Lys Gly Asn Gly Leu Ala Gly Val Pro Thr Leu Ser Phe Asn Pro
400                 405                 410                 415 ggc cgg atc gag cct ggc aac gcg gcg tgg aag gcc agc cgg aag cca      1400
Gly Arg Ile Glu Pro Gly Asn Ala Ala Trp Lys Ala Ser Arg Lys Pro
                420                 425                 430 ctc gcg gcc gtg tgg aag gca aag ggc gcc aag cgg ccg ttt tac acg      1448
Leu Ala Ala Val Trp Lys Ala Lys Gly Ala Lys Arg Pro Phe Tyr Thr
                435                 440                 445 gtc aat gtg cac tgg tcg agc aag ggc ggc ggc acg tcg ctc cat ggc      1496
Val Asn Val His Trp Ser Ser Lys Gly Gly Gly Thr Ser Leu His Gly
                450                 455                 460 gac cgc cgg ccg ccg gtt aac ggg gcg gtg gac gcg agg atg gcg cag      1544
Asp Arg Arg Pro Pro Val Asn Gly Ala Val Asp Ala Arg Met Ala Gln
465                 470                 475 gct aat gtc acg ggg gtgagcgctg agtgcattgg ttgagaaaag ggtgatgcta      1599
Ala Asn Val Thr Gly
480 acgggaaaca g acg ttt att gcg caa atc ctg tcc ctt gac ccg gcg gca     1649
            Thr Phe Ile Ala Gln Ile Leu Ser Leu Asp Pro Ala Ala
                        485                 490                 495 aac gtc att gcc gcg ggt gat ttc aac gag ttt gct ttt gtg cag ccg      1697
Asn Val Ile Ala Ala Gly Asp Phe Asn Glu Phe Ala Phe Val Gln Pro
            500                 505                 510 atg aag acg ttc tcg gcc atc tcg acg atg gtc gac ctc gac gag gcg      1745
Met Lys Thr Phe Ser Ala Ile Ser Thr Met Val Asp Leu Asp Glu Ala
```

```
                    515                 520                 525
gcc ggg atc cct gtc gag gaa cga tac acc ta gtgagtaacc ttctagggac    1797
Ala Gly Ile Pro Val Glu Glu Arg Tyr Thr Tyr
530                 535                 540 gatgtgcgag cttgtgctga ttgtgaacag t gcc tat gac atg aac gcc cag      1849
                                   Ala Tyr Asp Met Asn Ala Gln
                                                           545 gcc ctc gac cac atg tat gtt agc ccc gcg ctg gcg cac aag aag tcg    1897
Ala Leu Asp His Met Tyr Val Ser Pro Ala Leu Ala His Lys Lys Ser
            550                 555                 560 acg cgc ttc gag cat ctc cat gtc aac tcg tgg gca tcg tat gat gat    1945
Thr Arg Phe Glu His Leu His Val Asn Ser Trp Ala Ser Tyr Asp Asp
565                 570                 575 gtg gtc tcg gac cac gac cca agc att gcc ttg ttt gac gtg tgc ggt    1993
Val Val Ser Asp His Asp Pro Ser Ile Ala Leu Phe Asp Val Cys Gly
580                 585                 590                 595 tgc tga                                                            1999
Cys

<210> SEQ ID NO 62
<211> LENGTH: 616
<212> TYPE: PRT
<213> ORGANISM: Acrophialophora fusispora

<400> SEQUENCE: 62

Met Lys Pro Ser Pro Leu Phe Cys Cys Ala Phe Ala Gly Leu Gln Ser
-20                 -15                 -10                 -5

Leu Ala Ala Ala Leu Thr Ile Ala Glu Ile Asn Gly Asn Lys Phe Ile
            -1  1                   5                  10

Ser Ser Tyr Asn Gly Gln Ala Val Thr Asn Ile Thr Gly Leu Leu Ile
            15                  20                  25

Ala Lys Gly Pro Asn Gly Val Trp Ile Arg Ser Thr Thr Pro Asp Asp
30                  35                  40

Asp Gln Ala Thr Ser Glu Ala Ile Tyr Val Phe Ser Ser Ser Val Gly
45                  50                  55                  60

Ala Asn Leu Thr Val Gly Asp Ile Ile Ser Leu Asp Gly Lys Val Ser
            65                  70                  75

Glu Tyr Arg Ser Ser Ser Asn Tyr Met Tyr Leu Thr Glu Ile Thr Ser
            80                  85                  90

Pro Lys Asn Val Lys Val Val Ser Ser Gly Asn Thr Val Thr Pro Leu
            95                  100                 105

Val Ile Gly Gln Asp Thr Leu Ser Pro Pro Thr Val Gln Tyr Ser Ser
110                 115                 120

Leu Asp Asn Gly Asp Ile Tyr Asn Leu Pro Asn Gly Val Ala Asn Val
125                 130                 135                 140

Ser Ala Ala Asn Pro Val Leu Asp Pro Thr Lys Tyr Gly Leu Asp Phe
                145                 150                 155

Trp Glu Ser Leu Ser Gly Glu Leu Val Thr Val Lys Lys Pro Thr Ala
                160                 165                 170

Ile Lys Thr Pro Asn Gln Tyr Gly Asp Thr Trp Val Ile Gly Asp Trp
                175                 180                 185

Ala Val Thr Gly Arg Asn His His Gly Val Thr Met Ser Asp Lys
                190                 195                 200

Asp Ser Asn Pro Glu Ala Ile Ile Ile Gly Ser Pro Leu Asp Arg Thr
205                 210                 215                 220

Lys Asn Pro Thr Thr Ser Lys Met Gly Asp Gln Phe Glu Asp Ile Thr
```

```
                   225                 230                 235
Gly Val Val Gln His Ala Phe Gly Phe Tyr Ser Ile Leu Pro Leu Thr
                240                 245                 250

Ala Ile Lys Thr Thr Thr Ala Ala Ser Ala Ala Ala Pro Pro Thr Thr
                255                 260                 265

Leu Leu Ser Gln Gly Lys Cys Lys Ala Ile Thr Val Gly Ser Tyr Asn
            270                 275                 280

Val Glu Asn Leu Ala Pro Asn Ser Thr His Leu Pro Lys Val Ala Ala
285                 290                 295                 300

His Ile Val Asp Tyr Leu Lys Thr Pro Asp Leu Ile Phe Val Gln Glu
                305                 310                 315

Val Gln Asp Asn Ser Gly Pro Thr Asp Asp Gly Val Val Ser Ala Asn
                320                 325                 330

Thr Thr Leu Thr Thr Leu Val Asp Ala Ile His Ser Leu Ser Gly Val
                335                 340                 345

Thr Tyr Ala Phe Ala Asp Val Asp Pro Val Ser Asn Ala Asp Gly Gly
            350                 355                 360

Gln Pro Gly Gly Asn Ile Arg Gln Ala Tyr Leu Tyr Arg Pro Glu Val
365                 370                 375                 380

Val Ser Leu Tyr Lys Pro Asn Gln Gly Gly Ser Asn Asp Ala Thr Glu
                385                 390                 395

Val Val Pro Gly Lys Gly Asn Gly Leu Ala Gly Val Pro Thr Leu Ser
                400                 405                 410

Phe Asn Pro Gly Arg Ile Glu Pro Gly Asn Ala Ala Trp Lys Ala Ser
                415                 420                 425

Arg Lys Pro Leu Ala Ala Val Trp Lys Ala Lys Gly Ala Lys Arg Pro
            430                 435                 440

Phe Tyr Thr Val Asn Val His Trp Ser Ser Lys Gly Gly Thr Ser
445                 450                 455                 460

Leu His Gly Asp Arg Arg Pro Pro Val Asn Gly Ala Val Asp Ala Arg
                465                 470                 475

Met Ala Gln Ala Asn Val Thr Gly Thr Phe Ile Ala Gln Ile Leu Ser
                480                 485                 490

Leu Asp Pro Ala Ala Asn Val Ile Ala Ala Gly Asp Phe Asn Glu Phe
            495                 500                 505

Ala Phe Val Gln Pro Met Lys Thr Phe Ser Ala Ile Ser Thr Met Val
                510                 515                 520

Asp Leu Asp Glu Ala Ala Gly Ile Pro Val Glu Glu Arg Tyr Thr Tyr
525                 530                 535                 540

Ala Tyr Asp Met Asn Ala Gln Ala Leu Asp His Met Tyr Val Ser Pro
                545                 550                 555

Ala Leu Ala His Lys Lys Ser Thr Arg Phe Glu His Leu His Val Asn
                560                 565                 570

Ser Trp Ala Ser Tyr Asp Asp Val Val Ser Asp His Asp Pro Ser Ile
            575                 580                 585

Ala Leu Phe Asp Val Cys Gly Cys
            590                 595

<210> SEQ ID NO 63
<211> LENGTH: 596
<212> TYPE: PRT
<213> ORGANISM: Acrophialophora fusispora

<400> SEQUENCE: 63
```

```
Leu Thr Ile Ala Glu Ile Asn Gly Asn Lys Phe Ile Ser Ser Tyr Asn
1               5                   10                  15

Gly Gln Ala Val Thr Asn Ile Thr Gly Leu Leu Ile Ala Lys Gly Pro
            20                  25                  30

Asn Gly Val Trp Ile Arg Ser Thr Thr Pro Asp Asp Gln Ala Thr
            35                  40                  45

Ser Glu Ala Ile Tyr Val Phe Ser Ser Ser Val Gly Ala Asn Leu Thr
50                  55                  60

Val Gly Asp Ile Ile Ser Leu Asp Gly Lys Val Ser Glu Tyr Arg Ser
65                  70                  75                  80

Ser Ser Asn Tyr Met Tyr Leu Thr Glu Ile Thr Ser Pro Lys Asn Val
                85                  90                  95

Lys Val Val Ser Ser Gly Asn Thr Val Thr Pro Leu Val Ile Gly Gln
            100                 105                 110

Asp Thr Leu Ser Pro Pro Thr Val Gln Tyr Ser Ser Leu Asp Asn Gly
            115                 120                 125

Asp Ile Tyr Asn Leu Pro Asn Gly Val Ala Asn Val Ser Ala Ala Asn
            130                 135                 140

Pro Val Leu Asp Pro Thr Lys Tyr Gly Leu Asp Phe Trp Glu Ser Leu
145                 150                 155                 160

Ser Gly Glu Leu Val Thr Val Lys Lys Pro Thr Ala Ile Lys Thr Pro
                165                 170                 175

Asn Gln Tyr Gly Asp Thr Trp Val Ile Gly Asp Trp Ala Val Thr Gly
            180                 185                 190

Arg Asn His His Gly Val Thr Met Ser Asp Lys Asp Ser Asn Pro
            195                 200                 205

Glu Ala Ile Ile Ile Gly Ser Pro Leu Asp Arg Thr Lys Asn Pro Thr
210                 215                 220

Thr Ser Lys Met Gly Asp Gln Phe Glu Asp Ile Thr Gly Val Val Gln
225                 230                 235                 240

His Ala Phe Gly Phe Tyr Ser Ile Leu Pro Leu Thr Ala Ile Lys Thr
            245                 250                 255

Thr Thr Ala Ala Ser Ala Ala Ala Pro Pro Thr Thr Leu Leu Ser Gln
            260                 265                 270

Gly Lys Cys Lys Ala Ile Thr Val Gly Ser Tyr Asn Val Glu Asn Leu
            275                 280                 285

Ala Pro Asn Ser Thr His Leu Pro Lys Val Ala Ala His Ile Val Asp
            290                 295                 300

Tyr Leu Lys Thr Pro Asp Leu Ile Phe Val Gln Glu Val Gln Asp Asn
305                 310                 315                 320

Ser Gly Pro Thr Asp Asp Gly Val Val Ser Ala Asn Thr Thr Leu Thr
            325                 330                 335

Thr Leu Val Asp Ala Ile His Ser Leu Ser Gly Val Thr Tyr Ala Phe
            340                 345                 350

Ala Asp Val Asp Pro Val Ser Asn Ala Asp Gly Gln Pro Gly Gly
            355                 360                 365

Asn Ile Arg Gln Ala Tyr Leu Tyr Arg Pro Glu Val Val Ser Leu Tyr
            370                 375                 380

Lys Pro Asn Gln Gly Gly Ser Asn Asp Ala Thr Glu Val Val Pro Gly
385                 390                 395                 400

Lys Gly Asn Gly Leu Ala Gly Val Pro Thr Leu Ser Phe Asn Pro Gly
            405                 410                 415

Arg Ile Glu Pro Gly Asn Ala Ala Trp Lys Ala Ser Arg Lys Pro Leu
```

```
                420             425             430
Ala Ala Val Trp Lys Ala Lys Gly Ala Lys Arg Pro Phe Tyr Thr Val
            435             440             445

Asn Val His Trp Ser Ser Lys Gly Gly Gly Thr Ser Leu His Gly Asp
    450             455             460

Arg Arg Pro Pro Val Asn Gly Ala Val Asp Ala Arg Met Ala Gln Ala
465             470             475             480

Asn Val Thr Gly Thr Phe Ile Ala Gln Ile Leu Ser Leu Asp Pro Ala
                485             490             495

Ala Asn Val Ile Ala Ala Gly Asp Phe Asn Glu Phe Ala Phe Val Gln
            500             505             510

Pro Met Lys Thr Phe Ser Ala Ile Ser Thr Met Val Asp Leu Asp Glu
            515             520             525

Ala Ala Gly Ile Pro Val Glu Glu Arg Tyr Thr Tyr Ala Tyr Asp Met
            530             535             540

Asn Ala Gln Ala Leu Asp His Met Tyr Val Ser Pro Ala Leu Ala His
545             550             555             560

Lys Lys Ser Thr Arg Phe Glu His Leu His Val Asn Ser Trp Ala Ser
                565             570             575

Tyr Asp Asp Val Val Ser Asp His Asp Pro Ser Ile Ala Leu Phe Asp
                580             585             590

Val Cys Gly Cys
        595

<210> SEQ ID NO 64
<211> LENGTH: 2020
<212> TYPE: DNA
<213> ORGANISM: Chaetomium luteum
<220> FEATURE:
<221> NAME/KEY: CDS
<222> LOCATION: (1)..(673)
<220> FEATURE:
<221> NAME/KEY: sig_peptide
<222> LOCATION: (1)..(60)
<220> FEATURE:
<221> NAME/KEY: mat_peptide
<222> LOCATION: (61)..(2017)
<220> FEATURE:
<221> NAME/KEY: CDS
<222> LOCATION: (726)..(1570)
<220> FEATURE:
<221> NAME/KEY: CDS
<222> LOCATION: (1628)..(1794)
<220> FEATURE:
<221> NAME/KEY: CDS
<222> LOCATION: (1849)..(2017)

<400> SEQUENCE: 64 atg agg cta gca cca gtg ttc tgc tgg gtc ttt gtc agc ttc cag tcg      48
Met Arg Leu Ala Pro Val Phe Cys Trp Val Phe Val Ser Phe Gln Ser
-20             -15             -10             -5 ctg act gcg gcc ctg act atc tcg gag atc aac ggt aac aag ttc atc      96
Leu Thr Ala Ala Leu Thr Ile Ser Glu Ile Asn Gly Asn Lys Phe Ile
        -1  1           5               10 tcg ccg tac tcg ggc aag tct gtg acg aat gtg acg ggc ttg ctg att     144
Ser Pro Tyr Ser Gly Lys Ser Val Thr Asn Val Thr Gly Leu Leu Ile
            15              20              25 gcc aag gga ccc aac ggc atc tgg atc cgc tcg acg acg ccg gac gat     192
Ala Lys Gly Pro Asn Gly Ile Trp Ile Arg Ser Thr Thr Pro Asp Asp
        30              35              40 gac aag acc acc tcg gag gct gtc tac gtc ttc agc agc agt gtt ggt     240
Asp Lys Thr Thr Ser Glu Ala Val Tyr Val Phe Ser Ser Ser Val Gly
```

```
                    45                    50                    55                    60
atc aac ttg acc gtt ggg gac atc atc tca cta gac ggg aaa gtc tcc          288
Ile Asn Leu Thr Val Gly Asp Ile Ile Ser Leu Asp Gly Lys Val Ser
                         65                    70                    75 gag tac cgt tca agt tct agc tac atc tac ctg act gag atc acc tcg          336
Glu Tyr Arg Ser Ser Ser Ser Tyr Ile Tyr Leu Thr Glu Ile Thr Ser
                     80                    85                    90 cca aag aac gtg cat ata ctg tca tct gga aac acg gtg aca ccg ctc          384
Pro Lys Asn Val His Ile Leu Ser Ser Gly Asn Thr Val Thr Pro Leu
                 95                   100                   105 atc att ggc aaa gac acc cta tct ccc cca acg gtg cag tat agc aat          432
Ile Ile Gly Lys Asp Thr Leu Ser Pro Pro Thr Val Gln Tyr Ser Asn
            110                   115                   120 ctc gat ggc ggc gat atc tac agc ctg cca aat gct gtg gcc aac ata          480
Leu Asp Gly Gly Asp Ile Tyr Ser Leu Pro Asn Ala Val Ala Asn Ile
125                   130                   135                   140 tct gag gtt aac ccc gtg ctg gac ccg gct aag tac ggc ctg gac ttt          528
Ser Glu Val Asn Pro Val Leu Asp Pro Ala Lys Tyr Gly Leu Asp Phe
                        145                   150                   155 tgg gaa agc ctc agc ggt gag ctg gtc acg atc aac aag ccg cag gcc          576
Trp Glu Ser Leu Ser Gly Glu Leu Val Thr Ile Asn Lys Pro Gln Ala
                    160                   165                   170 att aag acg ccg aac gag tac ggc gac act tgg gtg gtg ggt gac tgg          624
Ile Lys Thr Pro Asn Glu Tyr Gly Asp Thr Trp Val Val Gly Asp Trp
                175                   180                   185 gcc gtg acg ggc aaa aac aaa cat ggc ggt ctg act atg tct gac aaa g        673
Ala Val Thr Gly Lys Asn Lys His Gly Gly Leu Thr Met Ser Asp Lys
            190                   195                   200 gtgagcccgt agcatgaccc tggatgctca atctcatact cacactcagc ag  ac  tcc        730
                                                        Asp Ser
                                                            205 aac cct gag gcc atc ata atc gga aca ccc ctg gat gga acc aag aat          778
Asn Pro Glu Ala Ile Ile Ile Gly Thr Pro Leu Asp Gly Thr Lys Asn
                210                   215                   220 ccc act atc tcc aaa atg gga gac caa ttc gaa gac atc acc ggc atc          826
Pro Thr Ile Ser Lys Met Gly Asp Gln Phe Glu Asp Ile Thr Gly Ile
            225                   230                   235 gtc cag caa acc ttc ggc ttc tat aat atc ctc ccc ctt acc gcc ctc          874
Val Gln Gln Thr Phe Gly Phe Tyr Asn Ile Leu Pro Leu Thr Ala Leu
        240                   245                   250 aaa acc acc agt tct gcc tcc gcg tcc gtc tcc ccg acc ttt ctt ctc          922
Lys Thr Thr Ser Ser Ala Ser Ala Ser Val Ser Pro Thr Phe Leu Leu
255                   260                   265                   270 agc cac ggc aag tgc aag gcc ctc acg gtt ggc agc tac aat gta gag          970
Ser His Gly Lys Cys Lys Ala Leu Thr Val Gly Ser Tyr Asn Val Glu
                        275                   280                   285 aac atg gcg cca aca tcc tcc cac ctc ccc aaa gtt gcc gcc cac ata         1018
Asn Met Ala Pro Thr Ser Ser His Leu Pro Lys Val Ala Ala His Ile
                    290                   295                   300 gtg gac tac ctc aag acg ccg gac ctc atg ttc gtc caa gag att caa         1066
Val Asp Tyr Leu Lys Thr Pro Asp Leu Met Phe Val Gln Glu Ile Gln
                305                   310                   315 gac aac agc gga ccc acg aat gac ggc atc gtc tcc gcc aac gcc acc         1114
Asp Asn Ser Gly Pro Thr Asn Asp Gly Ile Val Ser Ala Asn Ala Thr
            320                   325                   330 atc acc gct ctc gtt aaa gcc atc aag act ctc agc ggt gta acg tac         1162
Ile Thr Ala Leu Val Lys Ala Ile Lys Thr Leu Ser Gly Val Thr Tyr
335                   340                   345                   350 gct tgg act gac att gac ccc gtc tcc aac gag gac ggt ggt cag ccg         1210
```

```
Ala Trp Thr Asp Ile Asp Pro Val Ser Asn Glu Asp Gly Gly Gln Pro
            355                 360                 365 ggt ggt aac atc cgc cag gcg tat ctc tac cgc ccc gaa gtg ctg agc    1258
Gly Gly Asn Ile Arg Gln Ala Tyr Leu Tyr Arg Pro Glu Val Leu Ser
        370                 375                 380 ttg tac gaa gcc aac ccg ggc ggc tct aat gac gca aca gag gtt gtc    1306
Leu Tyr Glu Ala Asn Pro Gly Gly Ser Asn Asp Ala Thr Glu Val Val
            385                 390                 395 cct gct gaa ggc aag ggc aag ggc ttt ggc ggt gcc ccg acc ctg tcg    1354
Pro Ala Glu Gly Lys Gly Lys Gly Phe Gly Gly Ala Pro Thr Leu Ser
        400                 405                 410 ttc aac ccc ggc cgg att gac ccc gcc aac gct gcc tgg aag aac agc    1402
Phe Asn Pro Gly Arg Ile Asp Pro Ala Asn Ala Ala Trp Lys Asn Ser
415                 420                 425                 430 cgg aag cct ctt gct gct gtc tgg aag gct aag ggc gcc aag aga ccg    1450
Arg Lys Pro Leu Ala Ala Val Trp Lys Ala Lys Gly Ala Lys Arg Pro
                435                 440                 445 ttc tac act gtc aat gtg cac tgg tcg agc aaa ggc ggc ggc acg tca    1498
Phe Tyr Thr Val Asn Val His Trp Ser Ser Lys Gly Gly Gly Thr Ser
            450                 455                 460 ctg cat gga gat gtt agg ccg ccg atc aat ggc gct gtg gag gcg cgg    1546
Leu His Gly Asp Val Arg Pro Pro Ile Asn Gly Ala Val Glu Ala Arg
        465                 470                 475 atg gcg cag gcg aat gtt acg ggg gtgagtacaa cacttcgtgg tagcagggtg   1600
Met Ala Gln Ala Asn Val Thr Gly
        480                 485 tgttttgctg tcgctgacaa gaagcag tcg ttt att gcc aaa att ctg gct ctg  1654
                                Ser Phe Ile Ala Lys Ile Leu Ala Leu
                                                490                 495 gat ccg acc gcg aac atc att gcc gcc ggt gac ttc aac gag ttt tct    1702
Asp Pro Thr Ala Asn Ile Ile Ala Ala Gly Asp Phe Asn Glu Phe Ser
                500                 505                 510 ttc gtg cag cct ttg aag atg ttc tcg acc att tcg aag atg gtt gac    1750
Phe Val Gln Pro Leu Lys Met Phe Ser Thr Ile Ser Lys Met Val Asp
            515                 520                 525 att gac gag gcc acc gaa gtg ccc gcc gag gag cga tac act ta         1794
Ile Asp Glu Ala Thr Glu Val Pro Ala Glu Glu Arg Tyr Thr Tyr
        530                 535                 540 gtacgtggat tctgtctgtt gctgatggaa aaagacattc tgaccagggg acag c gca   1852
                                                             Ala tat gac atg aat gct caa gcc ctc gac cac att ttc atc agc cct gcg    1900
Tyr Asp Met Asn Ala Gln Ala Leu Asp His Ile Phe Ile Ser Pro Ala
        545                 550                 555 ctc gct ctt agc aag acc acg cgt gtc gac cac ctc cac ctc aac tcc    1948
Leu Ala Leu Ser Lys Thr Thr Arg Val Asp His Leu His Leu Asn Ser
560                 565                 570                 575 tgg gct gcc tat gat gac gtt gtg tcg gat cac gac ccg agc att gcc    1996
Trp Ala Ala Tyr Asp Asp Val Val Ser Asp His Asp Pro Ser Ile Ala
                580                 585                 590 ttg ttg gac gta tgc ggt tgt tga                                    2020
Leu Leu Asp Val Cys Gly Cys
            595

<210> SEQ ID NO 65
<211> LENGTH: 618
<212> TYPE: PRT
<213> ORGANISM: Chaetomium luteum

<400> SEQUENCE: 65

Met Arg Leu Ala Pro Val Phe Cys Trp Val Phe Val Ser Phe Gln Ser
```

```
        -20              -15              -10               -5
Leu Thr Ala Ala Leu Thr Ile Ser Glu Ile Asn Gly Asn Lys Phe Ile
           -1  1                  5                  10

Ser Pro Tyr Ser Gly Lys Ser Val Thr Asn Val Thr Gly Leu Leu Ile
            15                  20                  25

Ala Lys Gly Pro Asn Gly Ile Trp Ile Arg Ser Thr Thr Pro Asp Asp
            30                  35                  40

Asp Lys Thr Thr Ser Glu Ala Val Tyr Val Phe Ser Ser Ser Val Gly
 45                  50                  55                  60

Ile Asn Leu Thr Val Gly Asp Ile Ile Ser Leu Asp Gly Lys Val Ser
                65                  70                  75

Glu Tyr Arg Ser Ser Ser Tyr Ile Tyr Leu Thr Glu Ile Thr Ser
            80                  85                  90

Pro Lys Asn Val His Ile Leu Ser Ser Gly Asn Thr Val Thr Pro Leu
            95                 100                 105

Ile Ile Gly Lys Asp Thr Leu Ser Pro Pro Thr Val Gln Tyr Ser Asn
           110                 115                 120

Leu Asp Gly Gly Asp Ile Tyr Ser Leu Pro Asn Ala Val Ala Asn Ile
125                 130                 135                 140

Ser Glu Val Asn Pro Val Leu Asp Pro Ala Lys Tyr Gly Leu Asp Phe
                145                 150                 155

Trp Glu Ser Leu Ser Gly Glu Leu Val Thr Ile Asn Lys Pro Gln Ala
            160                 165                 170

Ile Lys Thr Pro Asn Glu Tyr Gly Asp Thr Trp Val Val Gly Asp Trp
            175                 180                 185

Ala Val Thr Gly Lys Asn Lys His Gly Gly Leu Thr Met Ser Asp Lys
            190                 195                 200

Asp Ser Asn Pro Glu Ala Ile Ile Gly Thr Pro Leu Asp Gly Thr
205                 210                 215                 220

Lys Asn Pro Thr Ile Ser Lys Met Gly Asp Gln Phe Glu Asp Ile Thr
                225                 230                 235

Gly Ile Val Gln Gln Thr Phe Gly Phe Tyr Asn Ile Leu Pro Leu Thr
            240                 245                 250

Ala Leu Lys Thr Thr Ser Ser Ala Ser Ala Ser Val Ser Pro Thr Phe
            255                 260                 265

Leu Leu Ser His Gly Lys Cys Lys Ala Leu Thr Val Gly Ser Tyr Asn
            270                 275                 280

Val Glu Asn Met Ala Pro Thr Ser Ser His Leu Pro Lys Val Ala Ala
285                 290                 295                 300

His Ile Val Asp Tyr Leu Lys Thr Pro Asp Leu Met Phe Val Gln Glu
                305                 310                 315

Ile Gln Asp Asn Ser Gly Pro Thr Asn Asp Gly Ile Val Ser Ala Asn
            320                 325                 330

Ala Thr Ile Thr Ala Leu Val Lys Ala Ile Lys Thr Leu Ser Gly Val
            335                 340                 345

Thr Tyr Ala Trp Thr Asp Ile Asp Pro Val Ser Asn Glu Asp Gly Gly
            350                 355                 360

Gln Pro Gly Gly Asn Ile Arg Gln Ala Tyr Leu Tyr Arg Pro Glu Val
365                 370                 375                 380

Leu Ser Leu Tyr Glu Ala Asn Pro Gly Gly Ser Asn Asp Ala Thr Glu
                385                 390                 395

Val Val Pro Ala Glu Gly Lys Gly Lys Gly Phe Gly Gly Ala Pro Thr
            400                 405                 410
```

```
Leu Ser Phe Asn Pro Gly Arg Ile Asp Pro Ala Asn Ala Ala Trp Lys
            415                 420                 425

Asn Ser Arg Lys Pro Leu Ala Ala Val Trp Lys Ala Lys Gly Ala Lys
        430                 435                 440

Arg Pro Phe Tyr Thr Val Asn Val His Trp Ser Ser Lys Gly Gly Gly
445                 450                 455                 460

Thr Ser Leu His Gly Asp Val Arg Pro Ile Asn Gly Ala Val Glu
                465                 470                 475

Ala Arg Met Ala Gln Ala Asn Val Thr Gly Ser Phe Ile Ala Lys Ile
                480                 485                 490

Leu Ala Leu Asp Pro Thr Ala Asn Ile Ile Ala Ala Gly Asp Phe Asn
            495                 500                 505

Glu Phe Ser Phe Val Gln Pro Leu Lys Met Phe Ser Thr Ile Ser Lys
        510                 515                 520

Met Val Asp Ile Asp Glu Ala Thr Glu Val Pro Ala Glu Glu Arg Tyr
525                 530                 535                 540

Thr Tyr Ala Tyr Asp Met Asn Ala Gln Ala Leu Asp His Ile Phe Ile
                545                 550                 555

Ser Pro Ala Leu Ala Leu Ser Lys Thr Thr Arg Val Asp His Leu His
            560                 565                 570

Leu Asn Ser Trp Ala Ala Tyr Asp Asp Val Val Ser Asp His Asp Pro
        575                 580                 585

Ser Ile Ala Leu Leu Asp Val Cys Gly Cys
590                 595

<210> SEQ ID NO 66
<211> LENGTH: 598
<212> TYPE: PRT
<213> ORGANISM: Chaetomium luteum

<400> SEQUENCE: 66

Leu Thr Ile Ser Glu Ile Asn Gly Asn Lys Phe Ile Ser Pro Tyr Ser
1               5                   10                  15

Gly Lys Ser Val Thr Asn Val Thr Gly Leu Leu Ile Ala Lys Gly Pro
                20                  25                  30

Asn Gly Ile Trp Ile Arg Ser Thr Thr Pro Asp Asp Asp Lys Thr Thr
            35                  40                  45

Ser Glu Ala Val Tyr Val Phe Ser Ser Ser Val Gly Ile Asn Leu Thr
        50                  55                  60

Val Gly Asp Ile Ile Ser Leu Asp Gly Lys Val Ser Glu Tyr Arg Ser
65                  70                  75                  80

Ser Ser Ser Tyr Ile Tyr Leu Thr Glu Ile Thr Ser Pro Lys Asn Val
                85                  90                  95

His Ile Leu Ser Ser Gly Asn Thr Val Thr Pro Leu Ile Ile Gly Lys
                100                 105                 110

Asp Thr Leu Ser Pro Pro Thr Val Gln Tyr Ser Asn Leu Asp Gly Gly
            115                 120                 125

Asp Ile Tyr Ser Leu Pro Asn Ala Val Ala Asn Ile Ser Glu Val Asn
        130                 135                 140

Pro Val Leu Asp Pro Ala Lys Tyr Gly Leu Asp Phe Trp Glu Ser Leu
145                 150                 155                 160

Ser Gly Glu Leu Val Thr Ile Asn Lys Pro Gln Ala Ile Lys Thr Pro
                165                 170                 175

Asn Glu Tyr Gly Asp Thr Trp Val Val Gly Asp Trp Ala Val Thr Gly
```

```
            180                 185                 190
Lys Asn Lys His Gly Leu Thr Met Ser Asp Lys Asp Ser Asn Pro
            195                 200             205
Glu Ala Ile Ile Ile Gly Thr Pro Leu Asp Gly Thr Lys Asn Pro Thr
        210                 215                 220
Ile Ser Lys Met Gly Asp Gln Phe Glu Asp Ile Thr Gly Ile Val Gln
225                 230                 235                 240
Gln Thr Phe Gly Phe Tyr Asn Ile Leu Pro Leu Thr Ala Leu Lys Thr
                245                 250                 255
Thr Ser Ser Ala Ser Ala Ser Val Ser Pro Thr Phe Leu Leu Ser His
            260                 265                 270
Gly Lys Cys Lys Ala Leu Thr Val Gly Ser Tyr Asn Val Glu Asn Met
        275                 280                 285
Ala Pro Thr Ser Ser His Leu Pro Lys Val Ala His Ile Val Asp
        290                 295                 300
Tyr Leu Lys Thr Pro Asp Leu Met Phe Val Gln Glu Ile Gln Asp Asn
305                 310                 315                 320
Ser Gly Pro Thr Asn Asp Gly Ile Val Ser Ala Asn Ala Thr Ile Thr
                325                 330                 335
Ala Leu Val Lys Ala Ile Lys Thr Leu Ser Gly Val Thr Tyr Ala Trp
            340                 345                 350
Thr Asp Ile Asp Pro Val Ser Asn Glu Asp Gly Gln Pro Gly Gly
        355                 360                 365
Asn Ile Arg Gln Ala Tyr Leu Tyr Arg Pro Glu Val Leu Ser Leu Tyr
370                 375                 380
Glu Ala Asn Pro Gly Gly Ser Asn Asp Ala Thr Glu Val Val Pro Ala
385                 390                 395                 400
Glu Gly Lys Gly Lys Gly Phe Gly Gly Ala Pro Thr Leu Ser Phe Asn
                405                 410                 415
Pro Gly Arg Ile Asp Pro Ala Asn Ala Ala Trp Lys Asn Ser Arg Lys
            420                 425                 430
Pro Leu Ala Ala Val Trp Lys Ala Lys Gly Ala Lys Arg Pro Phe Tyr
        435                 440                 445
Thr Val Asn Val His Trp Ser Ser Lys Gly Gly Thr Ser Leu His
        450                 455                 460
Gly Asp Val Arg Pro Pro Ile Asn Gly Ala Val Glu Ala Arg Met Ala
465                 470                 475                 480
Gln Ala Asn Val Thr Gly Ser Phe Ile Ala Lys Ile Leu Ala Leu Asp
                485                 490                 495
Pro Thr Ala Asn Ile Ile Ala Ala Gly Asp Phe Asn Glu Phe Ser Phe
            500                 505                 510
Val Gln Pro Leu Lys Met Phe Ser Thr Ile Ser Lys Met Val Asp Ile
        515                 520                 525
Asp Glu Ala Thr Glu Val Pro Ala Glu Arg Tyr Thr Tyr Ala Tyr
        530                 535                 540
Asp Met Asn Ala Gln Ala Leu Asp His Ile Phe Ile Ser Pro Ala Leu
545                 550                 555                 560
Ala Leu Ser Lys Thr Thr Arg Val Asp His Leu His Leu Asn Ser Trp
                565                 570                 575
Ala Ala Tyr Asp Asp Val Val Ser Asp His Asp Pro Ser Ile Ala Leu
            580                 585                 590
Leu Asp Val Cys Gly Cys
            595
```

```
<210> SEQ ID NO 67
<211> LENGTH: 2054
<212> TYPE: DNA
<213> ORGANISM: Arthrinium arundinis
<220> FEATURE:
<221> NAME/KEY: CDS
<222> LOCATION: (1)..(679)
<220> FEATURE:
<221> NAME/KEY: sig_peptide
<222> LOCATION: (1)..(60)
<220> FEATURE:
<221> NAME/KEY: mat_peptide
<222> LOCATION: (61)..(2051)
<220> FEATURE:
<221> NAME/KEY: CDS
<222> LOCATION: (736)..(1559)
<220> FEATURE:
<221> NAME/KEY: CDS
<222> LOCATION: (1638)..(1845)
<220> FEATURE:
<221> NAME/KEY: CDS
<222> LOCATION: (1927)..(2051)

<400> SEQUENCE: 67
```

| | | | | | | | | | | | | | | | | |
|---|---|---|---|---|---|---|---|---|---|---|---|---|---|---|---|---|
| atg | aag | ggc | ggt | tct | ctg | ttg | tcg | tgg | ctc | acc | acc | acc | ttg | gtc | gcc | 48 |
| Met | Lys | Gly | Gly | Ser | Leu | Leu | Ser | Trp | Leu | Thr | Thr | Thr | Leu | Val | Ala | |
| -20 | | | | | -15 | | | | | -10 | | | | | -5 | |

| | | | | | | | | | | | | | | | | |
|---|---|---|---|---|---|---|---|---|---|---|---|---|---|---|---|---|
| ggg | gtt | tcg | gcg | ctc | acc | att | gga | gag | atc | aac | ggc | aac | cgg | ttc | ttg | 96 |
| Gly | Val | Ser | Ala | Leu | Thr | Ile | Gly | Glu | Ile | Asn | Gly | Asn | Arg | Phe | Leu | |
| | | -1 | 1 | | | | | 5 | | | | | | 10 | | |

| | | | | | | | | | | | | | | | | |
|---|---|---|---|---|---|---|---|---|---|---|---|---|---|---|---|---|
| tct | cct | tac | aat | ggc | cag | gac | gtc | tcc | aac | gtg | acg | ggc | atc | gtg | acg | 144 |
| Ser | Pro | Tyr | Asn | Gly | Gln | Asp | Val | Ser | Asn | Val | Thr | Gly | Ile | Val | Thr | |
| | | 15 | | | | | 20 | | | | | 25 | | | | |

| | | | | | | | | | | | | | | | | |
|---|---|---|---|---|---|---|---|---|---|---|---|---|---|---|---|---|
| gca | aag | ggc | ccc | gac | ggt | ctt | tgg | gtc | cga | tcc | gtc | aga | aaa | ggt | tgc | 192 |
| Ala | Lys | Gly | Pro | Asp | Gly | Leu | Trp | Val | Arg | Ser | Val | Arg | Lys | Gly | Cys | |
| | 30 | | | | | 35 | | | | | 40 | | | | | |

| | | | | | | | | | | | | | | | | |
|---|---|---|---|---|---|---|---|---|---|---|---|---|---|---|---|---|
| gac | aga | cgc | gtc | tcg | gac | gct | gtc | tac | ata | tat | ggc | tct | gcc | ctc | gcc | 240 |
| Asp | Arg | Arg | Val | Ser | Asp | Ala | Val | Tyr | Ile | Tyr | Gly | Ser | Ala | Leu | Ala | |
| 45 | | | | | 50 | | | | | 55 | | | | | 60 | |

| | | | | | | | | | | | | | | | | |
|---|---|---|---|---|---|---|---|---|---|---|---|---|---|---|---|---|
| acg | aac | gcc | tcc | atc | agc | acg | ggc | gat | gtt | gtc | gtt | ctg | agc | ggt | aaa | 288 |
| Thr | Asn | Ala | Ser | Ile | Ser | Thr | Gly | Asp | Val | Val | Val | Leu | Ser | Gly | Lys | |
| | | | | 65 | | | | | 70 | | | | | 75 | | |

| | | | | | | | | | | | | | | | | |
|---|---|---|---|---|---|---|---|---|---|---|---|---|---|---|---|---|
| gtc | agc | gag | tac | aga | tca | aac | aag | gac | tac | ctg | tac | atg | acc | cag | atc | 336 |
| Val | Ser | Glu | Tyr | Arg | Ser | Asn | Lys | Asp | Tyr | Leu | Tyr | Met | Thr | Gln | Ile | |
| | | | 80 | | | | | 85 | | | | | 90 | | | |

| | | | | | | | | | | | | | | | | |
|---|---|---|---|---|---|---|---|---|---|---|---|---|---|---|---|---|
| acg | tcg | cca | aag | gtc | gca | gcc | att | cta | gaa | cat | ggc | aag | caa | gtc | gtg | 384 |
| Thr | Ser | Pro | Lys | Val | Ala | Ala | Ile | Leu | Glu | His | Gly | Lys | Gln | Val | Val | |
| | | | 95 | | | | | 100 | | | | | 105 | | | |

| | | | | | | | | | | | | | | | | |
|---|---|---|---|---|---|---|---|---|---|---|---|---|---|---|---|---|
| ccg | aag | gtc | att | ggc | aaa | gat | acg | tac | agc | cca | ccc | acg | gtg | cag | tac | 432 |
| Pro | Lys | Val | Ile | Gly | Lys | Asp | Thr | Tyr | Ser | Pro | Pro | Thr | Val | Gln | Tyr | |
| | 110 | | | | | 115 | | | | | 120 | | | | | |

| | | | | | | | | | | | | | | | | |
|---|---|---|---|---|---|---|---|---|---|---|---|---|---|---|---|---|
| aca | agc | ctt | gac | gaa | ggc | gat | atc | ttt | gcg | gtc | ccg | aac | aac | aaa | agc | 480 |
| Thr | Ser | Leu | Asp | Glu | Gly | Asp | Ile | Phe | Ala | Val | Pro | Asn | Asn | Lys | Ser | |
| 125 | | | | | 130 | | | | | 135 | | | | | 140 | |

| | | | | | | | | | | | | | | | | |
|---|---|---|---|---|---|---|---|---|---|---|---|---|---|---|---|---|
| ctt | gtc | tcg | gtg | gcg | aat | ccg | gtg | ttg | gag | ccc | gaa | aag | tac | ggc | ctg | 528 |
| Leu | Val | Ser | Val | Ala | Asn | Pro | Val | Leu | Glu | Pro | Glu | Lys | Tyr | Gly | Leu | |
| | | | | 145 | | | | | 150 | | | | | 155 | | |

| | | | | | | | | | | | | | | | | |
|---|---|---|---|---|---|---|---|---|---|---|---|---|---|---|---|---|
| gac | ttc | tgg | gag | agc | cta | tcg | ggc | caa | ttg | gta | aca | gtc | aag | agc | ccg | 576 |
| Asp | Phe | Trp | Glu | Ser | Leu | Ser | Gly | Gln | Leu | Val | Thr | Val | Lys | Ser | Pro | |
| | | | 160 | | | | | 165 | | | | | 170 | | | |

| | | | | | | | | | | | | | | | | |
|---|---|---|---|---|---|---|---|---|---|---|---|---|---|---|---|---|
| cga | gct | att | ggt | cga | ccg | aac | aaa | tac | ggt | gat | acc | tgg | gtt | gtg | ggc | 624 |
| Arg | Ala | Ile | Gly | Arg | Pro | Asn | Lys | Tyr | Gly | Asp | Thr | Trp | Val | Val | Gly | |
| | | 175 | | | | | 180 | | | | | 185 | | | | |

-continued

```
gat tgg aaa aca tcg ggc gag aat ggc cga ggg ggt cta act act atg      672
Asp Trp Lys Thr Ser Gly Glu Asn Gly Arg Gly Gly Leu Thr Thr Met
        190                 195                 200 tct atg g gtaagttatt aactgcaggc aattatttga ctacggagaa ctgatacaaa     729
Ser Met
205 gcacag at   agc aat ccc gag gga att gtc atc ggc tcg cct ttg gac      776
            Asp Ser Asn Pro Glu Gly Ile Val Ile Gly Ser Pro Leu Asp
                        210                 215                 220 gga tcc aag aac ccc aac gat acc aag ctc gga gac acc ctg gaa gac      824
Gly Ser Lys Asn Pro Asn Asp Thr Lys Leu Gly Asp Thr Leu Glu Asp
                225                 230                 235 atc acg ggc gtg gtg tat cag gca ttt ggc ttc tac aga atc ctg ccg      872
Ile Thr Gly Val Val Tyr Gln Ala Phe Gly Phe Tyr Arg Ile Leu Pro
            240                 245                 250 ctg acc aaa gtc gcc gtg gtt gcc tcc cag gag cct gca atg ccc cct      920
Leu Thr Lys Val Ala Val Val Ala Ser Gln Glu Pro Ala Met Pro Pro
        255                 260                 265 ccg aca tca ctg acc agc gat ggt gtg tgc tcc ggc ttg acc atc ggc      968
Pro Thr Ser Leu Thr Ser Asp Gly Val Cys Ser Gly Leu Thr Ile Gly
    270                 275                 280 tcg tac aat atc gaa aac ttc tgg cca ggc gac aca gct cac gtc caa     1016
Ser Tyr Asn Ile Glu Asn Phe Trp Pro Gly Asp Thr Ala His Val Gln
285                 290                 295                 300 gcc gtc gcc cac cac att gtt gac tac ctc aag acg ccc gat ctg gtc     1064
Ala Val Ala His His Ile Val Asp Tyr Leu Lys Thr Pro Asp Leu Val
                305                 310                 315 ttc ctg caa gag gtc cag gat gac aac ggg gcg act gat gac ggg acc     1112
Phe Leu Gln Glu Val Gln Asp Asp Asn Gly Ala Thr Asp Asp Gly Thr
            320                 325                 330 gtg agc tcg gac cta acc tta tcg acc ctg gcc gcc gct atc gag aag     1160
Val Ser Ser Asp Leu Thr Leu Ser Thr Leu Ala Ala Ala Ile Glu Lys
        335                 340                 345 gcg agt ggg ggc atc gga tac aac ttc acc tat gtc gcg ccc atc aac     1208
Ala Ser Gly Gly Ile Gly Tyr Asn Phe Thr Tyr Val Ala Pro Ile Asn
    350                 355                 360 aag aag gac ggc ggc gcc ccg ggt ggc aac atc cgc act gcg tac ctg     1256
Lys Lys Asp Gly Gly Ala Pro Gly Gly Asn Ile Arg Thr Ala Tyr Leu
365                 370                 375                 380 ttc cgc cga gat gtc ctg acg ctg cgg gac ccc aac ccg gct gac tcg     1304
Phe Arg Arg Asp Val Leu Thr Leu Arg Asp Pro Asn Pro Ala Asp Ser
                385                 390                 395 acc act gct aat gaa gtc ttg tcc ggc ggt gcg ctc aag tac aac ccg     1352
Thr Thr Ala Asn Glu Val Leu Ser Gly Gly Ala Leu Lys Tyr Asn Pro
            400                 405                 410 ggc cta atc gac cct acc aat gcg gcc ttc acc aat agt cgt aag cct     1400
Gly Leu Ile Asp Pro Thr Asn Ala Ala Phe Thr Asn Ser Arg Lys Pro
        415                 420                 425 ctc acc gca gcg tgg cag acg ctg gat ggc aac agc acc ttc tac acc     1448
Leu Thr Ala Ala Trp Gln Thr Leu Asp Gly Asn Ser Thr Phe Tyr Thr
    430                 435                 440 gtc aat gtg cac tgg ggc tct aag ggt ggc tcc tca tct atc cat ggc     1496
Val Asn Val His Trp Gly Ser Lys Gly Gly Ser Ser Ser Ile His Gly
445                 450                 455                 460 gat gct cgc cct cct gta aat ggc ggt gtc aag gat cgc att gcg caa     1544
Asp Ala Arg Pro Pro Val Asn Gly Gly Val Lys Asp Arg Ile Ala Gln
                465                 470                 475 gcg gcg gtt act gca gtatgtccct cttacctctt ttcctctcga aacccccaat    1599
Ala Ala Val Thr Ala
            480
```

```
cgcttgtgac gtcccaattg acatcccttt cctaacag aac ttc att gcc gca att    1655
                                         Asn Phe Ile Ala Ala Ile
                                                     485 ctg gcg gag gac cct gag gcc cac atc atc acg tcg ggc gac ttc aac     1703
Leu Ala Glu Asp Pro Glu Ala His Ile Ile Thr Ser Gly Asp Phe Asn
        490                 495                 500 gag tac ccg ttc gtc aag ccc atc acc gac ttc gag tcg cgt tcc aag     1751
Glu Tyr Pro Phe Val Lys Pro Ile Thr Asp Phe Glu Ser Arg Ser Lys
    505                 510                 515 atg gag gac ctc gat gtt gtc gcc ggc atc gat cct gtc gag cgc tac     1799
Met Glu Asp Leu Asp Val Val Ala Gly Ile Asp Pro Val Glu Arg Tyr
520                 525                 530                 535 agc tac ttg tac gac atg aac acc cag gag ctg gac cac atg ttt g       1845
Ser Tyr Leu Tyr Asp Met Asn Thr Gln Glu Leu Asp His Met Phe
                540                 545                 550 gtaagtaccc atcatcgatg attcaacgtt ctctatccta gaaagagaag tactctgctg   1905
acccactccg atgttgtgaa g tg agc cca gca ctg gcg aag acg aag ccc      1955
                       Val Ser Pro Ala Leu Ala Lys Thr Lys Pro
                                       555                 560 cag ttc gag cat atc cac gtc aat acg tgg atc gcg tac gac gac atg     2003
Gln Phe Glu His Ile His Val Asn Thr Trp Ile Ala Tyr Asp Asp Met
                565                 570                 575 gtc tca gac cat gac ccg agt gtg gct aag atg aat ctt tgc aag tat     2051
Val Ser Asp His Asp Pro Ser Val Ala Lys Met Asn Leu Cys Lys Tyr
                580                 585                 590 taa                                                                 2054

<210> SEQ ID NO 68
<211> LENGTH: 612
<212> TYPE: PRT
<213> ORGANISM: Arthrinium arundinis

<400> SEQUENCE: 68

Met Lys Gly Gly Ser Leu Leu Ser Trp Leu Thr Thr Leu Val Ala
-20                 -15                 -10                 -5

Gly Val Ser Ala Leu Thr Ile Gly Glu Ile Asn Gly Asn Arg Phe Leu
            -1  1                 5                  10

Ser Pro Tyr Asn Gly Gln Asp Val Ser Asn Val Thr Gly Ile Val Thr
        15                  20                  25

Ala Lys Gly Pro Asp Gly Leu Trp Val Arg Ser Val Arg Lys Gly Cys
    30                  35                  40

Asp Arg Arg Val Ser Asp Ala Val Tyr Ile Tyr Gly Ser Ala Leu Ala
45                  50                  55                  60

Thr Asn Ala Ser Ile Ser Thr Gly Asp Val Val Leu Ser Gly Lys
                65                  70                  75

Val Ser Glu Tyr Arg Ser Asn Lys Asp Tyr Leu Tyr Met Thr Gln Ile
            80                  85                  90

Thr Ser Pro Lys Val Ala Ala Ile Leu Glu His Gly Lys Gln Val Val
        95                  100                 105

Pro Lys Val Ile Gly Lys Asp Thr Tyr Ser Pro Pro Thr Val Gln Tyr
    110                 115                 120

Thr Ser Leu Asp Glu Gly Asp Ile Phe Ala Val Pro Asn Asn Lys Ser
125                 130                 135                 140

Leu Val Ser Val Ala Asn Pro Val Leu Glu Pro Glu Lys Tyr Gly Leu
                145                 150                 155

Asp Phe Trp Glu Ser Leu Ser Gly Gln Leu Val Thr Val Lys Ser Pro
```

```
                160                 165                 170
Arg Ala Ile Gly Arg Pro Asn Lys Tyr Gly Asp Thr Trp Val Val Gly
            175                 180                 185

Asp Trp Lys Thr Ser Gly Glu Asn Gly Arg Gly Leu Thr Thr Met
        190                 195                 200

Ser Met Asp Ser Asn Pro Glu Gly Ile Val Ile Gly Ser Pro Leu Asp
205                 210                 215                 220

Gly Ser Lys Asn Pro Asn Asp Thr Lys Leu Gly Asp Thr Leu Glu Asp
                225                 230                 235

Ile Thr Gly Val Val Tyr Gln Ala Phe Gly Phe Tyr Arg Ile Leu Pro
            240                 245                 250

Leu Thr Lys Val Ala Val Ala Ser Gln Glu Pro Ala Met Pro Pro
        255                 260                 265

Pro Thr Ser Leu Thr Ser Asp Gly Val Cys Ser Gly Leu Thr Ile Gly
    270                 275                 280

Ser Tyr Asn Ile Glu Asn Phe Trp Pro Gly Asp Thr Ala His Val Gln
285                 290                 295                 300

Ala Val Ala His His Ile Val Asp Tyr Leu Lys Thr Pro Asp Leu Val
                305                 310                 315

Phe Leu Gln Glu Val Gln Asp Asn Gly Ala Thr Asp Gly Thr
            320                 325                 330

Val Ser Asp Leu Thr Leu Ser Thr Leu Ala Ala Ile Glu Lys
        335                 340                 345

Ala Ser Gly Gly Ile Gly Tyr Asn Phe Thr Tyr Val Ala Pro Ile Asn
    350                 355                 360

Lys Lys Asp Gly Gly Ala Pro Gly Gly Asn Ile Arg Thr Ala Tyr Leu
365                 370                 375                 380

Phe Arg Arg Asp Val Leu Thr Leu Arg Asp Pro Asn Pro Ala Asp Ser
                385                 390                 395

Thr Thr Ala Asn Glu Val Leu Ser Gly Gly Ala Leu Lys Tyr Asn Pro
            400                 405                 410

Gly Leu Ile Asp Pro Thr Asn Ala Ala Phe Thr Asn Ser Arg Lys Pro
        415                 420                 425

Leu Thr Ala Ala Trp Gln Thr Leu Asp Gly Asn Ser Thr Phe Tyr Thr
    430                 435                 440

Val Asn Val His Trp Gly Ser Lys Gly Gly Ser Ser Ile His Gly
445                 450                 455                 460

Asp Ala Arg Pro Pro Val Asn Gly Gly Val Lys Asp Arg Ile Ala Gln
                465                 470                 475

Ala Ala Val Thr Ala Asn Phe Ile Ala Ala Ile Leu Ala Glu Asp Pro
            480                 485                 490

Glu Ala His Ile Ile Thr Ser Gly Asp Phe Asn Glu Tyr Pro Phe Val
        495                 500                 505

Lys Pro Ile Thr Asp Phe Glu Ser Arg Ser Lys Met Glu Asp Leu Asp
    510                 515                 520

Val Val Ala Gly Ile Asp Pro Val Glu Arg Tyr Ser Tyr Leu Tyr Asp
525                 530                 535                 540

Met Asn Thr Gln Glu Leu Asp His Met Phe Val Ser Pro Ala Leu Ala
                545                 550                 555

Lys Thr Lys Pro Gln Phe Glu His Ile His Val Asn Thr Trp Ile Ala
            560                 565                 570

Tyr Asp Asp Met Val Ser Asp His Asp Pro Ser Val Ala Lys Met Asn
        575                 580                 585
```

Leu Cys Lys Tyr
    590

<210> SEQ ID NO 69
<211> LENGTH: 592
<212> TYPE: PRT
<213> ORGANISM: Arthrinium arundinis

<400> SEQUENCE: 69

Leu Thr Ile Gly Glu Ile Asn Gly Asn Arg Phe Leu Ser Pro Tyr Asn
1               5                   10                  15

Gly Gln Asp Val Ser Asn Val Thr Gly Ile Val Thr Ala Lys Gly Pro
            20                  25                  30

Asp Gly Leu Trp Val Arg Ser Val Arg Lys Gly Cys Asp Arg Arg Val
        35                  40                  45

Ser Asp Ala Val Tyr Ile Tyr Gly Ser Ala Leu Ala Thr Asn Ala Ser
    50                  55                  60

Ile Ser Thr Gly Asp Val Val Leu Ser Gly Lys Val Ser Glu Tyr
65                  70                  75                  80

Arg Ser Asn Lys Asp Tyr Leu Tyr Met Thr Gln Ile Thr Ser Pro Lys
                85                  90                  95

Val Ala Ala Ile Leu Glu His Gly Lys Gln Val Val Pro Lys Val Ile
            100                 105                 110

Gly Lys Asp Thr Tyr Ser Pro Pro Thr Val Gln Tyr Thr Ser Leu Asp
        115                 120                 125

Glu Gly Asp Ile Phe Ala Val Pro Asn Asn Lys Ser Leu Val Ser Val
    130                 135                 140

Ala Asn Pro Val Leu Glu Pro Glu Lys Tyr Gly Leu Asp Phe Trp Glu
145                 150                 155                 160

Ser Leu Ser Gly Gln Leu Val Thr Val Lys Ser Pro Arg Ala Ile Gly
                165                 170                 175

Arg Pro Asn Lys Tyr Gly Asp Thr Trp Val Val Gly Asp Trp Lys Thr
            180                 185                 190

Ser Gly Glu Asn Gly Arg Gly Gly Leu Thr Thr Met Ser Met Asp Ser
        195                 200                 205

Asn Pro Glu Gly Ile Val Ile Gly Ser Pro Leu Asp Gly Ser Lys Asn
    210                 215                 220

Pro Asn Asp Thr Lys Leu Gly Asp Thr Leu Glu Asp Ile Thr Gly Val
225                 230                 235                 240

Val Tyr Gln Ala Phe Gly Phe Tyr Arg Ile Leu Pro Leu Thr Lys Val
                245                 250                 255

Ala Val Val Ala Ser Gln Glu Pro Ala Met Pro Pro Thr Ser Leu
            260                 265                 270

Thr Ser Asp Gly Val Cys Ser Gly Leu Thr Ile Gly Ser Tyr Asn Ile
        275                 280                 285

Glu Asn Phe Trp Pro Gly Asp Thr Ala His Val Gln Ala Val Ala His
    290                 295                 300

His Ile Val Asp Tyr Leu Lys Thr Pro Asp Leu Val Phe Leu Gln Glu
305                 310                 315                 320

Val Gln Asp Asp Asn Gly Ala Thr Asp Gly Thr Val Ser Ser Asp
                325                 330                 335

Leu Thr Leu Ser Thr Leu Ala Ala Ala Ile Glu Lys Ala Ser Gly Gly
            340                 345                 350

Ile Gly Tyr Asn Phe Thr Tyr Val Ala Pro Ile Asn Lys Lys Asp Gly

```
                355                 360                 365
Gly Ala Pro Gly Gly Asn Ile Arg Thr Ala Tyr Leu Phe Arg Arg Asp
            370                 375                 380

Val Leu Thr Leu Arg Asp Pro Asn Pro Ala Asp Ser Thr Thr Ala Asn
385                 390                 395                 400

Glu Val Leu Ser Gly Gly Ala Leu Lys Tyr Asn Pro Gly Leu Ile Asp
                405                 410                 415

Pro Thr Asn Ala Ala Phe Thr Asn Ser Arg Lys Pro Leu Thr Ala Ala
            420                 425                 430

Trp Gln Thr Leu Asp Gly Asn Ser Thr Phe Tyr Thr Val Asn Val His
            435                 440                 445

Trp Gly Ser Lys Gly Gly Ser Ser Ile His Gly Asp Ala Arg Pro
        450                 455                 460

Pro Val Asn Gly Gly Val Lys Asp Arg Ile Ala Gln Ala Ala Val Thr
465                 470                 475                 480

Ala Asn Phe Ile Ala Ala Ile Leu Ala Glu Asp Pro Glu Ala His Ile
                485                 490                 495

Ile Thr Ser Gly Asp Phe Asn Glu Tyr Pro Phe Val Lys Pro Ile Thr
            500                 505                 510

Asp Phe Glu Ser Arg Ser Lys Met Glu Asp Leu Asp Val Val Ala Gly
            515                 520                 525

Ile Asp Pro Val Glu Arg Tyr Ser Tyr Leu Tyr Asp Met Asn Thr Gln
530                 535                 540

Glu Leu Asp His Met Phe Val Ser Pro Ala Leu Ala Lys Thr Lys Pro
545                 550                 555                 560

Gln Phe Glu His Ile His Val Asn Thr Trp Ile Ala Tyr Asp Asp Met
                565                 570                 575

Val Ser Asp His Asp Pro Ser Val Ala Lys Met Asn Leu Cys Lys Tyr
            580                 585                 590

<210> SEQ ID NO 70
<211> LENGTH: 2349
<212> TYPE: DNA
<213> ORGANISM: Phialophora geniculate
<220> FEATURE:
<221> NAME/KEY: CDS
<222> LOCATION: (1)..(2346)
<220> FEATURE:
<221> NAME/KEY: sig_peptide
<222> LOCATION: (1)..(48)
<220> FEATURE:
<221> NAME/KEY: mat_peptide
<222> LOCATION: (49)..(2346)

<400> SEQUENCE: 70 atg cag agt ctg ttg gcc ttg ctc gcc ctc ggc act gcg gtg caa gcc      48
Met Gln Ser Leu Leu Ala Leu Leu Ala Leu Gly Thr Ala Val Gln Ala
    -15                 -10                 -5                  -1 cag agc atc cat gcc atc aat ggc aag aat ttc ctg tcg cca tat aat      96
Gln Ser Ile His Ala Ile Asn Gly Lys Asn Phe Leu Ser Pro Tyr Asn
1               5                   10                  15 ggg gct ttg gtc acc aat gtc aca ggt atc gtg acc gcc aag gcc tca     144
Gly Ala Leu Val Thr Asn Val Thr Gly Ile Val Thr Ala Lys Ala Ser
            20                  25                  30 aat ggc ttg tac ctc cgc agc ccg aag ccc gca tgc gat gtc cgc atc     192
Asn Gly Leu Tyr Leu Arg Ser Pro Lys Pro Ala Cys Asp Val Arg Ile
        35                  40                  45 ggg aac ggt ctg gtc gtc tac gac tca act atc ggt aag aac gag tct     240
Gly Asn Gly Leu Val Val Tyr Asp Ser Thr Ile Gly Lys Asn Glu Ser
```

-continued

```
            50                  55                  60
atc gcc gtc ggc gac acg ctg gtt ctg agc ggg aag atc acg gaa tat     288
Ile Ala Val Gly Asp Thr Leu Val Leu Ser Gly Lys Ile Thr Glu Tyr
65                  70                  75                  80 cgc tcg act gcg acc tat ctc tat ctg act gag ctg gag tca ccc gtc     336
Arg Ser Thr Ala Thr Tyr Leu Tyr Leu Thr Glu Leu Glu Ser Pro Val
                85                  90                  95 gtc cag agt tgg gtc aag gga gaa acg gcg ccg aag cct cgc gtc atc     384
Val Gln Ser Trp Val Lys Gly Glu Thr Ala Pro Lys Pro Arg Val Ile
            100                 105                 110 ggc aca gac acg atg agt cct cct acc gag cac ttt acc ggt ctg gac     432
Gly Thr Asp Thr Met Ser Pro Pro Thr Glu His Phe Thr Gly Leu Asp
    115                 120                 125 aat ggc gac gtc ttc ggg ata ccc aac gac gac agc cgt att tcg gtt     480
Asn Gly Asp Val Phe Gly Ile Pro Asn Asp Asp Ser Arg Ile Ser Val
130                 135                 140 gtc aac ccg gaa ctg cag ccc gac aaa tac ggc ctc gac ttc tgg aag     528
Val Asn Pro Glu Leu Gln Pro Asp Lys Tyr Gly Leu Asp Phe Trp Lys
145                 150                 155                 160 agc ttg aac gga gaa ctc gtc aca atg gcc aac ccc gtc gcc atc tcc     576
Ser Leu Asn Gly Glu Leu Val Thr Met Ala Asn Pro Val Ala Ile Ser
                165                 170                 175 aag atc acc aca tac ggc gag acg tgg atg gtg ggt agc tgg cct acg     624
Lys Ile Thr Thr Tyr Gly Glu Thr Trp Met Val Gly Ser Trp Pro Thr
            180                 185                 190 acc ggc cag aat aaa cga ggt ggc ttg acg ctg ggc gac aag gac ggc     672
Thr Gly Gln Asn Lys Arg Gly Gly Leu Thr Leu Gly Asp Lys Asp Gly
    195                 200                 205 aac cca gag gcc atc att gtc ggc gcg ccc ctc gac ggc agc agg gcc     720
Asn Pro Glu Ala Ile Ile Val Gly Ala Pro Leu Asp Gly Ser Arg Ala
210                 215                 220 gtc gac agc tac cgt atc ggc gat acg ttc cag aac atc act ggc gtg     768
Val Asp Ser Tyr Arg Ile Gly Asp Thr Phe Gln Asn Ile Thr Gly Val
225                 230                 235                 240 att cgt tat cag ttt ggc ttc tac tac ctt ctg cct ctg act tcg ccc     816
Ile Arg Tyr Gln Phe Gly Phe Tyr Tyr Leu Leu Pro Leu Thr Ser Pro
                245                 250                 255 gtc ctc gtg tcg tcg ccc agc ccg gcg ctg ccg cct cca act tca ctg     864
Val Leu Val Ser Ser Pro Ser Pro Ala Leu Pro Pro Pro Thr Ser Leu
            260                 265                 270 atc agc acg ggc gag tgc tcc ggc ctc acc ttt ggc gac tac aac atc     912
Ile Ser Thr Gly Glu Cys Ser Gly Leu Thr Phe Gly Asp Tyr Asn Ile
    275                 280                 285 gag aac ttc gca ccc tcg gat atg gcg cac gcc aac gac gtc gcg gcc     960
Glu Asn Phe Ala Pro Ser Asp Met Ala His Ala Asn Asp Val Ala Ala
290                 295                 300 cac atc gtg aat tac ctg aag agc cct gat gtg cta ttc gtc caa gag    1008
His Ile Val Asn Tyr Leu Lys Ser Pro Asp Val Leu Phe Val Gln Glu
305                 310                 315                 320 gtc cag gac aac agc ggc ccc acg aac aac ggt gtg gtt gac tct tca    1056
Val Gln Asp Asn Ser Gly Pro Thr Asn Asn Gly Val Val Asp Ser Ser
                325                 330                 335 gtg acc ctc agt gtt ctc gct tcg gtc att gcc aat atg ggg gga ccc    1104
Val Thr Leu Ser Val Leu Ala Ser Val Ile Ala Asn Met Gly Gly Pro
            340                 345                 350 aag tac tca tac act tgg atc aat ccg atc aat aac gca gat ggt ggc    1152
Lys Tyr Ser Tyr Thr Trp Ile Asn Pro Ile Asn Asn Ala Asp Gly Gly
    355                 360                 365 cag aat ggc ggg aat atc cgc gtg gcc tat ctg tac aac gca gat ctt    1200
```

```
                Gln Asn Gly Gly Asn Ile Arg Val Ala Tyr Leu Tyr Asn Ala Asp Leu
                    370                 375                 380 gtg cag ctg agc aac ggc agc ccc ggt ggt tcg ctc gac gcc aac gcc        1248
Val Gln Leu Ser Asn Gly Ser Pro Gly Gly Ser Leu Asp Ala Asn Ala
385                 390                 395                 400 gtg ctg gaa gac aag aat gga cgg cct act ctc aag tat aac ccg ggc        1296
Val Leu Glu Asp Lys Asn Gly Arg Pro Thr Leu Lys Tyr Asn Pro Gly
                405                 410                 415 ctc atc gac cct acc aac gcc gcg tgg gcg gca acc cgc aag ccg ttg        1344
Leu Ile Asp Pro Thr Asn Ala Ala Trp Ala Ala Thr Arg Lys Pro Leu
            420                 425                 430 gtt gct cag tgg cag act gtg gtt gga aac cac gtc ttc ttc acc gtc        1392
Val Ala Gln Trp Gln Thr Val Val Gly Asn His Val Phe Phe Thr Val
        435                 440                 445 aac gtg cac tgg agc tcc aag ggc ggc agc tcg agc ctc cag ggt gat        1440
Asn Val His Trp Ser Ser Lys Gly Gly Ser Ser Ser Leu Gln Gly Asp
    450                 455                 460 ccc cgc ccg ccc atc aac tca ccg att gag aag cgc atc cag cag gcc        1488
Pro Arg Pro Pro Ile Asn Ser Pro Ile Glu Lys Arg Ile Gln Gln Ala
465                 470                 475                 480 aat gtc acg gcc agc ttc atc gcc cag atc gtg gag tcg gac gca gac        1536
Asn Val Thr Ala Ser Phe Ile Ala Gln Ile Val Glu Ser Asp Ala Asp
                485                 490                 495 gcc cgt atc atc ttg gct ggc gat ctg aat gaa ttc gcg ttc gtc gag        1584
Ala Arg Ile Ile Leu Ala Gly Asp Leu Asn Glu Phe Ala Phe Val Glu
                500                 505                 510 ccc gtc aag acg ttt gcg gcc gtg tcc agc atg gtt gac ttg aac gat        1632
Pro Val Lys Thr Phe Ala Ala Val Ser Ser Met Val Asp Leu Asn Asp
            515                 520                 525 gct gcc aac atc cct gtt gag gag cgg tat acg tac acg ttt ggc gcc        1680
Ala Ala Asn Ile Pro Val Glu Glu Arg Tyr Thr Tyr Thr Phe Gly Ala
530                 535                 540 aac atg cag gag atc gac cac atg ttt gtc agt ccc gcc att gcc aac        1728
Asn Met Gln Glu Ile Asp His Met Phe Val Ser Pro Ala Ile Ala Asn
545                 550                 555                 560 ctg tcg ccg ctc cag gag cac atc cac gtc aac act tgg gtg tcg gtc        1776
Leu Ser Pro Leu Gln Glu His Ile His Val Asn Thr Trp Val Ser Val
                565                 570                 575 aag gac cag gtc tcc gat cac gac ccc acc gtg gcc aag ctc aac gtg        1824
Lys Asp Gln Val Ser Asp His Asp Pro Thr Val Ala Lys Leu Asn Val
                580                 585                 590 tgc ggc atc aat atc gga ccc aac gtc acc tcg acc acg aca agc            1872
Cys Gly Ile Asn Ile Gly Pro Asn Val Thr Ser Thr Thr Thr Ser
            595                 600                 605 acg gct acc att acg agc tcg acg tcc acc gtc act ggt gtc gtg acc        1920
Thr Ala Thr Ile Thr Ser Ser Thr Ser Thr Val Thr Gly Val Val Thr
610                 615                 620 aca acg aca cta acg acc tca aca act acc agc acg gct gcg ccc att        1968
Thr Thr Thr Leu Thr Thr Ser Thr Thr Thr Ser Thr Ala Ala Pro Ile
625                 630                 635                 640 gcc tcg ggc acg gcg ctc tcc ggc agg ggc cag ttc caa gta acc tcg        2016
Ala Ser Gly Thr Ala Leu Ser Gly Arg Gly Gln Phe Gln Val Thr Ser
                645                 650                 655 cca ggt gtg tct tcg ggc ggc agc ctg atc acc gca ggc acc tgg tac        2064
Pro Gly Val Ser Ser Gly Gly Ser Leu Ile Thr Ala Gly Thr Trp Tyr
                660                 665                 670 cgt ggc ggc ggc acc ccg gcc aca tac acg gcc acg ccc aac gca gac        2112
Arg Gly Gly Gly Thr Pro Ala Thr Tyr Thr Ala Thr Pro Asn Ala Asp
            675                 680                 685
```

```
ggc aaa acc ttc acg ctg gcc acc agc agg ggc aaa tgt gcg gtc ctc      2160
Gly Lys Thr Phe Thr Leu Ala Thr Ser Arg Gly Lys Cys Ala Val Leu
    690             695                 700 gct gac acg tcc ttc tcg tgc ggc acc ggc atc aca acc gcc agc agc      2208
Ala Asp Thr Ser Phe Ser Cys Gly Thr Gly Ile Thr Thr Ala Ser Ser
705             710                 715                 720 ttt ggc ttc gac ggc acg tac ctg acc ttc agc gga tcc aac gtc ttc      2256
Phe Gly Phe Asp Gly Thr Tyr Leu Thr Phe Ser Gly Ser Asn Val Phe
            725                 730                 735 cac gcc gct gct gtt ccc tct ggc acc acg cag gga act atc ttc acg      2304
His Ala Ala Ala Val Pro Ser Gly Thr Thr Gln Gly Thr Ile Phe Thr
                740                 745                 750 agc gaa cag gcc gtg act ctg cag gcg atc tgg aag cct ctc tag          2349
Ser Glu Gln Ala Val Thr Leu Gln Ala Ile Trp Lys Pro Leu
755                 760                 765
```

<210> SEQ ID NO 71
<211> LENGTH: 782
<212> TYPE: PRT
<213> ORGANISM: Phialophora geniculate

<400> SEQUENCE: 71

```
Met Gln Ser Leu Leu Ala Leu Leu Ala Leu Gly Thr Ala Val Gln Ala
    -15                 -10                 -5                  -1

Gln Ser Ile His Ala Ile Asn Gly Lys Asn Phe Leu Ser Pro Tyr Asn
1               5                   10                  15

Gly Ala Leu Val Thr Asn Val Thr Gly Ile Val Thr Ala Lys Ala Ser
                20                  25                  30

Asn Gly Leu Tyr Leu Arg Ser Pro Lys Pro Ala Cys Asp Val Arg Ile
            35                  40                  45

Gly Asn Gly Leu Val Val Tyr Asp Ser Thr Ile Gly Lys Asn Glu Ser
        50                  55                  60

Ile Ala Val Gly Asp Thr Leu Val Leu Ser Gly Lys Ile Thr Glu Tyr
65                  70                  75                  80

Arg Ser Thr Ala Thr Tyr Leu Tyr Leu Thr Glu Leu Glu Ser Pro Val
                85                  90                  95

Val Gln Ser Trp Val Lys Gly Glu Thr Ala Pro Lys Pro Arg Val Ile
            100                 105                 110

Gly Thr Asp Thr Met Ser Pro Pro Thr Glu His Phe Thr Gly Leu Asp
        115                 120                 125

Asn Gly Asp Val Phe Gly Ile Pro Asn Asp Asp Ser Arg Ile Ser Val
    130                 135                 140

Val Asn Pro Glu Leu Gln Pro Asp Lys Tyr Gly Leu Asp Phe Trp Lys
145                 150                 155                 160

Ser Leu Asn Gly Glu Leu Val Thr Met Ala Asn Pro Val Ala Ile Ser
                165                 170                 175

Lys Ile Thr Thr Tyr Gly Glu Thr Trp Met Val Gly Ser Trp Pro Thr
            180                 185                 190

Thr Gly Gln Asn Lys Arg Gly Gly Leu Thr Leu Gly Asp Lys Asp Gly
        195                 200                 205

Asn Pro Glu Ala Ile Ile Val Gly Ala Pro Leu Asp Gly Ser Arg Ala
    210                 215                 220

Val Asp Ser Tyr Arg Ile Gly Asp Thr Phe Gln Asn Ile Thr Gly Val
225                 230                 235                 240

Ile Arg Tyr Gln Phe Gly Phe Tyr Tyr Leu Leu Pro Leu Thr Ser Pro
                245                 250                 255
```

```
Val Leu Val Ser Ser Pro Ser Pro Ala Leu Pro Pro Thr Ser Leu
            260                 265                 270

Ile Ser Thr Gly Glu Cys Ser Gly Leu Thr Phe Gly Asp Tyr Asn Ile
            275                 280                 285

Glu Asn Phe Ala Pro Ser Asp Met Ala His Ala Asn Asp Val Ala Ala
290                 295                 300

His Ile Val Asn Tyr Leu Lys Ser Pro Asp Val Leu Phe Val Gln Glu
305                 310                 315                 320

Val Gln Asp Asn Ser Gly Pro Thr Asn Asn Gly Val Val Asp Ser Ser
                325                 330                 335

Val Thr Leu Ser Val Leu Ala Ser Val Ile Ala Asn Met Gly Gly Pro
            340                 345                 350

Lys Tyr Ser Tyr Thr Trp Ile Asn Pro Ile Asn Asn Ala Asp Gly Gly
            355                 360                 365

Gln Asn Gly Gly Asn Ile Arg Val Ala Tyr Leu Tyr Asn Ala Asp Leu
            370                 375                 380

Val Gln Leu Ser Asn Gly Ser Pro Gly Gly Ser Leu Asp Ala Asn Ala
385                 390                 395                 400

Val Leu Glu Asp Lys Asn Gly Arg Pro Thr Leu Lys Tyr Asn Pro Gly
                405                 410                 415

Leu Ile Asp Pro Thr Asn Ala Ala Trp Ala Ala Thr Arg Lys Pro Leu
            420                 425                 430

Val Ala Gln Trp Gln Thr Val Val Gly Asn His Val Phe Phe Thr Val
                435                 440                 445

Asn Val His Trp Ser Ser Lys Gly Gly Ser Ser Leu Gln Gly Asp
450                 455                 460

Pro Arg Pro Pro Ile Asn Ser Pro Ile Glu Lys Arg Ile Gln Gln Ala
465                 470                 475                 480

Asn Val Thr Ala Ser Phe Ile Ala Gln Ile Val Glu Ser Asp Ala Asp
                485                 490                 495

Ala Arg Ile Ile Leu Ala Gly Asp Leu Asn Glu Phe Ala Phe Val Glu
            500                 505                 510

Pro Val Lys Thr Phe Ala Ala Val Ser Ser Met Val Asp Leu Asn Asp
            515                 520                 525

Ala Ala Asn Ile Pro Val Glu Glu Arg Tyr Thr Tyr Thr Phe Gly Ala
530                 535                 540

Asn Met Gln Glu Ile Asp His Met Phe Val Ser Pro Ala Ile Ala Asn
545                 550                 555                 560

Leu Ser Pro Leu Gln Glu His Ile His Val Asn Thr Trp Val Ser Val
                565                 570                 575

Lys Asp Gln Val Ser Asp His Asp Pro Thr Val Ala Lys Leu Asn Val
            580                 585                 590

Cys Gly Ile Asn Ile Gly Pro Asn Val Thr Ser Thr Thr Thr Thr Ser
            595                 600                 605

Thr Ala Thr Ile Thr Ser Ser Thr Ser Thr Val Thr Gly Val Val Thr
            610                 615                 620

Thr Thr Thr Leu Thr Thr Ser Thr Thr Thr Ser Thr Ala Ala Pro Ile
625                 630                 635                 640

Ala Ser Gly Thr Ala Leu Ser Gly Arg Gly Gln Phe Gln Val Thr Ser
                645                 650                 655

Pro Gly Val Ser Ser Gly Gly Ser Leu Ile Thr Ala Gly Thr Trp Tyr
            660                 665                 670

Arg Gly Gly Gly Thr Pro Ala Thr Tyr Thr Ala Thr Pro Asn Ala Asp
```

```
            675                 680                 685
Gly Lys Thr Phe Thr Leu Ala Thr Ser Arg Gly Lys Cys Ala Val Leu
        690                 695                 700

Ala Asp Thr Ser Phe Ser Cys Gly Thr Gly Ile Thr Thr Ala Ser Ser
705                 710                 715                 720

Phe Gly Phe Asp Gly Thr Tyr Leu Thr Phe Ser Gly Ser Asn Val Phe
                725                 730                 735

His Ala Ala Val Pro Ser Gly Thr Thr Gln Gly Thr Ile Phe Thr
            740                 745                 750

Ser Glu Gln Ala Val Thr Leu Gln Ala Ile Trp Lys Pro Leu
        755                 760                 765

<210> SEQ ID NO 72
<211> LENGTH: 766
<212> TYPE: PRT
<213> ORGANISM: Phialophora geniculata

<400> SEQUENCE: 72

Gln Ser Ile His Ala Ile Asn Gly Lys Asn Phe Leu Ser Pro Tyr Asn
1               5                   10                  15

Gly Ala Leu Val Thr Asn Val Thr Gly Ile Val Thr Ala Lys Ala Ser
            20                  25                  30

Asn Gly Leu Tyr Leu Arg Ser Pro Lys Pro Ala Cys Asp Val Arg Ile
        35                  40                  45

Gly Asn Gly Leu Val Val Tyr Asp Ser Thr Ile Gly Lys Asn Glu Ser
    50                  55                  60

Ile Ala Val Gly Asp Thr Leu Val Leu Ser Gly Lys Ile Thr Glu Tyr
65                  70                  75                  80

Arg Ser Thr Ala Thr Tyr Leu Tyr Leu Thr Glu Leu Glu Ser Pro Val
                85                  90                  95

Val Gln Ser Trp Val Lys Gly Glu Thr Ala Pro Lys Pro Arg Val Ile
            100                 105                 110

Gly Thr Asp Thr Met Ser Pro Pro Thr Glu His Phe Thr Gly Leu Asp
        115                 120                 125

Asn Gly Asp Val Phe Gly Ile Pro Asn Asp Asp Ser Arg Ile Ser Val
    130                 135                 140

Val Asn Pro Glu Leu Gln Pro Asp Lys Tyr Gly Leu Asp Phe Trp Lys
145                 150                 155                 160

Ser Leu Asn Gly Glu Leu Val Thr Met Ala Asn Pro Val Ala Ile Ser
                165                 170                 175

Lys Ile Thr Thr Tyr Gly Glu Thr Trp Met Val Gly Ser Trp Pro Thr
            180                 185                 190

Thr Gly Gln Asn Lys Arg Gly Gly Leu Thr Leu Gly Asp Lys Asp Gly
        195                 200                 205

Asn Pro Glu Ala Ile Ile Val Gly Ala Pro Leu Asp Gly Ser Arg Ala
    210                 215                 220

Val Asp Ser Tyr Arg Ile Gly Asp Thr Phe Gln Asn Ile Thr Gly Val
225                 230                 235                 240

Ile Arg Tyr Gln Phe Gly Phe Tyr Tyr Leu Leu Pro Leu Thr Ser Pro
                245                 250                 255

Val Leu Val Ser Ser Pro Ser Pro Ala Leu Pro Pro Thr Ser Leu
            260                 265                 270

Ile Ser Thr Gly Glu Cys Ser Gly Leu Thr Phe Gly Asp Tyr Asn Ile
        275                 280                 285
```

```
Glu Asn Phe Ala Pro Ser Asp Met Ala His Ala Asn Asp Val Ala Ala
290                 295                 300

His Ile Val Asn Tyr Leu Lys Ser Pro Asp Val Leu Phe Val Gln Glu
305                 310                 315                 320

Val Gln Asp Asn Ser Gly Pro Thr Asn Asn Gly Val Val Asp Ser Ser
            325                 330                 335

Val Thr Leu Ser Val Leu Ala Ser Val Ile Ala Asn Met Gly Gly Pro
        340                 345                 350

Lys Tyr Ser Tyr Thr Trp Ile Asn Pro Ile Asn Asn Ala Asp Gly Gly
    355                 360                 365

Gln Asn Gly Gly Asn Ile Arg Val Ala Tyr Leu Tyr Asn Ala Asp Leu
370                 375                 380

Val Gln Leu Ser Asn Gly Ser Pro Gly Gly Ser Leu Asp Ala Asn Ala
385                 390                 395                 400

Val Leu Glu Asp Lys Asn Gly Arg Pro Thr Leu Lys Tyr Asn Pro Gly
                405                 410                 415

Leu Ile Asp Pro Thr Asn Ala Ala Trp Ala Ala Thr Arg Lys Pro Leu
            420                 425                 430

Val Ala Gln Trp Gln Thr Val Val Gly Asn His Val Phe Phe Thr Val
        435                 440                 445

Asn Val His Trp Ser Ser Lys Gly Gly Ser Ser Leu Gln Gly Asp
450                 455                 460

Pro Arg Pro Pro Ile Asn Ser Pro Ile Glu Lys Arg Ile Gln Gln Ala
465                 470                 475                 480

Asn Val Thr Ala Ser Phe Ile Ala Gln Ile Val Glu Ser Asp Ala Asp
                485                 490                 495

Ala Arg Ile Ile Leu Ala Gly Asp Leu Asn Glu Phe Ala Phe Val Glu
            500                 505                 510

Pro Val Lys Thr Phe Ala Ala Val Ser Ser Met Val Asp Leu Asn Asp
        515                 520                 525

Ala Ala Asn Ile Pro Val Glu Glu Arg Tyr Thr Tyr Thr Phe Gly Ala
530                 535                 540

Asn Met Gln Glu Ile Asp His Met Phe Val Ser Pro Ala Ile Ala Asn
545                 550                 555                 560

Leu Ser Pro Leu Gln Glu His Ile His Val Asn Thr Trp Val Ser Val
                565                 570                 575

Lys Asp Gln Val Ser Asp His Asp Pro Thr Val Ala Lys Leu Asn Val
            580                 585                 590

Cys Gly Ile Asn Ile Gly Pro Asn Val Thr Ser Thr Thr Thr Thr Ser
        595                 600                 605

Thr Ala Thr Ile Thr Ser Ser Thr Ser Thr Val Thr Gly Val Val Thr
610                 615                 620

Thr Thr Thr Leu Thr Thr Ser Thr Thr Thr Ser Thr Ala Ala Pro Ile
625                 630                 635                 640

Ala Ser Gly Thr Ala Leu Ser Gly Arg Gly Gln Phe Gln Val Thr Ser
                645                 650                 655

Pro Gly Val Ser Ser Gly Gly Ser Leu Ile Thr Ala Gly Thr Trp Tyr
            660                 665                 670

Arg Gly Gly Gly Thr Pro Ala Thr Tyr Thr Ala Thr Pro Asn Ala Asp
        675                 680                 685

Gly Lys Thr Phe Thr Leu Ala Thr Ser Arg Gly Lys Cys Ala Val Leu
690                 695                 700

Ala Asp Thr Ser Phe Ser Cys Gly Thr Gly Ile Thr Thr Ala Ser Ser
```

```
                705                 710                 715                 720
Phe Gly Phe Asp Gly Thr Tyr Leu Thr Phe Ser Gly Ser Asn Val Phe
                    725                 730                 735
His Ala Ala Ala Val Pro Ser Gly Thr Thr Gln Gly Thr Ile Phe Thr
                740                 745                 750
Ser Glu Gln Ala Val Thr Leu Gln Ala Ile Trp Lys Pro Leu
                755                 760                 765
```

<210> SEQ ID NO 73
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Gly (G) or Tyr (Y) or Trp (W) or Phe (F)
      or Ala (A) or His (H)
<220> FEATURE:
<221> NAME/KEY: MISC_FEATURE
<222> LOCATION: (4)..(4)
<223> OTHER INFORMATION: Xaa =Arg (R) or Gln (Q) or Asp (D) or Glu (E)
      or Val (V)

<400> SEQUENCE: 73

Xaa Asn Ile Xaa
1

<210> SEQ ID NO 74
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (4)..(4)
<223> OTHER INFORMATION: Xaa = Asp (D) or His(H) or Leu (L)

<400> SEQUENCE: 74

Ser Asp His Xaa Pro
1               5

<210> SEQ ID NO 75
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (5)..(5)
<223> OTHER INFORMATION: Xaa = Arg (R) or Gln (Q)

<400> SEQUENCE: 75

Gly Gly Asn Ile Xaa
1               5

The invention claimed is:

1. A detergent composition comprising a surfactant and a polypeptide having DNase activity, wherein the polypeptide having DNase activity has at least 90% sequence identity to the polypeptide of SEQ ID NO: 3 or is a fragment thereof having DNase activity.

2. The detergent composition of claim 1 which further comprises at least one additional component selected from:
   i. a polyol,
   ii. an additional enzyme, and
   iii. one or more polymer.

3. The detergent composition of claim 2, wherein the polyol is selected from glycerol, (mono, di, or tri) propylene glycol, ethylene glycol, polyethylene glycol, sugar alcohols, sorbitol, mannitol, erythritol, dulcitol, inositol, xylitol and adonitol.

4. The detergent composition of claim 2, comprising at least one additional enzyme, wherein the additional enzyme is selected from the group consisting of proteases, amylases and lipases.

5. The detergent composition according to claim 1, wherein the surfactant is selected from soap, LAS, AEOS and SLES.

6. The detergent composition of claim 2, wherein the polymer is selected from (carboxymethyl)cellulose (CMC), poly(vinyl alcohol) (PVA), poly(vinylpyrrolidone) (PVP), poly(ethyleneglycol) and poly(ethylene oxide) (PEG).

7. The detergent composition of claim 1, wherein the polypeptide having DNase activity has at least 98% sequence identity to the polypeptide of SEQ ID NO: 3.

8. The detergent composition of claim 1, wherein the polypeptide having DNase activity has at least 95% sequence identity to the polypeptide of SEQ ID NO: 3.

9. A laundering method for laundering an item comprising:
   a) exposing an item to a wash liquor comprising the detergent composition of claim 1;
   b) completing at least one wash cycle; and
   c) optionally rinsing the item,
wherein the item is a textile.

10. The method of claim 9, wherein the pH of the wash liquor is in the range 5.5 to 11.

11. The method of claim 9, wherein the temperature of the wash liquor is in the range of 5° C. to 95° C.

* * * * *